United States Patent
Chen et al.

(10) Patent No.: US 12,410,191 B2
(45) Date of Patent: Sep. 9, 2025

(54) MACROLIDE DERIVATIVES, PREPARATION METHOD AND APPLICATION THEREOF

(71) Applicants: ZHEJIANG HISUN PHARMACEUTICAL CO., LTD., Zhejiang (CN); SHANGHAI ARYL PHARMTECH CO., LTD., Shanghai (CN)

(72) Inventors: Youxi Chen, Shanghai (CN); Liang Gong, Shanghai (CN); Xingwu Zhu, Shanghai (CN); Qing Xiang, Shanghai (CN); Wentao Mao, Shanghai (CN); Cheng Ye, Shanghai (CN); Taishan Hu, Shanghai (CN); Lei Chen, Zhejiang (CN); Guoping Jiang, Shanghai (CN)

(73) Assignees: Zhejiang Hisun Pharmaceutical Co., Ltd., Zhejiang (CN); Shanghai Aryl Pharmtech Co., Ltd, Shanghai (CN)

( * ) Notice: Subject to any disclaimer, the term of this patent is extended or adjusted under 35 U.S.C. 154(b) by 894 days.

(21) Appl. No.: 17/612,315

(22) PCT Filed: May 20, 2020

(86) PCT No.: PCT/CN2020/091434
§ 371 (c)(1),
(2) Date: Nov. 18, 2021

(87) PCT Pub. No.: WO2020/233645
PCT Pub. Date: Nov. 26, 2020

(65) Prior Publication Data
US 2022/0235070 A1 Jul. 28, 2022

(30) Foreign Application Priority Data
May 21, 2019 (CN) .......................... 201910422337.4

(51) Int. Cl.
| | | |
|---|---|---|
| C07D 498/22 | (2006.01) | |
| A61P 25/00 | (2006.01) | |
| A61P 29/00 | (2006.01) | |
| A61P 35/00 | (2006.01) | |
| A61P 37/00 | (2006.01) | |
| C07D 487/04 | (2006.01) | |

(52) U.S. Cl.
CPC ............ *C07D 498/22* (2013.01); *A61P 35/00* (2018.01); *C07D 487/04* (2013.01)

(58) Field of Classification Search
CPC ..... C07D 498/22; C07D 487/04; A61P 35/00; A61P 29/00; A61P 37/00; A61P 25/00
See application file for complete search history.

(56) References Cited

U.S. PATENT DOCUMENTS 6,562,854 B2 * 5/2003 Church ................ C07D 401/14
 514/394
9,714,258 B2 * 7/2017 Cui ...................... C07D 498/18

FOREIGN PATENT DOCUMENTS

| | | |
|---|---|---|
| CN | 1251579 A | 4/2000 |
| CN | 102971322 A | 3/2013 |
| CN | 106170289 A | 11/2016 |
| CN | 107735399 A | 2/2018 |
| CN | 109715165 A | 5/2019 |
| CN | 111171049 A | 5/2020 |
| JP | 2001519806 A | 10/2001 |
| JP | 2002506072 A | 2/2002 |
| JP | 2013530142 A | 7/2013 |
| JP | 2017503867 A | 2/2017 |
| JP | 2018519343 A | 7/2018 |
| WO | 9845275 A1 | 10/1998 |
| WO | 2006082392 A1 | 8/2006 |
| WO | 2007123269 A1 | 11/2007 |
| WO | 2014022858 A1 | 2/2014 |
| WO | 2015089139 A1 | 6/2015 |
| WO | 2017007759 A1 | 1/2017 |
| WO | 2019023417 A1 | 1/2019 |
| WO | 2019037761 A1 | 2/2019 |
| WO | 2020185755 A1 | 9/2020 |

OTHER PUBLICATIONS

Notification of Reasons for Refusal for Japanese Patent Application 2021-569373 mailed Dec. 20, 2022; 15 pp.
English translation of the International Search Report for International Application No. PCT/CN2020/091434, mailed Aug. 19, 2020, 5 pages.
Notice of Reasons for Refusal for Japanese Patent Application No. 2023-117814 mailed Jul. 2, 2024; 9 pp.

* cited by examiner

*Primary Examiner* — Jeffrey S Lundgren
*Assistant Examiner* — Alexander K. Showalter
(74) *Attorney, Agent, or Firm* — Armstrong Teasdale LLP

(57) ABSTRACT

Provided are a macrolide derivative represented by formula (I), a preparation method thereof, and an application of the macrolide derivative as an inhibitor of one or more protein kinases of TRK, ALK and ROS1,

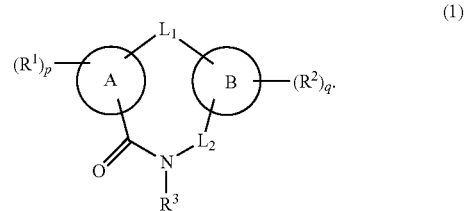

(I)

18 Claims, No Drawings

MACROLIDE DERIVATIVES, PREPARATION METHOD AND APPLICATION THEREOF

CROSS-REFERENCE TO RELATED APPLICATIONS

This application is a U.S. National Phase Application of PCT/CN2020/091434, filed May 20, 2020, which claims the benefit of priority to CN Application No. 201910422337.4, filed May 21, 2019, the contents of which are hereby expressly incorporated by reference in their entirety.

(A) TECHNICAL FIELD

The present invention relates to a novel macrolide derivative, a preparation method thereof, a pharmaceutical composition containing the derivative and application thereof as a therapeutic agent, especially as an inhibitor of one or more protein kinases of TRK, ALK and ROS1.

(B) BACKGROUND OF THE INVENTION

Tropomyosin-related receptor tyrosine kinase (TRK) is a high-affinity receptor of a neurotrophin (NT) (neurotrophic factor (NGF) family of protein). Neurotrophic factor receptor tyrosine kinase genes NTRK1, NTRK2 and NTRK3 encode TRKA, TRKB and TRKC proteins respectively, which are all tyrosine kinases, and collectively referred to as TRK family proteins. All the TRK proteins have a similar extracellular domain structure, but have respective different ligands: NGF binds to TRKA, a brain derived neurotrophic factor (BDNF) and a neurotrophic factor 4 (NT-4) bind to TRKB, and a neurotrophic factor 3 (NT-3) binds to TRKC.

Gene expression studies show that members of the TRK family are widely expressed in neuronal tissues and are related to the maintenance, signal transduction and survival of neuronal cells. NTRK gene is mainly expressed in a nervous system, and is also expressed in embryonic development and adults. When activated by signal induction, TRK may be subject to self-phosphorylation, and activates downstream signal pathways to implement various physiological functions. Downstream signal molecules of TRK comprise SHC, FRS2, PLCγ, MAPK, PI3K, PKC, or the like. Most of these signal molecules are closely related to functions including cell energy exchange, survival and proliferation. If TRK is dysfunctional, the physiological functions of cells may get out of control, and the cells may even become cancer cells. Overexpression, activation, amplification and mutation of the TRK protein and TRK gene fusion are related to many cancers, and the TRK gene fusion refers to the fusion of the members (NTRK1, NTRK2, NTRK3) of the NTRK gene family with another unrelated gene due to chromosome variation. A TRK fusion protein will be in a continuous active state, triggers a permanent signal cascade reaction, and drives the diffusion and growth of a TRK fusion tumor. The cancers comprise neuroblastoma, ovarian cancer, breast cancer, prostate cancer, gastric cancer, gastrointestinal cancer, liver cancer, cholangiocarcinoma, pancreatic cancer, multiple myeloma, astrocytoma, medulloblastoma, neuroglioma, melanoma, thyroid cancer, lung cancer, magnocellular neuroendocrine tumor, colorectal cancer, mammary analogue secretory carcinoma (MASC), sarcoma, head and neck tumor, renal carcinoma, and the like.

A TRK inhibitor is effective in a preclinical pain model, and especially, antagonistic NGF and TRKA antibodies (RN-624) are effective in animal models of inflammatory and neuropathic pain and human clinical trials. In addition, the activation of BDNF/TRKB pathways may be used as a regulator of various types of pains, including inflammatory pain, neuropathic pain and surgical pain. Since TRKA and RKB kinases may be used as mediators of NGF-driven biological reactions, TRKA and/or other TRK kinase inhibitors may provide effective treatment for chronic pains. The TRK inhibitor can effectively treat inflammatory pain, including but not limited to asthma, interstitial cystitis, ulcerative colitis, inflammatory bowel disease including Crohn's disease, eczema, psoriasis, or the like. The TRKA receptor is very important for a disease process of parasitic infection of Trypanosoma cruzi in a human host, therefore, the TRKA inhibitor may be used for treating a Chagas disease and related protozoan infection. TRK/neurotrophic factor pathway, which refers to BDNF/TRKB at the same time, is also related to the cause of neurodegenerative diseases, including multiple sclerosis, Parkinson's disease and Alzheimer's disease. The TRK inhibitor may also be used for treating diseases related to imbalance of bone remodeling regulation, such as osteoporosis, rheumatoid arthritis and bone metastasis.

Anaplastic lymphoma kinase (ALK) is a member of an insulin receptor superfamily of receptor tyrosine kinase, which is closely related to the tumorigenesis of hematopoietic and non-hematopoietic tumors. ALK gene is located on a No. 2 chromosome and mainly expressed in neurons, especially in the course of development. The ALK gene participates in the balanced chromosomal translocation of a nucleolar phosphoprotein (NPM) gene on a No. 5 chromosome in a large subset of anaplastic large cell lymphoma (ALCL). In ALK+ALCL, as a result of translocation, a ubiquitous promoter of NPM drives ectopic expression of the fusion protein, wherein NPM is partially dimerized and an ALK kinase domain is subject to self-phosphorylation and becomes constitutively active. It has been reported that the full-length ALK receptor protein is abnormally expressed in neuroblastoma and glioblastoma. Moreover, the ALK fusion protein has appeared in degenerative large cell lymphoma. The studies on the ALK fusion protein have promoted the possibility of a new treatment method for patients with ALK-positive malignant diseases. ROS1 belongs to the insulin receptor superfamily, and is similar to other tyrosine kinase receptor molecules, and ROS1 plays a role in transmitting growth signals from an external environment of cells into cell nucleuses. Genetic changes of ROS1, such as gene rearrangement, mutation or increased copy number, produce oncogenes that may cause cancers. It is found that ROS1 is in the form of fusion proteins (six different partners of ROS1) in NSCLC patients and exists in about 2% patients suffering NSCLC (Bergethon et al., 2012; Davies et al., 2012). Two other ROS1 gene rearrangements have been detected in various other cancers, and the cancers comprise glioblastoma multiforme, cholangiocarcinoma, ovarian cancer, gastric adenocarcinoma, colorectal cancer, inflammatory myofibroblastoma, angiosarcoma and epithelioid hemangioendothelioma. The ROS1 gene rearrangement results in a fusion protein with a constitutively active kinase domain, the kinase domain activates downstream signal transduction pathways leading to carcinogenic properties in cells, and the carcinogenic properties comprise uncontrolled proliferation and resistance to cell death by prolonging tumor cell survival.

In November, 2018, American FDA approved the listing of TRK inhibitor Larotrectinib, which was a novel oral drug for treating patients with abnormal variation of TRK. Previous studies have shown that the NTRK gene encoding

3

TRK may fuse abnormally with other genes, resulting in a cancer growing in many parts of a body, and the Larotrectinib can selectively inhibit TRK. Meanwhile, there are other TRK kinase inhibitors under study, including LOXO-195 (Loxo Oncology Inc, phase 2) and repotrectinib (TP therapeutics Inc, phase 2). At present, a series of TRK inhibitor patent applications have been published, including WO2015089139A1, WO2006082392A1, WO2007123269A1, and the like. The study and application of the TRK inhibitors have made some progress, but there is still a huge room for improvement. Therefore, it is still necessary to continue to study and develop novel TRK inhibitors.

(C) SUMMARY

In view of the above technical problems, the present invention provides a novel macrolide derivative represented by general formula (I), which can significantly improve the activity of wild-type and mutant TRKA, TRKB and TRKC enzymes. Meanwhile, the compound of the present invention has good pharmacokinetic absorption, significantly increased Cmax, low clearance rate, significantly improved bioavailability and preferable pharmacokinetic properties.

Therefore, in a first aspect, the present invention provides a compound represented by general formula (I) or a stereoisomer or a tautomer thereof, or a pharmaceutically acceptable salt thereof,

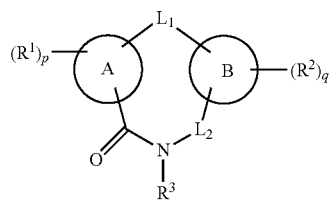

(I)

wherein:
ring A is selected from bicyclic heteroaryl;
ring B is selected from bicyclic aryl, bicyclic heteroaryl or bicyclic fused ring, wherein the bicyclic fused ring is preferably a fused ring of aryl or heteroaryl and monocyclic heterocyclyl or monocyclic cycloalkyl;
$L_1$ is selected from $—(CR^aR^b)_m—$, wherein any one of $—(CR^aR^b)—$ is optionally further replaced by $—N(R^c)—$, $—O—$ or $—S(O)_r—$;
$L_2$ is selected from $—(CR^dR^e)_n—$, wherein any one of $—(CR^dR^e)—$ is optionally further replaced by $—N(R^f)—$, $—O—$ or $—S(O)—$;
each $R^a$, $R^b$, $R^d$ and $R^e$ are the same or different and are each independently selected from hydrogen atom, deuterium, halogen, hydroxyl, alkoxy, alkyl, alkenyl, alkynyl, cycloalkyl, heterocyclyl, aryl, heteroaryl or $—NR^5R^6$, wherein the alkyl, alkenyl, alkynyl, cycloalkyl, heterocyclyl, aryl or heteroaryl is optionally further substituted by one or more substituents selected from hydroxyl, halogen, nitro, cyano, alkoxy, cycloalkyl, heterocyclyl, aryl, heteroaryl, $—C(O)R^4$, $—C(O)OR^4$, $—OC(O)R^4$, $—NR^5R^6$, $—C(O)NR^5R^6$, $—SO_2NR^5R^6$ or $—NR^5C(O)R^6$;
alternatively, $R^a$ and $R^b$ together with the same carbon atom bound therewith form a $C_3$-$C_8$ cycloalkyl or 3-8 membered heterocyclyl, wherein the 3-8 membered heterocyclyl internally contains one or more N, O or

4

$S(O)_r$, and the $C_3$-$C_8$ cycloalkyl or 3-8 membered heterocyclyl is optionally further substituted by one or more substituents selected from hydroxyl, halogen, nitro, cyano, alkyl, alkoxy, cycloalkyl, heterocyclyl, aryl, heteroaryl, =O, $—C(O)R^4$, $—C(O)OR^4$, $—OC(O)R^4$, $—NR^5R^6$, $—C(O)NR^5R^6$, $—SO_2NR^5R^6$ or $—NR^5C(O)R^6$;
alternatively, any two $R^a$ together with different carbon atoms respectively bound therewith form a $C_3$-$C_8$ cycloalkyl or 3-8 membered heterocyclyl, wherein the 3-8 membered heterocyclyl internally contains one or more N, O or $S(O)_r$, and the $C_3$-$C_8$ cycloalkyl or 3-8 membered heterocyclyl is optionally further substituted by one or more substituents selected from hydroxyl, halogen, nitro, cyano, alkyl, alkoxy, cycloalkyl, heterocyclyl, aryl, heteroaryl, =O, $—C(O)R^4$, $—C(O)OR^4$, $—OC(O)R^4$, $—NR^5R^6$, $—C(O)NR^5R^6$, $—SO_2NR^5R^6$ or $—NR^5C(O)R^6$;
alternatively, $R^d$ and $R^e$ together with the same carbon atom bound therewith form a $C_3$-$C_8$ cycloalkyl or 3-8 membered heterocyclyl, wherein the 3-8 membered heterocyclyl internally contains one or more N, O or $S(O)_r$, and the $C_3$-$C_8$ cycloalkyl or 3-8 membered heterocyclyl is optionally further substituted by one or more substituents selected from hydroxyl, halogen, nitro, cyano, alkyl, alkoxy, cycloalkyl, heterocyclyl, aryl, heteroaryl, =O, $—C(O)R^4$, $—C(O)OR^4$, $—OC(O)R^4$, $—NR^5R^6$, $—C(O)NR^5R^6$, $—SO_2NR^5R^6$ or $—NR^5C(O)R^6$;
alternatively, any two $R^d$ together with different carbon atoms respectively bound therewith form a $C_3$-$C_8$ cycloalkyl or 3-8 membered heterocyclyl, wherein the 3-8 membered heterocyclyl internally contains one or more N, O or $S(O)_r$, and the $C_3$-$C_8$ cycloalkyl or 3-8 membered heterocyclyl is optionally further substituted by one or more substituents selected from hydroxyl, halogen, nitro, cyano, alkyl, alkoxy, cycloalkyl, heterocyclyl, aryl, heteroaryl, =O, $—C(O)R^4$, $—C(O)OR^4$, $—OC(O)R^4$, $—NR^5R^6$, $—C(O)NR^5R^6$, $—SO_2NR^5R^6$ or $—NR^5C(O)R^6$;
each $R^c$ and $R^f$ are the same or different, and are each independently selected from hydrogen atom, alkyl or cycloalkyl, wherein the alkyl or cycloalkyl is optionally further substituted by one or more substituents selected from halogen, hydroxy, alkoxy or cycloalkyl; and $R^c$ and $R^f$ are preferably selected from hydrogen atom;
alternatively, when one $—(CR^aR^b)—$ is replaced by $—N(R^c)—$, $R^a$ or $R^b$ and $R^c$ together with the carbon atom and nitrogen atom respectively bound therewith form a 3-8 membered heterocyclyl, wherein the 3-8 membered heterocyclyl internally contains one or more N, O or $S(O)_r$, and the 3-8 membered heterocyclyl is optionally further substituted by one or more substituents selected from hydroxyl, halogen, nitro, cyano, alkyl, alkoxy, cycloalkyl, heterocyclyl, aryl, heteroaryl, =O, $—C(O)R^4$, $—C(O)OR^4$, $—OC(O)R^4$, $—NR^5R^6$, $—C(O)NR^5R^6$, $—SO_2NR^5R^6$ or $—NR^5C(O)R^6$;
alternatively, when one $—(CR^dR^e)—$ is replaced by $—N(R^f)—$, $R^d$ or $R^e$ and $R^f$ together with the carbon atom and nitrogen atom respectively bound therewith form a 3-8 membered heterocyclyl, wherein the 3-8 membered heterocyclyl internally contains one or more N, O or $S(O)_r$, and the 3-8 membered heterocyclyl is optionally further substituted by one or more substituents selected from hydroxyl, halogen, nitro, cyano, alkyl, alkoxy, cycloalkyl, heterocyclyl, aryl, heteroaryl, =O, —C(O)R⁴, —C(O)OR⁴, —OC(O)R⁴, —NR⁵R⁶, —C(O)NR⁵R⁶, —SO₂NR⁵R⁶ or —NR⁵C(O)R⁶;

each R¹ and R² are the same or different, and are each independently selected from hydrogen atom, hydroxyl, halogen, nitro, cyano, alkyl, alkoxy, cycloalkyl, heterocyclyl, aryl, heteroaryl, —C(O)R⁴, —C(O)OR⁴, —OC(O)R⁴, —NR⁵R⁶, —C(O)NR⁵R⁶, —SO₂NR⁵R⁶ or —NR⁵C(O)R⁶, wherein the alkyl, alkoxy, cycloalkyl, heterocyclyl, aryl or heteroaryl is optionally further substituted by one or more substituents selected from hydroxy, halogen, nitro, cyano, alkoxy, cycloalkyl, heterocyclyl, aryl, heteroaryl, =O, —C(O)R⁴, —C(O)OR⁴, —OC(O)R⁴, —NR⁵R⁶, —C(O)NR⁵R⁶, —SO₂NR⁵R⁶ or —NR⁵C(O)R⁶; preferably, R¹ and R² are each independently selected from hydrogen atom, halogen, amino, cyano, alkyl, alkoxy, haloalkyl, haloalkoxy, hydroxyalkyl or alkoxyalkyl; and more preferably, R¹ and R² are each independently selected from hydrogen atom, amino, cyano, F, Cl, Br, methyl, hydroxymethyl, halomethyl or methoxymethyl;

R³ is selected from hydrogen atom, alkyl or cycloalkyl, wherein the alkyl or cycloalkyl is optionally further substituted by one or more substituents selected from halogen, hydroxy, alkoxy or cycloalkyl;

R⁴, R⁵ and R⁶ are each independently selected from hydrogen atom, hydroxy, halogen, alkyl, alkoxy, cycloalkyl, heterocyclyl, aryl or heteroaryl, wherein the alkyl, alkoxy, cycloalkyl, heterocyclyl, aryl or heteroaryl is optionally further substituted by one or more substituents selected from hydroxyl, halogen, nitro, cyano, alkyl, alkoxy, cycloalkyl, heterocyclyl, aryl, heteroaryl, =O, —C(O)R⁷, —C(O)OR⁷, —OC(O)R⁷, —NR⁸R⁹, —C(O)NR⁸R⁹, —SO₂NR⁸R⁹ or —NR⁸C(O)R⁹;

alternatively, R⁵ and R⁶ together with the atom bound therewith form a 4-8 membered heterocyclyl, wherein the 4-8 membered heterocyclyl internally contains one or more N, O or S(O)ᵣ, and the 4-8 membered heterocyclyl is optionally further substituted by one or more substituents selected from hydroxyl, halogen, nitro, cyano, alkyl, alkoxy, cycloalkyl, heterocyclyl, aryl, heteroaryl, =O, —C(O)R⁷, —C(O)OR⁷, —OC(O)R⁷, —NR⁸R⁹, —C(O)NR⁸R⁹, —SO₂NR⁸R⁹ or —NR⁸C(O)R⁹;

R⁷, R⁸ and R⁹ are each independently selected from hydrogen atom, alkyl, cycloalkyl, heterocyclyl, aryl or heteroaryl, wherein the alkyl, cycloalkyl, heterocyclyl, aryl or heteroaryl is optionally further substituted by one or more substituents selected from hydroxyl, halogen, nitro, cyano, alkyl, alkoxy, cycloalkyl, heterocyclyl, aryl, heteroaryl, carboxyl or carboxylate;

m and n are the same or different and are each independently selected from 1, 2, 3 or 4;

p and q are the same or different and are each independently selected from 0, 1, 2, 3, 4 or 5; and r is selected from 0, 1 or 2.

In some preferred embodiments of the present invention, the compound represented by general formula (I) or the stereoisomer or the tautomer thereof, or the pharmaceutically acceptable salt thereof is a compound represented by general formula (II) or a stereoisomer or a tautomer thereof, or a pharmaceutically acceptable salt thereof,

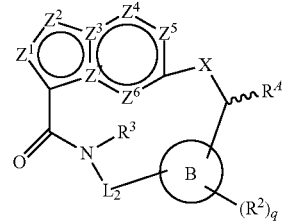

(II)

wherein:

ring B is selected from:

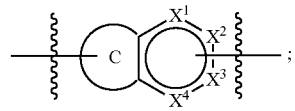

ring C is selected from monocyclic cycloalkyl, monocyclic heterocyclyl, monocyclic aryl or monocyclic heteroaryl, wherein ring C is bound with L₂;

X is selected from —N(Rᶜ)—, —O— or —S(O)ᵣ—; and preferably —NH—;

Z¹, Z², and Z⁴ to Z⁶ are the same or different and are each independently selected from N, NH, C(=O) or C(R¹);

Z³ and Z⁷ are the same or different and are each independently selected from N or C;

at least one of Z¹ to Z⁷ is not selected from N or NH;

X¹ to X⁴ are the same or different and are each independently selected from bonds, N, NH, C(=O) or C(R²);

at least one of X¹ to X⁴ is not selected from N or NH; and at most one of X¹ to X⁴ is selected from bonds;

Rᴬ is selected from hydrogen atom or alkyl, wherein the alkyl is optionally further substituted by one or more substituents selected from halogen, hydroxy, alkoxy or cycloalkyl; and Rᴬ is preferably methyl;

Rᶜ is selected from hydrogen atom, alkyl or cycloalkyl, wherein the alkyl or cycloalkyl is optionally further substituted by one or more substituents selected from halogen, hydroxy, alkoxy or cycloalkyl;

alternatively, when X is selected from —N(Rᶜ)—, Rᴬ and Rᶜ together with the carbon atom and nitrogen atom respectively bound therewith form a 4-8 membered heterocyclyl, wherein the 4-8 membered heterocyclyl internally contains one or more N, O or S(O)ᵣ, and the 4-8 membered heterocyclyl is optionally further substituted by one or more substituents selected from hydroxyl, halogen, nitro, cyano, alkyl, alkoxy, cycloalkyl, heterocyclyl, aryl, heteroaryl, =O, —C(O)R⁴, —C(O)OR⁴, —OC(O)R⁴, —NR⁵R⁶, —C(O)NR⁵R⁶, —SO₂NR⁵R⁶ or —NR⁵C(O)R⁶; and R¹ to R⁶, L₂, q and r are defined as in general formula (I).

In some preferred embodiments of the present invention, the compound represented by general formula (II) or the stereoisomer or the tautomer thereof, or the pharmaceutically acceptable salt thereof is a compound represented by general formula (III) or a stereoisomer or a tautomer thereof, or a pharmaceutically acceptable salt thereof,

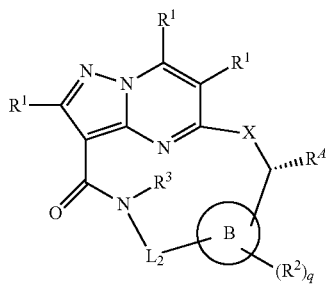

(III)

wherein: ring B, X, L₂, R¹ to R³, R⁴ and q are defined as in general formula (II).

In some preferred embodiments of the present invention, the compound represented by general formula (I), (II) or (III) or the stereoisomer or the tautomer thereof, or the pharmaceutically acceptable salt thereof, wherein ring B is selected from an 8-10 membered bicyclic fused ring, and preferably selected from:

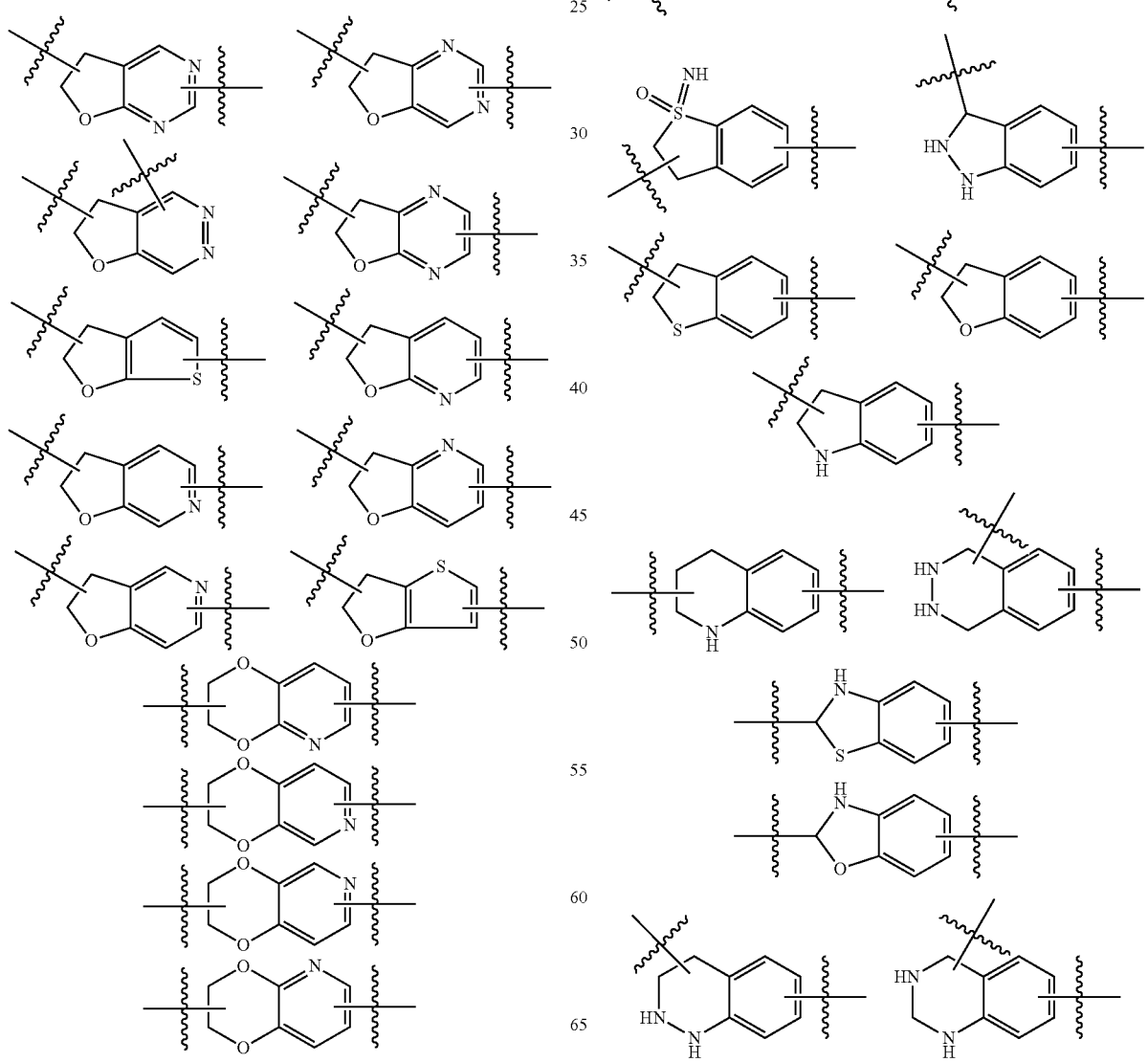

-continued
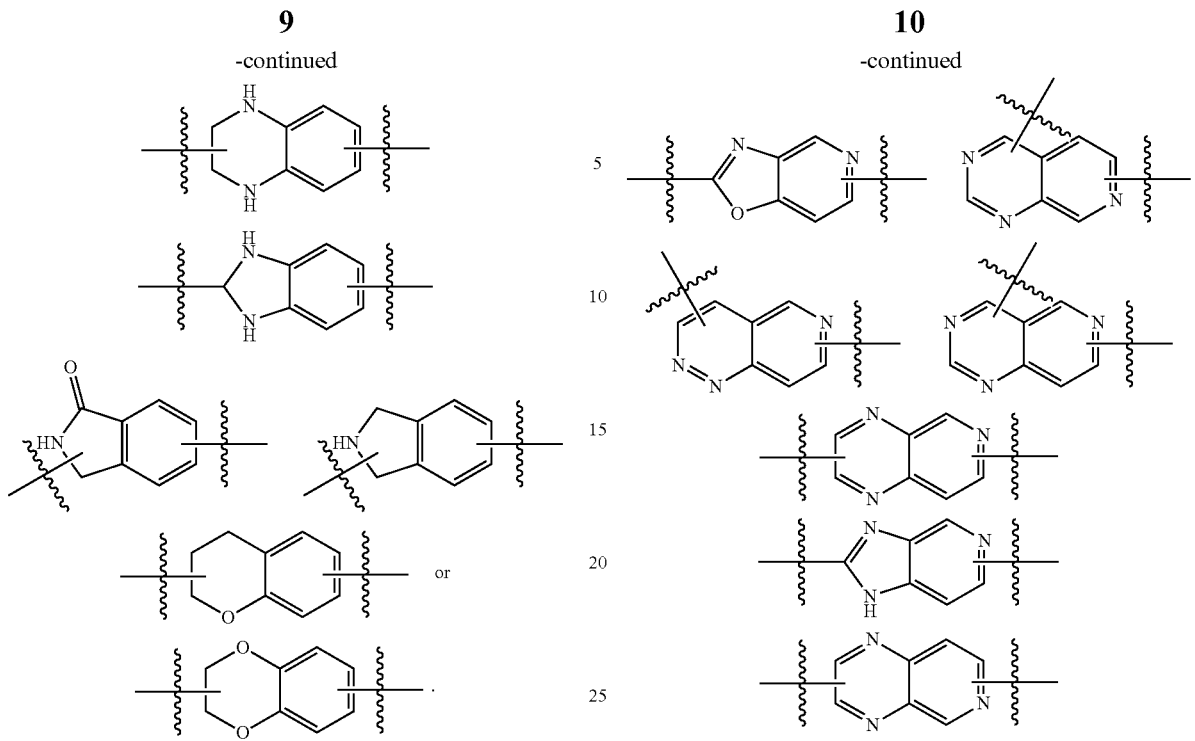
In some preferred embodiments of the present invention, the compound represented by general formula (I), (II) or (III) or the stereoisomer or the tautomer thereof, or the pharmaceutically acceptable salt thereof, wherein ring B is selected from an 8-10 membered bicyclic heteroaryl, and preferably selected from:
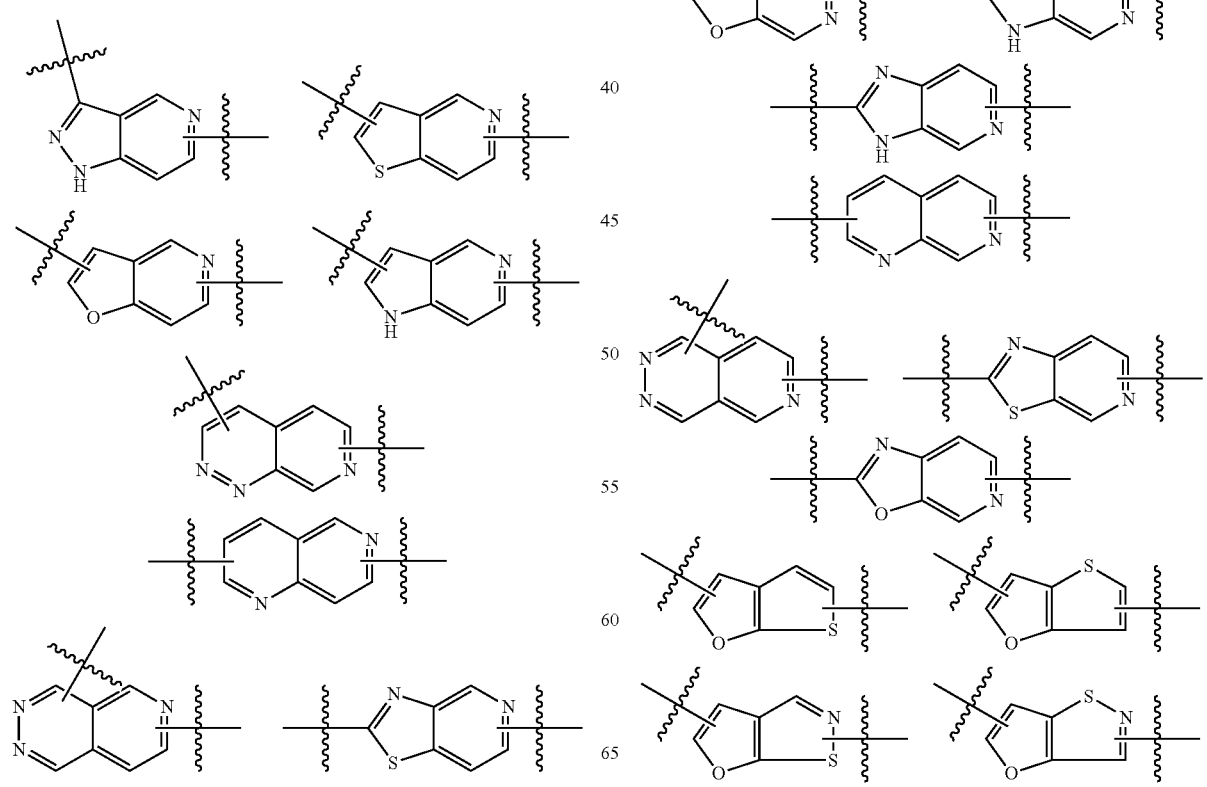

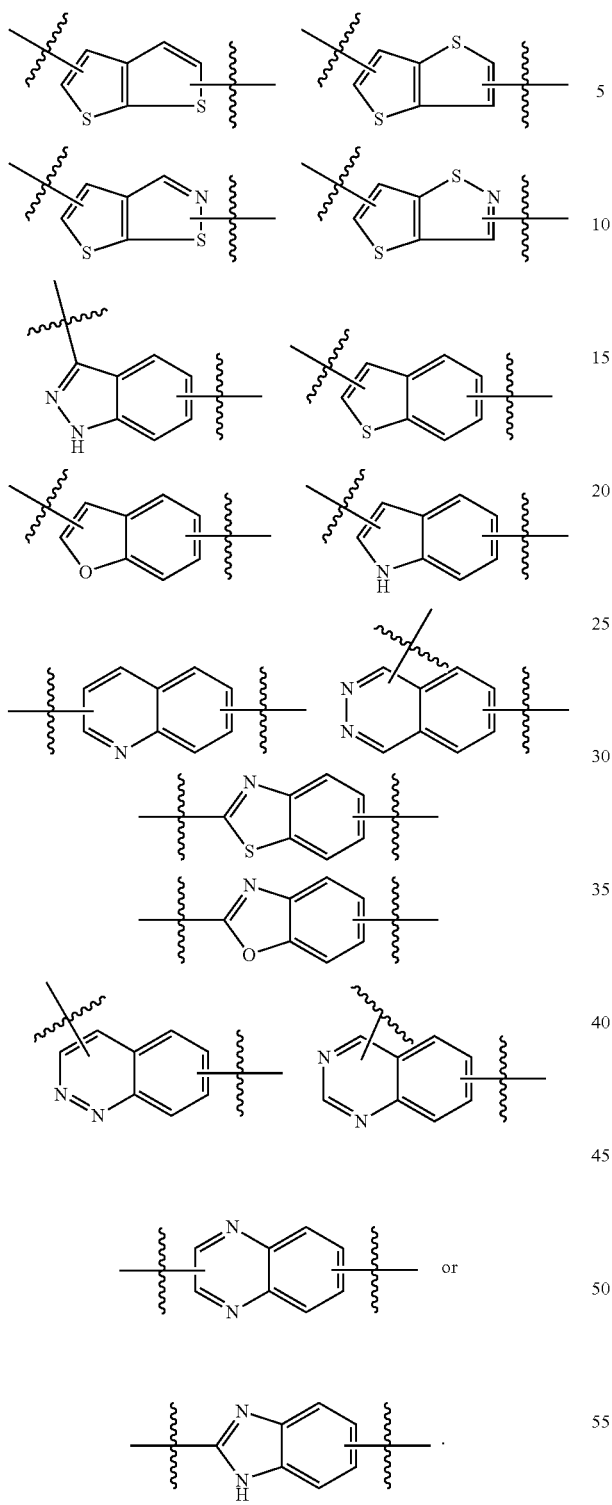

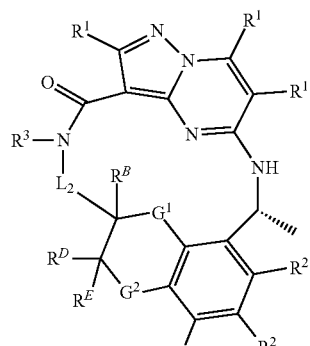

(IV)

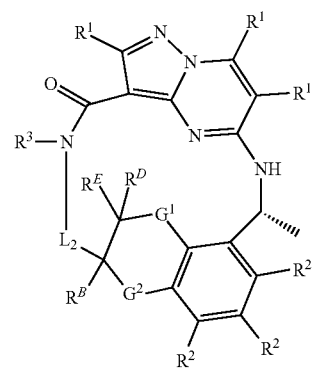

(V)

In some preferred embodiments of the present invention, the compound represented by general formula (III) or the stereoisomer or the tautomer thereof, or the pharmaceutically acceptable salt thereof is a compound represented by general formula (IV) or (V) or a stereoisomer or a tautomer thereof, or a pharmaceutically acceptable salt thereof, wherein:
$G^1$ and $G^2$ are the same or different, and are each independently selected from bonds, —N($R^g$)—, —(C$R^h R^i$)— or —O—;
$R^g$ is selected from hydrogen atom, alkyl or cycloalkyl, wherein the alkyl or cycloalkyl is optionally further substituted by one or more substituents selected from halogen, hydroxy or alkoxy;
$R^h$ and $R^i$ are the same or different and are each independently selected from hydrogen atom, deuterium, halogen, hydroxy, alkoxy, alkyl, alkenyl, alkynyl, cycloalkyl, heterocyclyl, aryl or heteroaryl, wherein the alkyl, alkenyl, alkynyl, cycloalkyl, heterocyclyl, aryl or heteroaryl is optionally further substituted by one or more substituents selected from hydroxy, halogen, nitro, cyano, alkoxy, cycloalkyl, heterocyclyl, aryl, heteroaryl, —C(O)$R^4$, —C(O)O$R^4$, —OC(O)$R^4$, —N$R^5 R^6$, —C(O)N$R^5 R^6$, —SO$_2$N$R^5 R^6$ or —N$R^5$C(O)$R^6$;
alternatively, $R^h$ and $R^i$ together with the carbon atom bound therewith form a $C_3$-$C_8$ cycloalkyl or 3-8 membered heterocyclyl, wherein the 3-8 membered heterocyclyl internally contains one or more N, O or S(O)$_r$, and the $C_3$-$C_8$ cycloalkyl or 3-8 membered heterocyclyl is optionally further substituted by one or more substituents selected from hydroxyl, halogen, nitro, cyano, alkyl, alkoxy, cycloalkyl, heterocyclyl, aryl, heteroaryl, =O, —C(O)$R^4$, —C(O)O$R^4$, —OC(O)$R^4$, —N$R^5 R^6$, —C(O)N$R^5 R^6$, —SO$_2$N$R^5 R^6$ or —N$R^5$C(O)$R^6$;
each $R^1$ and $R^2$ are the same or different, and are each independently selected from hydrogen atom, hydroxyl, halogen, nitro, cyano, alkyl, alkoxy, cycloalkyl, heterocyclyl, aryl, heteroaryl, —C(O)$R^4$, —C(O)O$R^4$, —OC(O)$R^4$, —N$R^5 R^6$, —C(O)N$R^5 R^6$, —SO$_2$N$R^5 R^6$ or —N$R^5$C(O)$R^6$, wherein the alkyl, alkoxy, cycloalkyl, heterocyclyl, aryl or heteroaryl is optionally further substituted by one or more substituents selected from hydroxy, halogen, nitro, cyano, alkoxy, cycloalkyl or heterocyclyl; preferably, $R^1$ and $R^2$ are each independently selected from hydrogen atom, halogen, amino, cyano, alkyl, alkoxy, haloalkyl, haloalkoxy, hydroxyalkyl or alkoxyalkyl; and more preferably, $R^1$ and $R^2$ are each independently selected from hydrogen atom, amino, cyano, F, Cl, Br, methyl, hydroxymethyl, halomethyl or methoxymethyl;

$R^B$ is selected from hydrogen atom, alkyl or alkoxy, wherein the alkyl or alkoxy is substituted by one or more substituents selected from hydroxy, halogen, nitro, cyano, alkoxy, cycloalkyl, heterocyclyl, aryl, heteroaryl, —C(O)$R^4$, —C(O)O$R^4$, —OC(O)$R^4$, —N$R^5R^6$, —C(O)N$R^5R^6$, —SO$_2$N$R^5R^6$ or —N$R^5$C(O)$R^6$; and $R^B$ is preferably selected from hydrogen atom or methyl, wherein the methyl is optionally further substituted by one or more substituents selected from halogen, hydroxy, cycloalkyl, alkoxy or —N$R^5R^6$;

$R^D$ and $R^E$ are the same or different, and are each independently selected from hydrogen atom, deuterium, halogen, hydroxy, alkoxy, alkyl, alkenyl, alkynyl, cycloalkyl, heterocyclyl, aryl, heteroaryl, —C(O)$R^4$, —C(O)O$R^4$, —OC(O)$R^4$, —N$R^5R^6$, —C(O)N$R^5R^6$, —SO$_2$N$R^5R^6$ or —N$R^5$C(O)$R^6$, wherein the alkyl, alkenyl, alkynyl, cycloalkyl, heterocyclyl, aryl or heteroaryl is optionally further substituted by one or more substituents selected from hydroxy, halogen, nitro, cyano, alkoxy, cycloalkyl, heterocyclyl, aryl, heteroaryl-C(O)$R^4$, —C(O)O$R^4$, —OC(O)$R^4$, —N$R^5R^6$, —C(O)N$R^5R^6$, —SO$_2$N$R^5R^6$ or —N$R^5$C(O)$R^6$;

alternatively, $R^D$ and $R^E$ together with the carbon atom bound therewith form a $C_3$-$C_6$ cycloalkyl or 3-6 membered heterocyclyl, wherein the 3-6 membered heterocyclyl internally contains one or more N, O or S(O)$_r$, and the $C_3$-$C_6$ cycloalkyl or 3-6 membered heterocyclyl is optionally further substituted by one or more substituents selected from hydroxyl, halogen, nitro, cyano, alkyl, alkoxy, cycloalkyl, heterocyclyl, aryl, heteroaryl, =O, —C(O)$R^4$, —C(O)O$R^4$, —OC(O)$R^4$, —N$R^5R^6$, —C(O)N$R^5R^6$, —SO$_2$N$R^5R^6$ or —N$R^5$C(O)$R^6$; and $L_2$, r, and $R^3$ to $R^6$ are defined as in general formula (III).

In some preferred embodiments of the present invention, the compound represented by general formula (III) or the stereoisomer or the tautomer thereof, or the pharmaceutically acceptable salt thereof is a compound represented by general formula (VI), (VII), (VIII) or (IX) or a stereoisomer or a tautomer thereof, or a pharmaceutically acceptable salt thereof,

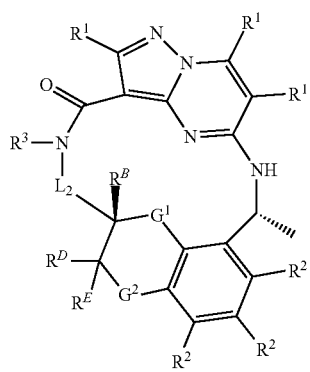

(VI)

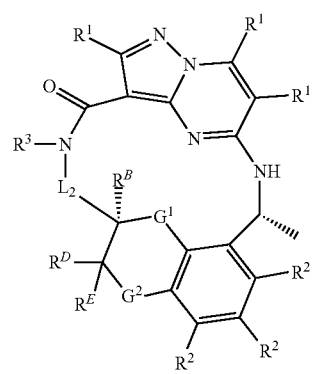

(VII)

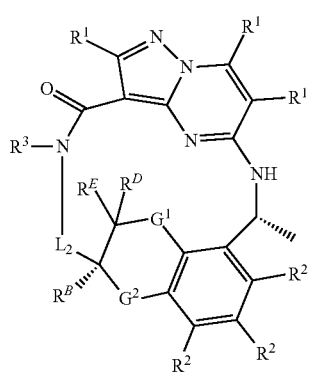

(VIII)

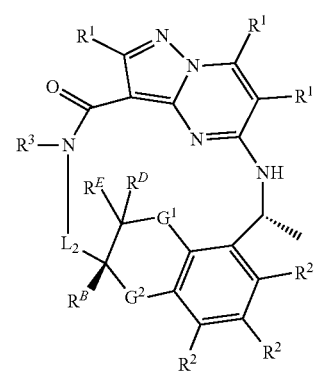

(IX)

wherein: $L_2$, $G^1$, $G^2$, $R^1$ to $R^3$, $R^B$, $R^D$ and $R^E$ are defined as in general formula (IV) or (V).

In some preferred embodiments of the present invention, the compound represented by general formula (I), (II), (III), (IV), (V), (VI), (VII), (VIII) or (IX) or the stereoisomer or the tautomer thereof, or the pharmaceutically acceptable salt thereof, wherein:

$L_2$ is selected from —(C$R^dR^e$)$_n$—;

$R^d$ is selected from hydrogen atom;

$R^e$ is selected from hydrogen atom, alkyl or alkoxy, and preferably hydrogen atom or methyl, wherein the alkyl or alkoxy is optionally further substituted by one or more halogens; and n is 1, 2 or 3.

Typical compounds of the present invention comprise, but are not limited to:

| Compound No. | Structure | Name |
|---|---|---|
| Example 1 | 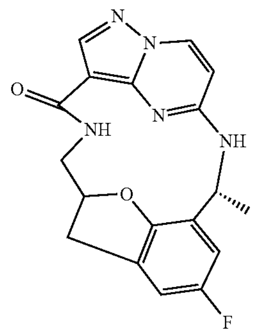 [SMILES: C[C@H]1Nc2ccn3ncc(c3n2)C(=O)NCC2Cc3cc(F)cc1c3O2] | (3R)-6-fluoro-3-methyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one |
| Example 2 | 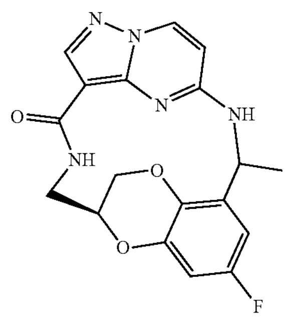 [SMILES: CC1Nc2ccn3ncc(c3n2)C(=O)NC[C@H]2COc3c(cc(F)cc31)O2] | (12S)-6-fluoro-3-methyl-10,24-dioxa-2,14,18,19,22-pentaazapentacyclo[14.5.2.1$^{8,12}$.0$^{4,9}$.0$^{19,23}$]tetracosa-1(22),4(9),5,7,16(23),17,20-heptaen-15-one |
| Example 3 | 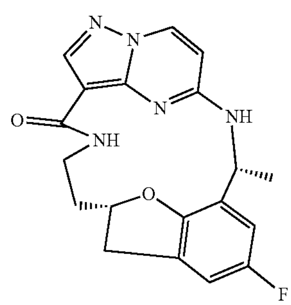 [SMILES: C[C@H]1Nc2ccn3ncc(c3n2)C(=O)NCC[C@H]2Cc3cc(F)cc1c3O2] | (3R,11R)-6-fluoro-3-methyl-10-oxa-2,14,18,19,22-pentaazapentacyclo[14.5.2.1$^{8,11}$.0$^{4,9}$.0$^{19,23}$]tetracosa-1(22),4,6,8,16(23),17,20-heptaen-15-one |
| Example 4 | 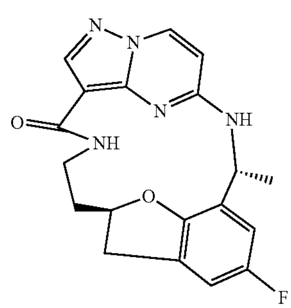 [SMILES: C[C@H]1Nc2ccn3ncc(c3n2)C(=O)NCC[C@@H]2Cc3cc(F)cc1c3O2] | (3R,11S)-6-fluoro-3-methyl-10-oxa-2,14,18,19,22-pentaazapentacyclo[14.5.2.1$^{8,11}$.0$^{4,9}$.0$^{19,23}$]tetracosa-1(22),4,6,8,16(23),17,20-heptaen-15-one |
| Example 5 | 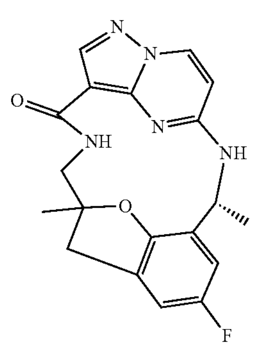 [SMILES: C[C@H]1Nc2ccn3ncc(c3n2)C(=O)NCC2(C)Cc3cc(F)cc1c3O2] | (3R)-6-fluoro-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one |

-continued

| Compound No. | Structure | Name |
|---|---|---|
| Example 6 | 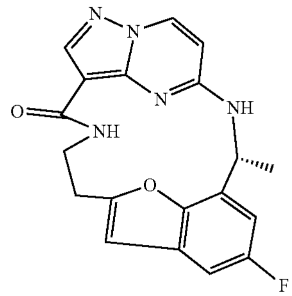 [SMILES: C[C@H]1Nc2ccn3ncc(c3n2)C(=O)NCCc2cc3cc(F)cc1c3o2] | (3R)-6-fluoro-3-methyl-10-oxa-2,14,18,19,22-pentaazapentacyclo[14.5.2.1$^{8,11}$.0$^{4,9}$.0$^{19,23}$]tetracosa-1(22),4,6,8,11(24),16(23),17,20-octaen-15-one |
| Example 7 | 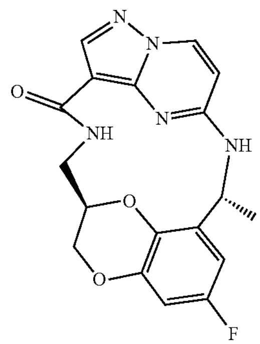 [SMILES: C[C@H]1Nc2ccn3ncc(c3n2)C(=O)NC[C@@H]2COc3cc(F)cc1c3O2] | (2R,14R)-19-fluoro-2-methyl-16,22-dioxa-3,5,7,8,12-pentaazapentacyclo[12.6.2.2$^{4,7}$.0$^{6,10}$.0$^{17,21}$]tetracosa-1(20),4,6(10),8,17(21),18,23-heptaen-11-one |
| Example 8 | 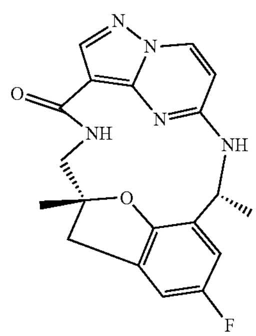 [SMILES: C[C@H]1Nc2ccn3ncc(c3n2)C(=O)NC[C@@]2(C)Cc3cc(F)cc1c3O2] | (3R,11R)-6-fluoro-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one |
| Example 9 | 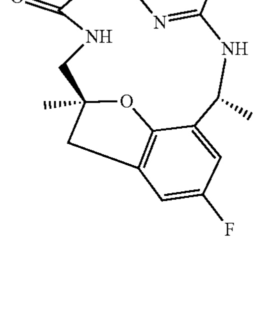 | (3R,11S)-6-fluoro-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one |

-continued

| Compound No. | Structure | Name |
|---|---|---|
| Example 10 | 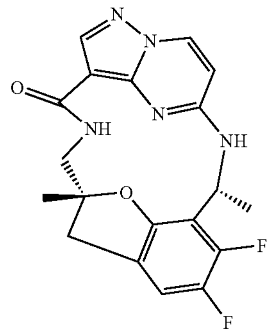 [SMILES: C[C@H]1Nc2ccn3ncc(c3n2)C(=O)NC[C@@]2(C)Cc3cc(F)c(F)c1c3O2] | (3R,11R)-5,6-difluoro-3,11-dimethyl-10-oxa-2,13, 17,18,21-pentaazapentacyclo[13.5.2.1$^{8,11}$.0$^{4,9}$.0$^{18,22}$] tricosa-1(21),4,6,8,15(22),16,19-heptaen-14-one |
| Example 11 | 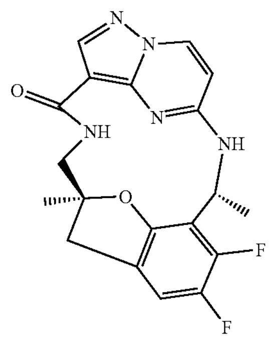 [SMILES: C[C@H]1Nc2ccn3ncc(c3n2)C(=O)NC[C@]2(C)Cc3cc(F)c(F)c1c3O2] | (3R,11S)-5,6-difluoro-3,11-dimethyl-10-oxa-2,13,17, 18,21-pentaazapentacyclo[13.5.2.1$^{8,11}$.0$^{4,9}$.0$^{18,22}$] tricosa-1(21),4,6,8,15(22),16,19-heptaen-14-one |
| Example 12 | 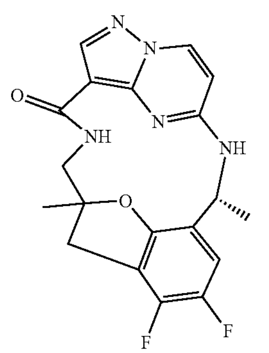 [SMILES: C[C@H]1Nc2ccn3ncc(c3n2)C(=O)NCC2(C)Cc3c(F)c(F)cc1c3O2] | (3R)-6,7-difluoro-3,11-dimethyl-10-oxa-2,13,17,18, 21-pentaazapentacyclo[13.5.2.1$^{8,11}$.0$^{4,9}$.0$^{18,22}$]tricosa-1(21),4,6,8,15(22),16,19-heptaen-14-one |
| Example 13 | 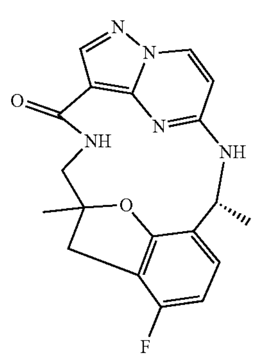 [SMILES: C[C@H]1Nc2ccn3ncc(c3n2)C(=O)NCC2(C)Cc3c(F)ccc1c3O2] | (3R)-7-fluoro-3,11-dimethyl-10-oxa-2,13,17,18,21-pentaazapentacyclo[13.5.2.1$^{8,11}$.0$^{4,9}$.0$^{18,22}$]-tricosa-1(21),4,6,8,15(22),16,19-heptaen-14-one |

-continued

| Compound No. | Structure | Name |
|---|---|---|
| Example 14 | 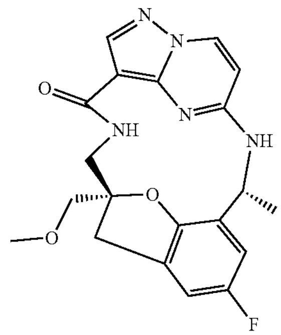 | (3R,11S)-6-fluoro-11-(methoxymethyl)-3-methyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one |
| Example 15 | 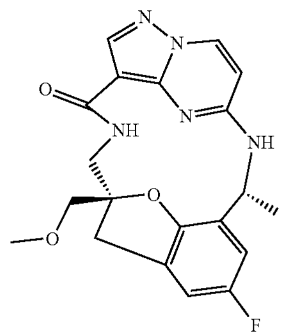 | (3R,11R)-6-fluoro-11-(methoxymethyl)-3-methyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one |
| Example 16 | 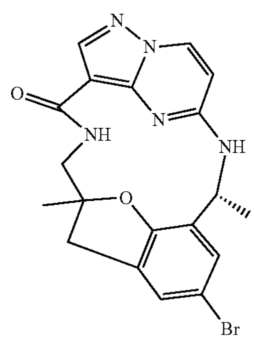 [SMILES: C[C@H]1Nc2ccn3ncc(c3n2)C(=O)NCC2(C)Cc3cc(Br)cc1c3O2] | (3R)-6-bromo-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one |
| Example 17 | 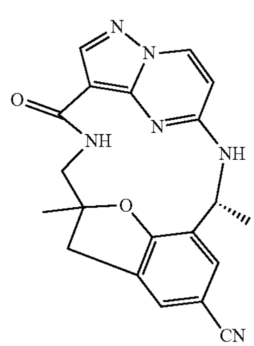 [SMILES: C[C@H]1Nc2ccn3ncc(c3n2)C(=O)NCC2(C)Cc3cc(C#N)cc1c3O2] | (3R)-6-Cyano-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one |

-continued

| Compound No. | Structure | Name |
|---|---|---|
| Example 18 | 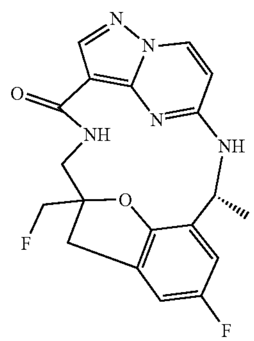 [SMILES: C[C@H]1Nc2ccn3ncc(c3n2)C(=O)NCC2(CF)Cc3cc(F)cc1c3O2] | (3R)-6-fluoro-11-(fluoromethyl)-3-methyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one |
| Example 19 | 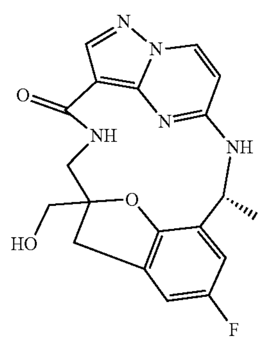 [SMILES: C[C@H]1Nc2ccn3ncc(c3n2)C(=O)NCC2(CO)Cc3cc(F)cc1c3O2] | (3R)-6-fluoro-11-(hydroxymethyl)-3-methyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one |
| Example 20 | 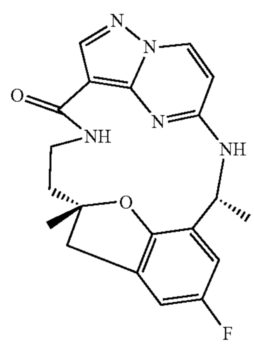 [SMILES: C[C@H]1Nc2ccn3ncc(c3n2)C(=O)NCC[C@@]2(C)Cc3cc(F)cc1c3O2] | (3R,11R)-6-fluoro-3,11-dimethyl-10-oxa-2,14,18,19,22-pentaazapentacyclo[14.5.2.1$^{8,11}$.0$^{4,9}$.0$^{19,23}$]tetracosa-1(22),4,6,8,16(23),17,20-heptaen-15-one |
| Example 21 | 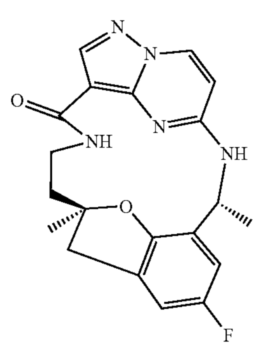 [SMILES: C[C@H]1Nc2ccn3ncc(c3n2)C(=O)NCC[C@]2(C)Cc3cc(F)cc1c3O2] | (3R,11S)-6-fluoro-3,11-dimethyl-10-oxa-2,14,18,19,22-pentaazapentacyclo[14.5.2.1$^{8,11}$.0$^{4,9}$.0$^{19,23}$]tetracosa-1(22),4,6,8,16(23),17,20-heptaen-15-one |

-continued

| Compound No. | Structure | Name |
|---|---|---|
| Example 22 | 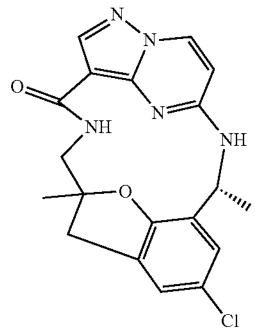 [SMILES: C[C@H]1Nc2ccn3ncc(c3n2)C(=O)NCC2(C)Cc3cc(Cl)cc1c3O2] | (3R)-6-chloro-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one |
| Example 23 | 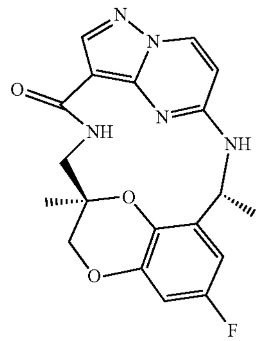 [SMILES: C[C@H]1Nc2ccn3ncc(c3n2)C(=O)NC[C@]2(C)COc3cc(F)cc1c3O2] | (2R,14R)-19-fluoro-2,14-dimethyl-16,22-dioxa-3,5,7,8,12-pentaazapentacyclo[12.6.2.2$^{4,7}$.0$^{6,10}$.0$^{17,21}$]tetracosa-1(20),4,6(10),8,17(21),18,23-heptaen-11-one |
| Example 24 | 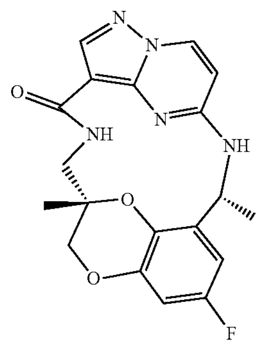 [SMILES: C[C@H]1Nc2ccn3ncc(c3n2)C(=O)NC[C@@]2(C)COc3cc(F)cc1c3O2] | (2R,14S)-19-fluoro-2,14-dimethyl-16,22-dioxa-3,5,7,8,12-pentaazapentacyclo[12.6.2.2$^{4,7}$.0$^{6,10}$.0$^{17,21}$]tetracosa-1(20),4,6(10),8,17(21),18,23-heptaen-11-one |
| Example 25 | 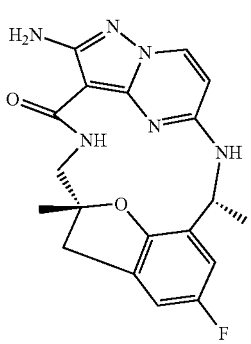 [SMILES: C[C@H]1Nc2ccn3nc(N)c(c3n2)C(=O)NC[C@@]2(C)Cc3cc(F)cc1c3O2] | (3R,11R)-16-amino-6-fluoro-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one |

| Compound No. | Structure | Name |
|---|---|---|
| Example 26 | 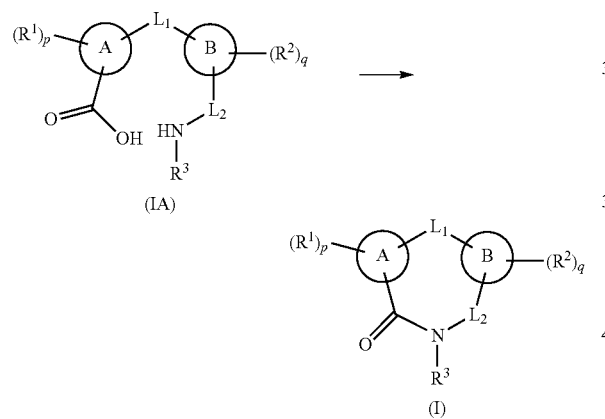 | (3R,11R)-6-fluoro-3,11-dimethyl-10-oxa-2,13,17,21,22-pentaazapentacyclo[13.5.2.1$^{8,11}$.0$^{4,9}$.0$^{18,22}$]tricosa-1(21),4,6,8,15,17,19-heptaen-14-one | or a stereoisomer, tautomer thereof or a pharmaceutically acceptable salt thereof.

In another aspect, the present invention provides a preparation method of the compound represented by general formula (I) or the stereoisomer or the tautomer thereof, or the pharmaceutically acceptable salt thereof, wherein the method comprises:

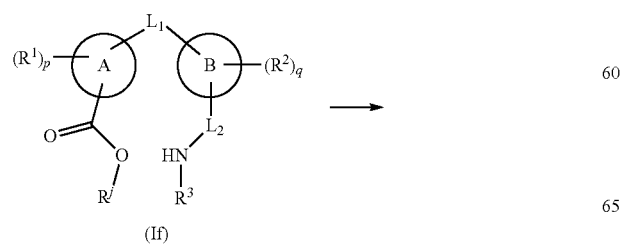

subjecting a compound represented by general formula (IA) to a condensation reaction under basic conditions to obtain a compound represented by general formula (I);

wherein: ring A, ring B, $R^1$ to $R^3$, $L_1$, $L_2$, p and q are defined as in general formula (I).

In another aspect, the present invention provides a preparation method of the compound represented by general formula (I) or the stereoisomer or the tautomer thereof, or the pharmaceutically acceptable salt thereof, wherein the method comprises:

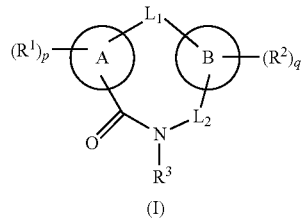

subjecting a compound represented by general formula (If) to a condensation reaction under basic conditions to obtain a compound represented by general formula (I);

wherein:

$R^j$ is selected from alkyl; and ring A, ring B, $R^1$ to $R^3$, $L_1$, $L_2$, p and q are defined as in general formula (I).

In another aspect, the present invention provides a compound represented by general formula (IA) or a stereoisomer or a tautomer thereof,

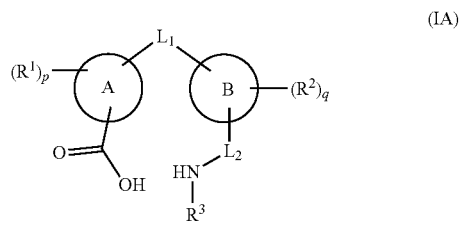

wherein: ring A, ring B, $R^1$ to $R^3$, $L_1$, $L_2$, p and q are defined as in general formula (I).

Typical compounds represented by general formula (IA) comprise, but are not limited to:

| Compound No. | Structure | Name |
|---|---|---|
| 1m | 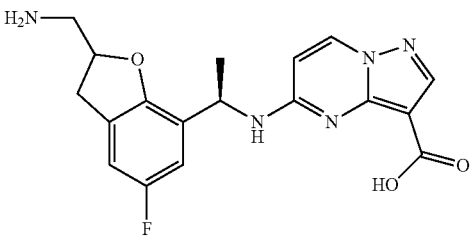 [SMILES: C[C@@H](Nc1ccn2ncc(C(=O)O)c2n1)c1cc(F)cc2c1OC(CN)C2] | 5-(((1R)-1-(2-(aminomethyl)-2,3-dihydrobenzofuran-7-yl)ethyl)amino)pyrazolo[1,5-a]pyrimidine-3-carboxylic acid |
| 2j | 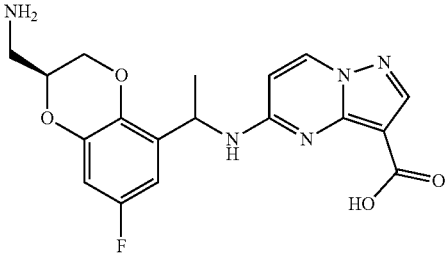 [SMILES: CC(Nc1ccn2ncc(C(=O)O)c2n1)c1cc(F)cc2c1OC[C@H](CN)O2] | 5-((1-((2S)-2-(aminomethyl)-7-fluoro-2,3-dihydrobenzo[b][1,4]dioxin-5-yl)ethyl)amino)pyrazolo[1,5-a]pyrimidine-3-carboxylic acid |
| 3l | 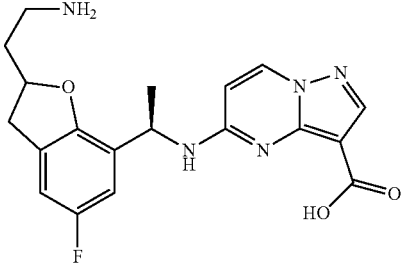 [SMILES: C[C@@H](Nc1ccn2ncc(C(=O)O)c2n1)c1cc(F)cc2c1OC(CCN)C2] | 5-(((1R)-1-(2-(2-aminoethyl)-5-fluoro-2,3-dihydrobenzofuran-7-yl)ethyl)amino)pyrazolo[1,5-a]pyrimidine-3-carboxylic acid |
| 5j | 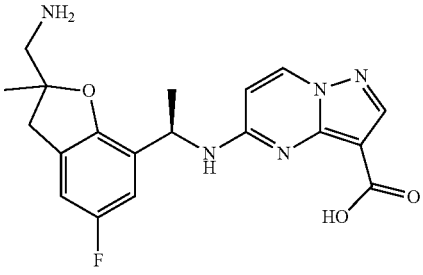 | 5-(((1R)-1-(2-(aminomethyl)-5-fluoro-2-methyl-2,3-dihydrobenzofuran-7-yl)ethyl)amino)pyrazolo[1,5-a]pyrimidine-3-carboxylic acid |
| 6n | 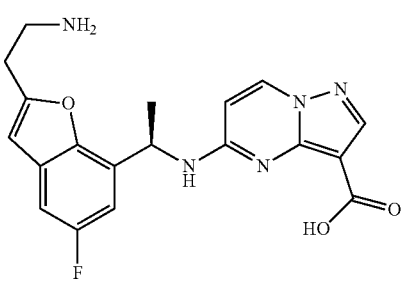 [SMILES: C[C@@H](Nc1ccn2ncc(C(=O)O)c2n1)c1cc(F)cc2cc(CCN)oc12] | (1R)-5-((1-(2-(2-aminoethyl)-5-fluorobenzofuran-7-yl)ethyl)amino)pyrazolo[1,5-a]pyrimidine-3-carboxylic acid |

-continued

| Compound No. | Structure | Name |
|---|---|---|
| 7j | 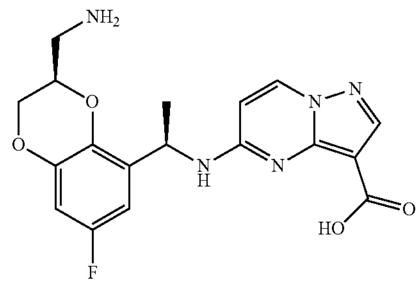 [SMILES: C[C@@H](Nc1ccn2ncc(C(=O)O)c2n1)c1cc(F)cc2c1O[C@H](CN)CO2] | 5-(((1R)-1-((3R)-3-(aminomethyl)-7-fluoro-2,3-dihydrobenzo[b][1,4]dioxin-5-yl)ethyl)amino)pyrazolo[1,5-a]pyrimidine-3-carboxylic acid |
| 8h | 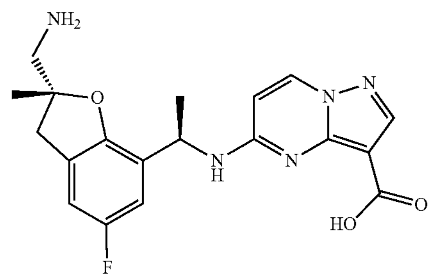 [SMILES: C[C@@H](Nc1ccn2ncc(C(=O)O)c2n1)c1cc(F)cc2c1O[C@@](C)(CN)C2] | 5-(((1R)-1-((2R)-2-(aminomethyl)-5-fluoro-2-methyl-2,3-dihydrobenzofuran-7-yl)ethyl)amino)pyrazolo[1,5-a]pyrimidine-3-carboxylic acid |
| 9f | 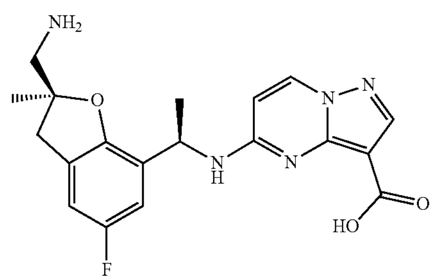 [SMILES: C[C@@H](Nc1ccn2ncc(C(=O)O)c2n1)c1cc(F)cc2c1O[C@](C)(CN)C2] | 5-(((1R)-1-((2S)-2-(aminomethyl)-5-fluoro-2-methyl-2,3-dihydrobenzofuran-7-yl)ethyl)amino)pyrazolo[1,5-a]pyrimidine-3-carboxylic acid |
| 10m | 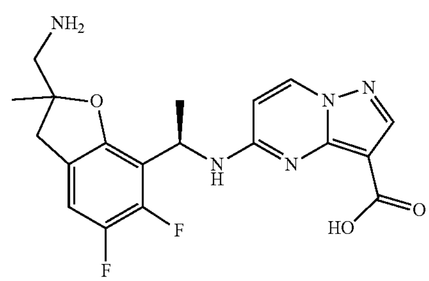 [SMILES: C[C@@H](Nc1ccn2ncc(C(=O)O)c2n1)c1c(F)c(F)cc2c1OC(C)(CN)C2] | 5-(((1R)-1-(2-(aminomethyl)-5,6-difluoro-2-methyl-2,3-dihydrobenzofuran-7-yl)ethyl)amino)pyrazolo[1,5-a]pyrimidine-3-carboxylic acid |
| 12i | 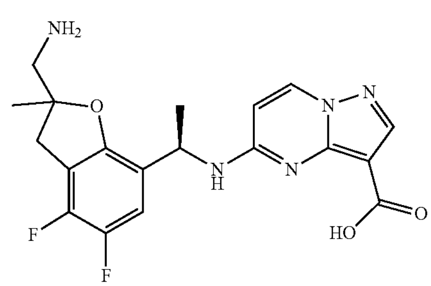 [SMILES: C[C@@H](Nc1ccn2ncc(C(=O)O)c2n1)c1cc(F)c(F)c2c1OC(C)(CN)C2] | 5-(((1R)-1-(2-(aminomethyl)-4,5-difluoro-2-methyl-2,3-dihydrobenzofuran-7-yl)ethyl)amino)pyrazolo[1,5-a]pyrimidine-3-carboxylic acid |

| Compound No. | Structure | Name |
|---|---|---|
| 13l | 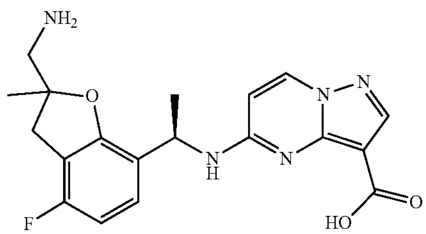 [SMILES: C[C@@H](Nc1ccn2ncc(C(=O)O)c2n1)c1ccc(F)c2c1OC(C)(CN)C2] | 5-(((1R)-1-(2-(aminomethyl)-4-fluoro-2-methyl-2,3-dihydrobenzofuran-7-yl)ethyl)amino)pyrazolo[1,5-a]pyrimidine-3-carboxylic acid |
| 14n | 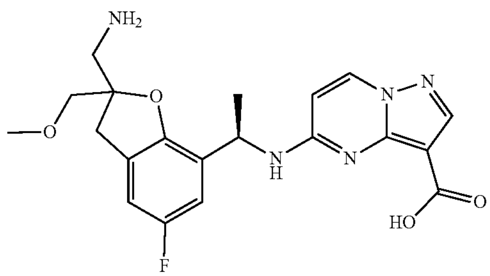 [SMILES: COCC1(CN)Cc2cc(F)cc([C@@H](C)Nc3ccn4ncc(C(=O)O)c4n3)c2O1] | 5-(((1R)-1-(2-(aminomethyl)-5-fluoro-2-(methoxymethyl)-2,3-dihydrobenzofuran-7-yl)ethyl)amino)pyrazolo[1,5-a]pyrimidine-3-carboxylic acid |
| 16l | 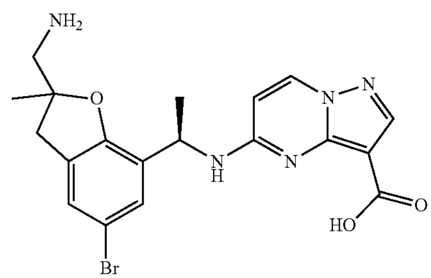 [SMILES: C[C@@H](Nc1ccn2ncc(C(=O)O)c2n1)c1cc(Br)cc2c1OC(C)(CN)C2] | 5-(((1R)-1-(2-(aminomethyl)-5-bromo-2-methyl-2,3-dihydrobenzofuran-7-yl)ethyl)amino)pyrazolo[1,5-a]pyrimidine-3-carboxylic acid |
| 18n | 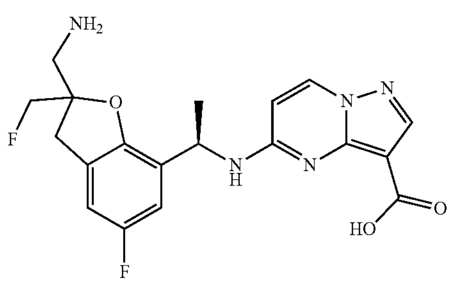 [SMILES: C[C@@H](Nc1ccn2ncc(C(=O)O)c2n1)c1cc(F)cc2c1OC(CN)(CF)C2] | 5-(((1R)-1-(2-(aminomethyl)-5-fluoro-2-(fluoromethyl)-2,3-dihydrobenzofuran-7-yl)ethyl)amino)pyrazolo[1,5-a]pyrimidine-3-carboxylic acid |
| 19h | 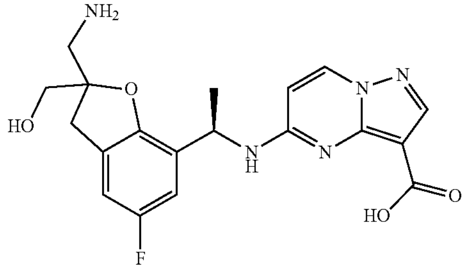 [SMILES: C[C@@H](Nc1ccn2ncc(C(=O)O)c2n1)c1cc(F)cc2c1OC(CN)(CO)C2] | 5-(((1R)-1-(2-(aminomethyl)-5-fluoro-2-(hydroxymethyl)-2,3-dihydrobenzofuran-7-yl)ethyl)amino)pyrazolo[1,5-a]pyrimidine-3-carboxylic acid |

-continued

| Compound No. | Structure | Name |
|---|---|---|
| 20k | 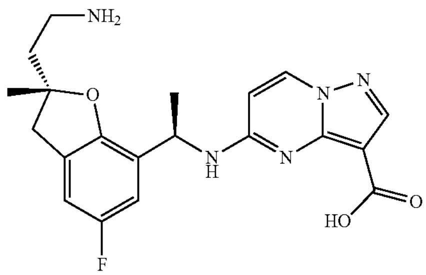 [SMILES: C[C@@H](Nc1ccn2ncc(C(=O)O)c2n1)c1cc(F)cc2c1O[C@@](C)(CCN)C2] | 5-(((R)-1-((R)-2-(2-aminoethyl)-5-fluoro-2-methyl-2,3-dihydrobenzofuran-7-yl)ethyl)amino)pyrazolo[1,5-a]pyrimidine-3-carboxylic acid |
| 21e | 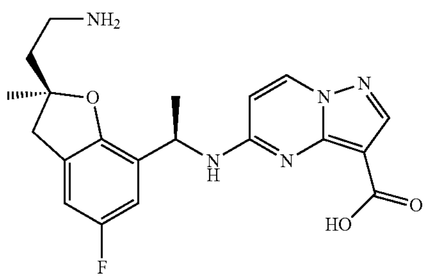 [SMILES: C[C@@H](Nc1ccn2ncc(C(=O)O)c2n1)c1cc(F)cc2c1O[C@](C)(CCN)C2] | 5-(((R)-1-((S)-2-(2-aminoethyl)-5-fluoro-2-methyl-2,3-dihydrobenzofuran-7-yl)ethyl)amino)pyrazolo[1,5-a]pyrimidine-3-carboxylic acid |
| 22l | 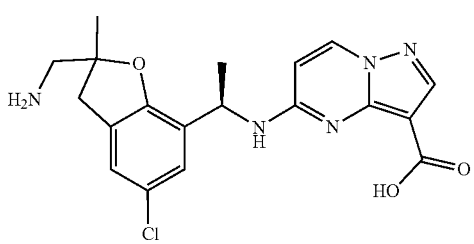 [SMILES: C[C@@H](Nc1ccn2ncc(C(=O)O)c2n1)c1cc(Cl)cc2c1OC(C)(CN)C2] | 5-(((1R)-1-(2-(aminomethyl)-5-chloro-2-methyl-2,3-dihydrobenzofuran-7-yl)ethyl)amino)pyrazolo[1,5-a]pyrimidine-3-carboxylic acid |
| 23k | 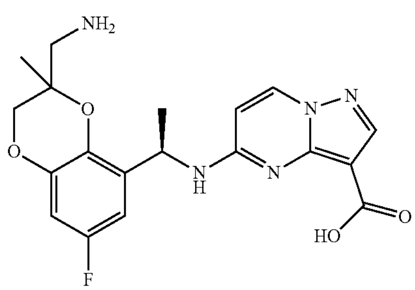 [SMILES: C[C@@H](Nc1ccn2ncc(C(=O)O)c2n1)c1cc(F)cc2c1OC(C)(CN)CO2] | 5-(((1R)-1-(3-(aminomethyl)-7-fluoro-3-methyl-2,3-dihydrobenzo[b][1,4]dioxin-5-yl)ethyl)amino)pyrazolo[1,5-a]pyrimidine-3-carboxylic acid |
| 25j | 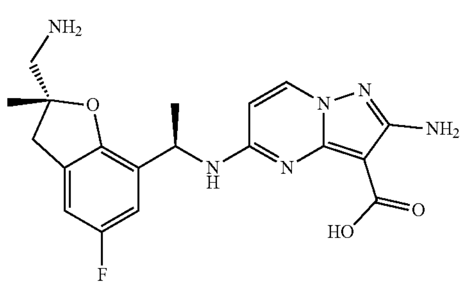 [SMILES: C[C@@H](Nc1ccn2nc(N)c(C(=O)O)c2n1)c1cc(F)cc2c1O[C@@](C)(CN)C2] | 2-amino-5-(((R)-1-((R)-2-(aminomethyl)-5-fluoro-2-methyl-2,3-dihydrobenzofuran-7-yl)ethyl)amino)pyrazolo[1,5-a]pyrimidine-3-carboxylic acid |

| Compound No. | Structure | Name |
|---|---|---|
| 26d | 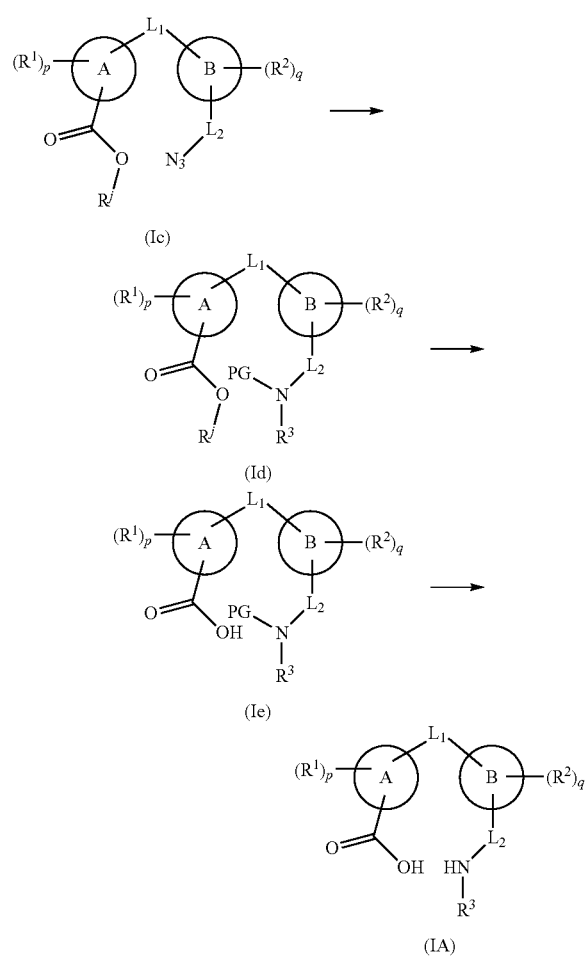 | 6-(((R)-1-((R)-2-(aminomethyl)-5-fluoro-2-methyl-2,3-dihydrobenzofuran-7-yl)ethyl)amino)imidazole[1,2-b]pyridazine-3-carboxylic acid | or a stereoisomer, tautomer thereof or a pharmaceutically acceptable salt thereof.

In another aspect, the present invention provides a preparation method of the compound represented by general formula (IA) or the stereoisomer or the tautomer thereof, wherein the method comprises:

reacting a compound represented by general formula (Ic) in the presence of di-tert-butyl dicarbonate under the conditions of hydrogen and catalyst to obtain a compound represented by general formula (Id); subjecting the compound represented by general formula (Id) to hydrolysis under basic conditions to obtain a compound represented by general formula (Ie); and further removing the protecting group PG from the compound represented by general formula (Ie) to obtain a compound represented by general formula (IA);

wherein:

$R^3$ is selected from hydrogen atom;

$R^j$ is selected from alkyl;

PG is an amino protecting group, and is preferably tert-butoxycarbonyl; and ring A, ring B, $R^1$ to $R^2$, $L_1$, $L_2$, p and q are defined as in general formula (I).

Further, the present invention provides a pharmaceutical composition, wherein the pharmaceutical composition comprises an effective amount of the compound represented by general formula (I), (II), (III), (IV), (V), (VI), (VII), (VIII) or (IX) or the stereoisomer or the tautomer thereof, or the pharmaceutically acceptable salt thereof, and a pharmaceutically acceptable carrier, an excipient or a combination thereof.

The present invention further provides a method for inhibiting an activity of one or more protein kinases of TRK, ALK and ROS1, comprising contacting the TRK receptor with a compound represented by general formula (I), (II), (III), (IV), (V), (VI), (VII), (VIII) or (IX) or the stereoisomer or the tautomer thereof, or the pharmaceutically acceptable salt thereof, or the pharmaceutical composition thereof.

The present invention further provides use of the compound represented by general formula (I), (II), (III), (IV), (V), (VI), (VII), (VIII) or (IX) or the stereoisomer or the tautomer thereof, or the pharmaceutically acceptable salt thereof, or the pharmaceutical composition thereof in preparing a medicament for treating a disease mediated by one or more protein kinases of TRK, ALK and ROS1, wherein the disease mediated by one or more protein kinases of TRK, ALK and ROS1 is preferably pain, cancer, inflammation, neurodegenerative disease or trypanosome infection, wherein the cancer is preferably neurocytoma, ovarian cancer, breast cancer, prostate cancer, gastric cancer, gastrointestinal cancer, liver cancer, cholangiocarcinoma, pancreatic cancer, multiple myeloma, astrocytoma, medulloblastoma, neuroglioma, melanoma, thyroid cancer, lung cancer, magnocellular neuroendocrine tumor, colorectal cancer, mammary analogue secretory carcinoma, sarcoma, head and neck tumor, and renal carcinoma.

The present invention further provides use of the compound represented by general formula (I), (II), (III), (IV), (V), (VI), (VII), (VIII) or (IX) or the stereoisomer or the tautomer thereof, or the pharmaceutically acceptable salt thereof, or the pharmaceutical composition thereof in preparing an inhibitor of one or more protein kinases of TRK, ALK and ROS1.

The present invention further provides use of the compound represented by general formula (I), (II), (III), (IV), (V), (VI), (VII), (VIII) or (IX) or the stereoisomer or the tautomer thereof, or the pharmaceutically acceptable salt thereof, or the pharmaceutical composition thereof in preparing a medicament for treating pain, cancer, inflammation, neurodegenerative disease or trypanosome infection, wherein the cancer is preferably neurocytoma, ovarian cancer, breast cancer, prostate cancer, gastric cancer, gastrointestinal cancer, liver cancer, cholangiocarcinoma, pancreatic cancer, multiple myeloma, astrocytoma, medulloblastoma, neuroglioma, melanoma, thyroid cancer, lung cancer, magnocellular neuroendocrine tumor, colorectal cancer, mammary analogue secretory carcinoma, sarcoma, head and neck tumor, and renal carcinoma.

The present invention further provides a method for treating a disease symptom of pain, inflammation, neurodegenerative diseases or trypanosome infection, comprising administering a therapeutically effective amount of the compound represented by general formula (I), (II), (III), (IV), (V), (VI), (VII), (VIII) or (IX) or the stereoisomer or the tautomer thereof, or the pharmaceutically acceptable salt thereof, or the pharmaceutical composition to a patient in need.

The present invention further provides a method for treating a cancer, comprising administering a therapeutically effective amount of the compound represented by general formula (I), (II), (III), (IV), (V), (VI), (VII), (VIII) or (IX) or the stereoisomer or the tautomer thereof, or the pharmaceutically acceptable salt thereof, or the pharmaceutical composition thereof to a patient in need, wherein the cancer is preferably neurocytoma, ovarian cancer, breast cancer, prostate cancer, gastric cancer, gastrointestinal cancer, liver cancer, cholangiocarcinoma, pancreatic cancer, multiple myeloma, astrocytoma, medulloblastoma, neuroglioma, melanoma, thyroid cancer, lung cancer, magnocellular neuroendocrine tumor, colorectal cancer, mammary analogue secretory carcinoma, sarcoma, head and neck tumor, and renal carcinoma.

DETAILED DESCRIPTION OF THE INVENTION

Unless stated to the contrary, some terms used in the specification and claims of the present invention are defined as follows:

"Bond" means that the indicated substituent does not exist, and both ends of the substituent are directly bound to form a bond.

"Alkyl", when regarded as a group or a part of a group, means to comprise $C_1$-$C_{20}$ linear chain or branched aliphatic hydrocarbon groups. It is preferably a $C_1$-$C_{10}$ alkyl, and more preferably a $C_1$-$C_6$ alkyl. Examples of alkyl groups comprise, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, or the like. The alkyl may be substituted or unsubstituted.

"Alkenyl" refers to an alkyl as defined above consisting of at least two carbon atoms and at least one carbon-carbon double bond, the representative examples of which comprise but are not limited to ethenyl, 1-propenyl, 2-propenyl, 1-, 2- or 3-butenyl, or the like. The alkenyl may be optionally substituted or unsubstituted.

"Alkynyl" refers to an aliphatic hydrocarbon group with one carbon-carbon triple bond, which may be a linear chain or branched chain. It is preferably a $C_2$-$C_{10}$ alkynyl, more preferably a $C_2$-$C_6$ alkynyl, and most preferably a $C_2$-$C_4$ alkynyl. Examples of alkynyl groups comprise, but are not limited to, ethynyl, 1-propynyl, 2-propynyl, 1-, 2- or 3-butynyl, or the like. The alkynyl may be substituted or unsubstituted "Cycloalkyl" refers to saturated or partially saturated monocyclic, fused, bridged and spirocyclic carbocycles. It is preferably a $C_3$-$C_{12}$ cycloalkyl, more preferably a $C_3$-$C_8$ cycloalkyl, and most preferably a $C_3$-$C_6$ cycloalkyl. Examples of monocyclic cycloalkyl comprise but are not limited to cyclopropyl, cyclobutyl, cyclopentyl, cyclopentenyl, cyclohexyl, cyclohexenyl, cyclohexadienyl, cycloheptyl, cyclohepttrienyl, cyclooctyl, or the like, and cyclopropyl and cyclohexenyl are preferred. The cycloalkyl may be optionally substituted or unsubstituted.

"Spirocycloalkyl" refers to a 5-18 membered polycyclic group with two or more cyclic structures, and single rings share one carbon atom (called spiro atom) with each other. The ring contains one or more double bonds, but none of the rings has a completely conjugated a electron aromatic system. It is preferably 6-14 membered, and more preferably 7-10 membered. According to the number of spiro atoms shared between rings, the spirocycloalkyl may be classified into mono-spiro, di-spiro or multi-spiro-cycloalkyls, preferably mono-spiro and di-spiro-cycloalkyls, and preferably 4 membered/5 membered, 4 membered/6 membered, 5 membered/5 membered, or 5 membered/6 membered. Non-limiting examples of "spirocycloalkyl" comprise, but are not limited to, spiro[4.5]decyl, spiro[4.4]nonyl, spiro[3.5]nonyl, and spiro[2.4]heptyl.

"Fused cycloalkyl" refers to a 5-18 membered all-carbon polycyclic group with two or more cyclic structures sharing a pair of carbon atoms, and one or more rings may contain one or more double bonds, but none of the rings has a completely conjugated R electron aromatic system. The fused cycloalkyl is preferably 6-12 membered, and more preferably 7-10 membered. According to the number of constituent rings, fused cycloalkyls may be classified into bicyclic, tricyclic, tetracyclic or polycyclic fused cycloalkyls, preferably bicyclic or tricyclic, and more preferably 5 membered/5 membered or 5 membered/6 membered bicycloalkyl. Non-limiting examples of "fused cycloalkyl" comprise, but are not limited to, bicyclo[3.1.0]hexyl, bicyclo[3.2.0]hept-1-enyl, bicyclo[3.2.0]heptyl, decalinyl or tetradecahydrophenanthrenyl.

"Bridged cycloalkyl" refers to a 5-18 membered all-carbon polycyclic group with two or more cyclic structures sharing two carbon atoms that are not directly bound with each other, one or more rings may contain one or more double bonds, but none of the rings has a completely conjugated a electron aromatic system. The bridged cycloalkyl is preferably 6-12 membered, and more preferably 7-10 membered. It is preferably 6-14 membered, and more preferably 7-10 membered. According to the number of constituent rings, bridged cycloalkyls may be classified into bicyclic, tricyclic, tetracyclic or polycyclic bridged cycloalkyls, preferably bicyclic, tricyclic or tetracyclic, and more preferably bicyclic or tricyclic. Non-limiting examples of "bridged cycloalkyl" comprise, but are not limited to, (1s, 4s)-bicyclo[2.2.1]heptyl, bicyclo[3.2.1]octyl, (1s,5s)-bicyclo[3.3.1]nonyl, bicyclo[2.2.2]octyl, and (1r,5r)-bicyclo[3.3.2]decyl.

"Heterocyclyl", "heterocycle" or "heterocyclic" are used interchangeably in this application, and all refer to non-aromatic heterocyclyls, wherein one or more ring-forming atoms are heteroatoms, such as oxygen, nitrogen, sulfur atoms, or the like, comprising monocyclic ring, fused ring, bridged ring and spiro ring. Non-aromatic heterocyclyls preferably have a 5-7 membered monocyclic ring or a 7-10 membered bicyclic or tricyclic ring, which may contain 1, 2 or 3 atoms selected from nitrogen, oxygen and/or sulfur. Examples of "heterocyclyl" comprise but are not limited to morpholinyl, oxetanyl, thiomorpholinyl, tetrahydropyranyl, 1,1-dioxo-thiomorpholinyl, piperidinyl, 2-oxo-piperidinyl, pyrrolidinyl, 2-oxo-pyrrolidinyl, piperazine-2-one, 8-oxa-3-azabicyclo[3.2.1]octyl and piperazinyl. The heterocyclyl may be substituted or unsubstituted.

"Spiroheterocyclyl" refers to a 5-18 membered polycyclic group with two or more cyclic structures, and single rings share one atom with each other. The ring contains one or more double bonds, but none of the rings has a completely conjugated n electron aromatic system, wherein one or more ring atoms are selected from heteroatoms of nitrogen, oxygen or S(O). (wherein n is selected from 0, 1 or 2), and the remaining ring atoms are carbon. Spiroheterocyclyl is preferably 6-14 membered, and more preferably 7-10 membered. According to the number of spiro atoms shared between rings, the spiroheterocyclyls may be classified into mono-spiroheterocyclyl, bi-spiroheterocyclyl or multi-spiroheterocyclyl, preferably mono-spiroheterocyclyl and bi-spiroheterocyclyl. Spiroheterocyclyl is more preferably a 4 membered/4 membered, 4 membered/5 membered, 4 membered/6 membered, 5 membered/5 membered, or 5 membered/6 membered mono-spiroheterocyclyl. Non-limiting examples of "spiroheterocyclyl" comprise, but are not limited to, 1,7-dioxaspiro[4.5]decyl, 2-oxa-7-azaspiro[4.4]nonyl, 7-oxaspiro[3.5]nonyl and 5-oxaspiro[2.4]heptyl.

"Fused heterocyclyl" refers to an all-carbon polycyclic group with two or more cyclic structures sharing a pair of atoms, and one or more rings may contain one or more double bonds, but none of the rings has a completely conjugated n electron aromatic system, wherein one or more ring atoms are selected from heteroatoms of nitrogen, oxygen or S(O)~(wherein n is selected from 0, 1 or 2), and the remaining ring atoms are carbon. Fused heterocyclyl is preferably 6-14 membered, and more preferably 7-10 membered. According to the number of constituent rings, fused heterocyclyls may be classified into bicyclic, tricyclic, tetracyclic or polycyclic fused heterocyclyls, preferably bicyclic or tricyclic, and more preferably 5 membered/5 membered or 5 membered/6 membered bicyclic fused heterocyclyl. Non-limiting examples of "fused heterocyclyl" comprise, but are not limited to, octahydropyrrolo[3,4-c]pyrrolyl, octahydro-1H-isoindolyl, 3-azabicyclo[3.1.0]hexyl, and octahydrobenzo[b][1,4]dioxine.

"Bridged heterocyclyl" refers to a 5-14 membered or 5-18 membered polycyclic group with two or more cyclic structures sharing two atoms that are not directly bound with each other. One or more rings may contain one or more double bonds, but none of the rings has a completely conjugated π electron aromatic system, wherein one or more ring atoms are selected from heteroatoms of nitrogen, oxygen or S(O)$_n$ (wherein n is selected from 0, 1 or 2), and the remaining ring atoms are carbon. Bridged heterocyclyl is preferably 6-14 membered, and more preferably 7-10 membered. According to the number of constituent rings, bridged heterocyclyls may be classified into bicyclic, tricyclic, tetracyclic or polycyclic bridged heterocyclyls, preferably bicyclic, tricyclic or tetracyclic, and more preferably bicyclic or tricyclic. Non-limiting examples of "bridged heterocyclyl" comprise, but are not limited to, 2-azabicyclo[2.2.1]heptyl, 2-azabicyclo[2.2.2]octyl and 2-azabicyclo[3.3.2]decyl.

"Aryl" refers to a carbocyclic aromatic system containing one or two rings, wherein the rings may be bound together in a fused manner. The term "aryl" comprises monocyclic or bicyclic aryls, such as aromatic groups of phenyl, naphthyl, and tetrahydronaphthyl. Preferably, the aryl is a $C_6$-$C_{10}$ aryl, more preferably, the aryl is phenyl and naphthyl, and most preferably, the aryl is naphthyl. The aryl may be substituted or unsubstituted.

"Heteroaryl" refers to a 5-6 membered monocyclic ring or an 8-10 membered bicyclic ring, which may contain 1 to 4 atoms selected from nitrogen, oxygen and/or sulfur. Heteroaryl is preferably bicyclic heteroaryl. Examples of "heteroaryl" comprise but are not limited to, furanyl, pyridinyl, 2-oxo-1,2-dihydropyridyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzodioxolyl, benzothienyl, benzimidazolyl, indolyl, isoindolyl, 1,3-dioxo-isoindolyl, quinolinyl, indazolyl, benzisothiazolyl, benzoxazolyl, and benzisoxazolyl,

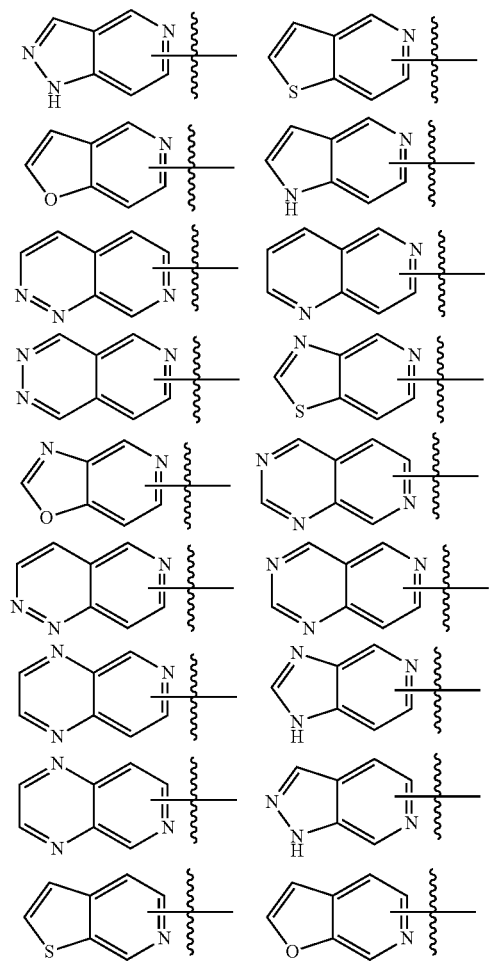

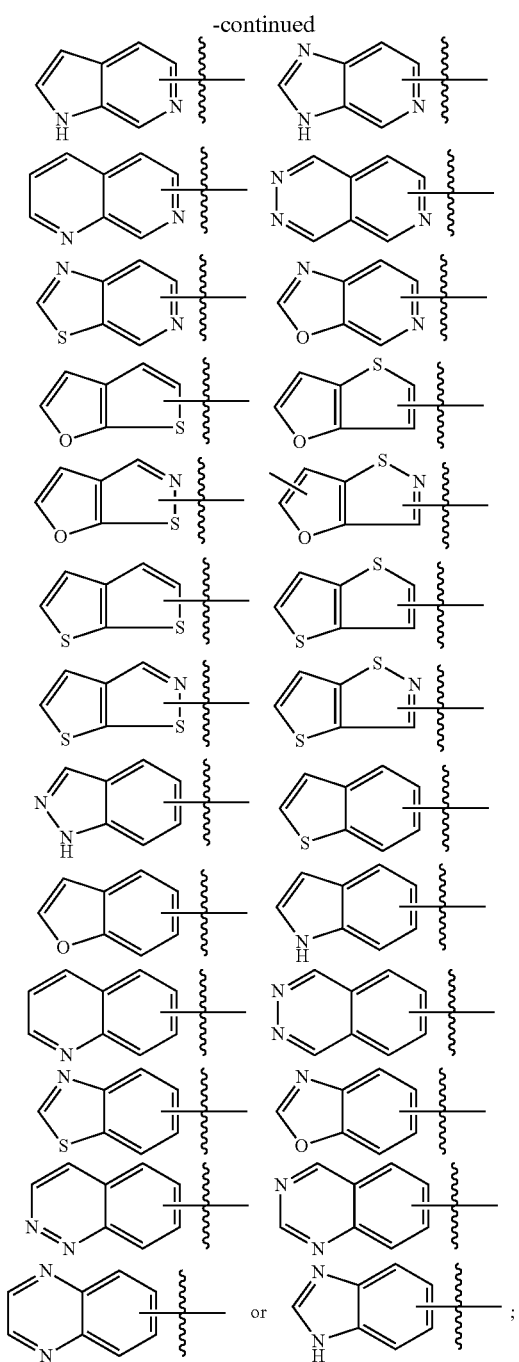

the heteroaryl may be substituted or unsubstituted.

"Fused ring" refers to a polycyclic group with two or more cyclic structures sharing a pair of atoms with each other. One or more rings may contain one or more double bonds, but at least one ring does not have a completely conjugated π electron aromatic system, and meanwhile, at least one ring has a completely conjugated π electron aromatic system, wherein zero, one or more ring atoms of the ring atoms are selected from heteroatoms of nitrogen, oxygen or $S(O)_n$ (wherein n is selected from 0, 1 or 2), and the remaining ring atoms are carbon. The fused ring is preferably a bicyclic or tricyclic fused ring, wherein the bicyclic fused ring is preferably a fused ring of aryl or heteroaryl and monocyclic heterocyclyl or monocyclic cycloalkyl. Fused ring is preferably 7-14 membered, and more preferably 8-10 membered. Examples of "fused ring" comprise, but not limited to:

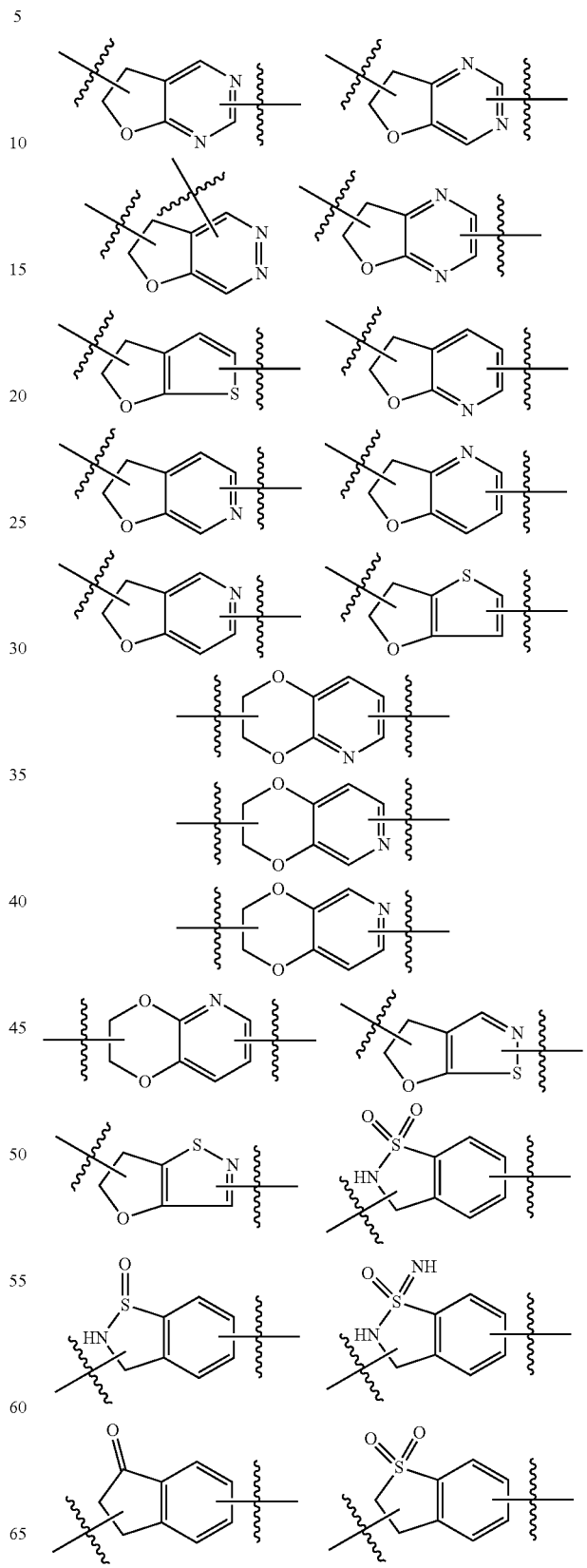

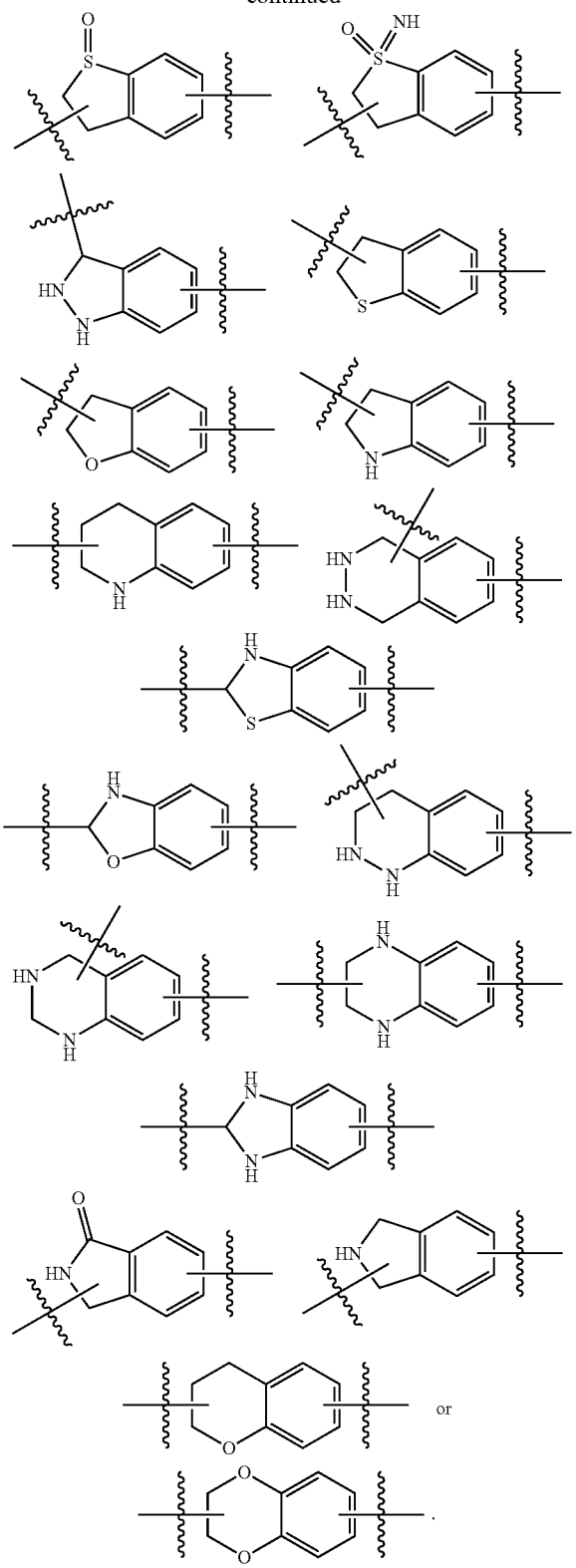

"Alkoxy" refers to a group of (alkyl-O—), wherein for the definition of alkyl, please refer to the relevant definitions herein. $C_1$-$C_6$ alkoxy is preferred. Examples of alkoxy comprise, but not limited to, methoxy, ethoxy, n-propoxy, isopropoxy, n-butoxy, isobutoxy, tert-butoxy, and the like.

"Haloalkyl" refers to an alkyl substituted by halogen, wherein, for the definitions of halogen and alkyl, please refer to the relevant definitions herein.

"Haloalkoxy" refers to an alkoxy substituted by halogen, wherein, for the definitions of halogen and alkoxy, please refer to the relevant definitions herein.

"Hydroxyalkyl" refers to an alkyl substituted by hydroxy, wherein, for the definition of alkyl, please refer to the relevant definitions herein.

"Alkoxyalkyl" refers to an alkyl substituted by alkoxy, wherein, for the definitions of alkyl and alkoxy, please refer to the relevant definitions herein.

"Hydroxy" refers to an —OH group.

"Halogen" refers to fluorine, chlorine, bromine and iodine.

"Amino" refers to —$NH_2$.

"Cyano" refers to —CN.

"Nitro" refers to —$NO_2$.

"Benzyl" refers to —$CH_2$— phenyl.

"Carboxyl" refers to —C(O)OH.

"Carboxylate" refers to —C(O)O— alkyl or —C(O)O— cycloalkyl, wherein the definitions of alkyl and cycloalkyl are as above.

"DMSO" refers to dimethyl sulfoxide.

"BOC" refers to tert-butoxycarbonyl.

"Ts" refers to p-toluenesulfonyl.

"Leaving group", is an atom or functional group separated from a larger molecule in a chemical reaction, which is a term used in nucleophilic substitution reaction and elimination reaction. In nucleophilic substitution reaction, a reactant attacked by a nucleophilic reagent is called substrate, while an atom or atomic group broken away with a pair of electrons in the substrate molecule is called a leaving group. A group that accepts electrons easily and has a strong ability of bearing negative charges is a good leaving group. When the pKa of a conjugate acid of the leaving group is smaller, it is easier for the leaving group to separate from other molecules. The reason is that when the pKa of the conjugated acid of the leaving group is smaller, the corresponding leaving group does not need to be combined with other atoms, and the tendency to exist in the form of anions (or electrically neutral leaving group) is enhanced. Common leaving groups comprise but are not limited to, halogen, —OTs or —OH.

"Substituted" means that one or more hydrogen atoms in a group, preferably at most 5, more preferably 1 to 3 hydrogen atoms, are independently replaced by a corresponding number of substituents. Obviously, substituents are only in their possible chemical positions, and those skilled in the art can determine (through experiments or theories) possible or impossible substitutions without going through much effort. For example, amino or hydroxyl with free hydrogen may be unstable when combined with carbon atoms with unsaturated (e.g., olefinic) bonds.

As used in this specification, "substitute" or "substituted", unless otherwise specified, means that a group may be substituted by one or more groups selected from the following: alkyl, alkenyl, alkynyl, alkoxy, alkylthio, alkylamino, halogen, mercapto, hydroxy, nitro, cyano, cycloalkyl, heterocyclic, aryl, heteroaryl, cycloalkoxy, heterocyclic alkoxy, cycloalkylthio, heterocycloalkylthio, amino, haloalkyl, hydroxyalkyl, carboxyl, carboxylate, =O, —C(O)$R^4$, —C(O)O$R^4$, —OC(O)$R^4$, —N$R^5R^6$, —C(O)N$R^5R^6$, —$SO_2$N$R^5R^6$ or —N$R^5$C(O)$R^6$.

$R^4$, $R^5$ and $R^6$ are each independently selected from hydrogen atom, hydroxy, halogen, alkyl, cycloalkyl, heterocyclyl, aryl or heteroaryl, wherein the alkyl, alkoxy, cycloalkyl, heterocyclyl, aryl or heteroaryl is optionally further substituted by one or more substituents selected from hydroxyl, halogen, nitro, cyano, alkyl, alkoxy, cycloalkyl, heterocyclyl, aryl, heteroaryl, =O, —C(O)$R^7$, —C(O)O$R^7$, —OC(O)$R^7$, —N$R^8R^9$, —C(O)N$R^8R^9$, —SO$_2$N$R^8R^9$ or —N$R^8$C(O)$R^9$.

Alternatively, $R^5$ and $R^6$ together with the atom bound therewith form a 4-8 membered heterocyclyl, wherein the 4-8 membered heterocyclyl internally contains one or more N, O or S(O)$_r$, and the 4-8 membered heterocyclyl is optionally further substituted by one or more substituents selected from hydroxyl, halogen, nitro, cyano, alkyl, alkoxy, cycloalkyl, heterocyclyl, aryl, heteroaryl, =O, —C(O)$R^7$, —C(O)O$R^7$, —OC(O)$R^7$, —N$R^8R^9$, —C(O)N$R^8R^9$, —SO$_2$N$R^8R^9$ or —N$R^8$C(O)$R^9$.

$R^7$, $R^8$ and $R^9$ are each independently selected from hydrogen atom, alkyl, cycloalkyl, heterocyclyl, aryl or heteroaryl, wherein the alkyl, cycloalkyl, heterocyclyl, aryl or heteroaryl, is optionally further substituted by one or more substituents selected from hydroxyl, halogen, nitro, cyano, alkyl, alkoxy, cycloalkyl, heterocyclyl, aryl, heteroaryl, carboxyl or carboxylate.

The compounds of the present invention may contain asymmetric centers or chiral centers, and therefore exist in different stereoisomeric forms. It is contemplated that all stereoisomeric forms of the compounds of the present invention, comprising but not limited to diastereomers, enantiomers and atropisomer and geometric (conformational) isomers and their mixtures, such as racemic mixtures, are within the scope of the present invention.

Unless otherwise stated, the structure described in the present invention also comprises all isomers of this structure (e.g., diastereomers, enantiomers and antimetamers and geometric (conformational) isomer forms; e.g., R and S configurations of each asymmetric center, (Z) and (E) double bond isomers, and (Z) and (E) conformational isomers. Therefore, the single stereoisomer and enantiomer mixtures, diastereomer mixtures and geometric (conformational) isomer mixtures of the compounds of the present invention are all within the scope of the present invention.

"Pharmaceutically acceptable salts" refer to some salts of the above-mentioned compounds which can keep the original biological activity and are suitable for medical use. The pharmaceutically acceptable salt of the compound represented by formula (I) may be a metal salt, an amine salt formed with a suitable acid.

"Pharmaceutical composition" represents a mixture containing one or more compounds described herein or physiologically acceptable salts or prodrugs thereof and other chemical components, as well as other components such as physiologically acceptable carriers and excipients. The object of the pharmaceutical composition is to promote the administration to organisms and facilitate the absorption of active ingredients to exert biological activity.

Synthesis Methods of the Compounds of the Present Invention

In order to achieve the objects of the present invention, the following technical solutions are adopted by the present invention.

Solution 1

A preparation method of the compound represented by general formula (I) or the stereoisomer or the tautomer thereof, or the pharmaceutically acceptable salt thereof according to the present invention comprises the following steps:

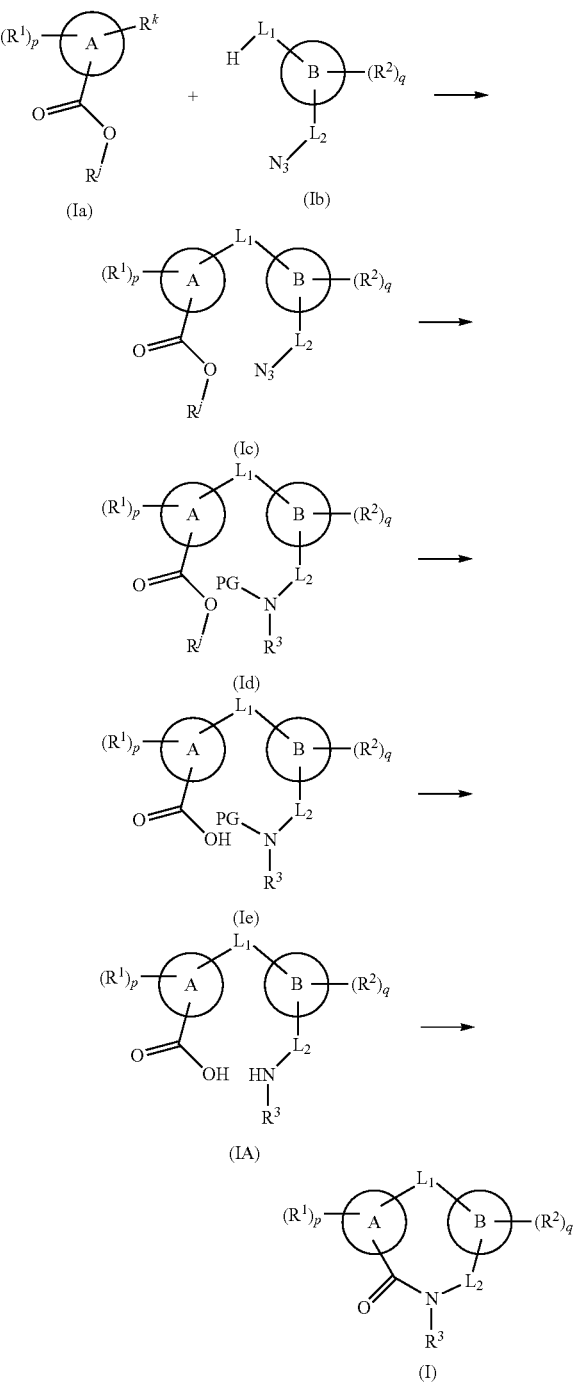

reacting a compound represented by general formula (Ia) with a compound represented by general formula (Ib) under basic conditions to obtain a compound represented by general formula (Ic); reacting the compound represented by general formula (Ic) in the presence of di-tert-butyl dicarbonate under the conditions of hydrogen and catalyst to obtain a compound represented by general formula (Id); subjecting the compound represented by general formula (Id) to hydrolysis under basic conditions to obtain a compound represented by general formula (Ie); further removing the protecting group PG from the compound represented by general formula (Ie) to obtain a compound represented by general formula (IA); and subjecting the compound represented by general formula (IA) to a condensation reaction in the presence of a condensation reagent under basic conditions to obtain a compound represented by general formula (I);
wherein:
$R^3$ is selected from hydrogen atom;
$R^j$ is selected from alkyl;
$R^k$ is a leaving group, preferably halogen;
PG is an amino protecting group, and is preferably tert-butoxycarbonyl; and
ring A, ring B, $R^1$ to $R^2$, $L_1$, $L_2$, p and q are defined as in general formula (I).

Solution 2

A preparation method of the compound represented by general formula (I) or the stereoisomer or the tautomer thereof, or the pharmaceutically acceptable salt thereof according to the present invention comprises the following steps:

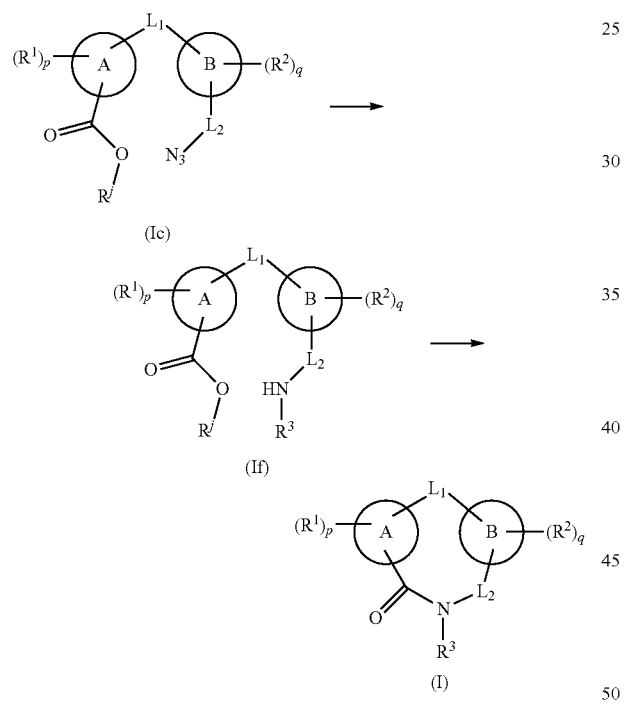

reacting a compound represented by general formula (Ic) under the conditions of triphenylphosphine and water to obtain a compound represented by general formula (If); and subjecting the compound represented by general formula (If) to a condensation reaction under basic conditions to obtain a compound represented by general formula (I);
$R^3$ is selected from hydrogen atom;
$R^j$ is selected from alkyl; and
ring A, ring B, $R^1$ to $R^2$, $L_1$, $L_2$, p and q are defined as in general formula (I).

Solution 3

A preparation method of the compound represented by general formula (II) or the stereoisomer or the tautomer thereof, or the pharmaceutically acceptable salt thereof according to the present invention comprises the following steps:

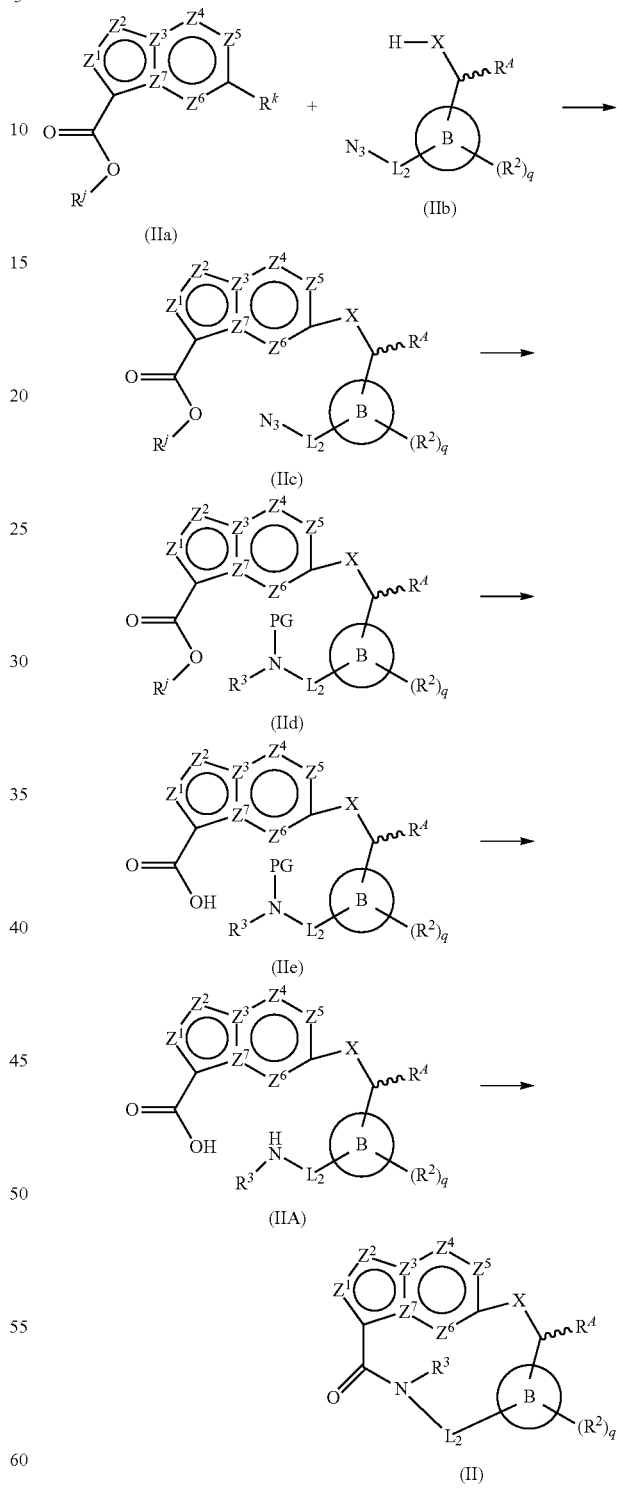

reacting a compound represented by general formula (IIa) with a compound represented by general formula (IIb) under basic conditions to obtain a compound represented by general formula (IIc); reacting the compound represented by general formula (IIc) in the presence of di-tert-butyl dicarbonate under the conditions of hydrogen and catalyst to obtain a compound represented by general formula (IId); subjecting the compound represented by general formula (IId) to hydrolysis under basic conditions to obtain a compound represented by general formula (IIe); further removing the protecting group PG from the compound represented by general formula (IIe) to obtain a compound represented by general formula (IIA); and subjecting the compound represented by general formula (IIA) to a condensation reaction in the presence of a condensation reagent under basic conditions to obtain ta compound represented by general formula (II); wherein:

$R^3$ is selected from hydrogen atom;
$R^j$ is selected from alkyl;
$R^k$ is a leaving group, preferably halogen;
PG is an amino protecting group, and is preferably tert-butoxycarbonyl; and
ring B, $R^1$ to $R^2$, $R^4$, $Z^1$ to $Z^7$, X, $L_2$, p and q are defined as in general formula (II).

Solution 4

A preparation method of the compound represented by general formula (II) or the stereoisomer or the tautomer thereof, or the pharmaceutically acceptable salt thereof according to the present invention comprises the following steps:

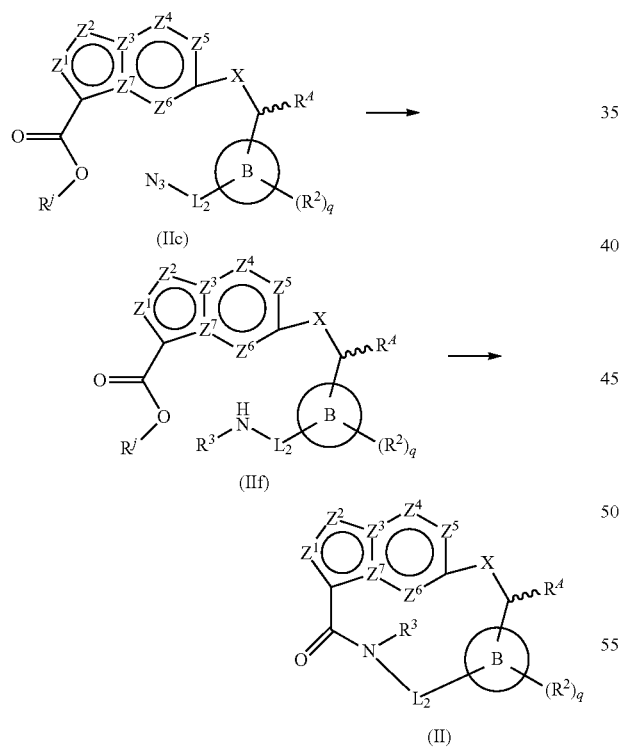

reacting a compound represented by general formula (IIc) under the conditions of triphenylphosphine and water to obtain a compound represented by general formula (IIf); and subjecting the compound represented by general formula (IIf) to a condensation reaction under basic conditions to obtain a compound represented by general formula (II);

$R^3$ is selected from hydrogen atom;
$R^j$ is selected from alkyl; and
ring B, $R^1$ to $R^2$, $R^4$, $Z^1$ to $Z^7$, X, $L_2$, p and q are defined as in general formula (II).

Solution 5

A preparation method of the compound represented by general formula (III) or the stereoisomer or the tautomer thereof, or the pharmaceutically acceptable salt thereof according to the present invention comprises the following steps:

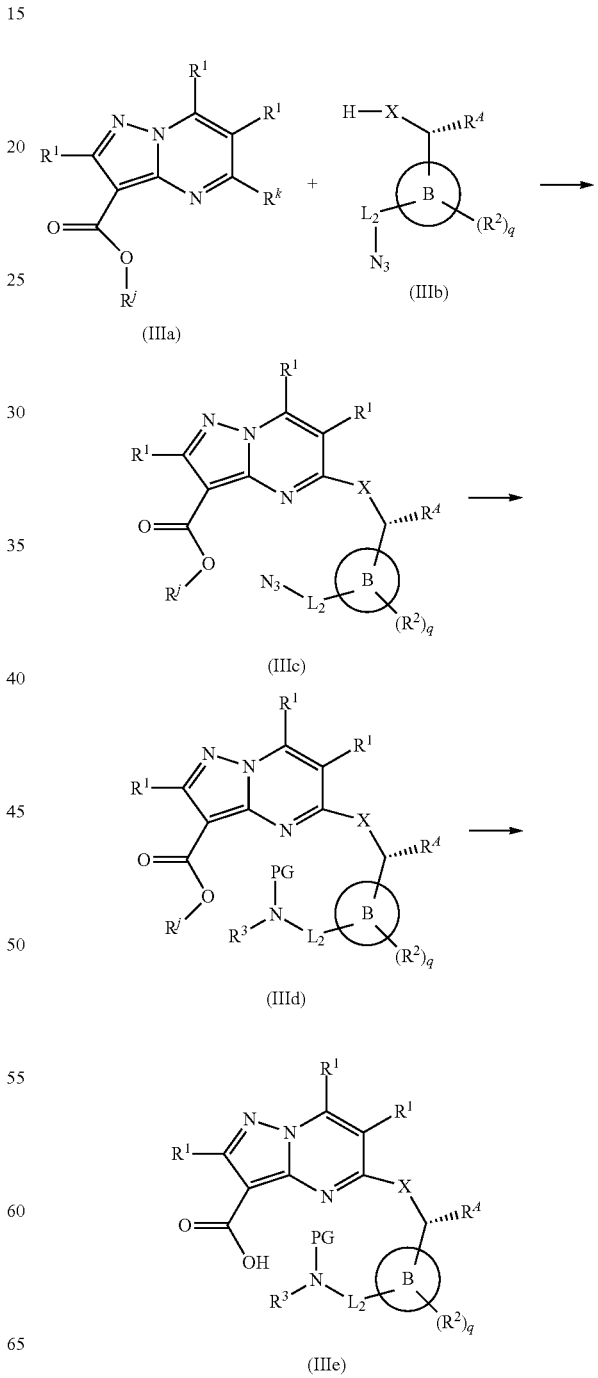

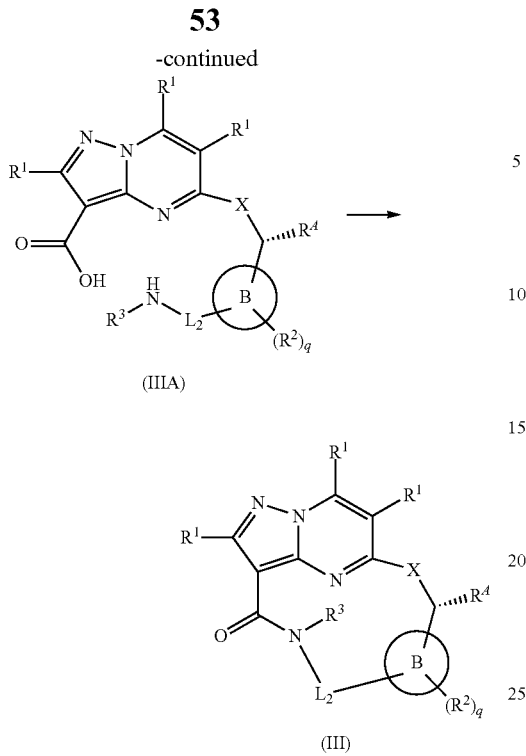

(IIIA)

(III)

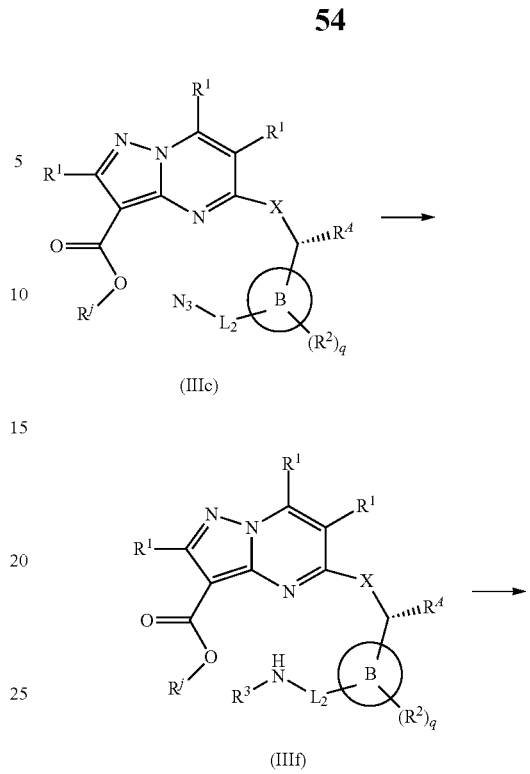

(IIIc)

(IIIf)

reacting a compound represented by general formula (IIIa) with a compound represented by general formula (IIIb) under basic conditions to obtain a compound represented by general formula (IIIc); reacting the compound represented by general formula (IIIc) in the presence of di-tert-butyl dicarbonate under the conditions of hydrogen and catalyst to obtain ta compound represented by general formula (IIId); subjecting the compound represented by general formula (IIId) to hydrolysis under basic conditions to obtain a compound represented by general formula (IIIe); further removing the protecting group PG from the compound represented by general formula (IIIe) to obtain a compound represented by general formula (IIIA); and subjecting the compound represented by general formula (IIIA) to a condensation reaction in the presence of a condensation reagent under basic conditions to obtain a compound represented by general formula (III);

wherein:

$R^3$ is selected from hydrogen atom;

$R^j$ is selected from alkyl;

$R^1$ is a leaving group, preferably halogen;

PG is an amino protecting group, and is preferably tert-butoxycarbonyl; and ring B, $R^1$ to $R^2$, $R^4$, X, $L_2$ and q are defined as in general formula (III).

Solution 6

A preparation method of the compound represented by general formula (III) or the stereoisomer or the tautomer thereof, or the pharmaceutically acceptable salt thereof according to the present invention comprises the following steps:

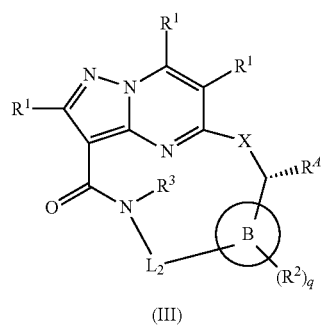

(III)

reacting a compound represented by general formula (IIIc) under the conditions of triphenylphosphine and water to obtain a compound represented by general formula (IIIf); and subjecting the compound represented by general formula (IIIf) to a condensation reaction under basic conditions to obtain a compound represented by general formula (III);

wherein:

$R^3$ is selected from hydrogen atom;

$R^j$ is selected from alkyl; and ring B, $R^1$ to $R^2$, $R^4$, X, $L_2$ and q are defined as in general formula (III).

Solution 7

A preparation method of the compound represented by general formula (IV) or the stereoisomer or the tautomer thereof, or the pharmaceutically acceptable salt thereof according to the present invention comprises the following steps:

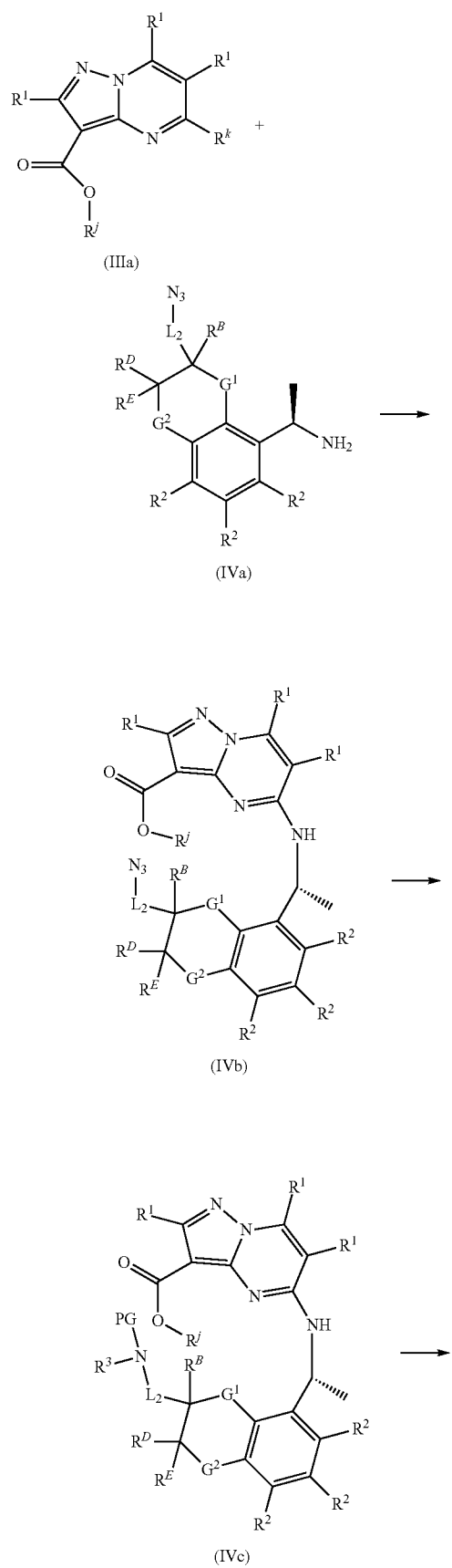

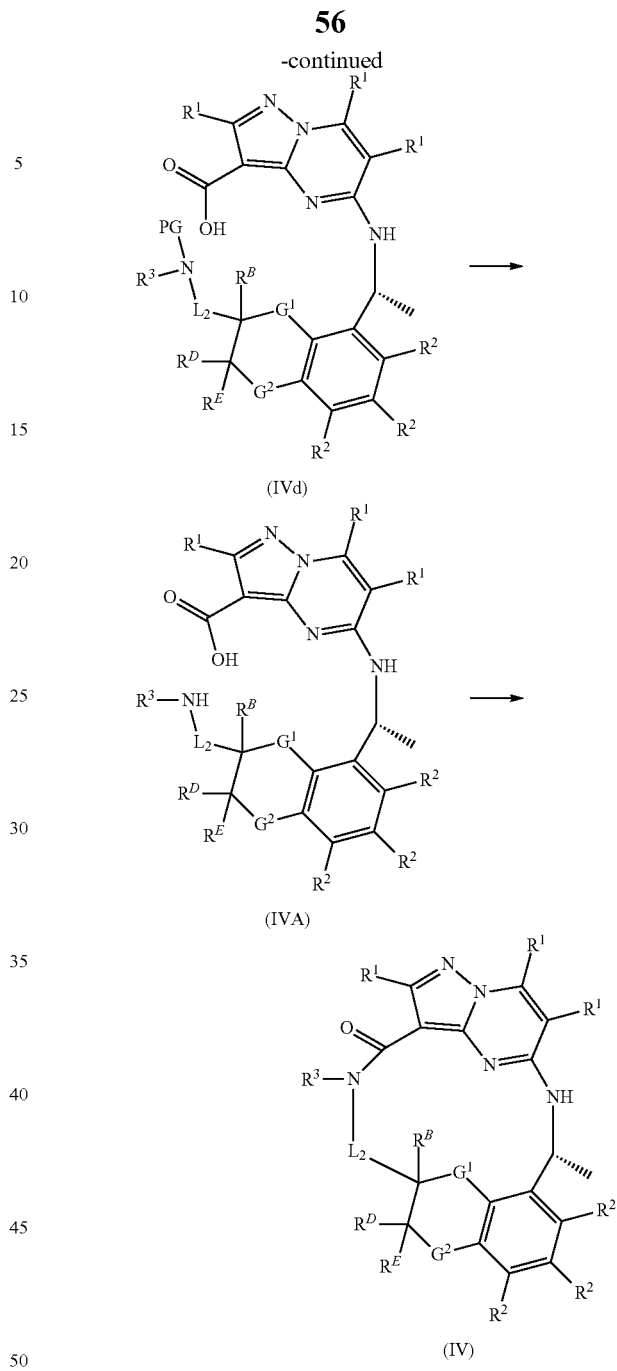

reacting a compound represented by general formula (IIIa) with a compound represented by general formula (IVa) under basic conditions to obtain a compound represented by general formula (IVb); reacting the compound represented by general formula (IVb) in the presence of di-tert-butyl dicarbonate under the conditions of hydrogen and catalyst to obtain a compound represented by general formula (IVc); subjecting the compound represented by general formula (IVc) to hydrolysis under basic conditions to obtain a compound represented by general formula (IVd); further removing the protecting group PG from the compound represented by general formula (IVd) to obtain a compound represented by general formula (IVA); and subjecting the compound represented by general formula (IVA) to a condensation reaction in the presence of a condensation reagent under basic conditions to obtain a compound represented by general formula (IV);

wherein:

R³ is selected from hydrogen atom;

R^j is selected from alkyl;

R^k is a leaving group, preferably halogen;

PG is an amino protecting group, and is preferably tert-butoxycarbonyl; and

R¹ to R², G¹, G², R^B, R^D, R^E and L₂ are defined as in general formula (IV).

Solution 8

A preparation method of the compound represented by general formula (IV) or the stereoisomer or the tautomer thereof, or the pharmaceutically acceptable salt thereof according to the present invention comprises the following steps:

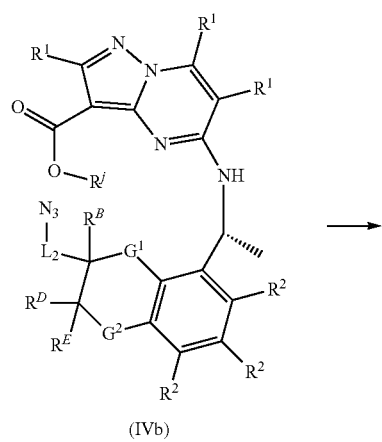

(IVb)

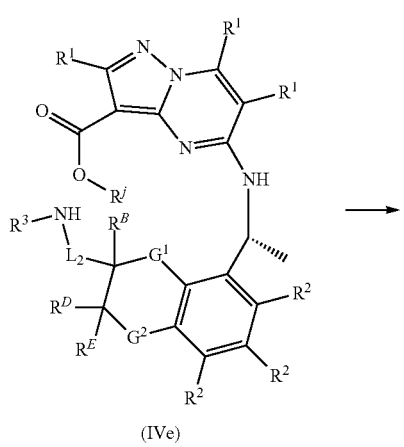

(IVe)

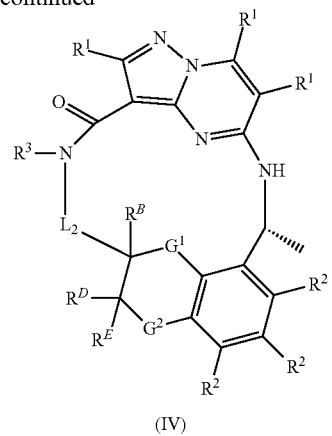

(IV)

reacting a compound represented by general formula (IVb) under the conditions of triphenylphosphine and water to obtain a compound represented by general formula (IVe); and subjecting the compound represented by general formula (IVe) to a condensation reaction under basic conditions to obtain a compound represented by general formula (IV);

wherein:

R³ is selected from hydrogen atom;

R^j is selected from alkyl; and

R¹ to R², G¹, G², R^B, R^D, R^E and L₂ are defined as in general formula (IV).

Solution 9

A preparation method of the compound represented by general formula (V) or the stereoisomer or the tautomer thereof, or the pharmaceutically acceptable salt thereof according to the present invention comprises the following steps:

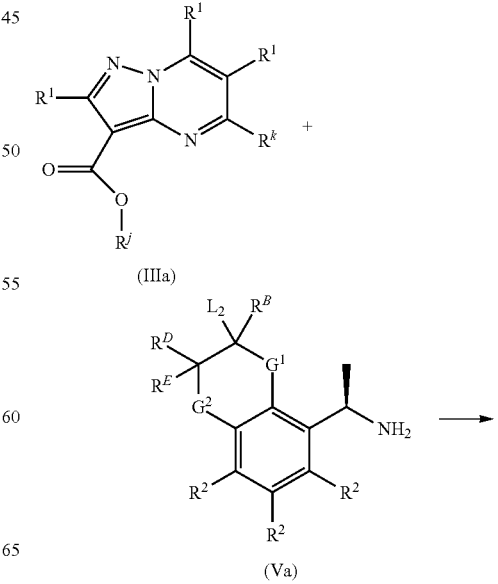

(IIIa)

(Va)

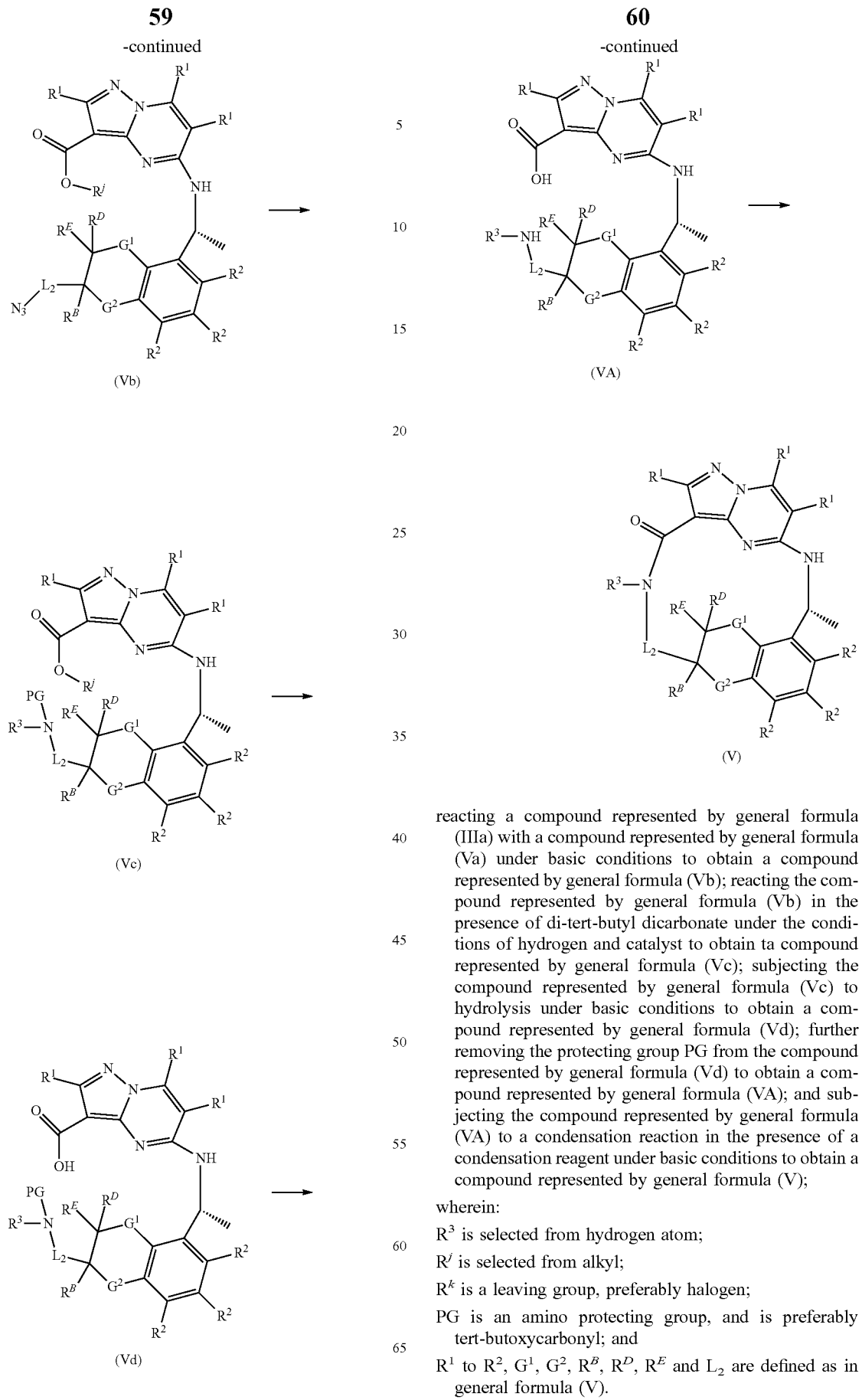

reacting a compound represented by general formula (IIIa) with a compound represented by general formula (Va) under basic conditions to obtain a compound represented by general formula (Vb); reacting the compound represented by general formula (Vb) in the presence of di-tert-butyl dicarbonate under the conditions of hydrogen and catalyst to obtain ta compound represented by general formula (Vc); subjecting the compound represented by general formula (Vc) to hydrolysis under basic conditions to obtain a compound represented by general formula (Vd); further removing the protecting group PG from the compound represented by general formula (Vd) to obtain a compound represented by general formula (VA); and subjecting the compound represented by general formula (VA) to a condensation reaction in the presence of a condensation reagent under basic conditions to obtain a compound represented by general formula (V);

wherein:

$R^3$ is selected from hydrogen atom;

$R^j$ is selected from alkyl;

$R^k$ is a leaving group, preferably halogen;

PG is an amino protecting group, and is preferably tert-butoxycarbonyl; and $R^1$ to $R^2$, $G^1$, $G^2$, $R^B$, $R^D$, $R^E$ and $L_2$ are defined as in general formula (V).

Solution 10

A preparation method of the compound represented by general formula (V) or the stereoisomer or the tautomer thereof, or the pharmaceutically acceptable salt thereof according to the present invention comprises the following steps:

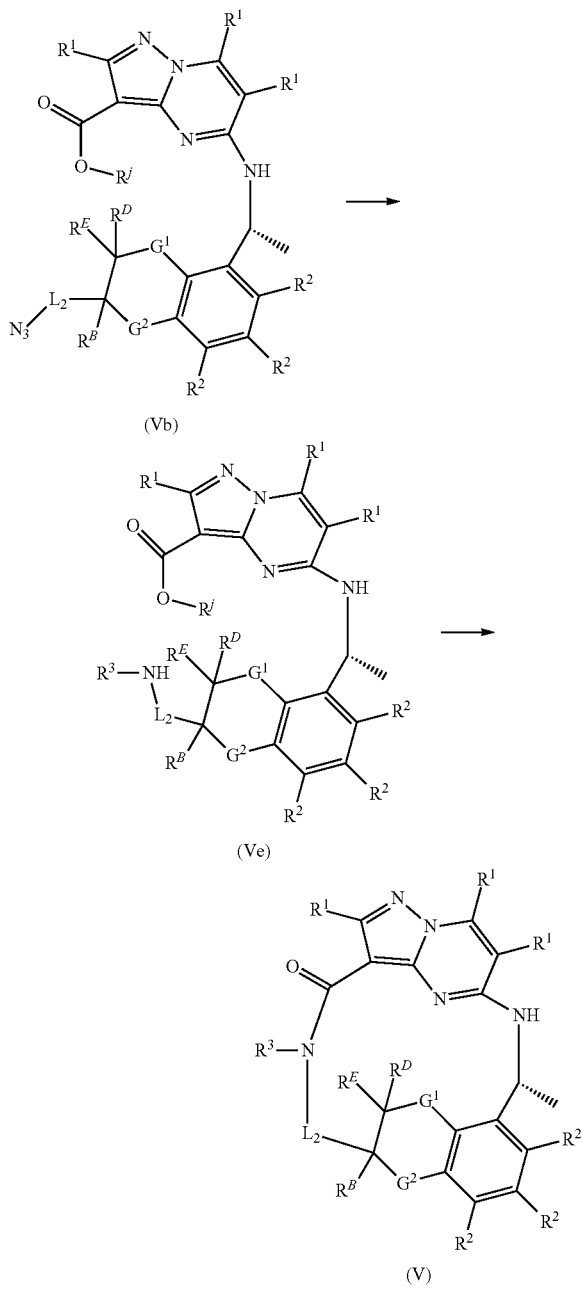

reacting a compound represented by general formula (Vb) under the conditions of triphenylphosphine and water to obtain a compound represented by general formula (Ve); and subjecting the compound represented by general formula (Ve) to a condensation reaction under basic conditions to obtain a compound represented by general formula (V);

wherein:
$R^3$ is selected from hydrogen atom;
$R^j$ is selected from alkyl; and
$R^1$ to $R^2$, $G^1$, $G^2$, $R^B$, $R^D$, $R^E$ and $L_2$ are defined as in general formula (V).

In the above reaction conditions for preparing the general formula (I), (II), (III), (IV) or (V), wherein:
the basic conditions are provided by an organic base or an inorganic base. The organic base is selected from N,N-diisopropylethylamine, pyridine, triethylamine, piperidine, N-methylpiperazine and 4-dimethylaminopyridine, and the inorganic base is selected from potassium phosphate, potassium phosphate trihydrate, potassium acetate, sodium hydroxide, potassium hydroxide, lithium hydroxide, sodium carbonate, potassium carbonate, cesium carbonate, sodium hydride and potassium hydride, and preferably N,N-diisopropylethylamine, sodium hydroxide, potassium hydroxide or lithium hydroxide.

The condensation reagent is selected from 2-(7-benzotriazole oxide)-N,N,N',N'-tetramethyluronium, dicyclohexylcarbodiimide, 1-(3-dimethylaminopropyl)-3-ethylcarbodiimide hydrochloride, N,N'-dicyclohexylcarbodiimide, N,N'-diisopropylcarbodiimide, 1-hydroxy-7-azobenzotriazole, 2-(7-azabenzotriazol-1-yl)-N,N,N',N'-tetramethyluronium hexafluorophosphate, pentafluorophenyl diphenyl phosphinate, benzotriazol-1-yl-oxytris(dimethylamino)phosphonium hexafluorophosphate or benzotriazol-1-yl-oxytripyrrolidinophosphonium hexafluorophosphate; and preferably pentafluorophenyl diphenyl phosphinate.

(D) EMBODIMENTS

The following examples are used to further describe the present invention, but these examples do not limit the scope of the present invention.

EXAMPLES

The examples show the preparation of representative compounds represented by formula (I) and related structural identification data. It should be noted that the following examples are only used to illustrate the present invention, but not to limit the present invention. $^1$H NMR spectrum was measured by Bruker instrument (400 MHz), and chemical shift was expressed in ppm. Tetramethylsilane internal standard (0.00 ppm) was employed. $^1$H NMR was expressed as follows: s=singlet, d=doublet, t=triplet, m=multiplet, br=broadened, dd=doublet of doublet, and dt=doublet of triplets. If a coupling constant was provided, it was in the unit of Hz.

A mass spectrum was determined by LC/MS, and an ionization method may be ESI or APCI. Yantai Huanghai HSGF254 or Qingdao GF254 silica gel plate was used as silica gel plates for thin layer chromatography. The silica gel plates used for thin layer chromatography (TLC) had a specification of 0.15 mm to 0.2 mm, and products separated and purified by TLC had a specification of 0.4 mm to 0.5 mm.

In general, Yantai Huanghai silica gel with 200-300 meshes was used as a carrier for column chromatography.

In the following examples, unless otherwise specified, all temperatures are in Celsius. Unless otherwise specified, various starting materials and reagents are commercially available or synthesized according to known methods, and the commercially available materials and reagents are directly used without further purification. Unless otherwise specified, the commercially available manufacturers comprise but are not limited to Shanghai Hao Hong Biomedical Technology Co., Ltd., Shanghai Accela ChemBio Inc., and Shanghai Han Feng Chemical Co., Ltd., and the like.

CD$_3$OD: Deuterated methanol.

CDCl$_3$: Deuterated chloroform.

DMSO-d$_6$: Deuterated dimethyl sulfoxide.

Argon atmosphere refers to that a reaction flask is connected with an argon balloon with a volume of about 1 L.

Unless otherwise specified in the examples, a solution in the reaction refers to an aqueous solution.

A compound is purified by silica gel column chromatography eluent system and thin layer chromatography, wherein the eluent system is selected from A: petroleum ether and ethyl acetate system; B: dichloromethane and methanol system; and C: dichloromethane and ethyl acetate system. The volume ratio of the solvent varies according to the difference of the polarity of the compound, and may also be adjusted by adding a small amount of acidic or basic reagents, such as acetic acid or triethylamine, or the like.

Example 1

(3R)-6-fluoro-3-methyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one

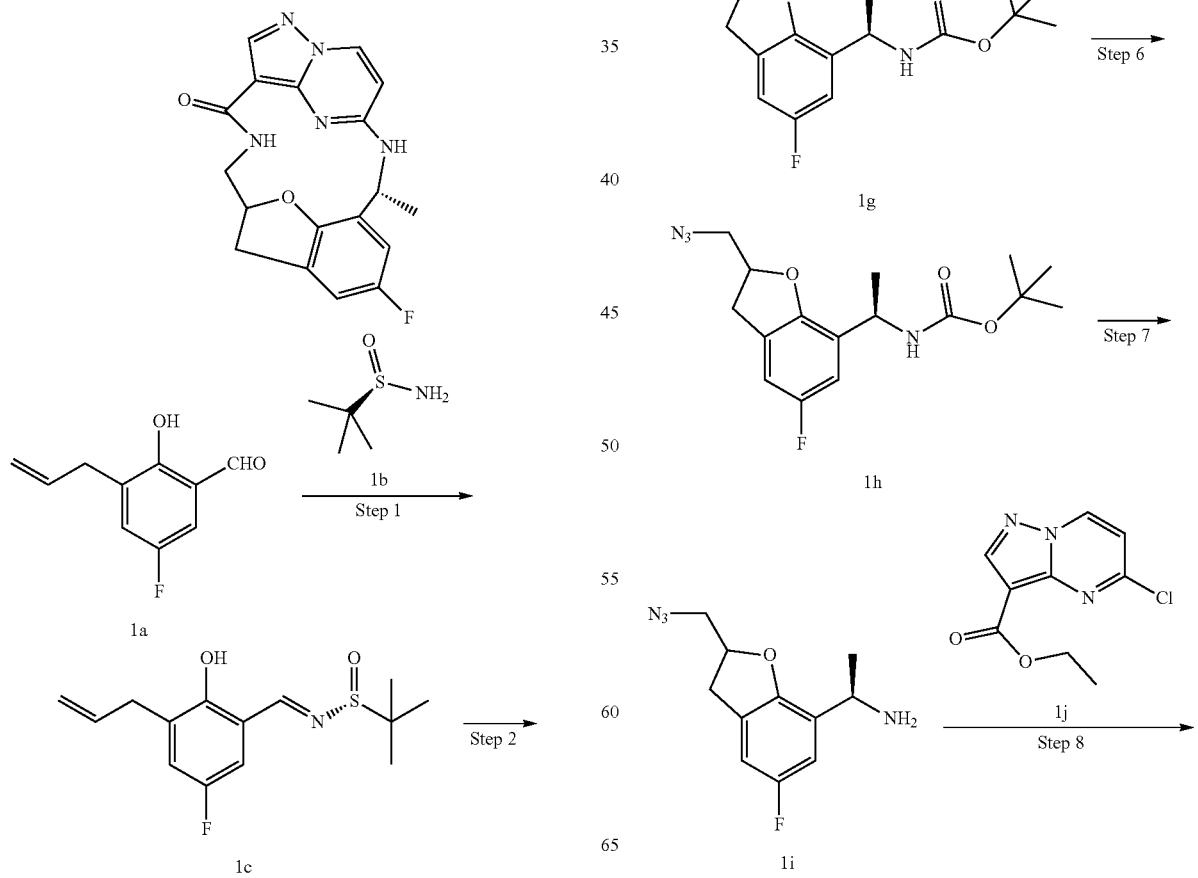

-continued

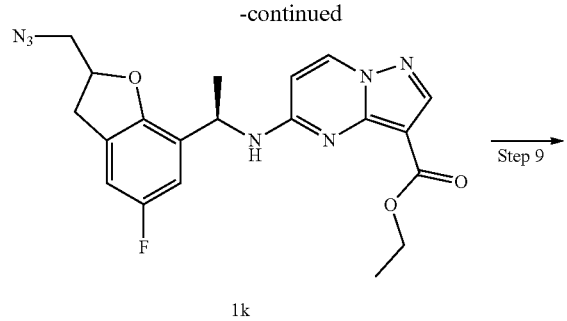

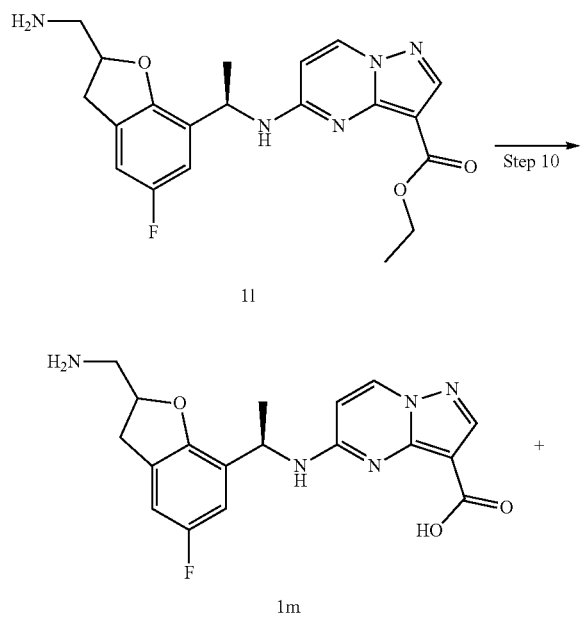

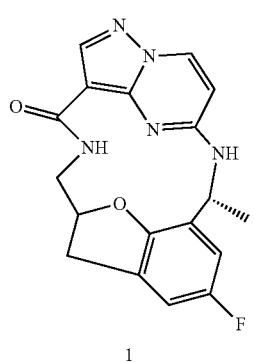

Step 1

(R,1E)-N-(3-allyl-5-fluoro-2-hydroxybenzylidene)-2-methylpropane-2-sulfenamide 3-allyl-5-fluoro-2-hydroxybenzaldehyde 1a (2.80 g, 15.5 mmol) (prepared according to patent application WO2014022858), (R)-2-methylpropane-2-sulfinamide 1b (2.07 g, 17.1 mmol) and cesium carbonate (8.08 g, 24.8 mmol) were added to 50 mL of dichloromethane, and reacted overnight at room temperature. After the reaction was completed, the reaction solution was added with water (30 mL), and extracted with dichloromethane (30 mL×3), and then organic phases were combined, dried with anhydrous sodium sulfate, filtered, and concentrated under reduced pressure. The obtained residue was further separated and purified by silica gel column chromatography (eluent: system A) to obtain (R,1E)-N-(3-allyl-5-fluoro-2-hydroxybenzylidene)-2-methylpropane-2-sulfenamide 1c (4.39 g, yellow semisolid) with a yield of 100%.

MS m/z(ESI): 284.1 [M+1]

Step 2

(R)—N-((1R)-1-(3-allyl-5-fluoro-2-hydroxyphenyl)ethyl)-2-methylpropane-2-sulfenamide (R,1E)-N-(3-allyl-5-fluoro-2-hydroxybenzylidene)-2-methylpropane-2-sulfenamide 1c (4.39 g, 15.5 mmol) was added into 50 mL of tetrahydrofuran, the temperature was controlled at −65° C., and then methylmagnesium bromide (77.5 ml, 77.5 mmol, 1 mol/L) was added dropwise. After the addition, the mixture was transferred to room temperature and reacted overnight. After the reaction was completed, the reaction solution was quenched with water (30 mL), and extracted with ethyl acetate (30 mL×3), and then organic phases were combined, dried with anhydrous sodium sulfate, filtered, and concentrated under reduced pressure. The obtained residue was further separated and purified by silica gel column chromatography (eluent: system A) to obtain (R)—N-((1R)-1-(3-allyl-5-fluoro-2-hydroxyphenyl)ethyl)-2-methylpropane-2-sulfenamide 1d (1.5 g, yellow viscous substance) with a yield of 32.6%.

MS m/z(ESI): 300.1 [M+1]

Step 3

(1R)-2-allyl-6-(1-aminoethyl)-4-fluorophenol (R)—N-((1R)-1-(3-allyl-5-fluoro-2-hydroxyphenyl)ethyl)-2-methylpropane-2-sulfenamide 1d (0.50 g, 1.67 mmol) was added to 5 mL of dichloromethane, then added with 2 mL of hydrochloride 1,4-dioxane solution (4 mol/L), and reacted at room temperature for 2 hours. After monitoring that the reaction was completed by LC-MS, the reaction solution was filtered, and then a filter cake was taken, dissolved in 10 mL of water, and the pH was adjusted to neutrality with a sodium carbonate solution. The reaction solution was extracted with ethyl acetate (20 mL×3), then organic phases were combined, dried with anhydrous sodium sulfate, filtered, and concentrated under reduced pressure to obtain crude product of (1R)-2-allyl-6-(1-aminoethyl)-4-fluorophenol 1e (yellow and viscous).

MS m/z(ESI): 178.1 [M−16]

Step 4

(1R)-1-(2-(iodomethyl)-5-fluoro-2,3-dihydrobenzofuran-7-yl)ethan-1-amine

Crude product of (1R)-2-allyl-6-(1-aminoethyl)-4-fluorophenol 1e (300 mg) was added to 5 mL of tetrahydrofuran, cooled to 0° C., and then added with iodosuccinimide (516 mg, 2.29 mmol), and reacted at room temperature overnight. After the reaction was completed, the reaction solution was added with 30 mL of water, and extracted with ethyl acetate (30 mL×3), then organic phases were combined, dried with anhydrous sodium sulfate, filtered, and concentrated under reduced pressure. The obtained residue was further separated and purified by silica gel column chromatography (eluent: system B) to obtain (1R)-1-(2-(iodomethyl)-5- fluoro-2,3-dihydrobenzofuran-7-yl)ethan-1-amine 1f (100 g, brown viscous substance) with a yield of 20%.

MS m/z(ESI): 304.0 [M−16]

Step 5

Tert-butyl ((1R)-1-(2-(iodomethyl)-5-fluoro-2,3-dihydrobenzofuran-7-yl)ethyl) carbamate (1R)-1-(2-(iodomethyl)-5-fluoro-2,3-dihydrobenzofuran-7-yl)ethan-1-amine 1f (500 mg, 1.56 mmol) and triethylamine (316 mg, 3.12 mmol) were dissolved in 5 mL of dichloromethane, then added with di-tert-butyl dicarbonate (374 mg, 1.71 mmol), and reacted at room temperature for 4 hours. After the reaction was completed, a saturated ammonium chloride solution was added for washing, then the reaction solution was dried with anhydrous sodium sulfate, filtered and concentrated to obtain crude product of tert-butyl ((1R)-1-(2-(iodomethyl)-5-fluor-2,3-dihydrobenzofuran-7-yl)ethyl) carbamate 1g (yellow, viscous).

MS m/z(ESI): 422.1 [M+1]

Step 6

Tert-butyl ((1R)-1-(2-(azidomethyl)-5-fluoro-2,3-dihydrobenzofuran-7-yl)ethyl) carbamate Crude product of tert-butyl ((1R)-1-(2-(iodomethyl)-5-fluoro-2,3-dihydrobenzofuran-7-yl)ethyl) carbamate 1g (170 mg) was added to 2 mL of N,N-dimethylformamide, and then added with sodium azide (32 mg, 0.49 mmol), and reacted at room temperature overnight. The reaction solution was added with 20 mL of water, and extracted with ethyl acetate (20 mL×3), then organic phases were combined, and washed with a saturated sodium chloride solution, dried with anhydrous sodium sulfate, filtered, and concentrated under reduced pressure to obtain crude product of tert-butyl ((1R)-1-(2-(azidomethyl)-5-fluoro-2,3-dihydrobenzofuran-7-yl) ethyl) carbamate 1h (yellow liquid).

MS m/z(ESI): 337.2 [M+1]

Step 7

(1R)-1-(2-(azidomethyl)-5-fluoro-2,3-dihydrobenzofuran-7-yl)ethan-1-amine

Crude product of tert-butyl ((1R)-1-(2-(azidomethyl)-5-fluoro-2,3-dihydrobenzofuran-7-yl)ethyl) carbamate 1h (120 mg) was added to 3 mL of dichloromethane, then added with 1.5 mL of hydrochloride 1,4-dioxane solution, and reacted at room temperature for 2 hours. The reaction solution was concentrated under reduced pressure to obtain crude product of (1R)-1-(2-(azidomethyl)-5-fluoro-2,3-dihydrobenzofuran-7-yl)ethan-1-amine 1i (yellow, viscous).

Step 8

Ethyl 5-(((1R)-1-(2-(azidomethyl)-5-fluoro-2,3-dihydrobenzofuran-7-yl)ethyl)amino)pyrazolo [1,5-a]pyrimidine-3-carboxylate Crude product of (1R)-1-(2-(azidomethyl)-5-fluoro-2,3-dihydrobenzofuran-7-yl)ethan-1-amine 1i (84 mg), N,N-diisopropylethylamine (280 mg, 2.16 mmol) and ethyl 5-chloropyrazolo[1,5-a]pyrimidine-3-carboxylate 1j (84 mg, 0.4 mmol) were dissolved in 3 mL of n-butylalcohol, and reacted at 120° C. for 5 hours. The reaction solution was concentrated under reduced pressure, and the obtained residue was further separated and purified by silica gel column chromatography (eluent: system A) to obtain ethyl 5-(((1R)-1-(2-(azidomethyl)-5-fluor-2,3-dihydrobenzofuran-7-yl) ethyl)amino)pyrazolo[1,5-a]pyrimidine-3-carboxylate 1k (120 mg, yellow solid).

MS m/z(ESI): 426.2 [M+1]

Step 9

Ethyl 5-(((1R)-1-(2-(aminomethyl)-5-fluoro-2,3-dihydrobenzofuran-7-yl)ethyl)amino)pyrazolo [1,5-a]pyrimidine-3-carboxylate Ethyl 5-(((1R)-12(azidomethyl)-5-fluoro-2,3(hydrobenzofuran-7-yl)ethyl)amino)pyrazolo[1,5-a]pyrimidine-3-carboxylate 1k (120 mg, 0.28 mmol) and triphenylphosphine (82 mg, 0.31 mmol) were added to 6 mL of mixed solution (tetrahydrofuran:water=2:1), and reacted at room temperature overnight. After the reaction was completed, the reaction solution was added with 20 mL of water, and extracted with ethyl acetate (20 mL×3), and then organic phases were combined, dried with anhydrous sodium sulfate, filtered, and concentrated under reduced pressure. The obtained residue was further separated and purified by silica gel column chromatography (eluent: system A) to obtain ethyl 5-(((1R)-1-(2-(aminomethyl)-5-fluoro-2,3-dihydrobenzofuran-7-yl) ethyl)amino)pyrazolo[1,5-a]pyrimidine-3-carboxylate 1l (76 g, yellow solid) with a yield of 67.25%.

MS m/z(ESI): 400.2 [M+1]

Step 10

(3R)-6-fluoro-3-methyl-10-oxa-2,13,17,18,21-pentaazapentacyclo[13.5.2.1$^{8,11}$.0$^{4,9}$.0$^{18,22}$]tricosa-1(21), 4,6,8,15(22),16,19-heptaen-14-one Ethyl 5-(((1R)-1-(2-(aminomethyl-5-fluor-2,3-dihydrobenzofuran-7-yl)ethyl)amino)pyrazolo[1,5-a]pyrimidine-3-carboxylate 1l (76 mg, 0.19 mmol) was dissolved in 3 mL of mixed solution (tetrahydrofuran:methanol:water=1:4:1), added with lithium hydroxide monohydrate (48 mg, 1.14 mmol), and stirred at 70° C. overnight. After monitoring that the reaction was completed by LC-MS, the reaction solution was added with 20 mL of water, and extracted with ethyl acetate (20 mL×3), and then organic phases were combined, dried with anhydrous sodium sulfate, filtered, and concentrated under reduced pressure. The obtained residue was further separated and purified by silica gel column chromatography (eluent: system A) to obtain 5-(((1R)-1-(2-(aminomethyl)-2,3-dihydrobenzofuran-7-yl)ethyl)amino)pyrazolo[1,5-a]pyrimidine-3-carboxylic acid 1m and the title product (3R)-6-fluoro-3-methyl-10-oxa-2,13,17,18,21-pentaazapentacyclo[13.5.2.1$^{8,11}$.0$^{4,9}$.0$^{18,22}$]tricosa-1(21),4,6,8, 15(22),16,19-heptaen-14-one 1 (5 mg) with a yield of 7%.

1m MS m/z(ESI): 372.0 [M+1]

1 MS m/z(ESI): 354.3 [M+1]

$^1$H NMR (400 MHz, DMSO-d$_6$) δ 8.88 (d, J=9.3 Hz, 1H), 8.65 (d, J=4.9 Hz, 1H), 8.55 (d, J=7.6 Hz, 1H), 8.01 (s, 1H), 6.84 (dd, J=8.5, 2.5 Hz, 1H), 6.75 (dd, J=9.9, 2.7 Hz, 1H), 6.38 (d, J=7.6 Hz, 1H), 5.36 (dt, J=10.0, 4.7 Hz, 1H), 4.92-5.04 (m, 1H), 3.56-3.70 (m, 2H), 3.50 (dd, J=13.4, 4.9 Hz, 1H), 2.83 (dd, J=16.9, 4.8 Hz, 1H), 1.55 (d, J=7.0 Hz, 3H).

Example 2
(12S)-6-fluoro-3-methyl-10,24-dioxa-2,14,18,19,22-pentaazapentacyclo[14.5.2.1^{8,12}.0^{4,9}.0^{19,23}]tetracosa-1(22),4(9),5,7,16(23),17,20-heptaen-15-one
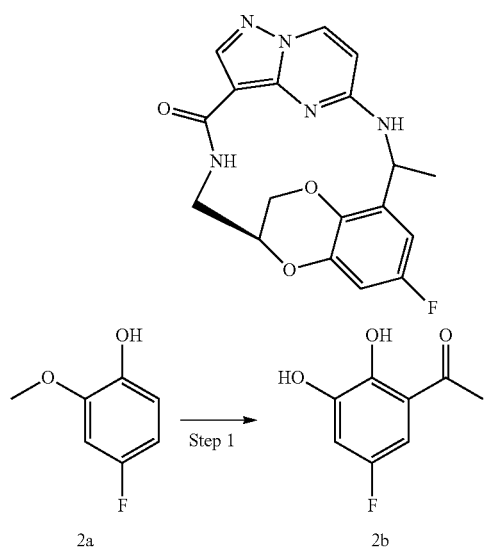
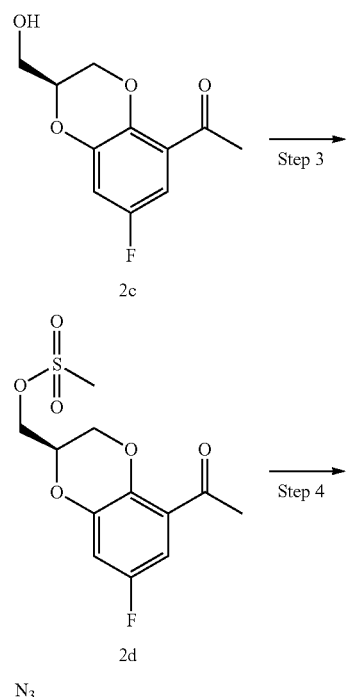
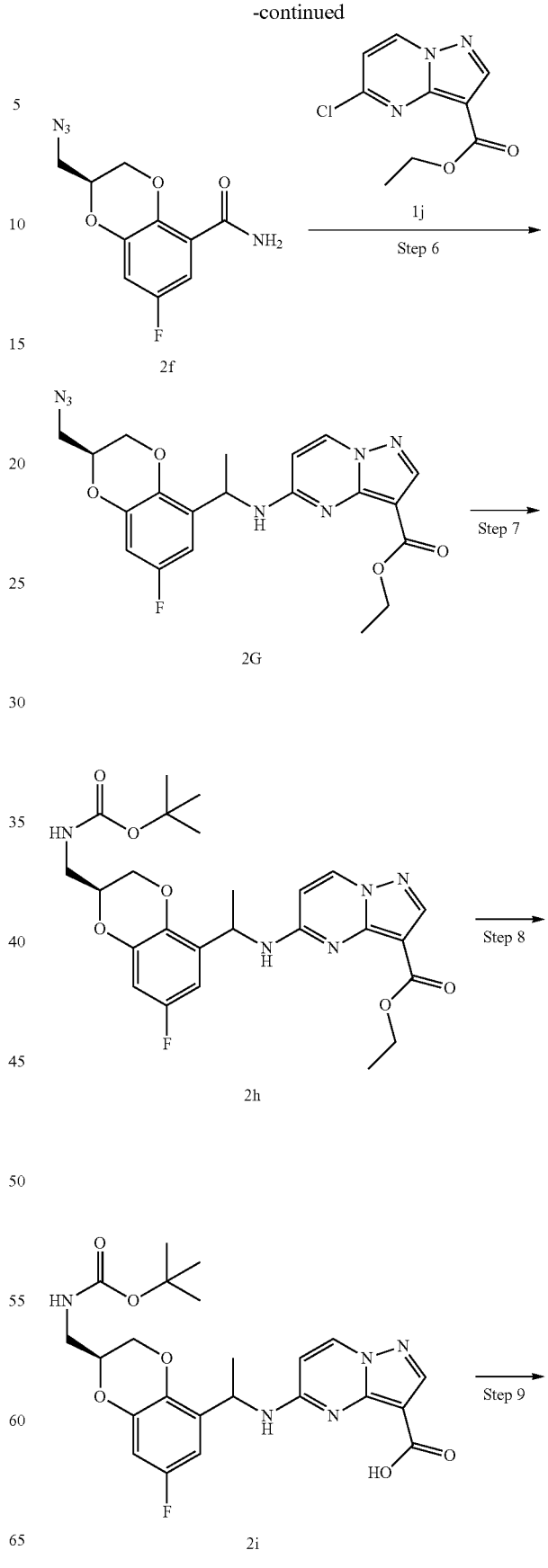

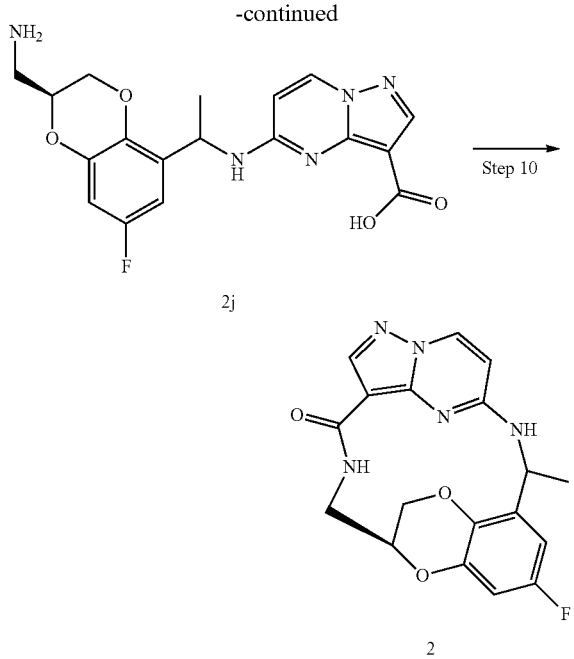

Step 1

1-(5-fluoro-2,3-dihydroxyphenyl)ethan-1-one 4-fluoro-2-methoxyphenol 2a (13.5 g, 95 mmol) was added to 200 mL of boron trifluoride-acetic acid complex, heated to 135° C., and reacted for 16 hours. After the reaction was completed, the reaction solution was added with 100 mL of water, and extracted with ethyl acetate (80 mL×3), then organic phases were combined, washed with saturated sodium chloride solution, dried with anhydrous sodium sulfate, filtered, and concentrated under reduced pressure. The obtained residue was further separated and purified by silica gel column chromatography (eluent: system A) to obtain 1-(5-fluoro-2,3-dihydroxyphenyl)ethan-1-one 2b (1.2 g, yellow solid) with a yield of 7.5%.

MS m/z(ESI): 171.0 [M+1]

Step 2

(2S)-1-(7-fluoro-2-(hydroxymethyl)-2,3-dihydrobenzo[b][1,4]dioxin-5-yl)ethan-1-one Sodium hydroxide (564 mg, 14.1 mmol) was dissolved in 20 mL of water, added with 1-(5-fluoro-2,3-dihydroxyphenyl)ethan-1-one 2b (1.2 g, 7.05 mmol) and (R)-2-(chloromethyl)oxirane, heated to 105° C., and reacted overnight. After the reaction was completed, the reaction was cooled down, the reaction solution was added with 20 mL of water, and extracted with ethyl acetate (30 mL×3), then organic phases were combined, washed with saturated sodium chloride solution, dried with anhydrous sodium sulfate, filtered, and concentrated under reduced pressure. The obtained residue was further separated and purified by silica gel column chromatography (eluent: system A) to obtain (2S)-1-(7-fluoro-2-(hydroxymethyl)-2,3-dihydrobenzo[b][1,4]dioxin-5-yl)ethan-1-one 2c (320 mg, yellow viscous substance) with a yield of 20.5%.

MS m/z(ESI): 227.0 [M+1]

Step 3

(2R)-(5-acetyl-7-fluoro-2,3-dihydrobenzo[b][1,4]dioxin-2-yl)methyl methanesulfonic acid (2S)-1-(7-fluoro-2-(hydroxymethyl)-2,3-dihydrobenzo[b][1,4]dioxin-5-yl)ethan-1-one 2c (320 mg, 1.41 mmol) was added to 1.5 mL of dichloromethane, cooled to 0° C., added with 4-dimethylaminopyridine (350 mg, 2.86 mmol), dropwise added with methylsulfonyl chloride (243 mg, 2.12 mmol), and then transferred to react at room temperature overnight. After the reaction was completed, the reaction solution was added with 30 mL of saturated ammonium chloride solution, extracted with dichloromethane (30 mL×3), washed with saturated ammonium chloride solution, and dried with anhydrous sodium sulfate, then the reaction solution was concentrated under reduced pressure to obtain crude product of (2R)-(5-acetyl-7-fluoro-2,3-dihydrobenzo[b][1,4]dioxin-2-yl)methyl methanesulfonic acid 2d (430 mg, yellow viscous substance) with a yield of 100%.

MS m/z(ESI): 305.0 [M+1]

Step 4

(2S)-1-(2-(azidomethyl)-7-fluoro-2,3-dihydrobenzo[b][1,4]dioxin-5-yl)ethan-1-one (2R)-(5-acetyl-7-fluoro-2,3-dihydrobenzo[b][1,4]dioxin-2-yl)methyl methanesulfonic acid 2d (430 mg) was added to 10 mL of N,N-dimethylformamide solution, and then added with sodium azide (193 mg, 2.97 mmol), heated to 55° C., and reacted overnight. After the reaction was completed, the reaction solution was added with 30 mL of water, and extracted with ethyl acetate (30 mL×3), then organic phases were combined, washed with a saturated sodium chloride solution, dried with anhydrous sodium sulfate, filtered and concentrated under reduced pressure. The obtained residue was further separated and purified by silica gel column chromatography (eluent: system A) to obtain (2S)-1-(2-(azidomethyl)-7-fluoro-2,3-dihydrobenzo[b][1,4]dioxin-5-yl)ethan-1-one 2e (230 g, yellow semisolid) with a yield of 65%.

MS m/z(ESI): 252.0 [M+1]

Step 5

1-((2S)-2-(azidomethyl)-7-fluoro-2,3-dihydrobenzo[b][1,4]dioxin-5-yl)ethan-1-amine (2S)-1-(2-(azidomethyl)-7-fluoro-2,3-dihydrobenzo[b][1,4]dioxin-5-yl)ethan-1-one 2e (230 mg, 0.92 mmol), ammonium acetate (710 mg, 9.2 mmol) and sodium cyanoborohydride (116 mg, 1.84 mmol) were added to 5 mL of methanol, reacted at room temperature for 1 hour, and then heated to reflux, and then reacted overnight. The reaction solution was concentrated under reduced pressure, added with 30 mL of water, and extracted with ethyl acetate (30 mL×3), then organic phases were combined, washed with a saturated sodium chloride solution, dried with anhydrous sodium sulfate, filtered, and concentrated under reduced pressure to obtain 230 mg of crude product of 1-((2S)-2-(azidomethyl)-7-fluoro-2,3-dihydrobenzo[b][1,4]dioxin-5-yl)ethan-1-amine 2f, and the product was subjected to the next reaction without purification.

MS m/z(ESI): 253.1 [M+1]

Step 6

Ethyl 5-((1-((2S)-2-(azidomethyl)-7-fluoro-2,3-dihydrobenzo[b][1,4]dioxin-5-yl)ethyl)amino) pyrazole[1,5]-a]pyrimidine-3-carboxylate Crude product of 1-((2S)-2-(azidomethyl)-7-fluoro-2,3-dihydrobenzo[b][1,4]dioxin-5-yl)ethan-1-amine 2f (230 mg), N,N-diisopropylethylamine (95 mg, 0.74 mmol) and ethyl 5-chloropyrazolo[1,5-a]pyrimidine-3-carboxylate 1j (248 mg, 1.10 mmol) were dissolved in 5 mL of n-butanol, and reacted at 120° C. for 5 hours. The reaction solution was concentrated under reduced pressure, and the obtained residue was further separated and purified by silica gel column chromatography (eluent: system A) to obtain ethyl 5-((1-((2S)-2-(azidomethyl)-7-fluoro-2,3-dihydrobenzo[b][1,4]dioxin-5-yl)ethyl)amino)pyrazole[1,5]-a]pyrimidine-3-carboxylate 2g (50 mg, yellow semisolid) with a yield of 12.4%.

MS m/z(ESI): 442.2 [M+1]

Step 7

Ethyl 5-((1-((2S)-2-(((tert-butoxycarbonyl)amino)methyl)-7-fluoro-2,3-dihydrobenzo [b][1,4]dioxin-5-yl)ethyl)amino)pyrazolo[1,5-a]pyrimidine-3-carboxylate Ethyl 5-((1-((2S)-2-(azidomethyl)-7-fluoro-2,3-dihydrobenzo[b][1,4]dioxin-5-yl)ethyl) amino)pyrazole[1,5]-a]pyrimidine-3-carboxylate 2g (50 mg, 0.11 mmol) was added to 5 mL of methanol, and then added with di-tert-butyl dicarbonate (30 mg, 0.14 mmol) and 10 mg of 10% palladium carbon, and reacted at room temperature for 5 hours under the protection of hydrogen. The reaction solution was filtered, and the filtrate was directly concentrated to obtain crude product of Ethyl 5-((1-((2S)-2-(((tert-butoxycarbonyl)amino)methyl)-7-fluoro-2,3-dihydrobenzo[b][1,4]dioxin-5-yl)ethyl)amino)pyrazolo[1,5-a]pyrimidine-3-carboxylate 2h (58 mg, yellow viscous substance), and the product was subjected to the next reaction without purification.

MS m/z(ESI): 516.2 [M+1]

Step 8

5-((1-((2S)-2-(((tert-butoxycarbonyl)amino)methyl)-7-fluoro-2,3-dihydrobenzo[b][1,4]dioxin-5-yl)ethyl)amino)pyrazolo[1,5-a]pyrimidine-3-carboxylic acid Crude product of ethyl 5-((1-((2S)-2-(((tert-butoxycarbonyl)amino)methyl)-7-fluoro-2,3-dihydrobenzo[b][1,4]dioxin-5-yl)ethyl)amino)pyrazolo[1,5-a]pyrimidine-3-carboxylate 2h (58 mg) was dissolved in 3 mL of mixed solution (tetrahydrofuran:methanol:water=1:4:1), added with lithium hydroxide monohydrate (46 mg, 1.10 mmol), and stirred at 75° C. overnight. After the reaction was completed, the reaction solution was added with 20 mL of water, and extracted with ethyl acetate (20 mL×3), then organic phases were combined, dried with anhydrous sodium sulfate, filtered, and concentrated under reduced pressure to obtain crude product of 5-((1-((2S)-2-(((tert-butoxycarbonyl)amino)methyl)-7-fluoro-2,3-dihydrobenzo[b][1,4]dioxin-5-yl)ethyl)amino)pyrazolo[1,5-a]pyrimidine-3-carboxylic acid 2i (54 mg, yellow viscous substance), and the product was subjected to the next reaction without purification.

MS m/z(ESI): 488.2 [M+1]

Step 9

5-((1-((2S)-2-(aminomethyl)-7-fluoro-2,3-dihydrobenzo[b][1,4]dioxin-5-yl)ethyl)amino)pyrazolo[1,5-a]pyrimidine-3-carboxylic acid Crude product of 5-((1-((2S)-2-(((tert-butoxycarbonyl)amino)methyl)-7-fluoro-2,3-dihydrobenzo[b][1,4]dioxin-5-yl)ethyl)amino)pyrazolo[1,5-a]pyrimidine-3-carboxylic acid 2i (54 mg) was added to 2 mL of dichloromethane, and then added with 2 mL of hydrochloride 1,4-dioxane solution (4 mol/L), and reacted at room temperature for 1 hour. The reaction solution was concentrated under reduced pressure to obtain crude product of 5-((1-((2S)-2-(aminomethyl)-7-fluoro-2,3-dihydrobenzo[b][1,4]dioxin-5-yl)ethyl)amino) pyrazolo[1,5-a]pyrimidine-3-carboxylic acid 2j, and the product was subjected to the next reaction without purification.

MS m/z(ESI): 388.1 [M+1]

Step 10

(12S)-6-fluoro-3-methyl-10,24-dioxa-2,14,18,19,22-pentaazapentacyclo[14.5.2.1$^{8,12}$.0$^{4,9}$.0$^{19,23}$]tetracosa-1(22),4(9),5,7,16(23),17,20-heptaen-15-one Crude product of 5-((1-((2S)-2-(aminomethyl)-7-fluoro-2,3-dihydrobenzo[b][1,4]dioxin-5-yl)ethyl)amino)pyrazolo[1,5-a]pyrimidine-3-carboxylic acid 2j (43 mg), pentafluorobenzene diphenyl phosphate (51 mg, 0.13 mmol) and N,N-diisopropylethylamine (142 mg, 1.10 mmol) were dissolved in 4 mL of mixed solution (dichloromethane:N.N-dimethylformamide=3:1), and reacted at room temperature overnight. After the reaction was completed, the reaction solution was added with 20 mL of saturated aqueous ammonium chloride solution and extracted with dichloromethane (20 mL×3), then organic phases were combined, dried with anhydrous sodium sulfate, filtered, and concentrated under reduced pressure to obtain the title product (12S)-6-fluoro-3-methyl-10,24-dioxa-2,14,18,19,22-pentaazapentacyclo [14.5.2.1$^{8,12}$.0$^{4,9}$.0$^{19,23}$]tetracosa-1(22),4(9),5,7,16(23),17,20-heptaen-15-one 2 (3 mg) with a yield of 7.5% by preparing a liquid phase (separation column AKZONOBEL Kromasil; 250×21.2 mm I.D.; 5 μm, 20 mL/min; mobile phase A: 0.05% TFA+H$_2$O, and mobile phase B: CH$_3$CN).

MS m/z(ESI): 370.3 [M+1] $^1$H NMR (400 MHz, DMSO-d$_6$) δ 8.56 (d, J=7.6 Hz, 1H), 8.52 (d, J=3.8 Hz, 1H), 8.08 (d, J=6.4 Hz, 2H), 6.65 (dd, J=9.6, 3.0 Hz, 1H), 6.56 (dd, J=9.2, 3.0 Hz, 114), 6.43 (d, J=7.6 Hz, 1H), 5.16-5.21 (m, 1H), 4.80-4.86 (m, 2H), 4.35-4.38 (m, 1H), 4.16-4.22 (m, 2H), 3.55 (d, J=14.8 Hz, 1H), 1.57 (d, J=7.0 Hz, 311).

Examples 3 and 4
(3R,11R)-6-fluoro-3-methyl-10-oxa-2,14,18,19,22-pentaazapentacyclo[14.5.2.1^{8,11}.0^{4,9}.0^{19,23}]tetracosa-1(22),4,6,8,16(23),17,20-heptaen-15-one 3
(3R,11S)-6-fluoro-3-methyl-10-oxa-2,14,18,19,22-pentaazapentacyclo[14.5.2.1^{8,11}.0^{4,9}.0^{19,23}]tetracosa-1(22),4,6,8,16(23),17,20-heptaen-15-one 4
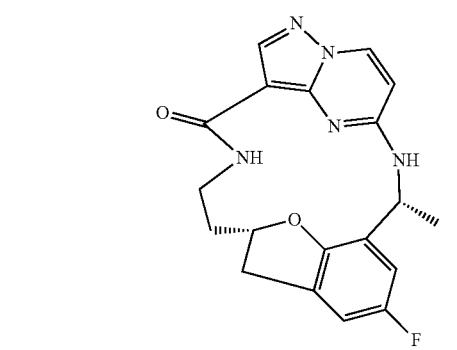
3
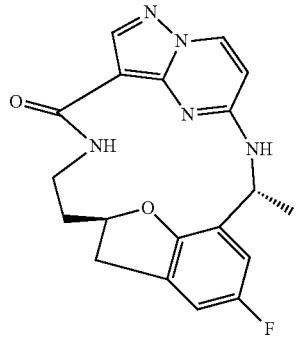
4
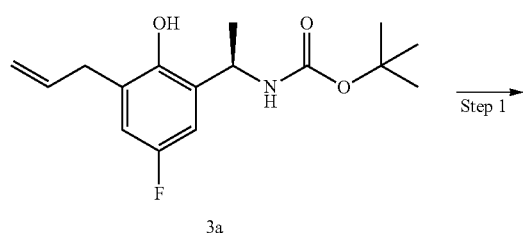
3a
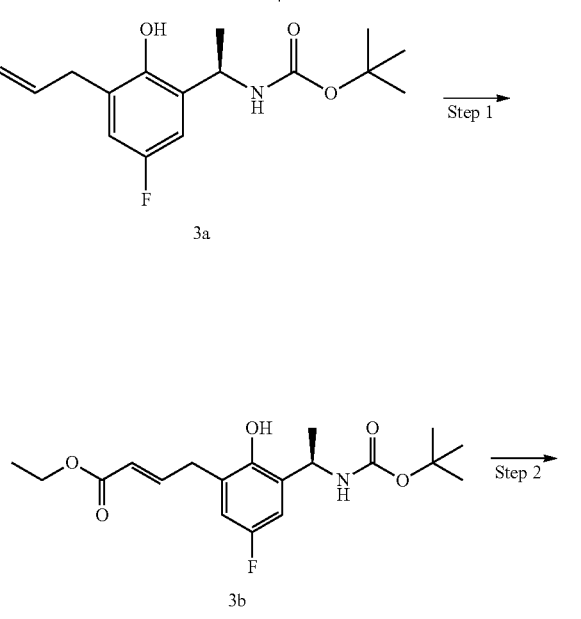
3b
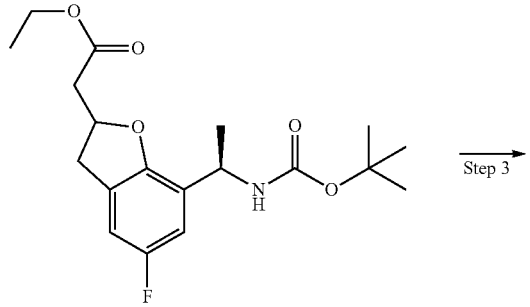
3c
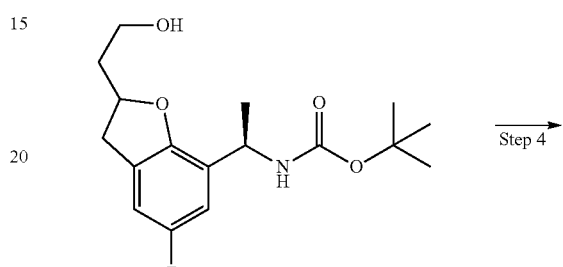
3d
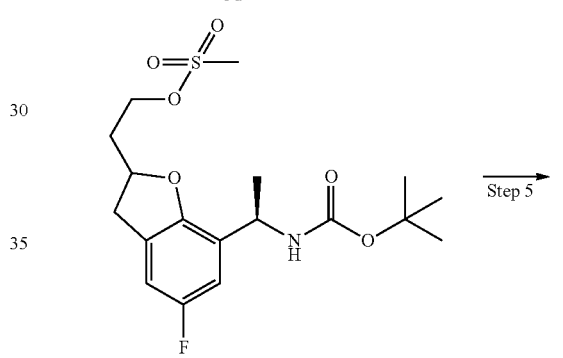
3e
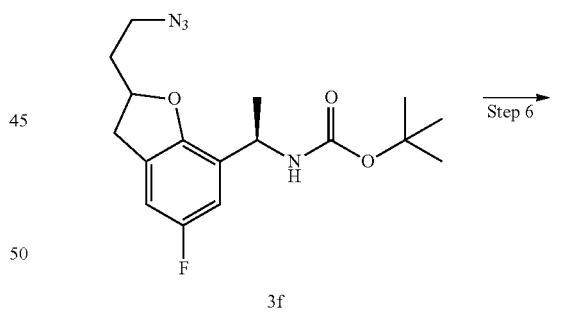
3f
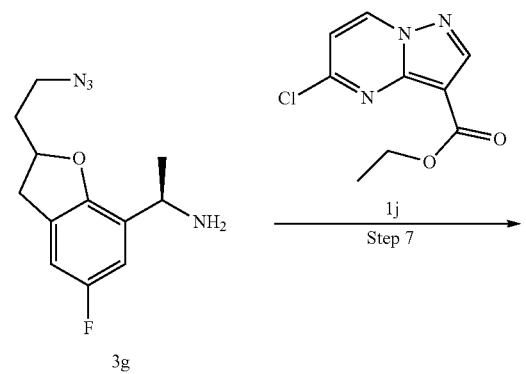
3g 77
-continued

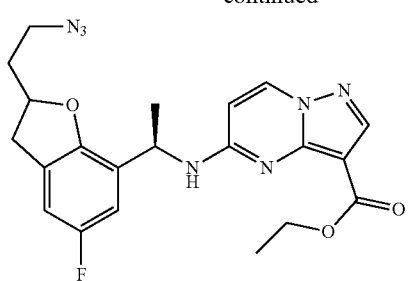
3h

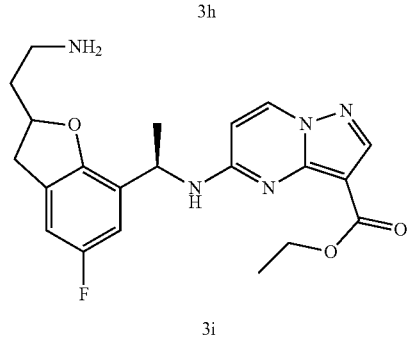
3i

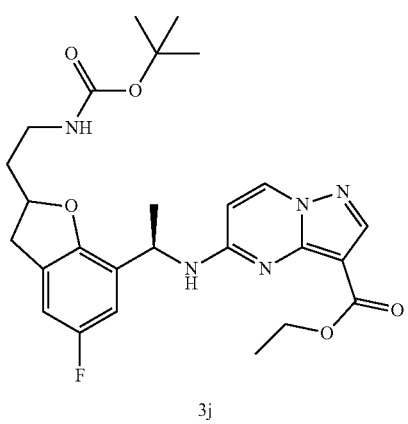
3j

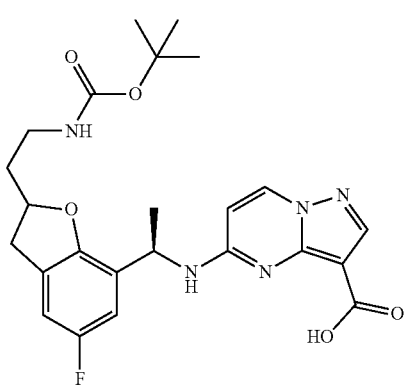
3k

78
-continued

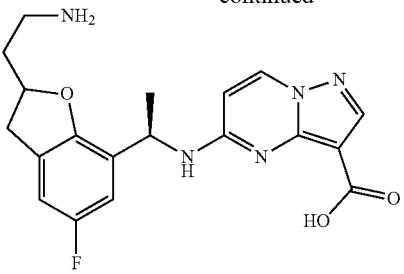
3l

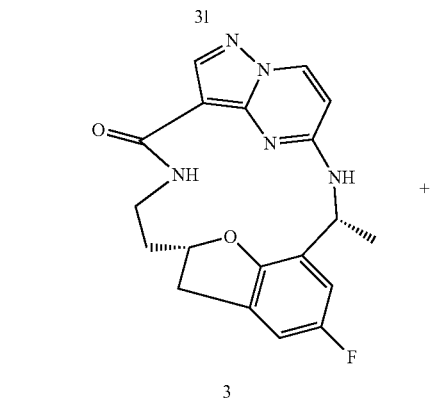
3

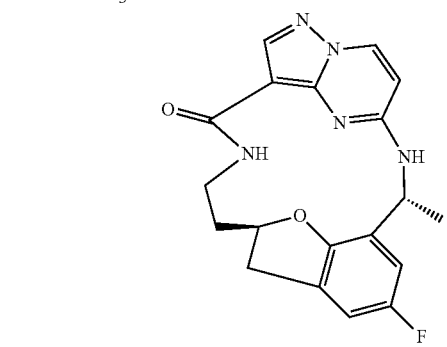
4

Ethyl (1R,2E)-4-(3-(1-((tert-butoxycarbonyl)amino) ethyl)-5-fluoro-2-hydroxyphenyl) but-2-enoate Tert-butyl (1R)-(1-(3-allyl-5-fluoro-2-hydroxyphenyl) ethyl) carbamate 3a (2.95 g, 10 mmol, prepared with reference to the preparation method of 1e), ethyl acrylate (2.5 g, 25 mmol), benzylidene-bis(tricyclohexylphosphine)dichlororuthenium (170 mg, 0.2 mmol) and cuprous iodide (40 mg, 0.2 mmol) were added to 50 mL of diethyl ether, heated to 40° C., and reacted overnight. The reaction solution was concentrated under reduced pressure, and the obtained residue was further separated and purified by silica gel column chromatography (eluent: system A) to obtain ethyl (1R,2E)-4-(3-(1-((tert-butoxycarbonyl)amino)ethyl)-5-fluoro-2-hydroxyphenyl)but-2-enoate 3b (2.3 g, yellow liquid) with a yield of 57.07%.

MS m/z(ESI): 368.2 [M+1]

Step 2

Ethyl 2-(7-((1R)-1-((tert-butoxycarbonyl)amino) ethyl)-5-fluoro-2,3-dihydrobenzofuran-2-yl) acetate Ethyl (1R,2E)-4-(3-(1-((tert-butoxycarbonyl)amino) ethyl)-5-fluoro-2-hydroxyphenyl)but-2-enoate 3b (2.18 g, 5.95 mmol) and caesium carbonate (1.94 g, 5.95 mmol) were dissolved in 4 mL of acetonitrile, and reacted at room temperature overnight. After the reaction was completed, the reaction solution was added with 20 mL of water, and extracted with ethyl acetate (20 mL×3), then organic phases were combined, and dried with anhydrous sodium sulfate, filtered, and concentrated under reduced pressure to obtain ethyl 2-(7-((1R)-1-((tert-butoxycarbonyl)amino)ethyl)-5-fluoro-2,3-dihydrobenzofuran-2-yl) acetate 3c (1.18 g, yellow solid) with a yield of 53.63%.

MS m/z(ESI): 368.2 [M+1]

Step 3

Tert-butyl ((1R)-1-(5-fluoro-2-(2-hydroxyethyl)-2,3-dihydrobenzofuran-7-yl)ethyl) carbamate Ethyl 2-(7-((1R)-1-((tert-butoxycarbonyl)amino)ethyl)-5-fluoro-2,3-dihydrobenzofuran-2-yl) acetate 3c (1.18 g, 3.2 mmol) was dissolved in 15 mL of dichloromethane, cooled to −78° C. under the protection of argon, dropwise added with diisobutylaluminum hydride (3.84 mL, 3.84 mmol, 1M). After the dropwise addition, the mixture was transferred to react at room temperature. After the reaction was completed, the reaction solution was quenched with 30 mL of water, and extracted with ethyl acetate (20 mL×3), then organic phases were combined, and dried with anhydrous sodium sulfate, filtered, and concentrated under reduced pressure to obtain crude product of tert-butyl ((1R)-1-(5-fluoro-2-(2-hydroxyethyl)-2,3-dihydrobenzofuran-7-yl) ethyl) carbamate 3d (yellow, viscous).

MS m/z(ESI): 326.2 [M+1]

Step 4

2-(7-((1R)-1-((tert-butoxycarbonyl)amino)ethyl)-5-fluor-2,3-dihydrobenzofuran-2-yl)ethyl methanesulfonic acid Tert-butyl ((1R)-1-(5-fluoro-2-(2-hydroxyethyl)-2,3-dihydrobenzofuran-7-yl)ethyl) carbamate 3d (1.05 g) and triethylamine (1.34 mL, 9.6 mmol) were dissolved in 20 mL of dichloromethane, dropwise added with methylsulfonyl chloride (440 mg, 3.84 mmol) slowly at 0° C., and then the mixture was transferred to react at room temperature for 2 hours. After the reaction was completed, the reaction solution was quenched with 30 mL of water, and extracted with ethyl acetate (20 mL×3), then organic phases were combined, and dried with anhydrous sodium sulfate, filtered, and concentrated under reduced pressure to obtain crude product of 2-(7-((1R)-1-((tert-butoxycarbonyl)amino)ethyl)-5-fluor-2,3-dihydrobenzofuran-2-yl)ethyl methanesulfonic acid 3e (yellow, viscous).

MS m/z(ESI): 404.2 [M+1]

Step 5

Tert-butyl ((1R)-1-(2-(2-azidoethyl)-5-fluoro-2,3-dihydrobenzofuran-7-yl)ethyl) carbamate Crude product of 2-(7-((1R)-1-((tert-butoxycarbonyl)amino)ethyl)-5-fluor-2,3-dihydrobenzofuran-2-yl)ethyl methanesulfonic acid 3e (300 mg) was added to 3 mL of N,N-dimethylformamide solution, and then added with sodium azide (64 mg, 0.98 mmol), and reacted at room temperature overnight. After the reaction was completed, the reaction solution was added with 30 mL of water, and extracted with ethyl acetate (20 mL×3), then organic phases were combined, and dried with anhydrous sodium sulfate, filtered, and concentrated under reduced pressure to obtain crude product of tert-butyl ((1R)-1-(2-(2-azidoethyl)-5-fluoro-2,3-dihydrobenzofuran-7-yl)ethyl) carbamate 3f (yellow liquid).

MS m/z(ESI): 351.2 [M+1]

Step 6

(1R)-1-(2-(2-azidoethyl)-5-fluoro-2,3-dihydrobenzofuran-7-yl)ethan-1-amine

Crude product of tert-butyl ((1R)-1-(2-(2-azidoethyl)-5-fluoro-2,3-dihydrobenzofuran-7-yl)ethyl) carbamate 3f was added to 5 mL of dichloromethane, then added with 2 mL of hydrochloride 1,4-dioxane solution (4 mol/L), and reacted at room temperature for 2 hours. After the reaction was completed, the reaction solution was directly concentrated under reduced pressure to obtain crude product of (1R)-1-(2-(2-azidoethyl)-5-fluoro-2,3-dihydrobenzofuran-7-yl)ethan-1-amine 3g.

MS m/z(ESI): 233.1 [M−16]

Step 7

Ethyl 5-(((1R)-1-(2-(2-azidoethyl)-5-fluoro-2,3-dihydrobenzofuran-7-yl)ethyl)amino) pyrazolo[1,5-a]pyrimidine-3-carboxylate Crude product of (1R)-1-(2-(2-azidoethyl)-5-fluoro-2,3-dihydrobenzofuran-7-yl)ethan-1-amine 3g (193 mg), N,N-diisopropylethylamine (597 mg, 4.62 mmol) and ethyl 5-chloropyrazolo[1,5-a]pyrimidine-3-carboxylate 1j (182 mg, 0.81 mmol) were dissolved in 5 mL of n-butanol, and reacted at 120° C. for 5 hours. After the reaction was completed, the reaction solution was directly concentrated under reduced pressure to obtain crude product of ethyl 5-(((1R)-1-(2-(2-azidoethyl)-5-fluoro-2,3-hydrobenzofuran-7-yl)ethyl)amino)pyrazolo[1,5-a]pyrimidine-3-carboxylate 3h.

MS m/z(ESI): 440.2 [M+1]

Step 8

Ethyl 5-(((1R)-1-(2-(2-aminoethyl)-5-fluoro-2,3-dihydrobenzofuran-7-yl)ethyl)amino) pyrazolo[1,5-a]pyrimidine-3-carboxylate Crude product of ethyl 5-(((1R)-1-(2-(2-azidoethyl)-5-fluoro-2,3-dihydrobenzofuran-7-yl)ethyl)amino)pyrazolo[1,5-a]pyrimidine-3-carboxylate 3 h and triphenylphosphine (200 mg, 0.92 mmol) were added to 6 mL of mixed solution (tetrahydrofuran:water=2:1), and reacted at room temperature overnight. The reaction solution was concentrated under reduced pressure, and the obtained residue was further separated and purified by silica gel column chromatography (eluent: system A) to obtain ethyl 5-(((1R)-1-(2-(2-aminoethyl)-5-fluoro-2,3-dihydrobenzofuran-7-yl)ethyl)amino) pyrazolo[1,5-a]pyrimidine-3-carboxylate 3i (280 mg, yellow foamy solid) with a yield of 88%.

MS m/z(ESI): 414.2 [M+1]

Step 9

Ethyl 5-(((1R)-1-(2-(2-((tert-butoxycarbonyl)amino)ethyl)-5-fluoro-2,3-dihydrobenzofuran-7-yl)ethyl)amino)pyrazolo[1,5-a]pyrimidine-3-carboxylate Ethyl 5-(((1R)-1-(2-(2-aminoethyl)-5-fluoro-2,3-dihydrobenzofuran-7-yl)ethyl)amino) pyrazolo[1,5-a]pyrimidine-3-carboxylate 3i (110 mg, 0.27 mmol) and triethylamine (55 mg, 0.54 mmol) were dissolved in 5 mL of dichloromethane, then added with di-tert-butyl dicarbonate (69 mg, 0.32 mmol), and reacted at room temperature for 3 hours. After the reaction was completed, the reaction solution was added with saturated ammonium chloride solution for washing, dried with anhydrous sodium sulfate, filtered, and concentrated under reduced pressure to obtain crude product of ethyl 5-(((1R)-1-(2-(2-((tert-butoxycarbonyl)amino)ethyl)-5-fluoro-2,3-dihydrobenzofuran-7-yl)ethyl)amino)pyrazolo[1,5-a]pyrimidine-3-carboxylate 3j (yellow liquid).

MS m/z(ESI): 514.2 [M+1]

Step 10

5-(((1R)-1-(2-(2-((tert-butoxycarbonyl)amino)ethyl)-5-fluoro-2,3-dihydrobenzofuran-7-yl)ethyl)amino)pyrazolo[1,5-a]pyrimidine-3-carboxylic acid Ethyl 5-(((1R)-1-(2-(2-((tert-butoxycarbonyl)amino)ethyl)-5-fluoro-2,3-dihydrobenzofuran-7-yl)ethyl)amino)pyrazolo[1,5-a]pyrimidine-3-carboxylate 3j (100 mg) was dissolved in 5 mL of mixed solution (tetrahydrofuran:methanol:water=1:3:1), added with lithium hydroxide monohydrate (50 mg, 1.19 mmol), and stirred at 70° C. overnight. After the reaction was completed, the reaction solution was added with 20 mL of water, and extracted with ethyl acetate (20 mL×3), then organic phases were combined, and dried with anhydrous sodium sulfate, filtered, and concentrated under reduced pressure to obtain crude product of 5-(((1R)-1-(2-(2-((tert-butoxycarbonyl)amino)ethyl)-5-fluoro-2,3-dihydrobenzofuran-7-yl)ethyl)amino)pyrazolo[1,5-a]pyrimidine-3-carboxylic acid 3k.

MS m/z(ESI): 486.2 [M+1]

Step 11

5-(((1R)-1-(2-(2-aminoethyl)-5-fluoro-2,3-dihydrobenzofuran-7-yl)ethyl)amino)pyrazolo[1,5-a]pyrimidine-3-carboxylic acid 5-(((1R)-1-(2-(2-((tert-butoxycarbonyl)amino)ethyl)-5-fluoro-2,3-dihydrobenzofuran-7-yl)ethyl)amino)pyrazolo[1,5-a]pyrimidine-3-carboxylic acid 3k (80 mg) was added to 3 mL of dichloromethane, and then added with 3 mL of hydrochloride 1,4-dioxane solution (4 mol/L), and reacted at room temperature for 2 hours. The reaction solution was concentrated under reduced pressure to obtain crude product of 5-(((1R)-1-(2-(2-aminoethyl)-5-fluoro-2,3-dihydrobenzofuran-7-yl)ethyl)amino)pyrazolo[1,5-a]pyrimidine-3-carboxylic acid 3l.

MS m/z(ESI): 386.2 [M+1]

Step 12

(3R,11R)-6-fluoro-3-methyl-10-oxa-2,14,18,19,22-pentaazapentacyclo[14.5.2.1$^{8,11}$.0$^{4,9}$.0$^{23}$]tetracosa-1(22),4,6,8,16(23),17,20-heptaen-15-one 3 (3R,11S)-6-fluoro-3-methyl-10-oxa-2,14,18,19,22-pentaazapentacyclo[14.5.2.1$^{8,11}$.0$^{4,9}$.0$^{19,23}$]tetracosa-(22),4,6,8,16(23),17,20-heptaen-15-one 4

5-(((1R)-1-(2-(2-aminoethyl)-5-fluoro-2,3-dihydrobenzofuran-7-yl)ethyl)amino)pyrazolo[1,5-a]pyrimidine-3-carboxylic acid 3l, pentafluorophenyl diphenyl phosphinate (97 mg, 0.19 mmol) and N,N-diisopropylethylamine (170 mg, 1.31 mmol) were dissolved in 5 mL of mixed solution (dichloromethane:N.N-dimethylformamide=1.5:1), and reacted at room temperature overnight. After the reaction was completed, the reaction solution was added with 20 mL of water, and extracted with dichloromethane (20 mL×3), then organic phases were combined, dried with anhydrous sodium sulfate, filtered, and concentrated under reduced pressure to obtain the title product (3R,11R)-6-fluoro-3-methyl-10-oxa-2,14,18,19,22-pentaazapentacyclo[14.5.2.1$^{8,11}$.0$^{4,9}$.0$^{19,23}$]tetracosa-1(22),4,6,8,16(23),17,20-heptaen-15-one 3 (8 mg) and (3R,11S)-6-fluoro-3-methyl-10-oxa-2,14,18,19,22-pentaazapentacyclo[14.5.2.1$^{8,11}$.0$^{4,9}$.0$^{19,23}$]tetracosa-1(22),4,6,8,16(23),17,20-heptaen-15-one 4 (6 mg) by preparing a liquid phase (separation column AKZONOBEL Kromasil; 250×21.2 mm I.D.; 5 μm, 20 mL/min; mobile phase A: 0.05% TFA+H$_2$O, and mobile phase B: CH$_3$CN).

3 MS m/z(ESI): 368.3 [M+1]

$^1$H NMR (400 MHz, DMSO-d$_6$) δ 8.64 (s, 1H), 8.16 (s, 1H), 8.04 (d, J=17.2 Hz, 1H), 7.63-7.72 (m, 1H), 6.78 (t, J=9.5 Hz, 1H), 6.68 (t, J=7.7 Hz, 1H), 6.28 (t, J=7.3 Hz, 1H), 5.32 (d, J=8.6 Hz, 1H), 5.07 (s, 1H), 3.94-4.30 (m, 1H), 3.31 (dt, J=9.9, 5.5 Hz, 2H), 2.90 (dt, J=16.1, 8.0 Hz, 1H), 2.10-2.18 (m, 1H), 1.71-1.75 (m, 1H), 1.42 (d, J=6.3 Hz, 3H). 4 MS m/z(ESI): 368.3 [M+1]

$^1$H NMR (400 MHz, DMSO-d$_6$) δ 8.90 (d, J=9.1 Hz, 1H), 8.52 (d, J=7.6 Hz, 1H), 8.43 (d, J=8.3 Hz, 1H), 8.08 (s, 1H), 6.98 (t, J=9.3 Hz, 2H), 6.28 (d, J=7.1 Hz, 1H), 5.55 (q, J=7.6 Hz, 1H), 4.37-4.42 (m, 1H), 4.11 (d, J=11.6 Hz, 1H), 3.22-3.24 (m, 1H), 2.99 (dd, J=14.7, 6.3 Hz, 1H), 2.87 (t, J=13.9 Hz, 1H), 2.18 (d, J=11.5 Hz, 1H), 1.97-2.12 (m, 1H), 1.54 (d, J=7.1 Hz, 3H).

Example 5

(3R)-6-fluoro-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one

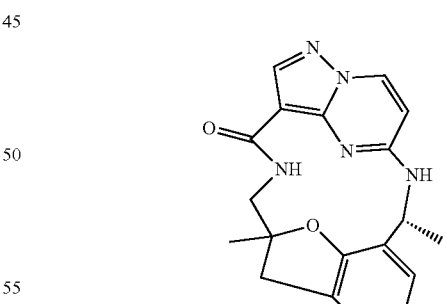

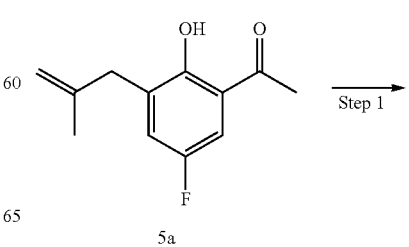

5a

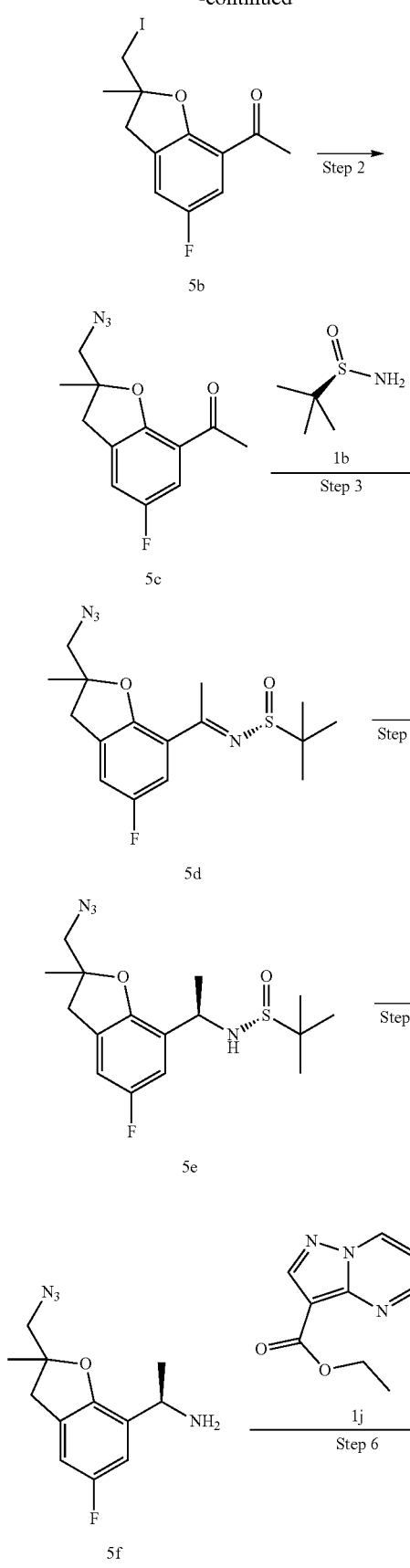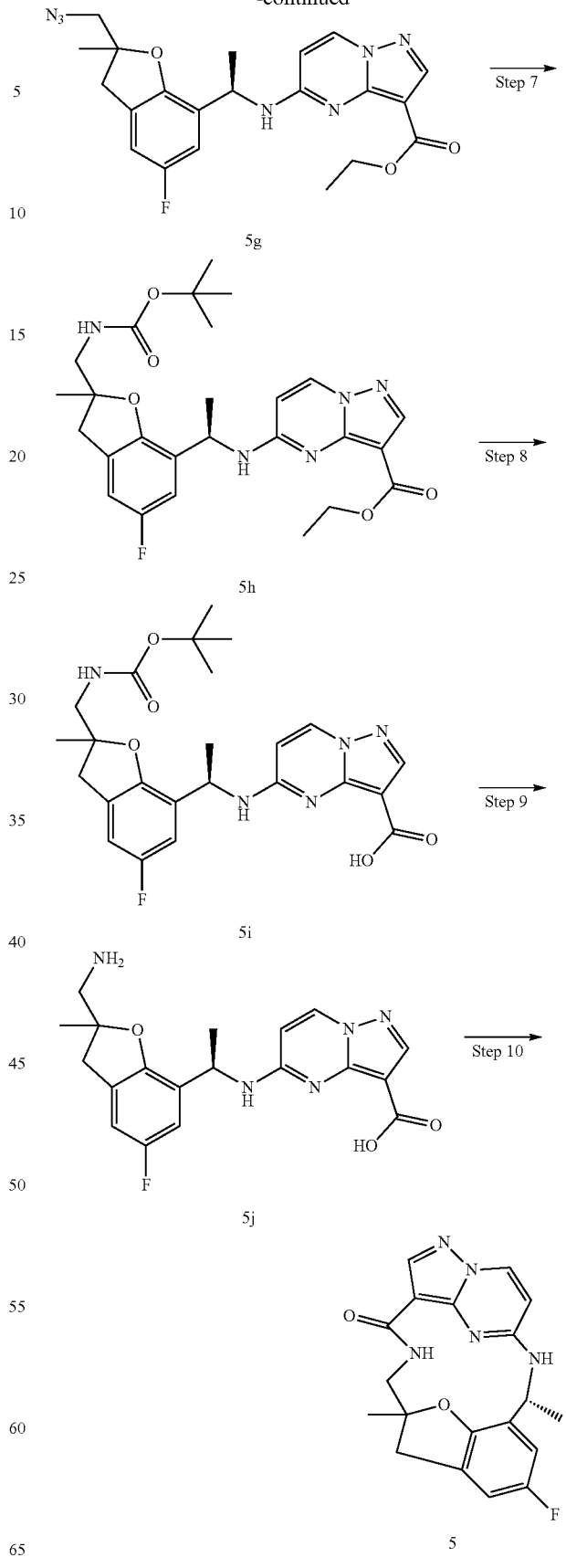

Step 1

1-(5-fluoro-2-(iodomethyl)-2-methyl-2,3-dihydrobenzofuran-7-yl)ethan-1-one 1-(5-fluoro-2-hydroxy-3-(2-methylallyl)phenyl)ethan-1-one 5a (12 g, 57.67 mmol) (prepared according to patent application WO2014022858) was added to 75 mL of tetrahydrofuran, and then added with iodosuccinimide (25.95 g, 115.33 mmol), and reacted at room temperature overnight. After the reaction was completed, the reaction solution was added with 100 mL of water, and extracted with ethyl acetate (50 mL×3), and then organic phases were combined, dried with anhydrous sodium sulfate, filtered, and concentrated under reduced pressure. The obtained residue was further separated and purified by silica gel column chromatography (eluent: system A) to obtain 1-(5-fluoro-2-(iodomethyl)-2-methyl-2,3-dihydrobenzofuran-7-yl)ethan-1-one 5b (15.2 g, yellow solid) with a yield of 78.9%.

MS m/z(ESI): 335.0 [M+1]

Step 2

1-(2-(azidomethyl)-5-fluoro-2-methyl-2,3-dihydrobenzofuran-7-yl)ethan-1-one 1-(5-fluoro-2-(iodomethyl)-2-methyl-2,3-dihydrobenzofuran-7-yl)ethan-1-one 5b (3 g, 8.98 mmol) was added to 20 mL of N,N-dimethylformamide, stirred for dissolution, then added with sodium azide (1.17 g, 17.96 mmol), heated to 75° C., and then reacted overnight. After the reaction was completed, the reaction solution was added with 60 mL of water, and extracted with ethyl acetate (50 mL×3), then organic phases were combined, washed with 30 mL of water for three times, dried with anhydrous sodium sulfate, filtered, and concentrated under reduced pressure. The obtained residue was further separated and purified by silica gel column chromatography (eluent: system A) to obtain 1-(2-(azidomethyl)-5-fluoro-2-methyl-2,3-dihydrobenzofuran-7-yl)ethan-1-one 5c (1.2 g, yellow liquid) with a yield of 60%.

MS m/z(ESI): 250.1 [M+1]

Step 3

(R)—N-((1E)-1-(2-(azidomethyl)-5-fluoro-2-methyl-2,3-dihydrobenzofuran-7-yl)ethylidene)-2-methylpropane-2-sulfenamide 1-(2-(azidomethyl)-5-fluoro-2-methyl-2,3-dihydrobenzofuran-7-yl)ethan-1-one 5c (1.2 g, 4.8 mmol), (R)-2-methylpropane-2-sulfinamide 1b (1.17 g, 9.6 mmol) and tetraethyl titanate (4.4 g, 19.3 mmol) were dissolved in 20 mL of tetrahydrofuran, and reacted at 75° C. overnight. After the reaction was completed, the reaction solution was added with 30 mL of water, and extracted with ethyl acetate (30 mL×3), and then organic phases were combined, dried with anhydrous sodium sulfate, filtered, and concentrated under reduced pressure. The obtained residue was further separated and purified by silica gel column chromatography (eluent: system A) to obtain (R)—N-((1E)-1-(2-(azidomethyl)-5-fluoro-2-methyl-2,3-dihydrobenzofuran-7-yl) ethylidene)-2-methylpropane-2-sulfenamide 5d (1.02 g, yellow liquid) with a yield of 60.3%.

MS m/z(ESI): 353.1 [M+1]

Step 4

(R)—N-((1R)-1-(2-(azidomethyl)-5-fluoro-2-methyl-2,3-dihydrobenzofuran-7-yl)ethyl)-2-methylpropane-2-sulfenamide (R)—N-((1E)-1-(2-(azidomethyl)-5-fluoro-2-methyl-2,3-dihydrobenzofuran-7-yl) ethylidene)-2-methylpropane-2-sulfenamide 5d (1.02 g, 2.90 mmol) was added to 20 mL of tetrahydrofuran, and then added with 9-boronbicyclo[3,3,1]-nonane (11.6 mL, 5.80 mmol, 0.5 mol/L), and reacted at room temperature for 4 hours. After the reaction was completed, the reaction solution was quenched with 30 mL of water, and extracted with ethyl acetate (30 mL×3), and then organic phases were combined, dried with anhydrous sodium sulfate, filtered, and concentrated under reduced pressure. The obtained residue was further separated and purified by silica gel column chromatography (eluent: system A) to obtain (R)—N-((1R)-1-(2-(azidomethyl)-5-fluoro-2-methyl-2,3-dihydrobenzofuran-7-yl)ethyl)-2-methylpropane-2-sulfenamide 5e (840 mg, yellow solid) with a yield of 81.9%.

MS m/z(ESI): 355.1 [M+1]

Step 5

(1R)-1-(2-(azidomethyl)-5-fluoro-2-methyl-2,3-dihydrobenzofuran-7-yl)ethan-1-amine (R)—N-((1R)-1-(2-(azidomethyl)-5-fluoro-2-methyl-2,3-dihydrobenzofuran-7-yl)ethyl)-2-methylpropane-2-sulfenamide 5e (840 mg, 2.37 mmol) was added to 5 mL of dichloromethane solution, then added with 2 mL of hydrochloride 1,4-dioxane solution (4 mol/L), and reacted at room temperature for 2 hours. After monitoring that the reaction was completed by LC-MS, the reaction solution was concentrated under reduced pressure to obtain crude product of (1R)-1-(2-(azidomethyl)-5-fluoro-2-methyl-2,3-dihydrobenzofuran-7-yl)ethan-1-amine 5f, and the product was subjected to the next reaction without purification.

MS m/z(ESI): 234.1 [M−16]

Step 6

Ethyl 5-(((1R)-1-(2-(azidomethyl)-5-fluoro-2-methyl-2,3-dihydrobenzofuran-7-yl)ethyl)amino)pyrazolo[1,5-a]pyrimidine-3-carboxylate Crude product of (1R)-1-(2-(azidomethyl)-5-fluoro-2-methyl-2,3-dihydrobenzofuran-7-yl)ethan-1-amine 5f (593 mg), ethyl 5-chloropyrazolo[1,5-a]pyrimidine-3-carboxylate 1j (533 mg, 2.37 mmol) and N,N-diisopropylethylamine (2.45 g, 18.96 mmol) were dissolved in 5 mL of n-butanol, and reacted at 125° C. for 3 hours. After monitoring that the reaction was completed by LC-MS, the reaction solution was added with 20 mL of water, and extracted with ethyl acetate (20 mL×3), then organic phases were combined, dried with anhydrous sodium sulfate, filtered, and concentrated under reduced pressure to obtain crude product of ethyl 5-(((1R)-1-(2-(azidomethyl)-5-fluoro-2-methyl-2,3-dihydrobenzofuran-7-yl)ethyl)amino)pyrazolo[1,5-a]pyrimidine-3-carboxylate 5g, and the product was subjected to the next reaction without purification.

MS m/z(ESI): 440.1 [M+1]

Step 7

Ethyl 5-(((1R)-1-(2-(((tert-butoxycarbonyl)amino)
methyl)-5-fluoro-2-methyl-2,3-dihydrobenzofuran-
7-yl)ethyl)amino)pyrazolo[1,5-a]pyrimidine-3-car-
boxylate Ethyl 5-(((1R)-1-(2-(azidomethyl)-5-fluoro-2-methyl-2,3-dihydrobenzofuran-7-yl)ethyl) amino)pyrazolo[1,5-a]pyrimidine-3-carboxylate 5g (410 mg, 0.93 mmol) was added to 5 mL of methanol, and then added with di-tert-butyl dicarbonate (244 mg, 1.12 mmol) and 100 mg of 10% palladium carbon, and reacted at room temperature for 4 hours under the protection of hydrogen. After the reaction was completed, the reaction solution was filtered, and the filtrate was directly concentrated to obtain crude product of ethyl 5-(((1R)-1-(2-(((tert-butoxycarbonyl)amino)methyl)-5-fluoro-2-methyl-2,3-dihydrobenzofuran-7-yl)ethyl) amino) pyrazolo[1,5-a]pyrimidine-3-carboxylate 5h, and the product was subjected to the next reaction without purification.

MS m/z(ESI): 514.2 [M+1]

Step 8

5-(((1R)-1-(2-(((tert-butoxycarbonyl)amino)methyl)-
5-fluoro-2-methyl-2,3-dihydrobenzofuran-7-yl)
ethyl)amino)pyrazolo[1,5-a]pyrimidine-3-carboxylic
acid Crude product of ethyl 5-(((1R)-1-(2-(((tert-butoxycarbonyl)amino)methyl)-5-fluoro-2-methyl-2,3-dihydrobenzofuran-7-yl)ethyl)amino) pyrazolo[1,5-a]pyrimidine-3-carboxylate 5h (479 mg) was dissolved in 6 mL of mixed solution (tetrahydrofuran:ethanol:water 2:2:1), added with lithium hydroxide monohydrate (310 mg, 7.39 mmol), and stirred at 80° C. overnight. After monitoring that the reaction was completed by LC-MS, the reaction solution was cooled, and dropwise added with diluted hydrochloric acid slowly to adjust the solution to acidity, then added with 10 mL of water, and extracted with ethyl acetate (20 mL×3), then organic phases were combined, dried with anhydrous sodium sulfate, filtered, and concentrated under reduced pressure to obtain crude product of 5-(((1R)-1-(2-(((tert-butoxycarbonyl)amino)methyl)-5-fluoro-2-methyl-2,3-dihydrobenzofuran-7-yl)ethyl)amino)pyrazolo[1,5-a]pyrimidine-3-carboxylic acid 5i, and the product was subjected to the next reaction without purification.

MS m/z(ESI): 486.2 [M+1]

Step 9

5-(((1R)-1-(2-(aminomethyl)-5-fluoro-2-methyl-2,3-
dihydrobenzofuran-7-yl)ethyl)amino)pyrazolo[1,5-a]
pyrimidine-3-carboxylic acid 5-(((1R)-1-(2-(((tert-butoxycarbonyl)amino)methyl)-5-fluoro-2-methyl-2,3-dihydrobenzofuran-7-yl)ethyl)amino) pyrazolo[1,5-a]pyrimidine-3-carboxylic acid 5i (451 mg) was added to 10 mL of dichloromethane solution, and then added with 3 mL of hydrochloride 1,4-dioxane solution, and reacted at room temperature for 1 hour. After monitoring that the reaction was completed by LC-MS, the reaction solution was concentrated under reduced pressure to obtain crude product of 5-(((1R)-1-(2-(aminomethyl)-5-fluoro-2-methyl-2,3-dihydrobenzofuran-7-yl)ethyl)amino)pyrazolo[1,5-a]pyrimidine-3-carboxylic acid 5j, and the product was subjected to the next reaction without purification.

MS m/z(ESI): 386.1 [M+1]

Step 10 (3R)-6-fluoro-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 5-(((1R)-1-(2-(aminomethyl)-5-fluoro-2-methyl-2,3-dihydrobenzofuran-7-yl)amino)pyrazolo[1,5-a]pyrimidine-3-carboxylic acid 5j (358 mg), pentafluorophenyl diphenyl phosphinate (428 mg, 1.12 mmol) and N,N-diisopropylethylamine (961 mg, 7.44 mmol) were dissolved in 6 mL of mixed solution (dichloromethane:N.N-dimethylformamide=5:1), and reacted at room temperature overnight. After monitoring that the reaction was completed by LC-MS, the reaction solution was added with 20 mL of saturated aqueous ammonium chloride solution and extracted with dichloromethane (20 mL×3), then organic phases were combined, dried with anhydrous sodium sulfate, filtered, and concentrated under reduced pressure to obtain the title product (3R)-6-fluoro-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 5 (20 mg) by preparing a liquid phase (separation column AKZONOBEL Kromasil; 250×21.2 mm I.D.; 5 µm, 20 mL/min; mobile phase A: 0.05% TFA+H$_2$O, and mobile phase B: CH$_3$CN).

MS m/z(ESI): 368.1 [M+1]

$^1$H NMR (400 MHz, DMSO-d$_6$) δ 8.92 (d, J=9.5 Hz, 1H), 8.64 (d, J=5.0 Hz, 1H), 8.53 (d, J=7.6 Hz, 1H), 8.00 (s, 1H), 6.75-6.89 (m, 1H), 6.74 (d, J=10.0 Hz, 1H), 6.37 (d, J=7.6 Hz, 1H), 4.93-5.12 (m, 1H), 3.68-3.93 (m, 2H), 3.58-3.66 (m, 2H), 1.59 (s, 3H), 1.54 (d, J=7.0 Hz, 3H).

Example 6

(3R)-6-fluoro-3-methyl-10-oxa-2,14,18,19,22-pentaazapentacyclo[14.5.2.1$^{8,11}$.0$^{4,9}$.0$^{19,23}$]tetracosa-1(22),4,6,8,11(24),16(23),17,20-octaen-15-one

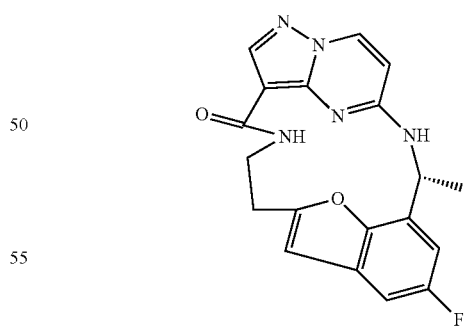

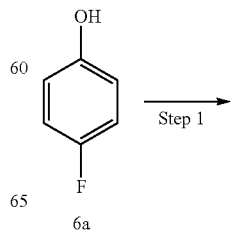

Step 1

6a

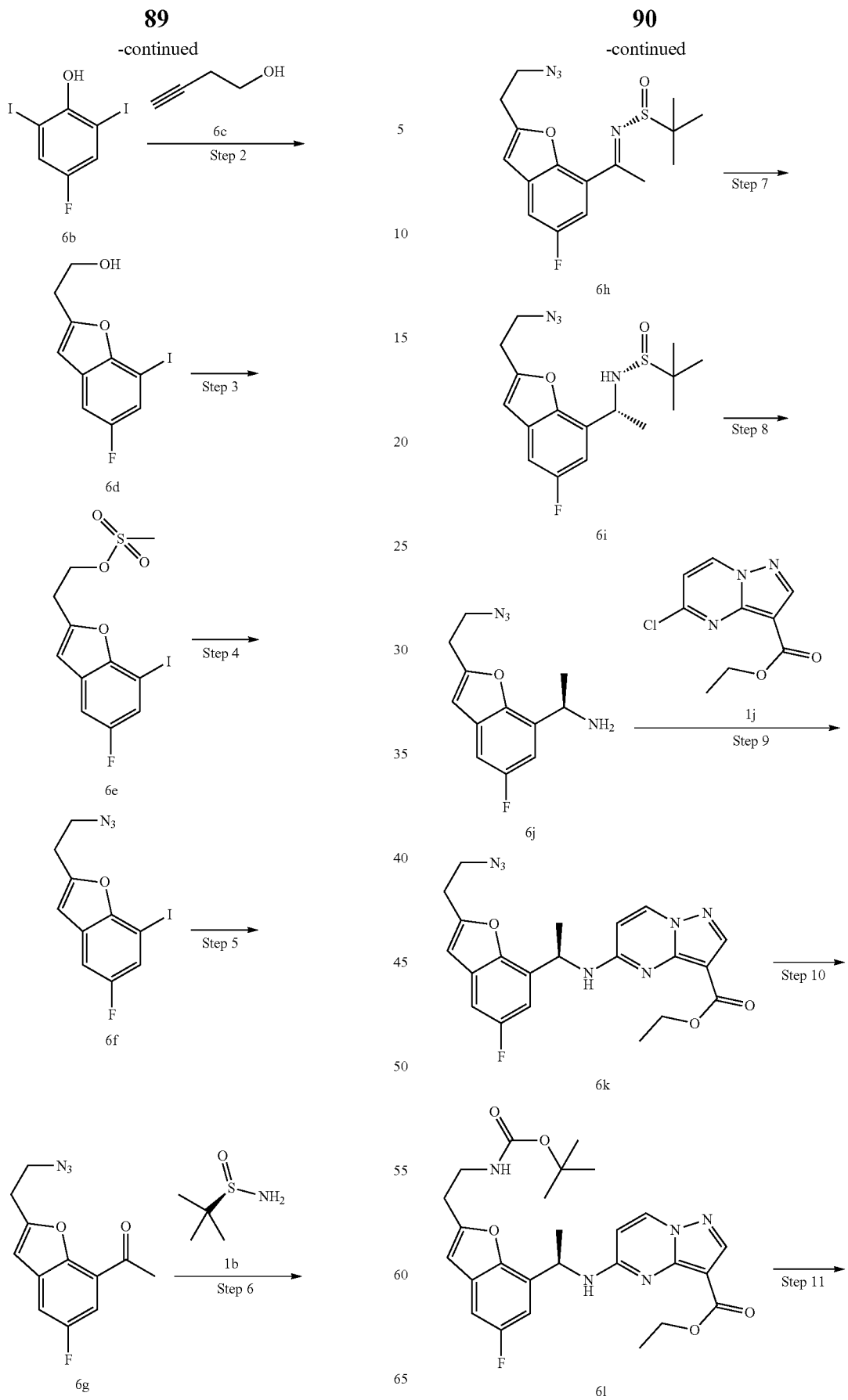

-continued

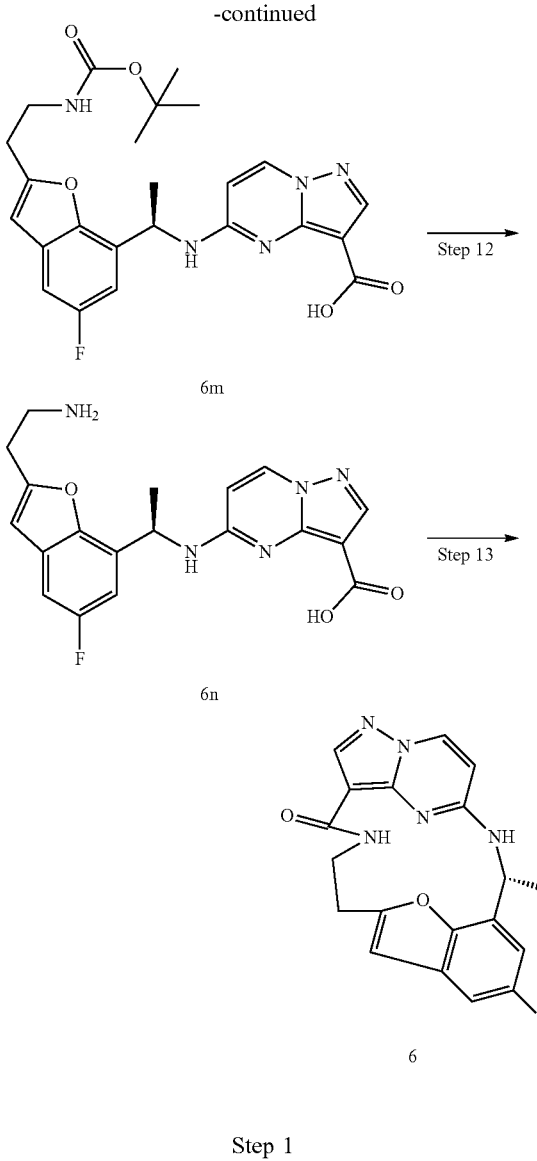

6m

6n

6

Step 1

4-fluoro-2,6-diiodophenol 4-fluorophenol 6a (1.12 g, 0.01 mol), iodine (3.81 g, 0.015 mol) and potassium iodide (2.50 g, 0.015 mol) were added to 50 mL of water, cooled to 0° C., and dropwise added with aqueous sodium hydroxide (800 mg, 0.02 mol, 50 mL of water), transferred to room temperature, and reacted overnight. After the reaction was completed, the pH of the solution was adjusted to weak acidity with dilute hydrochloric acid, and then the solution was extracted with ethyl acetate (30 mL×3); then organic phases were combined, washed with a saturated sodium chloride solution, dried with anhydrous sodium sulfate, filtered, and concentrated under reduced pressure to obtain 4-fluoro-2,6-diiodophenol 6b (3.5 g, brown viscous substance) with a yield of 96.25%.

MS m/z(ESI): 364.8 [M+1]

Step 2

2-(5-fluoro-7-iodobenzofuran-2-yl)ethan-1-ol 4-fluoro-2,6-diiodophenol 6b (960 mg, 2.64 mmol), but-3-yn-1-ol 6c (185 mg, 2.64 mmol), potassium acetate (778 mg, 7.92 mmol), triphenylphosphine (104 mg, 0.40 mmol), palladium acetate (30 mg, 0.13 mmol) and cuprous iodide (50 mg, 0.26 mmol) were added to 10 mL of acetonitrile, heated to 80° C. under the protection of argon, and reacted overnight. The reaction solution was concentrated under reduced pressure, and the obtained residue was further separated and purified by silica gel column chromatography (eluent: system A) to obtain 2-(5-fluoro-7-iodobenzofuran-2-yl)ethan-1-ol 6d (510 mg, yellow solid) with a yield of 63.1%.

MS m/z(ESI): 307.0 [M+1]

Step 3

Ethyl 2-(5-fluoro-7-iodobenzofuran-2-yl)methanesulfonic acid 2-(5-fluoro-7-iodobenzofuran-2-yl)ethan-1-ol 6d (6.7 g, 21.9 mmol) was dissolved in 70 mL of dichloromethane, added with triethylamine (6.1 mL, 44.0 mmol), dropwise added with methanesulfonyl chloride (3.0 g, 26.2 mmol) slowly at 0° C., transferred to room temperature and reacted for 4 hours. After the reaction was completed, the reaction solution was quenched with 50 mL of saturated aqueous ammonium chloride solution, and extracted with dichloromethane (30 mL×3), then organic phases were combined, and dried with anhydrous sodium sulfate, filtered, and concentrated under reduced pressure to obtain crude product of ethyl 2-(5-fluoro-7-iodobenzofuran-2-yl) methanesulfonic acid 6e (7.7 g, yellow liquid).

MS m/z(ESI): 384.9 [M+1]

Step 4

2-(2-azidoethyl)-5-fluoro-7-iodobenzofuran

Crude product of ethyl 2-(5-fluoro-7-iodobenzofuran-2-yl)methanesulfonic acid 6e (7.7 g) was added to 60 mL of N,N-dimethylformamide solution, and then added with sodium azide (1.56 g, 24.0 mmol), and reacted at room temperature overnight. The reaction solution was added with 150 mL of water, and extracted with ethyl acetate (80 mL×3), then organic phases were combined, and washed with a saturated sodium chloride solution, dried with anhydrous sodium sulfate, filtered, and concentrated under reduced pressure to obtain crude product of 2-(2-azidoethyl)-5-fluoro-7-iodobenzofuran 6f (yellow liquid).

MS m/z(ESI): 332.0 [M+1]

Step 5

1-(2-(2-azidoethyl)-5-fluorobenzofuran-7-yl)ethan-1-one 2-(2-azidoethyl)-5-fluoro-7-iodobenzofuran 6f, tributyl-(1-ethoxyvinyl)stannane (2.78 g, 7.7 mmol) and dichlorob(triphenylphosphine)palladium (250 mg, 0.36 mmol) was added to 25 mL of 1,4-dioxane, heated to 90° C. under the protection of argon, and reacted overnight. After the reaction was completed, the reaction solution was cooled to room temperature, added with 10% aqueous solution of potassium fluoride (405 mg, 7 mmol), and stirred at room temperature for 2 hours. The reaction solution was filtered, and then the filtrate was concentrated, added with 10 mL of 1 mol/L diluted hydrochloric acid, and stirred at room temperature for 2 hours. The pH of the solution was adjusted to basicity with a saturated sodium hydroxide solution, and then the solution was extracted with ethyl acetate (30 mL×3), then organic phases were combined, washed with a saturated sodium chloride solution, dried with anhydrous sodium sulfate, filtered, and concentrated under reduced pressure. The obtained residue was further separated and purified by silica gel column chromatography (eluent: system A) to obtain 1-(2-(2-azidoethyl)-5-fluorobenzofuran-7-yl)ethan-1-one 6g (580 mg, yellow liquid) with a yield of 33.7%.

MS m/z(ESI): 248.0 [M+1]

Step 6

(R,1E)-N-(1-(2-(2-azidoethyl)-5-fluorobenzofuran-7-yl)ethylidene)-2-methylpropane-2-sulfinamide 1-(2-(2-azidoethyl)-5-fluorobenzofuran-7-yl)ethan-1-one 6g (580 mg, 2.35 mmol), (R)-2-methylpropane-2-sulfinamide 1b (287 mg, 2.37 mmol) and tetraethyl titanate (1.07 g, 4.69 mmol) were dissolved in 8 mL of tetrahydrofuran, and reacted at 75° C. overnight. The reaction solution was concentrated under reduced pressure, and the obtained residue was further separated and purified by silica gel column chromatography (eluent: system A) to obtain (R,1E)-N-(1-(2-(2-azidoethyl)-5-fluorobenzofuran-7-yl) ethylidene)-2-methylpropane-2-sulfinamide 6h (750 mg, yellow semisolid) with a yield of 91.2%.

MS m/z(ESI): 351.1 [M+1]

Step 7

(R)—N-((1R)-1-(2-(2-azidoethyl)-5-fluorobenzofuran-7-yl)ethyl)-2-methylpropane-2-sulfinamide (R,1E)-N-(1-(2-(2-azidoethyl)-5-fluorobenzofuran-7-yl) ethylidene)-2-methylpropane-2-sulfinamide 6h (750 mg, 2.14 mmol) was dissolved in 15 mL of methanol, added with sodium borohydride (162 mg, 4.28 mmol), and reacted at room temperature overnight. After the reaction was completed, the reaction solution was quenched with 50 mL of water, and extracted with ethyl acetate (30 mL×3), and then organic phases were combined, dried with anhydrous sodium sulfate, filtered, and concentrated under reduced pressure. The obtained residue was further separated and purified by silicagel column chromatography (eluent: system A) to obtain (R)—N-((1R)-1-(2-(2-azidoethyl)-5-fluorobenzofuran-7-yl)ethyl)-2-methylpropane-2-sulfinamide 6i (262 mg, yellow semisolid) with a yield of 34.7%.

MS m/z(ESI): 353.1 [M+1]

Step 8

(1R)-1-(2-(2-azidoethyl)-5-fluorobenzofuran-7-yl) ethan-1-amine (R)—N-((1R)-1-(2-(2-azidoethyl)-5-fluorobenzofuran-7-yl)ethyl)-2-methylpropane-2-sulfinamide 6i (262 mg, 0.74 mmol) was added to 2 mL of dichloromethane, then added with 3 mL of hydrochloride 1,4-dioxane solution (4 mol/L), and reacted at room temperature for 1 hour. After the reaction was completed, the reaction solution was concentrated under reduced pressure to obtain 183 mg of crude product of (1R)-1-(2-(2-azidoethyl)-5-fluorobenzofuran-7-yl)ethan-1-amine 6j, and the product was subjected to the next reaction without purification.

Step 9

Ethyl (1R)-5-((1-(2-(2-azidoethyl)-5-fluorobenzofuran-7-yl)ethyl)amino)pyrazolo[1,5-a]pyrimidine-3-carboxylate Crude product of (1R)-1-(2-(2-azidoethyl)-5-fluorobenzofuran-7-yl)ethan-1-amine 6j (183 mg), N,N-diisopropylethylamine (597 mg, 4.62 mmol) and ethyl 5-chloropyrazolo[1,5-a]pyrimidine-3-carboxylate 1j (200 mg, 0.89 mmol) were dissolved in 3 mL of n-butanol, and reacted at 120° C. for 6 hours. The reaction solution was concentrated under reduced pressure, and the obtained residue was further separated and purified by silica gel column chromatography (eluent: system A) to obtain ethyl (1R)-5-((1-(2-(2-azidoethyl)-5-fluorobenzofuran-7-yl)ethyl)amino)pyrazolo[1,5-a]pyrimidine-3-carboxylate 6k (300 mg, yellow solid) with a yield of 92.8%.

MS m/z(ESI): 438.2 [M+1]

Step 10

Ethyl (1R)-5-((1-(2-(2-((tert-butoxycarbonyl)amino) ethyl)-5-fluorobenzofuran-7-yl)ethyl) amino)pyrazolo[1,5-a]pyrimidine-3-carboxylate Ethyl (1R)-5-((1-(2-(2-azidoethyl)-5-fluorobenzofuran-7-yl)ethyl)amino)pyrazolo[1,5-a]pyrimidine-3-carboxylate 6k (300 mg, 0.69 mmol) was added to 5 mL of methanol, and then added with di-tert-butyl dicarbonate (180 mg, 0.82 mmol) and 60 mg of 10% palladium carbon, and reacted at room temperature overnight under the protection of hydrogen. After the reaction was completed, the reaction solution was filtered, and the filtrate was directly concentrated to obtain crude product of ethyl (1R)-5-((1-(2-(2-((tert-butoxycarbonyl)amino)ethyl)-5-fluorobenzofuran-7-yl)ethyl) amino)pyrazolo[1,5-a]pyrimidine-3-carboxylate 6l(353 mg, yellow viscous substance), and the product was subjected to the next reaction without purification.

MS m/z(ESI): 512.2 [M+1]

Step 11

(1R)-5-((1-(2-(2-((tert-butoxycarbonyl)amino)ethyl)-5-fluorobenzofuran-7-yl)ethyl)amino)pyrazolo[1,5-a]pyrimidine-3-carboxylic acid Crude product of ethyl (1R)-5-((1-(2-(2-((tert-butoxycarbonyl)amino)ethyl)-5-fluorobenzofuran-7-yl)ethyl)amino) pyrazolo[1,5-a]pyrimidine-3-carboxylate 6l (353 mg) was dissolved in 5 mL of mixed solution (tetrahydrofuran:methanol:water=1:3:1), added with lithium hydroxide monohydrate (290 mg, 6.9 mmol), and stirred at 70° C. overnight. After the reaction was completed, the reaction solution was added with 20 mL of water, and extracted with ethyl acetate (20 mL×3), then organic phases were combined, and dried with anhydrous sodium sulfate, filtered, and concentrated under reduced pressure to obtain crude product of (1R)-5-((1-(2-(2-((tert-butoxycarbonyl)amino)ethyl)-5-fluorobenzofuran-7-yl)ethyl)amino)pyrazolo[1,5-a]pyrimidine-3-carboxylic acid 6m, and the product was subjected to the next reaction without purification.

MS m/z(ESI): 484.2 [M+1]

Step 12

(1R)-5-((1-(2-(2-aminoethyl)-5-fluorobenzofuran-7-yl)ethyl)amino)pyrazolo[1,5-a]pyrimidine-3-carboxylic acid (1R)-5-((1-(2-(2-((tert-butoxycarbonyl)amino)ethyl)-5-fluorobenzofuran-7-yl)ethyl)amino)pyrazolo[1,5-a]pyrimidine-3-carboxylic acid 6m was added to 2 mL of dichloromethane, and then added with 4 mL of hydrochloride 1,4-dioxane solution (4 mol/L), and reacted at room temperature for 1 hour. After the reaction was completed, the reaction solution was directly concentrated under reduced pressure to obtain crude product of (1R)-5-((1-(2-(2-aminoethyl)-5-fluorobenzofuran-7-yl)ethyl)amino)pyrazolo[1,5-a]pyrimidine-3-carboxylic acid 6n.

MS m/z(ESI): 384.1 [M+1]

Step 13

(3R)-6-fluoro-3-methyl-10-oxa-2,14,18,19,22-pentaazapentacyclo[14.5.2.1$^{1,11}$.0$^{4,9}$.0$^{19,23}$]tetracosa-1(22),4,6,8,11(24),16(23),17,20-octaen-15-one (1R)-5-((1-(2-(2-aminoethyl)-5-fluorobenzofuran-7-yl)ethyl)amino)pyrazolo[1,5-a]pyrimidine-3-carboxylic acid 6n (265 mg), pentafluorophenyl diphenyl phosphinate (318 mg, 0.83 mmol) and N,N-diisopropylethylamine (713 mg, 5.52 mmol) were dissolved in 4 mL of mixed solution (dichloromethane:N.N-dimethylformamide=3:1), and reacted at room temperature overnight. After the reaction was completed, the reaction solution was added with 20 mL of saturated aqueous ammonium chloride solution and extracted with dichloromethane (20 mL×3), then organic phases were combined, dried with anhydrous sodium sulfate, filtered, and concentrated under reduced pressure to obtain the title product (3R)-6-fluoro-3-methyl-10-oxa-2,14,18,19,22-pentaazapentacyclo[14.5.2.1$^{8,11}$.0$^{4,9}$.0$^{19,23}$]tetracosa-1(22),4,6,8,11(24),16(23),17,20-octaen-15-one 6 (64 mg) with a yield of 25.4% by preparing a liquid phase (separation column AKZONOBEL Kromasil; 250×21.2 mm I.D.; 5 μm, 20 mL/min; mobile phase A: 0.05% TFA+H$_2$O, and mobile phase B: CH$_3$CN).

MS m/z(ESI): 366.3 [M+1]

$^1$H NMR (400 MHz, DMSO-d$_6$) δ 8.60 (d, J=7.2 Hz, 1H), 8.51 (d, J=7.6 Hz, 1H), 8.16 (s, 1H), 8.04 (s, 1H), 7.22-7.30 (m, 1H), 7.02-7.14 (m, 1H), 6.72 (s, 11H), 6.34 (d, J=7.7 Hz, 1H), 5.74 (t, J=7.2 Hz, 1H), 3.74 (dd, J=13.0, 5.5 Hz, 1H), 3.46-3.59 (m, 1H), 3.24 (dd, J=15.4, 5.4 Hz, 1H), 3.19-3.04 (m, 1H), 1.64 (d, J=7.1 Hz, 3H).

Example 7

(2R,14R)-19-fluoro-2-methyl-16,22-dioxa-3,5,7,8,12-pentaazapentacyclo[12.6.2.2$^{4,7}$.0$^{6,10}$.0$^{17,21}$]tetracosa-1(20),4,6(10),8,17(21),18,23-heptaen-11-one

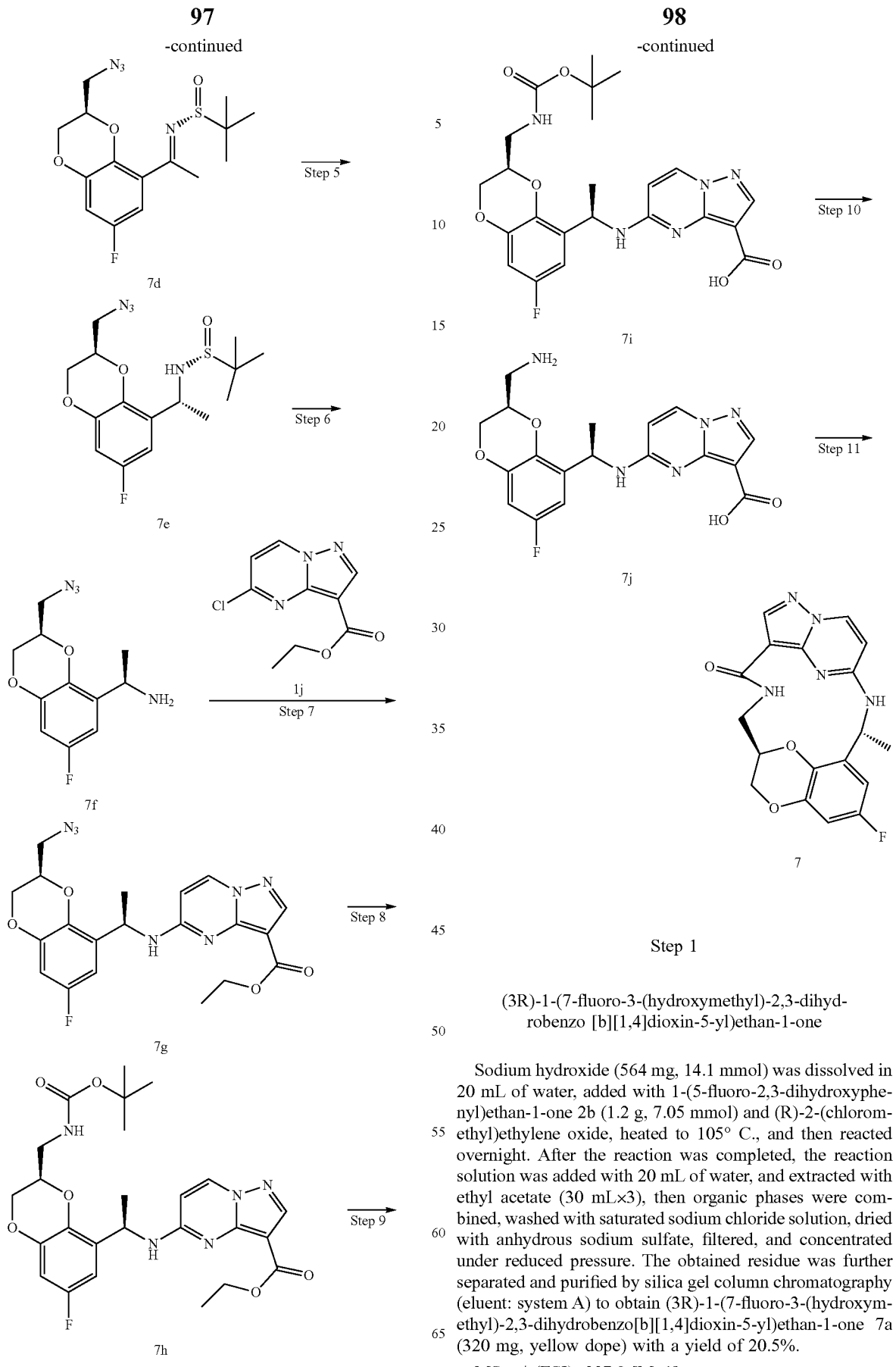

Step 1

(3R)-1-(7-fluoro-3-(hydroxymethyl)-2,3-dihydrobenzo [b][1,4]dioxin-5-yl)ethan-1-one Sodium hydroxide (564 mg, 14.1 mmol) was dissolved in 20 mL of water, added with 1-(5-fluoro-2,3-dihydroxyphenyl)ethan-1-one 2b (1.2 g, 7.05 mmol) and (R)-2-(chloromethyl)ethylene oxide, heated to 105° C., and then reacted overnight. After the reaction was completed, the reaction solution was added with 20 mL of water, and extracted with ethyl acetate (30 mL×3), then organic phases were combined, washed with saturated sodium chloride solution, dried with anhydrous sodium sulfate, filtered, and concentrated under reduced pressure. The obtained residue was further separated and purified by silica gel column chromatography (eluent: system A) to obtain (3R)-1-(7-fluoro-3-(hydroxymethyl)-2,3-dihydrobenzo[b][1,4]dioxin-5-yl)ethan-1-one 7a (320 mg, yellow dope) with a yield of 20.5%.

MS m/z(ESI): 227.0 [M+1]

Step 2

(2S)-(8-acetyl-6-fluoro-2,3-dihydrobenzo[b][1,4]dioxin-2-yl)methyl methanesulfonic acid (3R)-1-(7-fluoro-3-(hydroxymethyl)-2,3-dihydrobenzo[b][1,4]dioxin-5-yl)ethan-1-one 7a (320 mg, 1.41 mmol) was added to 1.5 mL of dichloromethane, cooled to 0° C., added with 4-dimethylaminopyridine (350 mg, 2.86 mmol), dropwise added with methylsulfonyl chloride (243 mg, 2.12 mmol), and then transferred to react at room temperature overnight. After the reaction was completed, the reaction solution was added with 30 mL of saturated ammonium chloride solution, extracted with dichloromethane (30 mL×3), then organic phases were combined, washed with saturated ammonium chloride solution, and dried with anhydrous sodium sulfate, then the reaction solution was concentrated under reduced pressure to obtain crude product of (2S)-(8-acetyl-6-fluoro-2,3-dihydrobenzo[b][1,4]dioxin-2-yl)methyl methanesulfonic acid 7b (430 mg, yellow viscous substance) with a yield of 100%.

MS m/z(ESI): 305.0 [M+1]

Step 3

(3R)-1-(3-(azidomethyl)-7-fluoro-2,3-dihydrobenzo[b][1,4]dioxin-5-yl)ethan-1-one (2S)-(8-acetyl-6-fluoro-2,3-dihydrobenzo[b][1,4]dioxin-2-yl)methyl methanesulfonic acid 7b (430 mg, 1.41 mmol) was added to 10 mL of N,N-dimethylformamide solution, and then added with sodium azide (193 mg, 2.97 mmol), heated to 55° C., and reacted overnight. After the reaction was completed, the reaction solution was added with 30 mL of water, and extracted with ethyl acetate (30 mL×3), then organic phases were combined, washed with a saturated sodium chloride solution, dried with anhydrous sodium sulfate, filtered, and concentrated under reduced pressure. The obtained residue was further separated and purified by silica gel column chromatography (eluent: system A) to obtain (3R)-1-(3-(azidomethyl)-7-fluoro-2,3-dihydrobenzo[b][1,4]dioxin-5-yl)ethan-1-one 7c (230 g, yellow semisolid) with a yield of 65%.

MS m/z(ESI): 252.0 [M+1]

Step 4

(R)—N-((1E)-1-((3R)-3-(azidomethyl)-7-fluoro-2,3-dihydrobenzo[b][1,4]dioxin-5-yl)ethylidene)-2-methylpropane-2-sulfinamide (3R)-1-(3-(azidomethyl)-7-fluoro-2,3-dihydrobenzo[b][1,4]dioxain-5-yl)ethan-1-one 7c (230 mg, 0.92 mmol), (R)-2-methylpropane-2-sulfinamide 1b (333 mg, 2.75 mmol) and tetraethyl titanate (836 mg, 3.66 mmol) were dissolved in 5 mL of tetrahydrofuran, and reacted at 75° C. overnight. The reaction solution was concentrated under reduced pressure, and the obtained residue was further separated and purified by silica gel column chromatography (eluent: system A) to obtain (R)—N-((1E)-1-((3R)-3-(azidomethyl)-7-fluoro-2,3-dihydrobenzo[b][1,4]dioxin-5-yl)ethylidene)-2-methylpropane-2-sulfinamide 7d (218 mg, yellow solid) with a yield of 66.9%.

MS m/z(ESI): 355.1 [M+1]

Step 5

(R)—N-((1R)-1-((3R)-3-(azidomethyl)-7-fluoro-2,3-dihydrobenzo[b][1,4]dioxin-5-yl)ethyl)-2-methylpropane-2-sulfinamide (R)—N-((1E)-1-((3R)-3-(azidomethyl)-7-fluoro-2,3-dihydrobenzo[b][1,4]dioxin-5-yl)ethylidene)-2-methylpropane-2-sulfinamide 7d (1.0 g, 2.82 mmol) was added to 10 mL of tetrahydrofuran, and then added with 9-borabicyclo[3,3,1]-nonane (11.3 mL, 5.65 mmol, 0.5 mol/L), and reacted at room temperature overnight. After the reaction was completed, the reaction solution was quenched with 30 mL of water, and extracted with ethyl acetate (30 mL×3), then organic phases were combined, dried with anhydrous sodium sulfate, filtered, and concentrated under reduced pressure to obtain crude product of (R)—N-((1R)-1-((3R)-3-(azidomethyl)-7-fluoro-2,3-dihydrobenzo[b][1,4]dioxin-5-yl)ethyl)-2-methylpropane-2-sulfinamide 7e (1.0 g, yellow viscous substance) with a yield of 100%.

MS m/z(ESI): 357.1 [M+1]

Step 6

(1R)-1-((3R)-3-(azidomethyl)-7-fluoro-2,3-dihydrobenzo[b][1,4]dioxin-5-yl)ethan-1-amine Crude product of (R)—N-((1R)-1-((3R)-3-(azidomethyl)-7-fluoro-2,3-dihydrobenzo[b][1,4]dioxin-5-yl)ethyl)-2-methylpropane-2-sulfinamide 7e (1.0 g) was added to 10 mL of dichloromethane, then added with 10 mL of hydrochloride 1,4-dioxane solution (4 mol/L), and reacted at room temperature for 1 hour. After the reaction was completed, the reaction solution was concentrated under reduced pressure to obtain 708 mg of crude product of (1R)-1-((3R)-3-(azidomethyl)-7-fluoro-2,3-dihydrobenzo[b][1,4]dioxin-5-yl)ethan-1-amine 7f with a yield of 100%, and the product was subjected to the next reaction without purification.

MS m/z(ESI): 253.1 [M+1]

Step 7

Ethyl 5-(((1R)-1-((3R)-3-(azidomethyl)-7-fluoro-2,3-dihydrobenzo[b][1,4]dioxin-5-yl)ethyl) amino)pyrazolo[1,5-a]pyrimidine-3-carboxylate Crude product of (1R)-1-((3R)-3-(azidomethyl)-7-fluoro-2,3-dihydrobenzo[b][1,4]dioxin-5-yl)ethan-1-amine 7f (708 mg), N,N-diisopropylethylamine (3.62 g, 28.0 mmol) and ethyl 5-chloropyrazolo[1,5-a]pyrimidine-3-carboxylate 1j (695 mg, 3.09 mmol) were dissolved in 10 mL of n-butanol, and reacted at 120° C. for 5 hours. After the reaction was completed, the reaction solution was concentrated under reduced pressure, and the obtained residue was further separated and purified by silica gel column chromatography (eluent: system A) to obtain ethyl 5-(((1R)-1-((3R)-3-(azidomethyl)-7-fluoro-2,3-dihydrobenzo[b][1,4]dioxin-5-yl)ethyl) amino)pyrazolo[1,5-a]pyrimidine-3-carboxylate 7g (570 mg, yellow viscous substance) with a yield of 46%.

MS m/z(ESI): 442.2 [M+1]

Step 8

Ethyl 5-(((1R)-1-((3R)-3-(((tert-butoxycarbonyl)amino)methyl)-7-fluoro-2,3-dihydrobenzo[b][1,4]dioxin-5-yl)ethyl)amino)pyrazolo[1,5-a]pyrimidine-3-carboxylate Ethyl 5-(((1R)-1-((3R)-3-(azidomethyl)-7-fluoro-2,3-dihydrobenzo[b][1,4]dioxin-5-yl) ethyl)amino)pyrazolo[1,5-a]pyrimidine-3-carboxylate 7g (570 mg, 1.29 mmol) was added to 5 mL of methanol, and then added with di-tert-butyl dicarbonate (338 mg, 1.55 mmol) and 100 mg of 10% palladium carbon, and reacted at room temperature for 5 hours under the protection of hydrogen. After the reaction was completed, the reaction solution was filtered, and the filtrate was directly concentrated to obtain crude product of ethyl 5-(((1R)-1-((3R)-3-(((tert-butoxycarbonyl)amino)methyl)-7-fluoro-2,3-dihydrobenzo[b][1,4]dioxin-5-yl)ethyl)amino)pyrazolo[1,5-a]pyrimidine-3-carboxylate 7h (666 mg, yellow viscous substance) with a yield of 100%, and the product was subjected to the next reaction without purification.

MS m/z(ESI): 516.2 [M+1]

Step 9

5-(((1R)-1-((3R)-3-(((tert-butoxycarbonyl)amino)methyl)-7-fluoro-2,3-dihydrobenzo[b][1,4]dioxin-5-yl)ethyl)amino)pyrazolo[1,5-a]pyrimidine-3-carboxylic acid Crude product of ethyl 5-(((1R)-1-((3R)-3-(((tert-butoxycarbonyl)amino)methyl)-7-fluoro-2,3-dihydrobenzo[b][1,4]dioxin-5-yl)ethyl)amino)pyrazolo[1,5-a]pyrimidine-3-carboxylate 7h (666 mg) was dissolved in 5 mL of mixed solution (tetrahydrofuran:methanol:water=1:3:1), added with lithium hydroxide monohydrate (845 mg, 13.0 mmol), and stirred at 75° C. overnight. After the reaction was completed, the reaction solution was added with 30 mL of water, and extracted with ethyl acetate (30 mL×3), then organic phases were combined, dried with anhydrous sodium sulfate, filtered, and concentrated under reduced pressure to obtain crude product of 5-(((1R)-1-((3R)-3-(((tert-butoxycarbonyl)amino)methyl)-7-fluoro-2,3-dihydrobenzo[b][1,4]dioxin-5-yl)ethyl)amino)pyrazolo[1,5-a]pyrimidine-3-carboxylic acid 7i with a yield of 100%, and the product was subjected to the next reaction without purification.

MS m/z(ESI): 488.2 [M+1]

Step 10

5-(((1R)-1-((3R)-3-(aminomethyl)-7-fluoro-2,3-dihydrobenzo[b][1,4]dioxin-5-yl)ethyl)amino)pyrazolo[1,5-a]pyrimidine-3-carboxylic acid Crude product of 5-(((1R)-1-((3R)-3-(((tert-butoxycarbonyl)amino)methyl)-7-fluoro-2,3-dihydrobenzo[b][1,4]dioxin-5-yl)ethyl)amino)pyrazolo[1,5-a]pyrimidine-3-carboxylic acid 7i (630 mg) was added to 3 mL of dichloromethane, and then added with 5 mL of hydrochloride 1,4-dioxane solution (4 mol/L), and reacted at room temperature for 1 hour. The reaction solution was concentrated under reduced pressure to obtain 500 mg of crude product of 5-(((1R)-1-((3R)-3-(aminomethyl)-7-fluoro-2,3-dihydrobenzo[b][1,4]dioxin-5-yl)ethyl)amino)pyrazolo[1,5-a]pyrimidine-3-carboxylic acid 7j with a yield of 100%.

MS m/z(ESI): 388.1 [M+1]

Step 11

(2R,14R)-19-fluoro-2-methyl-16,22-dioxa-3,5,7,8,12-pentaazapentacyclo[12.6.2.2$^{4,7}$.0$^{6,10}$.0$^{17,21}$]tetracosa-1(20),4,6(10),8,17(21),18,23-heptaen-11-one Crude product of 5-(((1R)-1-((3R)-3-(aminomethyl)-7-fluoro-2,3-dihydrobenzo[b][1,4]dioxin-5-yl)ethyl)amino)pyrazolo[1,5-a]pyrimidine-3-carboxylic acid 7j (500 mg), pentafluorophenyl diphenyl phosphinate (600 mg, 1.56 mmol) and N,N-diisopropylethylamine (1.35 g, 10.44 mmol) were dissolved in 6 mL of mixed solution (dichloromethane:N,N-dimethylformamide=5:1), and reacted at room temperature overnight. After the reaction was completed, the reaction solution was added with 20 mL of saturated aqueous ammonium chloride solution and extracted with dichloromethane (20 mL×3), then organic phases were combined, dried with anhydrous sodium sulfate, filtered, and concentrated under reduced pressure to obtain the title product (2R,14R)-19-fluoro-2-methyl-16,22-dioxa-3,5,7,8,12-pentaazapentacyclo[12.6.2.2$^{4,7}$.0$^{6,10}$.0$^{17,21}$]tetracosa-1(20),4,6(10),8,17(21),18,23-heptaen-11-one 7 (200 mg) with a yield of 42% by preparing a liquid phase (separation column AKZONOBEL Kromasil; 250×21.2 mm I.D.; 5 μm, 20 mL/min; mobile phase A: 0.05% TFA+H$_2$O, and mobile phase B: CH$_3$CN).

MS m/z(ESI): 370.3 [M+1]

$^1$H NMR (400 MHz, DMSO-d$_6$) δ 9.39 (t, J=4.9 Hz, 1H), 8.74 (d, J=6.0 Hz, 1H), 8.58 (d, J=7.6 Hz, 11H), 8.05 (s, 1H), 6.68 (ddd, J=14.1, 9.4, 3.0 Hz, 2H), 6.38 (d, J=7.6 Hz, 1H), 5.45 (q, J=6.9 Hz, 1H), 4.91 (dt, J=9.3, 4.5 Hz, 1H), 4.38 (dd, J=11.8, 3.3 Hz, 1H), 3.90 (dd, J=11.8, 5.4 Hz, 1H), 3.67 (dt, J=13.7, 5.5 Hz, 1H), 3.48 (dt, J=13.5, 5.5 Hz, 1H), 1.47 (d, J=7.0 Hz, 3H).

Example 8

(3R,11R)-6-fluoro-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one

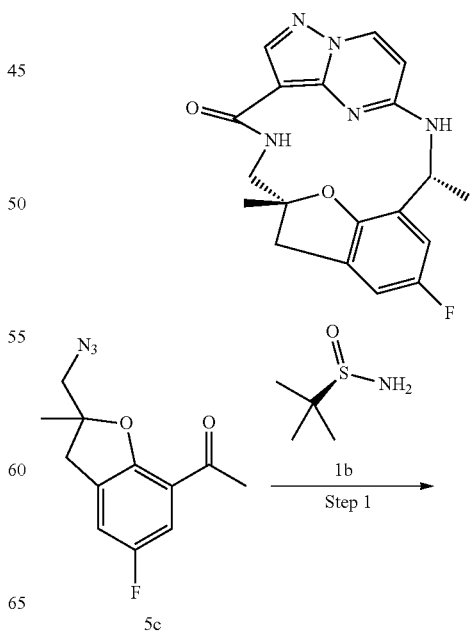

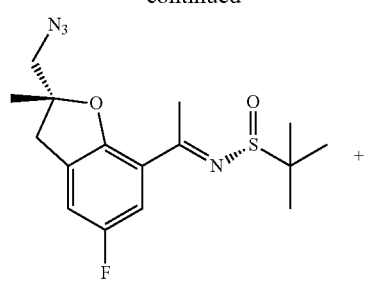
8a
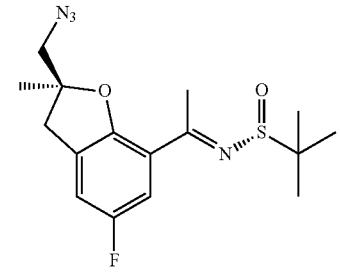
8b
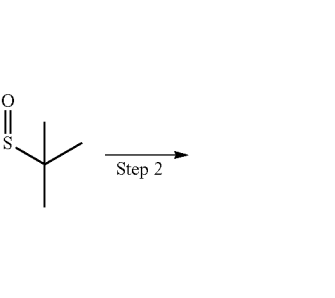
8a
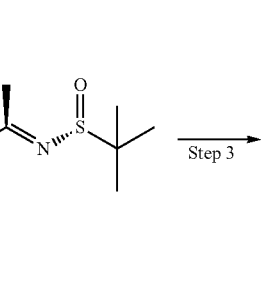
8c
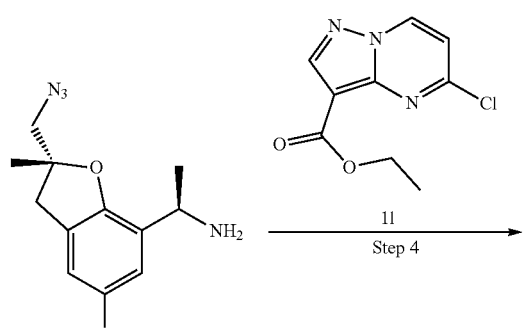
8d
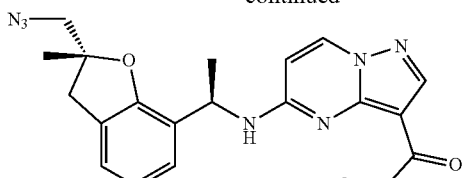
8e
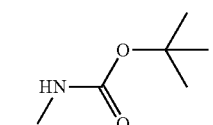
8f
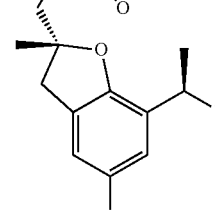
8g
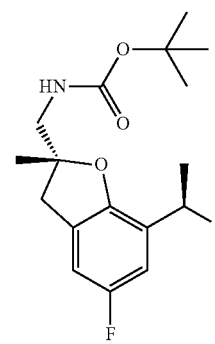
8h
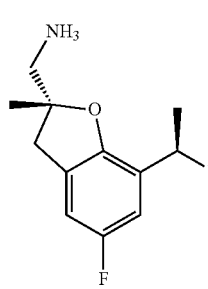
8

Step 1

(R)—N-((1E)-1-((2R)-2-(azidomethyl)-5-fluoro-2-methyl-2,3-dihydrobenzofuran-7-yl)ethylidene)-2-methylpropane-2-sulfinamide 8a (R)—N-((1K)-1-((2S)-2-(azidomethyl)-5-fluoro-2-methyl-2,3-dihydrobenzofuran-7-yl)ethylidene)-2-methylpropane-2-sulfinamide 8b 1-(2-(azidomethyl)-5-fluoro-2-methyl-2,3-dihydrobenzofuran-7-yl)ethan-1-one 5c (1.92 g, 7.71 mmol), (R)-2-methylpropane-2-sulfinamide 1b (1.87 g, 15.4 mmol) and tetraethyl titanate (7.03 g, 30.8 mmol) were dissolved in 20 mL of tetrahydrofuran, and reacted at 75° C. overnight. After the reaction was completed, the reaction solution was added with 30 mL of water, and extracted with ethyl acetate (30 mL×3), and then organic phases were combined, dried with anhydrous sodium sulfate, filtered, and concentrated under reduced pressure. The obtained residue was further separated and purified by silica gel column chromatography (eluent:petroleum ether:ethyl acetate=10:1) to obtain (R)—N-((1E)-1-((2R)-2-(azidomethyl)-5-fluoro-2-methyl-2,3-dihydrobenzofuran-7-yl)ethylidene)-2-methylpropane-2-sulfinamide 8a (1.32 g, yellow liquid, yield: 48.8%) which was eluted faster and (R)—N-((1E)-1-((2S)-2-(azidomethyl)-5-fluoro-2-methyl-2,3-dihydrobenzofuran-7-yl)ethylidene)-2-methylpropane-2-sulfinamide 8b (1.02 g, yellow liquid) with a yield of 37.4% which was eluted slower.

MS m/z(ESI): 353.2 [M+1]

Step 2

(R)—N-((1R)-1-((2R)-2-(azidomethyl)-5-fluoro-2-methyl-2,3-dihydrobenzofuran-7-yl)ethyl)-2-methylpropane-2-sulfinamide (R)—N-((1E)-1-((2R)-2-(azidomethyl)-5-fluoro-2-methyl-2,3-dihydrobenzofuran-7-yl)ethylidene)-2-methylpropane-2-sulfinamide 8a (1.32 g, 3.77 mmol) was added to 20 mL of tetrahydrofuran, and then added with 9-boronbicyclo[3,3,1]-nonane (15.08 mL, 7.54 mmol, 0.5 mol/L), and reacted at room temperature for 4 hours. After the reaction was completed, the reaction solution was quenched with 30 mL of water, and extracted with ethyl acetate (30 mL×3), and then organic phases were combined, dried with anhydrous sodium sulfate, filtered, and concentrated under reduced pressure. The obtained residue was further separated and purified by silica gel column chromatography (eluent: system A) to obtain (R)—N-((1R)-1-((2R)-2-(azidomethyl)-5-fluoro-2-methyl-2,3-dihydrobenzofuran-7-yl)ethyl)-2-methylpropane-2-sulfinamide 8c (1.22 g, yellow solid) with a yield of 91.1%.

MS m/z(ESI): 355.1 [M+1]

Step 3

(1R)-1-((2R)-2-(azidomethyl)-5-fluoro-2-methyl-2,3-dihydrobenzofuran-7-yl)ethan-1-amine (R)—N-((1R)-1-((2R)-2-(azidomethyl)-5-fluoro-2-methyl-2,3-dihydrobenzofuran-7-yl)ethyl)-2-methylpropane-2-sulfinamide 8c (1.22 g, 3.46 mmol) was added to 5 mL of dichloromethane solution, then added with 3 mL of hydrochloride 1,4-dioxane solution (4 mol/L), and reacted at room temperature for 1 hour. After monitoring that the reaction was completed by LC-MS, the reaction solution was concentrated under reduced pressure to obtain crude product of (1R)-1-((2R)-2-(azidomethyl)-5-fluoro-2-methyl-2,3-dihydrobenzofuran-7-yl)ethan-1-amine 8d, and the product was subjected to the next reaction without purification.

MS m/z(ESI): 234.1 [M−16]

Step 4

Ethyl 5-(((1R)-1-((2R)-2-(azidomethyl)-5-fluoro-2-methyl-2,3-dihydrobenzofuran-7-yl)ethyl) amino) pyrazolo[1,5-a]pyrimidine-3-carboxylate Crude product of (1R)-1-((2R)-2-(azidomethyl)-5-fluoro-2-methyl-2,3-dihydrobenzofuran-7-yl)ethan-1-amine 8d (866 mg), ethyl 5-chloropyrazolo[1,5-a]pyrimidine-3-carboxylate 1j (810 mg, 3.46 mmol) and N,N-diisopropylethylamine (3.58 g, 27.68 mmol) were dissolved in 10 mL of n-butanol, and reacted at 125° C. for 3 hours. After monitoring that the reaction was completed by LC-MS, the reaction solution was concentrated under reduced pressure, and the obtained residue was further separated and purified by silica gel column chromatography (eluent: system A) to obtain ethyl 5-(((1R)-1-((2R)-2-(azidomethyl)-5-fluoro-2-methyl-2,3-dihydrobenzofuran-7-yl)ethyl)amino)pyrazolo[1,5-a]pyrimidine-3-carboxylate 8e (910 mg, faint yellow solid) with a yield of 59.8%.

MS m/z(ESI): 440.0 [M+1]

Step 5

Ethyl 5-(((1R)-1-((2R)-2-(((tert-butoxycarbonyl)amino)methyl)-5-fluoro-2-methyl-2,3-dihydrobenzofuran-7-yl)ethyl)amino)pyrazolo[1,5-a]pyrimidine-3-carboxylate Ethyl 5-(((1R)-1-((2R)-2-(azidomethyl)-5-fluoro-2-methyl-2,3-dihydrobenzofuran-7-yl) ethyl)amino)pyrazolo[1,5-a]pyrimidine-3-carboxylate 8e (910 mg, 2.07 mmol) was added to 10 mL of methanol, and then added with di-tert-butyl dicarbonate (543 mg, 2.49 mmol) and 200 mg of 10% palladium carbon, and reacted at room temperature for 6 hours under the protection of hydrogen. After the reaction was completed, the reaction solution was filtered, and the filtrate was concentrated under reduced pressure to obtain crude product of ethyl 5-(((1R)-1-((2R)-2-(((tert-butoxycarbonyl)amino)methyl)-5-fluoro-2-methyl-2,3-dihydrobenzofuran-7-yl)ethyl)amino)pyrazolo[1,5-a]pyrimidine-3-carboxylate 8f, and the product was subjected to the next reaction without purification.

MS m/z(ESI): 514.2 [M+1]

Step 6

5-(((1R)-1-((2R)-2-(((tert-butoxycarbonyl)amino)methyl)-5-fluoro-2-methyl-2,3-dihydrobenzofuran-7-yl)ethyl)amino)pyrazolo[1,5-a]pyrimidine-3-carboxylic acid Crude product of ethyl 5-(((1R)-1-((2R)-2-(((tert-butoxycarbonyl)amino)methyl)-5-fluoro-2-methyl-2,3-dihydrobenzofuran-7-yl)ethyl)amino)pyrazolo[1,5-a]pyrimidine-3-carboxylate 8f (1.06 g) was dissolved in 5 mL of mixed solution (tetrahydrofuran:ethanol:water=2:2:1), added with lithium hydroxide monohydrate (868 mg, 20.7 mmol), and stirred at 80° C. overnight. After monitoring that the reaction was completed by LC-MS, the reaction solution was cooled, and dropwise added with diluted hydrochloric acid slowly to adjust the solution to acidity, then added with 20 mL of water, and extracted with ethyl acetate (20 mL×3), then organic phases were combined, dried with anhydrous sodium sulfate, filtered, and concentrated under reduced pressure to obtain crude product of 5-(((1R)-1-((2R)-2-(((tert-butoxycarbonyl)amino)methyl)-5-fluoro-2-methyl-2,3-dihydrobenzofuran-7-yl)ethyl)amino)pyrazolo[1,5-a]pyrimidine-3-carboxylic acid 8g, and the product was subjected to the next reaction without purification.

MS m/z(ESI): 486.2 [M+1]

Step 7

5-(((1R)-1-((2R)-2-(aminomethyl)-5-fluoro-2-methyl-2,3-dihydrobenzofuran-7-yl)ethyl)amino)pyrazolo[1,5-a]pyrimidine-3-carboxylic acid 5-(((1R)-1-((2R)-2-(((tert-butoxycarbonyl)amino)methyl)-5-fluoro-2-methyl-2,3-dihydrobenzofuran-7-yl)ethyl)amino)pyrazolo[1,5-a]pyrimidine-3-carboxylic acid 8g (1.00 g) was added to 10 mL of dichloromethane solution, and then added with 10 mL of hydrochloride 1,4-dioxane solution, and reacted at room temperature for 1 hour. After monitoring that the reaction was completed by LC-MS, the reaction solution was concentrated under reduced pressure to obtain crude product of 5-(((1R)-1-((2R)-2-(aminomethyl)-5-fluoro-2-methyl-2,3-dihydrobenzofuran-7-yl)ethyl)amino)pyrazolo[1,5-a]pyrimidine-3-carboxylic acid 8h, and the product was subjected to the next reaction without purification.

MS m/z(ESI): 386.1 [M+1]

Step 8

(3R,11R)-6-fluoro-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 5-(((1R)-1-((2R)-2-(aminomethyl)-5-fluoro-2-methyl-2,3-dihydrobenzofuran-7-yl)ethyl)amino)pyrazolo[1,5-a]pyrimidine-3-carboxylic acid 8h (797 mg), pentafluorophenyl diphenyl phosphinate (1.08 g, 2.48 mmol) and N,N-diisopropylethylamine (2.14 g, 16.56 mmol) were dissolved in 12 mL of mixed solution (dichloromethane:N.N-dimethylformamide=5:1), and reacted at room temperature overnight. After monitoring that the reaction was completed by LC-MS, the reaction solution was added with 30 mL of saturated aqueous ammonium chloride solution and extracted with dichloromethane (30 mL×3), then organic phases were combined, dried with anhydrous sodium sulfate, filtered, and concentrated under reduced pressure to obtain the title product (3R,11R)-6-fluoro-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 8 (200 mg) by preparing a liquid phase (separation column AKZONOBEL Kromasil; 250×21.2 mm I.D.; 5 μm, 20 mL/min; mobile phase A: 0.05% TFA+H$_2$O, and mobile phase B: CH$_3$CN).

MS m/z(ESI): 368.1 [M+1]

$^1$H NMR (400 MHz, DMSO-d$_6$) δ 8.62 (d, J=4.9 Hz, 1H), 8.53 (d, J=7.7 Hz, 11H), 8.00 (s, 11H), 6.80 (d, J=7.9 Hz, 1H), 6.73 (d, J=10.1 Hz, 11H), 6.37 (d, J=7.6 Hz, 1H), 4.94 (s, 1H), 4.03 (d, J=7.1 Hz, 1H), 3.79 (d, J=9.5 Hz, 2H), 3.24-3.15 (m, 2H), 1.59 (s, 3H), 1.54 (d, J=7.0 Hz, 3H).

Example 9

(3R,11S)-6-fluoro-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one

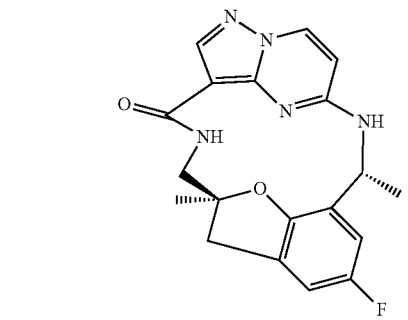

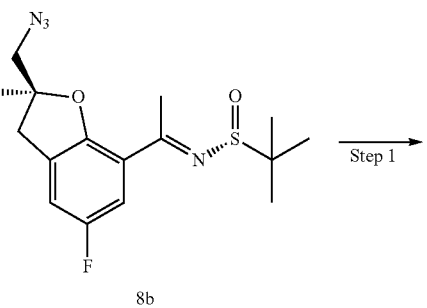

8b

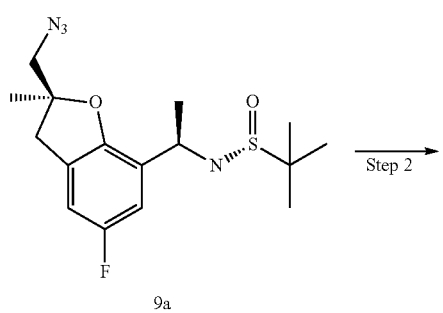

9a

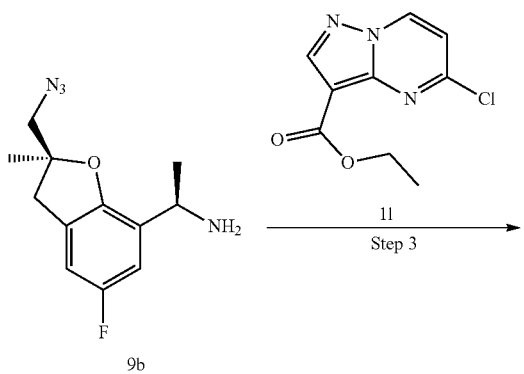

9b

109
-continued

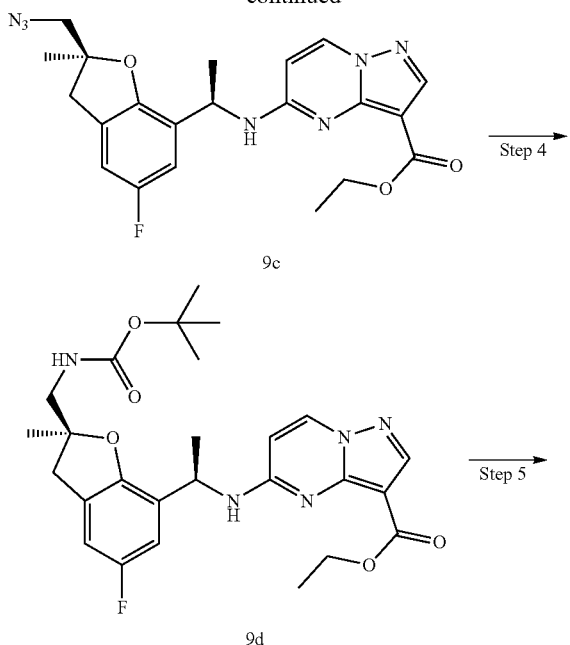

9c

9d

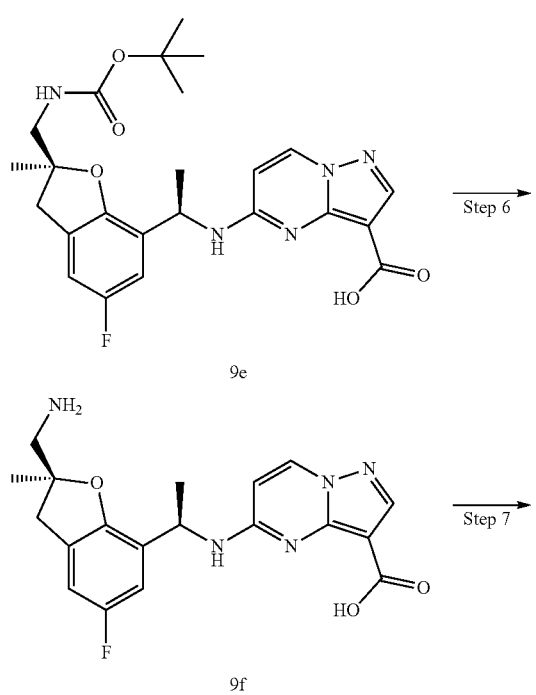

9e

9f

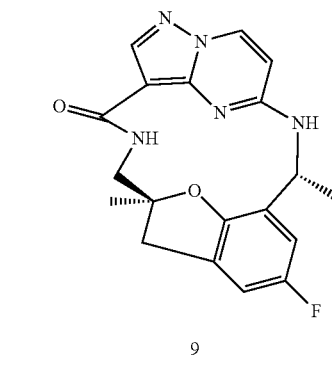

9

110

Step 1

(R)—N-((1R)-1-((2S)-2-(azidomethyl)-5-fluoro-2-methyl-2,3-dihydrobenzofuran-7-yl)ethyl)-2-methyl-propane-2-sulfinamide (R)—N-((1E)-1-((2S)-2-(azidomethyl)-5-fluoro-2-methyl-2,3-dihydrobenzofuran-7-yl)ethylidene)-2-methyl-propane-2-sulfinamide 8b (1.02 g, 2.90 mmol) was added to 10 mL of tetrahydrofuran, and then added with 9-borabicyclo[3,3,1]-nonane (11.6 mL, 5.80 mmol, 0.5 mol/L), and reacted at room temperature for 4 hours. After the reaction was completed, the reaction solution was quenched with 30 mL of water, and extracted with ethyl acetate (30 mL×3), and then organic phases were combined, dried with anhydrous sodium sulfate, filtered, and concentrated under reduced pressure. The obtained residue was further separated and purified by silica gel column chromatography (eluent: system A) to obtain (R)—N-((1R)-1-((2S)-2-(azidomethyl)-5-fluoro-2-methyl-2,3-dihydrobenzofuran-7-yl)ethyl)-2-methylpropane-2-sulfinamide 9a (793 mg) with a yield of 77.5%.

MS m/z(ESI): 355.1 [M+1]

Step 2

(1R)-1-((2S)-2-(azidomethyl)-5-fluoro-2-methyl-2,3-dihydrobenzofuran-7-yl)ethan-1-amine (R)—N-((1R)-1-((2S)-2-(azidomethyl)-5-fluoro-2-methyl-2,3-dihydrobenzofuran-7-yl)ethyl)-2-methylpropane-2-sulfinamide 9a (793 mg, 2.24 mmol) was added to 3 mL of dichloromethane solution, then added with 3 mL of hydrochloride 1,4-dioxane solution (4 mol/L), and reacted at room temperature for 1 hour. After monitoring that the reaction was completed by LC-MS, the reaction solution was concentrated under reduced pressure to obtain crude product of (1R)-1-((2S)-2-(azidomethyl)-5-fluoro-2-methyl-2,3-dihydrobenzofuran-7-yl)ethan-1-amine 9b, and the product was subjected to the next reaction without purification.

MS m/z(ESI): 234.1 [M−16]

Step 3

Ethyl 5-(((1R)-1-((2S)-2-(azidomethyl)-5-fluoro-2-methyl-2,3-dihydrobenzofuran-7-yl)ethyl) amino) pyrazolo[1,5-a]pyrimidine-3-carboxylate Crude product of (1R)-1-((2S)-2-(azidomethyl)-5-fluoro-2-methyl-2,3-dihydrobenzofuran-7-yl)ethan-1-amine 9b (560 mg), ethyl 5-chloropyrazolo[1,5-a]pyrimidine-3-carboxylate 1j (504 mg, 2.24 mmol) and N,N-diisopropylethylamine (2.32 g, 17.92 mmol) were dissolved in 10 mL of n-butanol, and reacted at 125° C. for 4 hours. After monitoring that the reaction was completed by LC-MS, the reaction solution was concentrated under reduced pressure, and the obtained residue was further separated and purified by silica gel column chromatography (eluent: system A) to obtain ethyl 5-(((1R)-1-((2S)-2-(azidomethyl)-5-fluoro-2-methyl-2,3-dihydrobenzofuran-7-yl)ethyl)amino)pyrazolo[1,5-a]pyrimidine-3-carboxylate 9c (610 mg, faint yellow solid) with a yield of 61.9%.

MS m/z(ESI): 440.0 [M+1]

Step 4

Ethyl 5-(((1R)-1-((2S)-2-(((tert-butoxycarbonyl) amino)methyl)-5-fluoro-2-methyl-2,3-dihydrobenzofuran-7-yl)ethyl)amino)pyrazolo[1,5-a]pyrimidine-3-carboxylate Ethyl 5-(((1R)-1-((2S)-2-(azidomethyl)-5-fluoro-2-methyl-2,3-dihydrobenzofuran-7-yl) ethyl)amino)pyrazolo [1,5-a]pyrimidine-3-carboxylate 9c (610 mg, 1.39 mmol) was added to 10 mL of methanol, and then added with di-tert-butyl dicarbonate (364 mg, 1.67 mmol) and 200 mg of wet palladium carbon, and reacted at room temperature for 6 hours under the protection of hydrogen. After the reaction was completed, the reaction solution was filtered, and the filtrate was concentrated under reduced pressure to obtain crude product of ethyl 5-(((1R)-1-((2S)-2-(((tert-butoxycarbonyl)amino)methyl)-5-fluoro-2-methyl-2,3-dihydrobenzofuran-7-yl)ethyl)amino)pyrazolo[1,5-a]pyrimidine-3-carboxylate 9d, and the product was subjected to the next reaction without purification.

MS m/z(ESI): 514.2 [M+1]

Step 5

5-(((1R)-1-((2S)-2-(((tert-butoxycarbonyl)amino) methyl)-5-fluoro-2-methyl-2,3-dihydrobenzofuran-7-yl)ethyl)amino)pyrazolo[1,5-a]pyrimidine-3-carboxylic acid Crude product of ethyl 5-(((1R)-1-((2S)-2-(((tert-butoxycarbonyl)amino)methyl)-5-fluoro-2-methyl-2,3-dihydrobenzofuran-7-yl)ethyl)amino)pyrazolo[1,5-a]pyrimidine-3-carboxylate 9d (713 mg) was dissolved in 5 mL of mixed solution (tetrahydrofuran:ethanol:water=2:2:1), added with lithium hydroxide monohydrate (583 mg, 13.9 mmol), and stirred at 80° C. overnight. After monitoring that the reaction was completed by LC-MS, the reaction solution was cooled, and dropwise added with diluted hydrochloric acid slowly to adjust the solution to acidity, then added with 20 mL of water, and extracted with ethyl acetate (20 mL×3), then organic phases were combined, dried with anhydrous sodium sulfate, filtered, and concentrated under reduced pressure to obtain crude product of 5-(((1R)-1-((2S)-2-(((tert-butoxycarbonyl)amino)methyl)-5-fluoro-2-methyl-2,3-dihydrobenzofuran-7-yl)ethyl)amino)pyrazolo[1,5-a]pyrimidine-3-carboxylic acid 9e, and the product was subjected to the next reaction without purification.

MS m/z(ESI): 486.2 [M+1]

Step 6

5-(((1R)-1-((2S)-2-(aminomethyl)-5-fluoro-2-methyl-2,3-dihydrobenzofuran-7-yl)ethyl)amino) pyrazolo[1,5-a]pyrimidine-3-carboxylic acid 5-(((1R)-1-((2S)-2-(((tert-butoxycarbonyl)amino) methyl)-5-fluoro-2-methyl-2,3-dihydrobenzofuran-7-yl) ethyl)amino)pyrazolo[1,5-a]pyrimidine-3-carboxylic acid 9e (674 mg) was added to 8 mL of dichloromethane solution, and then added with 8 mL of hydrochloride 1,4-dioxane solution (4 mol/L), and reacted at room temperature for 1 hour. After monitoring that the reaction was completed by LC-MS, the reaction solution was concentrated under reduced pressure to obtain crude product of 5-(((1R)-1-((2S)-2-(aminomethyl)-5-fluoro-2-methyl-2,3-dihydrobenzofuran-7-yl)ethyl)amino)pyrazolo[1,5-a]pyrimidine-3-carboxylic acid 9f, and the product was subjected to the next reaction without purification.

MS m/z(ESI): 386.1 [M+1]

Step 7

(3R,11S)-6-fluoro-3,11-dimethyl-10-oxa-2,13,17,18, 21-pentaazapentacyclo[13.5.2.1$^{8,11}$.0$^{4,9}$.0$^{18,22}$]tricosa-1(21),4,6,8,15(22),16,19-heptaen-14-one 5-(((1R)-1-((2S)-2-(aminomethyl)-5-fluoro-2-methyl-2, 3-dihydrobenzofuran-7-yl)ethyl)amino)pyrazolo[1,5-a]pyrimidine-3-carboxylic acid 9f (535 mg), pentafluorophenyl diphenyl phosphinate (641 mg, 1.67 mmol) and N,N-diisopropylethylamine (1.44 g, 11.12 mmol) were dissolved in 6 mL of mixed solution (dichloromethane:N.N-dimethylformamide=5:1), and reacted at room temperature overnight. After monitoring that the reaction was completed by LC-MS, the reaction solution was added with 20 mL of saturated aqueous ammonium chloride solution and extracted with dichloromethane (20 mL×3), then organic phases were combined, dried with anhydrous sodium sulfate, filtered, and concentrated under reduced pressure to obtain the title product (3R,11S)-6-fluoro-3,11-dimethyl-10-oxa-2,13,17, 18,21-pentaazapentacyclo[13.5.2.1$^{8,11}$.0$^{4,9}$.0$^{18,22}$]tricosa-1 (21),4,6,8,15(22),16,19-heptaen-14-one 9 (90 mg) by preparing a liquid phase (separation column AKZONOBEL Kromasil; 250×21.2 mm I.D.; 5 μm, 20 mL/min; mobile phase A: 0.05% TFA+H$_2$O, and mobile phase B: CH$_3$CN).

MS m/z(ESI): 368.1 [M+1]

$^1$H NMR (400 MHz, DMSO-d$_6$) δ 8.64 (d, J=5.0 Hz, 1H), 8.37 (d, J=8.0 Hz, 1H), 8.10 (s, 1H), 6.8 0 (d, J=7.9 Hz, 1H), 6.74 (d, J=10.0 Hz, 1H), 6.37 (d, J=7.6 Hz, 1H), 4.93 (s, 1H), 4.03 (d, J=7.1 Hz, 1H), 3.93-3.68 (m, 2H), 3.66-3.58 (m, 2H), 1.60 (m, 3H), 1.53 (d, J=7.0 Hz, 3H).

Examples 10 and 11

(3R,11R)-5,6-difluoro-3,11-dimethyl-10-oxa-2,13, 17,18,21-pentaazapentacyclo[13.5.2.1$^{8,11}$.0$^{4,9}$.0$^{18,22}$] tricosa-1(21),4,6,8,15(22),16,19-heptaen-14-one 10

(3R,11S)-5,6-difluoro-3,11-dimethyl-10-oxa-2,13, 17,18,21-pentaazapentacyclo[13.5.2.1$^{8,11}$.0$^{4,9}$.0$^{18,22}$] tricosa-1(21),4,6,8,15(22),16,19-heptaen-14-one 11

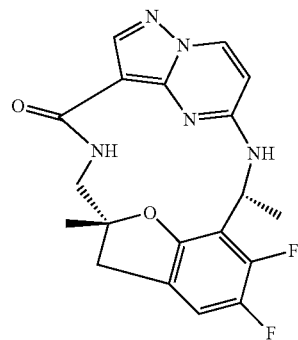

10

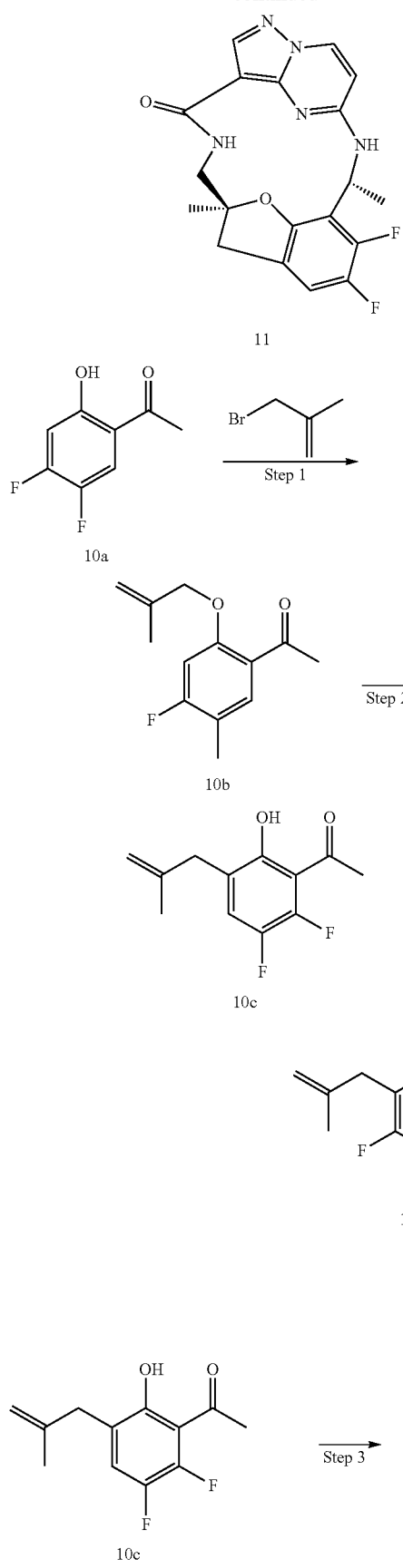
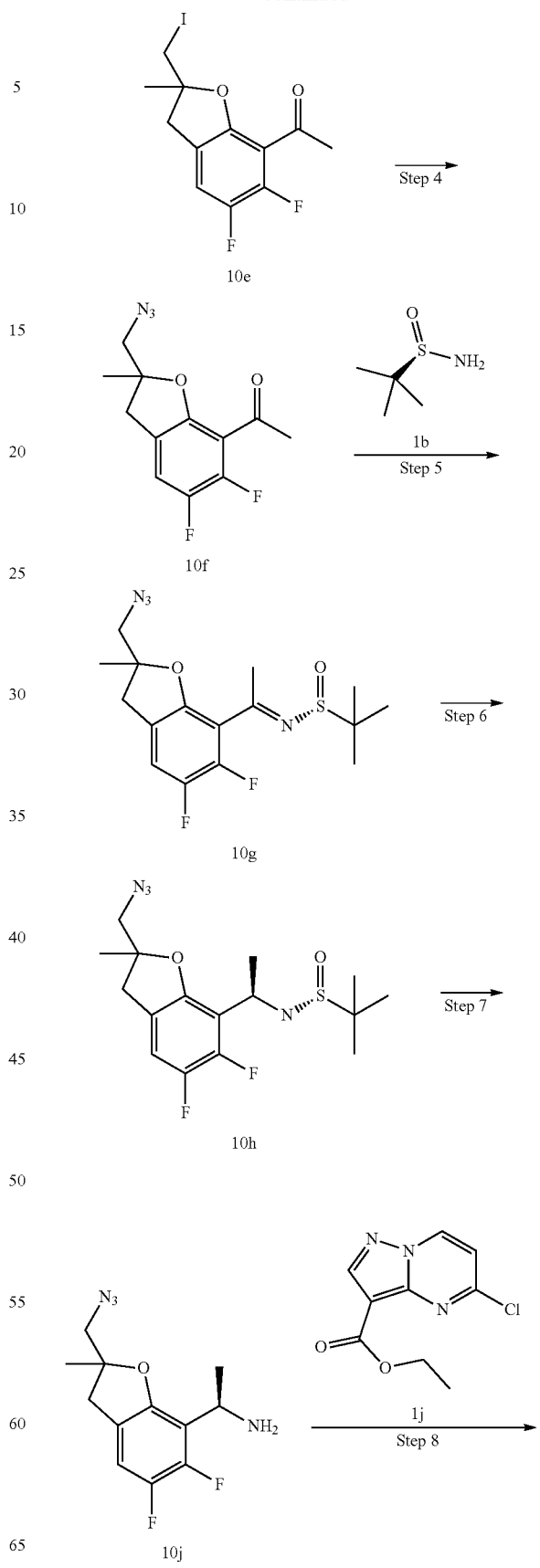

-continued

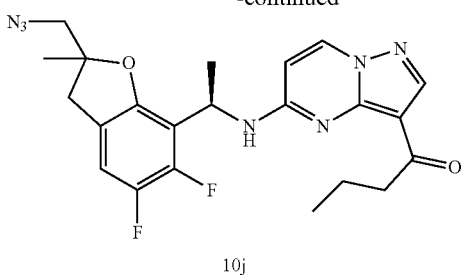

10j

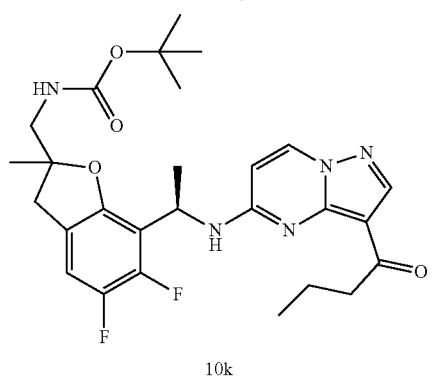

10k

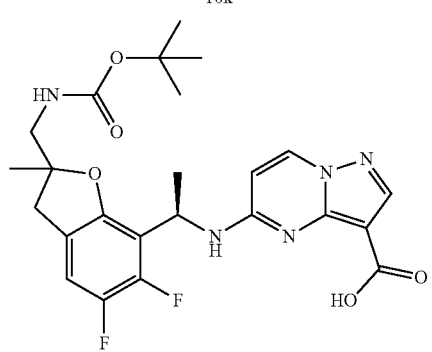

10i

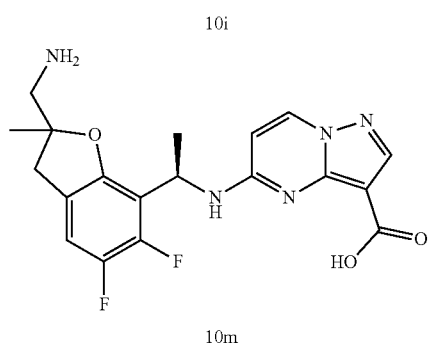

10m

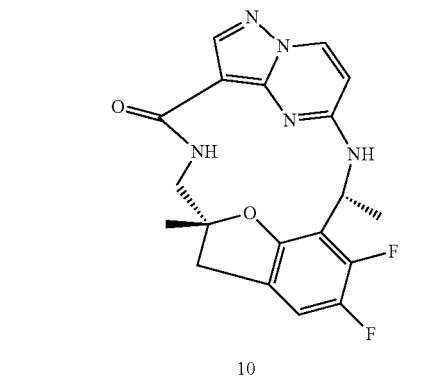

10

Step 9 →

Step 10 →

Step 11 →

Step 12 →

-continued

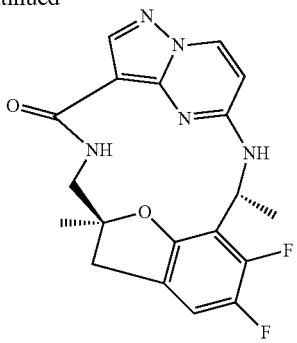

11

Step 1

1-(4,5-difluoro-2-((2-methylallyl)oxy)phenyl)ethan-1-one 1-(4,5-difluoro-2-hydroxyphenyl)ethan-1-one 10a (5.8 g, 33.7 mmol) was dissolved in 30 mL of N,N-dimethylformamide, then added with 3-bromo-2-methylpropene (4.5 g, 33.7 mmol) and potassium carbonate (9.3 g, 67.4 mmol) sequentially, and reacted at room temperature for 4 hours. After the reaction was completed, the reaction solution was added with 200 mL of water and extracted with ethyl acetate (100 mL×3), then organic phases were combined, washed with saturated brine (300 mL), dried with anhydrous sodium sulfate, filtered, and concentrated under reduced pressure to obtain 1-(4,5-difluoro-2-((2-methylallyl)oxy)phenyl)ethan-1-one 10b (7.2 g, grey liquid) with a yield of 94.5%.

MS m/z(ESI): 227.1 [M+1]

Step 2

1-(2,3-difluoro-6-hydroxy-5-(2-methylallyl)phenyl)ethan-1-one 10c 1-(4,5-difluoro-2-hydroxy-3-(2-methylallyl)phenyl)ethan-1-one 10d 1-(4,5-difluoro-2-((2-methylallyl)oxy)phenyl)ethan-1-one 10b (7.2 g, 31.8 mmol) was heated to 220° C., and then stirred and reacted for 10 hours. After the reaction was completed, the reaction solution was cooled to room temperature, added with 100 mL of dichloromethane to dissolve, and concentrated under reduced pressure. The obtained residue was purified by silica gel column chromatography (eluent: system A) to obtain 1-(2,3-difluoro-6-hydroxy-5-(2-methylallyl)phenyl)ethan-1-one 10c (700 mg, yellow liquid) with a yield of 9.7%, and 1-(4,5-difluoro-2-hydroxy-3-(2-methylallyl)phenyl)ethan-1-one 10d (2.7 g, yellow liquid) with a yield of 37.6%.

10c
MS m/z(ESI): 227.1 [M+1]
10d
MS m/z(ESI): 227.1 [M+1]

Step 3

1-(5,6-difluoro-2-(iodomethyl)-2-methyl-2,3-dihydrobenzofuran-7-yl)ethan-1-one 1-(2,3-difluoro-6-hydroxy-5-(2-methylallyl)phenyl)ethan-1-one 10c (700 mg, 3.08 mmol) was dissolved in 10 mL of tetrahydrofuran, added with N-iodosuccinimide (1.39 g, 6.16 mmol), and reacted at room temperature overnight. After the reaction was completed, the reaction solution was added with 100 mL of water, and then slowly added with sodium thiosulfate solid, and stirred for dissolution until the color of the solution was no longer light, then the solution was extracted with ethyl acetate (50 mL×3), then organic phases were combined, washed with 100 mL of saturated brine, dried with anhydrous sodium sulfate, filtered, and concentrated under reduced pressure. The obtained residue was purified by silica gel column chromatography (eluent: system A) to obtain 1-(5,6-difluoro-2-(iodomethyl)-2-methyl-2,3-dihydrobenzofuran-7-yl)ethan-1-one 10e (440 mg, yellow viscous substance) with a yield of 40.7%.

MS m/z(ESI): 353.2 [M+1]

Step 4

1-(2-(azidomethyl)-5,6-difluoro-2-methyl-2,3-dihydrobenzofuran-7-yl)ethan-1-one 1-(5,6-difluoro-2-(iodomethyl)-2-methyl-2,3-dihydrobenzofuran-7-yl)ethan-1-one 10e (440 mg, 1.25 mmol) was dissolved in 3 mL of N,N-dimethylformamide, and then added with sodium azide (98 mg, 1.5 mmol), heated to 60° C., and reacted overnight. After the reaction was completed, the reaction solution was cooled to room temperature, added with 100 mL of water, and extracted with ethyl acetate (50 mL×3), then organic phases were combined, washed with 100 mL of saturated brine, dried with anhydrous sodium sulfate, filtered, and concentrated under reduced pressure. The obtained residue was purified by silica gel column chromatography (eluent: system A) to obtain 1-(2-(azidomethyl)-5,6-difluoro-2-methyl-2,3-dihydrobenzofuran-7-yl)ethan-1-one 10f (300 mg, light brown viscous substance) with a yield of 90.9%.

MS m/z(ESI): 268.0 [M+1]

Step 5

(R)—N-((E)-1-(2-(azidomethyl)-5,6-difluoro-2-methyl-2,3-dihydrobenzofuran-7-yl)ethylidene)-2-methylpropane-2-sulfinamide 1-(2-(azidomethyl)-5,6-difluoro-2-methyl-2,3-dihydrobenzofuran-7-yl)ethan-1-one 10f (300 mg, 1.12 mmol) was dissolved in 5 mL of tetrahydrofuran, added with (R)-2-methylpropane-2-sulfinamide 1b (272 mg, 2.25 mmol) and tetraethyl titanate (1.02 g, 4.48 mmol) sequentially, then refluxed and reacted for 4 hours. After the reaction was completed, the reaction solution was cooled to room temperature and concentrated under reduced pressure. The obtained residue was purified by silica gel column chromatography (eluent: system A) to obtain (R)—N-((E)-1-(2-(azidomethyl)-5,6-difluoro-2-methyl-2,3-dihydrobenzofuran-7-yl)ethylidene)-2-methylpropane-2-sulfinamide 10g (370 mg, yellow viscous substance) with a yield of 89.16%.

MS m/z(ESI): 371.2 [M+1]

Step 6

(R)—N-((1R)-1-(2-(azidomethyl)-5,6-difluoro-2-methyl-2,3-dihydrobenzofuran-7-yl)ethyl)-2-methylpropane-2-sulfinamide (R)—N-((E)-1-(2-(azidomethyl)-5,6-difluoro-2-methyl-2,3-dihydrobenzofuran-7-yl)ethylidene)-2-methylpropane-2-sulfinamide 10g (370 mg, 1.0 mmol) was dissolved in 5 mL of tetrahydrofuran, and then added with 9-borabicyclo[3,3,1]-nonane (4 mL, 2.0 mmol, 0.5 mol/L), and reacted at room temperature for 2 hours. After the reaction was completed, the reaction solution was quenched with 30 mL of methanol and concentrated under reduced pressure to obtain crude product of (R)—N-((1R)-1-(2-(azidomethyl)-5,6-difluoro-2-methyl-2,3-dihydrobenzofuran-7-yl)ethyl)-2-methylpropane-2-sulfinamide 10h (372 mg, yellow viscous substance), which was directly used for the next reaction.

MS m/z(ESI): 373.2 [M+1]

Step 7

(1R)-1-(2-(azidomethyl)-5,6-difluoro-2-methyl-2,3-dihydrobenzofuran-7-yl)ethan-1-amine (R)—N-((1R)-1-(2-(azidomethyl)-5,6-difluoro-2-methyl-2,3-dihydrobenzofuran-7-yl)ethyl)-2-methylpropane-2-sulfinamide 10h (372 mg, 1.0 mmol) was dissolved in 5 mL of dichloromethane, then added with 3 mL of hydrochloride 1,4-dioxane solution (4 mol/L), and reacted at room temperature for 1 hour. After the reaction was completed, the reaction solution was concentrated under reduced pressure to obtain crude product of (1R)-1-(2-(azidomethyl)-5,6-difluoro-2-methyl-2,3-dihydrobenzofuran-7-yl)ethan-1-amine 10i (268 mg), which was directly used for the next reaction without purification.

MS m/z(ESI): 268.2 [M+1]

Step 8

Ethyl 5-(((1R)-1-(2-(azidomethyl)-5,6-difluoro-2-methyl-2,3-dihydrobenzofuran-7-yl)ethyl) amino) pyrazolo[1,5-a]pyrimidine-3-carboxylate (1R)-1-(2-(azidomethyl)-5,6-difluoro-2-methyl-2,3-dihydrobenzofuran-7-yl)ethan-1-amine 10i (268 mg, 1.0 mmol) and ethyl 5-chloropyrazolo[1,5-a]pyrimidine-3-carboxylate 1j (225 mg, 1.0 mmol) were dissolved in 3 mL of n-butanol, added with N,N-diisopropylethylamine (1.03 g, 8.0 mmol), heated to 125° C., and reacted for 6 hours. After the reaction was completed, the reaction solution was concentrated under reduced pressure. The obtained residue was purified by silica gel column chromatography (eluent: system A) to obtain ethyl 5-(((1R)-1-(2-(azidomethyl)-5,6-difluoro-2-methyl-2,3-dihydrobenzofuran-7-yl)ethyl) amino)pyrazolo[1,5-a]pyrimidine-3-carboxylate 10j (120 mg, yellow viscous substance) with a yield of 26.2%.

MS m/z(ESI): 458.2 [M+1]

Step 9

Ethyl 5-(((1R)-1-(2-(((tert-butoxycarbonyl)amino)methyl)-5,6-difluoro-2-methyl-2,3-dihydrobenzofuran-7-yl)ethyl)amino)pyrazolo[1,5-a]pyrimidine-3-carboxylate Ethyl 5-(((1R)-1-(2-(azidomethyl)-5,6-difluoro-2-methyl-2,3-dihydrobenzofuran-7-yl)ethyl) amino)pyrazolo[1,5-a]pyrimidine-3-carboxylate 10j (120 mg, 0.26 mmol) was dissolved in 5 mL of methanol, and then added with di-tert-butyl dicarbonate (338 mg, 1.55 mmol) and 10% palladium carbon (30 mg, containing 30% of water) sequentially, hydrogen gas was replaced for three times, and a hydrogen balloon was inserted to react at room temperature for 5 hours. After the reaction was completed, the reaction solution was filtered with diatomite, and the filtrate was concentrated under reduced pressure to obtain crude product of ethyl 5-(((1R)-1-(2-(((tert-butoxycarbonyl)amino) methyl)-5,6-difluoro-2-methyl-2,3-dihydrobenzofuran-7-yl) ethyl)amino)pyrazolo[1,5-a]pyrimidine-3-carboxylate 10k (138 mg, yellow viscous substance), which was directly used for the next reaction without purification.

MS m/z(ESI): 532.2 [M+1]

Step 10

5-(((1R)-1-(2-(((tert-butoxycarbonyl)amino)methyl)-5,6-difluoro-2-methyl-2,3-dihydrobenzofuran-7-yl) ethyl)amino)pyrazolo[1,5-a]pyrimidine-3-carboxylic acid Ethyl 5-(((1R)-1-(2-(((tert-butoxycarbonyl)amino) methyl)-5,6-difluoro-2-methyl-2,3-dihydrobenzofuran-7-yl) ethyl)amino)pyrazolo[1,5-a]pyrimidine-3-carboxylate 10k (138 mg, 0.26 mmol) was dissolved in 4 mL of mixed solvent of ethanol, tetrahydrofuran and water (V:V:V=2:1: 1), added with lithium hydroxide monohydrate (110 mg, 2.6 mmol), heated to 80° C., and reacted overnight. After the reaction was completed, the reaction solution was concentrated under reduced pressure to remove ethanol and tetrahydrofuran, then added with 20 mL of water, and adjusted to acidity with 1.0 M diluted hydrochloric acid, and extracted with ethyl acetate (15 mL×3), then organic phases were combined, washed with 50 mL of saturated brine, dried with anhydrous sodium sulfate, filtered, and concentrated under reduced pressure to obtain 5-(((1R)-1-(2-(((tert-butoxycarbonyl)amino)methyl)-5,6-difluoro-2-methyl-2,3-dihydrobenzofuran-7-yl)ethyl)amino)pyrazolo[1,5-a]pyrimidine-3-carboxylic acid 10l (123 mg, yellow viscous substance), which was directly used for the next reaction without further purification.

MS m/z(ESI): 504.2 [M+1]

Step 11

5-(((1R)-1-(2-(aminomethyl)-5,6-difluoro-2-methyl-2,3-dihydrobenzofuran-7-yl)ethyl)amino)pyrazolo[1, 5-a]pyrimidine-3-carboxylic acid 5-(((1R)-1-(2-(((tert-butoxycarbonyl)amino)methyl)-5,6-difluoro-2-methyl-2,3-dihydrobenzofuran-7-yl)ethyl) amino)pyrazolo[1,5-a]pyrimidine-3-carboxylic acid 10l (123 mg, 0.24 mmol) was dissolved in 2 mL of dichloromethane, and then added with 4 mL of hydrochloride 1,4-dioxane solution (4 mol/L), and reacted at room temperature for 1 hour. After the reaction was completed, the reaction solution was concentrated under reduced pressure to obtain crude product of 5-(((1R)-1-(2-(aminomethyl)-5, 6-difluoro-2-methyl-2,3-dihydrobenzofuran-7-yl)ethyl) amino)pyrazolo[1,5-a]pyrimidine-3-carboxylic acid 10m (98 mg), which was directly used for the next reaction without purification.

MS m/z(ESI): 404.2 [M+1]

Step 12

(3R,11R)-5,6-difluoro-3,11-dimethyl-10-oxa-2,13, 17,18,21-pentaazapentacyclo[13.5.2.1$^{8,11}$.0$^{4,9}$.0$^{18,22}$] tricosa-1(21),4,6,8,15(22),16,19-heptaen-14-one 10

(3R,11S)-5,6-difluoro-3,11-dimethyl-10-oxa-2,13, 17,18,21-pentaazapentacyclo[13.5.2.1$^{8,11}$.0$^{4,9}$.0$^{18,22}$] tricosa-1(21),4,6,8,15(22),16,19-heptaen-14-one 11

5-(((1R)-1-(2-(aminomethyl)-5,6-difluoro-2-methyl-2,3-dihydrobenzofuran-7-yl)ethyl)amino)pyrazolo[1,5-a]pyrimidine-3-carboxylic acid 10m (98 mg, 0.24 mmol), pentafluorophenyl diphenyl phosphinate (111 mg, 0.28 mmol) and N,N-diisopropylethylamine (248 mg, 1.92 mmol) were dissolved in 6 mL of mixed solvent of dichloromethane and N,N-dimethylformamide (V:V=5:1), and reacted at room temperature overnight. After the reaction was completed, the reaction solution was added with 20 mL of saturated aqueous ammonium chloride solution and extracted with dichloromethane (20 mL×3), and then organic phases were combined, dried with anhydrous sodium sulfate, filtered, and concentrated under reduced pressure. (3R,11R)-5,6-difluoro-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16, 19-heptaen-14-one 10 (20 mg) with a yield of 20.4% and (3R,11S)-5,6-difluoro-3,11-dimethyl-10-oxa-2,13,17,18,21-pentaazapentacyclo[13.5.2.1$^{8,11}$.0$^{4,9}$.0$^{18,22}$]tricosa-1(21),4, 6,8,15(22),16,19-heptaen-14-one 11(40 mg) with a yield of 40.8% were obtained by preparing a liquid phase (separation column AKZONOBEL Kromasil; 250×21.2 mm I.D.; 5 μm, 20 mL/min; mobile phase A: 0.05% TFA+H$_2$O, and mobile phase B: CH$_3$CN) from the obtained residue.

10

MS m/z(ESI): 386.2 [M+1]

$^1$H NMR (400 MHz, DMSO-d$_6$) δ 8.97 (d, J=6.7 Hz, 1H), 8.86 (d, J=9.7 Hz, 1H), 8.49 (d, J=7.4 Hz, 1H), 8.00 (d, J=5.9 Hz, 1H), 7.31 (s, 1H), 7.08 (d, J=8.7 Hz, 1H), 4.98-4.89 (m, 1H), 3.83 (dd, J=16.3, 7.3 Hz, 1H), 3.16-3.15 (m, 1H), 3.03-3.01 (m, 1H), 2.98-2.96 (m, 1H), 1.82 (s, 3H), 1.56 (d, J=18.1 Hz, 3H).

11

MS m/z(ESI): 386.2 [M+1]

$^1$H NMR (400 MHz, DMSO-d$_6$) δ 8.92 (d, J=9.5 Hz, 1H), 8.75 (d, J=5.2 Hz, 1H), 8.55 (d, J=7.6 Hz, 1H), 8.01 (s, 1H), 7.06 (t, J=8.9 Hz, 1H), 6.41 (d, J=7.6 Hz, 1H), 5.01 (t, J=6.7 Hz, 1H), 3.81 (dd, J=13.3, 9.8 Hz, 1H), 3.27-3.15 (m, 2H), 3.00 (d, J=16.6 Hz, 1H), 1.67 (d, J=7.2 Hz, 3H), 1.59 (s, 3H).

Example 12

(3R)-6,7-difluoro-3,11-dimethyl-10-oxa-2,13,17,18, 21-pentaazapentacyclo[13.5.2.1$^{8,11}$.0$^{4,9}$.0$^{18,22}$]tricosa-1(21),4,6,8,15(22),16,19-heptaen-14-one

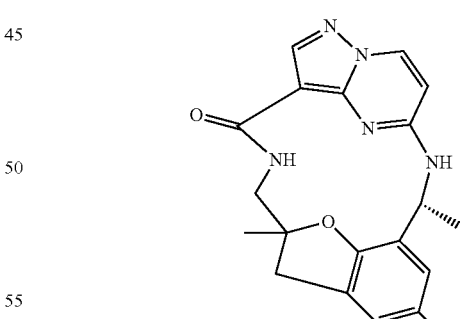

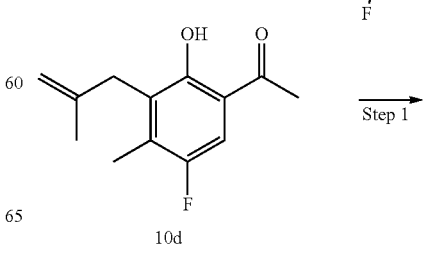

10d

121
-continued
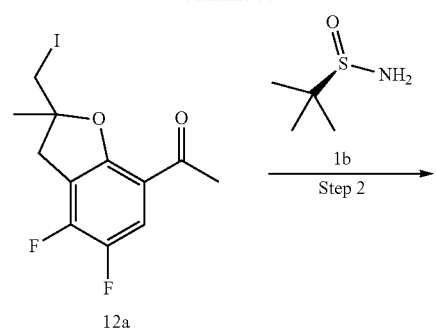
12a
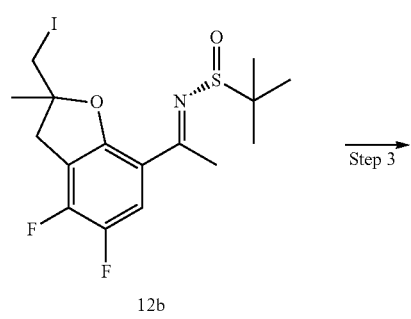
12b
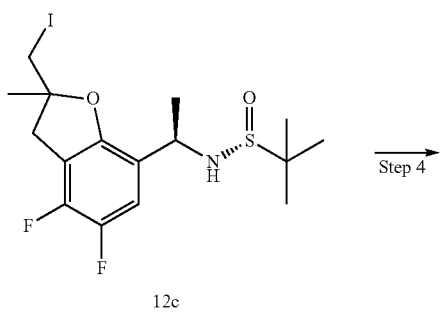
12c
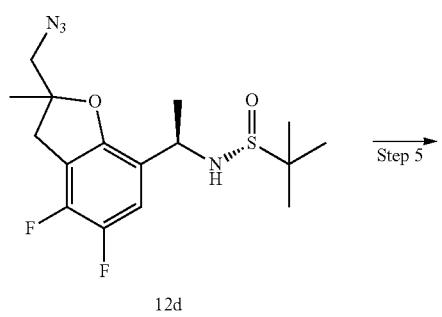
12d
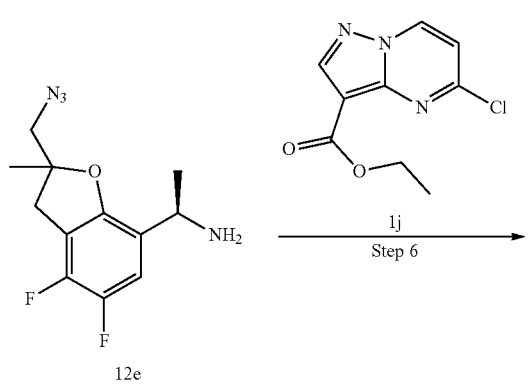
12e
122
-continued
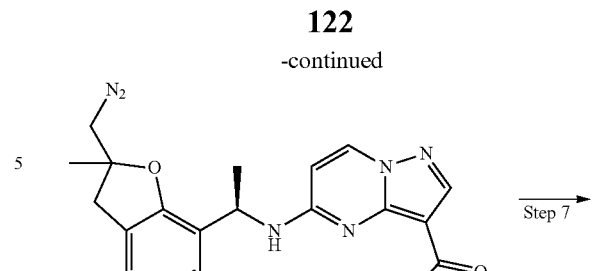
12f
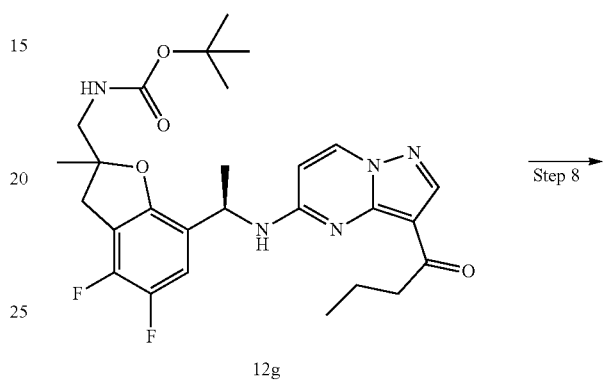
12g
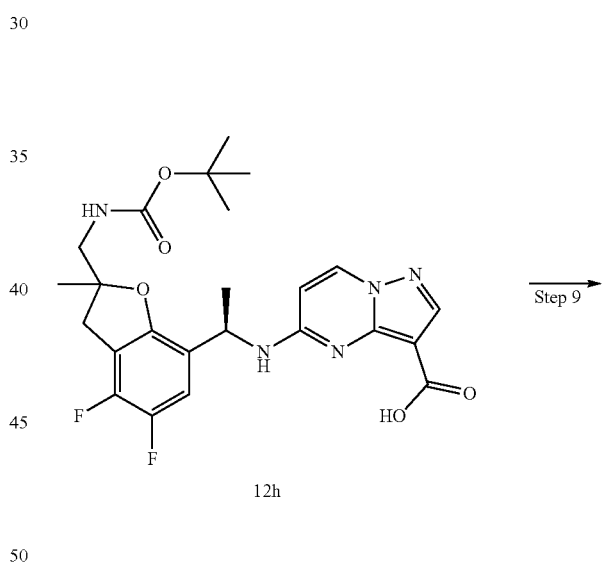
12h
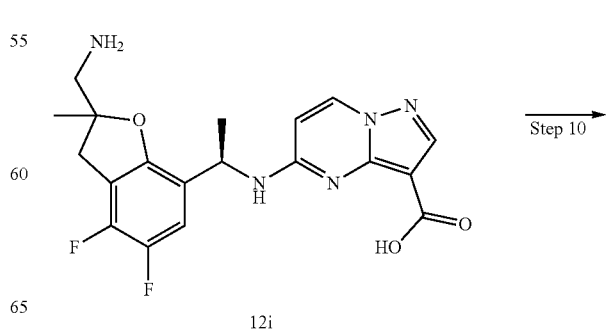
12i -continued

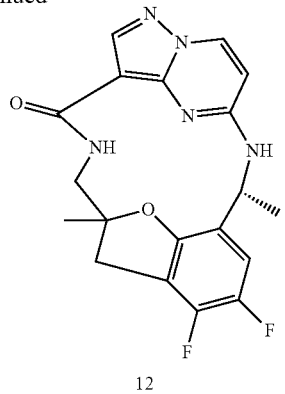

12

Step 1

1-(4,5-difluoro-2-(iodomethyl)-2-methyl-2,3-dihydrobenzofuran-7-yl)ethan-1-one 1-(4,5-difluoro-2-hydroxy-3-(2-methylallyl)phenyl)ethan-1-one 10d (2.7 g, 11.9 mmol) was dissolved in 50 mL of tetrahydrofuran, added with N-iodosuccinimide (5.4 g, 23.8 mmol), and reacted at room temperature overnight. After the reaction was completed, the reaction solution was added with sodium thiosulfate for decoloration, then added with 50 mL of water and extracted with ethyl acetate (100 mL×3), then organic phases were combined, washed with 300 mL of saturated brine, dried with anhydrous sodium sulfate, filtered, and concentrated under reduced pressure. The obtained residue was further separated and purified by silica gel column chromatography (eluent: system A) to obtain 1-(4,5-difluoro-2-(iodomethyl)-2-methyl-2,3-dihydrobenzofuran-7-yl)ethan-1-one 12a (1.35 g, white solid) with a yield of 37.5%.

MS m/z(ESI): 353.0 [M+1]

Step 2

(R)—N-((E)-1-(4,5-difluoro-2-(iodomethyl)-2-methyl-2,3-dihydrobenzofuran-7-yl)ethylidene)-2-methylpropane-2-sulfinamide 1-(4,5-difluoro-2-(iodomethyl)-2-methyl-2,3-dihydrobenzofuran-7-yl)ethan-1-one 12a (352 mg, 1.0 mmol) was dissolved in 5 mL of tetrahydrofuran, added with (R)-2-methylpropane-2-sulfinamide 1b (242 mg, 2.0 mmol) and tetraethyl titanate (912 g, 4.0 mmol) sequentially, and then reacted at 75° C. for 6 hours. After the reaction was completed, the reaction solution was cooled to room temperature, added with 20 mL of water, and filtered. The filtrate was extracted with ethyl acetate (20 mL×3), and then organic phases were combined, dried with anhydrous sodium sulfate, filtered, and concentrated under reduced pressure. The obtained residue was purified by silica gel column chromatography (eluent: system A) to obtain (R)—N-((E)-1-(4,5-difluoro-2-(iodomethyl)-2-methyl-2,3-dihydrobenzofuran-7-yl)ethylidene)-2-methylpropane-2-sulfinamide 12b (162 mg, yellow oily substance) with a yield of 36%.

MS m/z(ESI): 456.0[M+1]

Step 3

(R)—N-((1R)-1-(4,5-difluoro-2-(iodomethyl)-2-methyl-2,3-dihydrobenzofuran-7-yl)ethyl)-2-methylpropane-2-sulfinamide (R)—N-((E)-1-(4,5-difluoro-2-(iodomethyl)-2-methyl-2,3-dihydrobenzofuran-7-yl)ethylidene)-2-methylpropane-2-sulfinamide 12b (162 mg, 0.36 mmol) was dissolved in 5 mL of tetrahydrofuran, and then added with 9-borabicyclo[3,3,1]-nonane (1.4 mL, 0.72 mmol, 0.5 mol/L), and reacted at room temperature overnight. After the reaction was completed, the reaction solution was quenched with 30 mL of methanol and concentrated under reduced pressure to obtain (R)—N-((1R)-1-(4,5-difluoro-2-(iodomethyl)-2-methyl-2,3-dihydrobenzofuran-7-yl)ethyl)-2-methylpropane-2-sulfinamide 12c (130 mg, yellow oily substance) with a yield of 78%.

MS m/z(ESI): 458.0 [M+1]

Step 4

(R)—N-((1R)-1-(2-(azidomethyl)-4,5-difluoro-2-methyl-2,3-dihydrobenzofuran-7-yl)ethyl)-2-methylpropane-2-sulfinamide (R)—N-((1R)-1-(4,5-difluoro-2-(iodomethyl)-2-methyl-2,3-dihydrobenzofuran-7-yl)ethyl)-2-methylpropane-2-sulfinamide 12c (1.65 g, 3.6 mmol) was dissolved in 20 mL of N,N-dimethylformamide, added with sodium azide (351 mg, 5.4 mmol), heated to 95° C., and then reacted overnight. After the reaction was completed, the reaction solution was cooled to room temperature, added with 50 mL of water, and extracted with ethyl acetate (50 mL×3), then organic phases were combined, washed with 100 mL of saturated brine, dried with anhydrous sodium sulfate, filtered, and concentrated under reduced pressure. The obtained residue was purified by silica gel column chromatography (eluent: system A) to obtain (R)—N-((1R)-1-(2-(azidomethyl)-4,5-difluoro-2-methyl-2,3-dihydrobenzofuran-7-yl)ethyl)-2-methylpropane-2-sulfinamide 12d (700 mg, yellow oily substance) with a yield of 52%.

MS m/z(ESI): 373.1 [M+1]

Step 5

(1R)-1-(2-(azidomethyl)-4,5-difluoro-2-methyl-2,3-dihydrobenzofuran-7-yl)ethan-1-amine (R)—N-((1R)-1-(2-(azidomethyl)-4,5-difluoro-2-methyl-2,3-dihydrobenzofuran-7-yl)ethyl)-2-methylpropane-2-sulfinamide 12d (700 mg, 1.9 mmol) was dissolved in 5 mL of dichloromethane, then added with 2 mL of hydrochloride 1,4-dioxane solution (4 mol/L), and reacted at room temperature for 1 hour. After the reaction was completed, the reaction solution was concentrated under reduced pressure to obtain crude product of (1R)-1-(2-(azidomethyl)-4,5-difluoro-2-methyl-2,3-dihydrobenzofuran-7-yl)ethan-1-amine 12e (500 mg), which was directly used for the next reaction without purification.

MS m/z(ESI): 269.1 [M+1]

Step 6

Ethyl 5-(((1R)-1-(2-(azidomethyl)-4,5-difluoro-2-methyl-2,3-dihydrobenzofuran-7-yl)ethyl) amino) pyrazolo[1,5-a]pyrimidine-3-carboxylate (1R)-1-(2-(azidomethyl)-4,5-difluoro-2-methyl-2,3-dihydrobenzofuran-7-yl)ethan-1-amine 12e (500 mg, 1.87 mmol) and ethyl 5-chloropyrazolo[1,5-a]pyrimidine-3-carboxylate 1j (420.75 mg, 1.87 mmol) were dissolved in 10 mL of n-butanol, added with N,N-diisopropylethylamine (1.45 g, 11.22 mmol), heated to 125° C., and reacted for 5 hours. After the reaction was completed, the reaction solution was concentrated under reduced pressure. The obtained residue was purified by silica gel column chromatography (eluent: system A) to obtain ethyl 5-(((1R)-1-(2-(azidomethyl)-4,5-difluoro-2-methyl-2,3-dihydrobenzofuran-7-yl)ethyl)amino)pyrazolo[1,5-a]pyrimidine-3-carboxylate 12f (550 mg, yellow oily substance) with a yield of 64%.

MS m/z(ESI): 458.0 [M+1]

Step 7

Ethyl 5-(((1R)-1-(2-(((tert-butoxycarbonyl)amino)methyl)-4,5-difluoro-2-methyl-2,3-dihydrobenzofuran-7-yl)ethyl)amino)pyrazolo[1,5-a]pyrimidine-3-carboxylate Ethyl 5-(((1R)-1-(2-(azidomethyl)-4,5-difluoro-2-methyl-2,3-dihydrobenzofuran-7-yl)ethyl) amino)pyrazolo[1,5-a]pyrimidine-3-carboxylate 12f (550 mg, 1.2 mmol) was dissolved in 10 mL of methanol, and then added with di-tert-butyl dicarbonate (315 mg, 1.2 mmol) and 10% palladium carbon (100 mg, containing 50% of water) sequentially, hydrogen gas was replaced for three times, and a hydrogen balloon was inserted to react at room temperature for 4 hours. After the reaction was completed, the reaction solution was filtered, and the filtrate was concentrated under reduced pressure to obtain crude product of ethyl 5-(((1R)-1-(2-(((tert-butoxycarbonyl)amino)methyl)-4,5-difluoro-2-methyl-2,3-dihydrobenzofuran-7-yl)ethyl)amino)pyrazolo[1,5-a]pyrimidine-3-carboxylate 12g (637 mg, yellow oily substance), which was directly used for the next reaction without purification.

MS m/z(ESI): 532.1[M+1]

Step 8

5-(((1R)-1-(2-(((tert-butoxycarbonyl)amino)methyl)-4,5-difluoro-2-methyl-2,3-dihydrobenzofuran-7-yl)ethyl)amino)pyrazolo[1,5-a]pyrimidine-3-carboxylic acid Ethyl 5-(((1R)-1-(2-(((tert-butoxycarbonyl)amino)methyl)-4,5-difluoro-2-methyl-2,3-dihydrobenzofuran-7-yl)ethyl)amino)pyrazolo[1,5-a]pyrimidine-3-carboxylate 12g (637 mg, 1.2 mmol) was dissolved in 12 mL of mixed solvent of ethanol, tetrahydrofuran and water (V:V:V=5:5:2), added with lithium hydroxide monohydrate (503.5 mg, 12 mmol), heated to 80° C., and reacted overnight. After the reaction was completed, the reaction solution was concentrated under reduced pressure to remove ethanol and tetrahydrofuran, then added with 50 mL of water, and adjusted to acidity with 2.0 M diluted hydrochloric acid, and extracted with ethyl acetate (20 mL×3), then organic phases were combined, washed with 50 mL of saturated brine, dried with anhydrous sodium sulfate, filtered, and concentrated under reduced pressure to obtain crude product of 5-(((1R)-1-(2-(((tert-butoxycarbonyl)amino)methyl)-4,5-difluoro-2-methyl-2,3-dihydrobenzofuran-7-yl)ethyl)amino)pyrazolo[1,5-a]pyrimidine-3-carboxylic acid 12h (603 mg, yellow solid) with a yield of 99%.

MS m/z(ESI): 504.2 [M+1]

Step 9

5-(((1R)-1-(2-(aminomethyl)-4,5-difluoro-2-methyl-2,3-dihydrobenzofuran-7-yl)ethyl)amino)pyrazolo[1,5-a]pyrimidine-3-carboxylic acid 5-(((1R)-1-(2-(((tert-butoxycarbonyl)amino)methyl)-4,5-difluoro-2-methyl-2,3-dihydrobenzofuran-7-yl)ethyl)amino)pyrazolo[1,5-a]pyrimidine-3-carboxylic acid 12h (603 mg, 1.2 mmol) was dissolved in 5 mL of dichloromethane, and then added with 5 mL of hydrochloride 1,4-dioxane solution (4 mol/L), and reacted at room temperature for 1 hour. After the reaction was completed, the reaction was concentrated under reduced pressure to obtain crude product of 5-(((1R)-1-(2-(aminomethyl)-4,5-difluoro-2-methyl-2,3-dihydrobenzofuran-7-yl)ethyl)amino)pyrazolo[1,5-a]pyrimidine-3-carboxylic acid 12i (484 mg, yellow oily substance), which was directly used for the next reaction without purification.

MS m/z(ESI): 404.2 [M+1]

Step 10

(3R)-6,7-difluoro-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 5-(((1R)-1-(2-(aminomethyl)-4,5-difluoro-2-methyl-2,3-dihydrobenzofuran-7-yl)ethyl)amino)pyrazolo[1,5-a]pyrimidine-3-carboxylic acid 12i (484 mg, 1.2 mmol), pentafluorophenyl diphenyl phosphinate (554 mg, 1.44 mmol) and N,N-diisopropylethylamine (1.24 g, 9.6 mmol) were dissolved in 10 mL of mixed solvent of dichloromethane and N,N-dimethylformamide (V:V=1:1), and reacted at room temperature overnight. After the reaction was completed, the reaction solution was added with 20 mL of saturated aqueous ammonium chloride solution and extracted with dichloromethane (20 mL×3), and then organic phases were combined, dried with anhydrous sodium sulfate, filtered, and concentrated under reduced pressure. (3R)-6,7-difluoro-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 12 (20 mg) with a yield of 5% was obtained by preparing a liquid phase (separation column AKZONOBEL Kromasil; 250×21.2 mm I.D.; 5 μm, 20 mL/min; mobile phase A: 0.05% TFA+H$_2$O, and mobile phase B: CH$_3$CN) from the obtained residue.

MS m/z(ESI): 386.1 [M+1]

$^1$H NMR (400 MHz, DMSO-d$_6$) δ 8.88 (d, J=9.5 Hz, 1H), 8.60 (d, J=4.7 Hz, 1H), 8.58-8.52 (m, 1H), 8.01 (d, J=2.3 Hz, 1H), 6.98 (dd, J=11.5, 8.1 Hz, 1H), 6.38 (d, J=7.8 Hz, 1H), 4.89 (t, J=6.4 Hz, 1H), 3.84 (dd, J=13.4, 9.8 Hz, 1H), 3.56 (dd, J=14.2, 7.2 Hz, 1H), 3.25 (s, 1H), 3.10 (d, J=16.8 Hz, 1H), 1.62 (s, 3H), 1.53 (d, J=7.3 Hz, 3H).

Example 13
(3R)-7-fluoro-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one
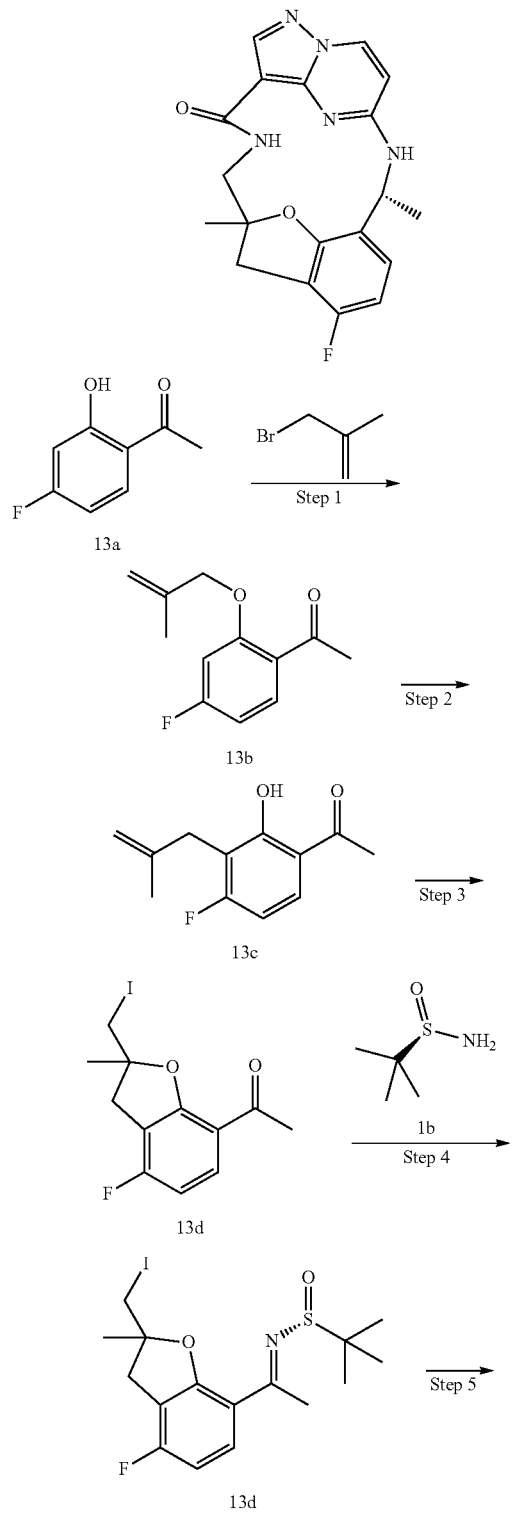
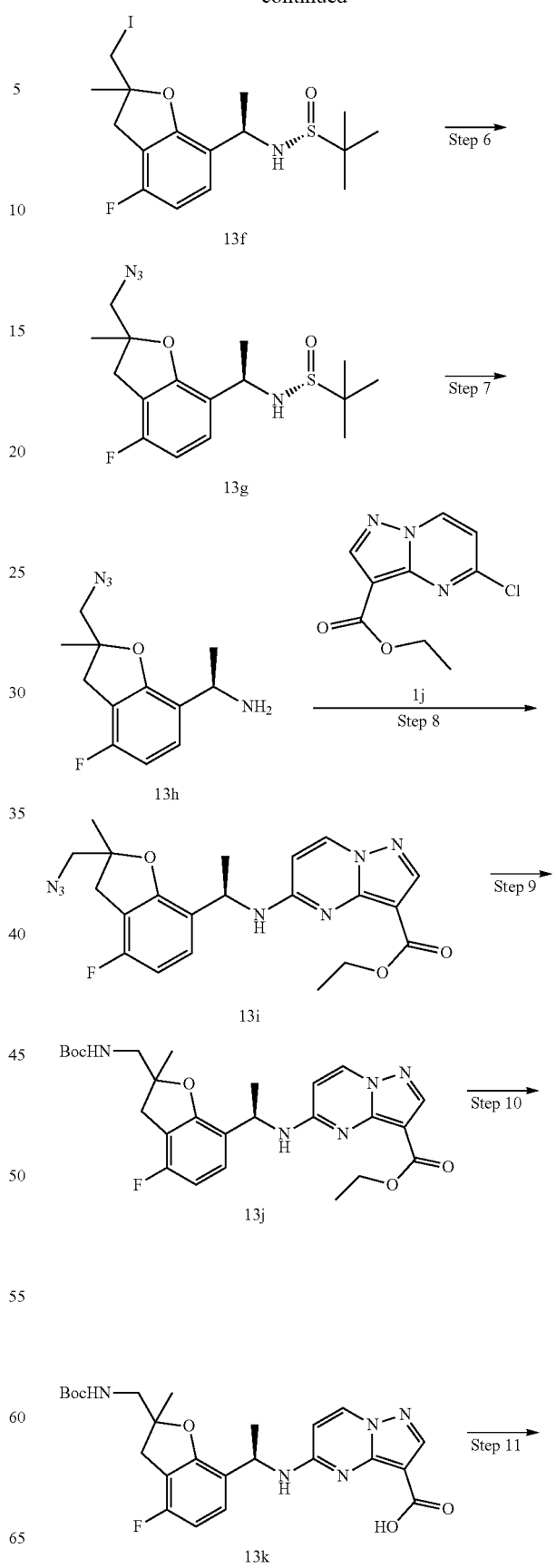

-continued

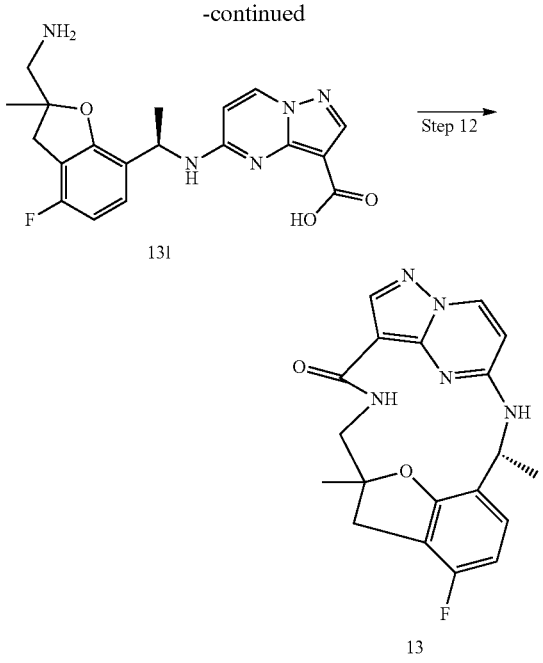

Step 1

1-(4-fluoro-2-((2-methylallyl)oxy)phenyl)ethan-1-one 1-(4-fluoro-2-hydroxyphenyl)ethan-1-one 13a (1.54 g, 10 mmol) was dissolved in 30 ml of N,N-dimethylformamide, then added with 3-bromo-2-methylpropene (1.62 g, 12 mmol) and potassium carbonate (2.76 g, 20 mmol) sequentially, and reacted at room temperature overnight. After the reaction was completed, the reaction solution was added with 100 mL of water and extracted with ethyl acetate (50 mL×2), then organic phases were combined, washed with saturated brine (30 mL), dried with anhydrous sodium sulfate, filtered, and concentrated under reduced pressure to obtain crude product of 1-(4-fluoro-2-((2-methylallyl)oxy)phenyl)ethan-1-one 13b (2.08 g, white solid), which was directly used for the next reaction without further purification.

MS m/z(ESI): 209.0 [M+1]

Step 2

1-(4-fluoro-2-hydroxy-3-(2-methylallyl)phenyl)ethan-1-one

Crude product of 1-(4-fluoro-2-((2-methylallyl)oxy)phenyl)ethan-1-one 13b (2.08 g) was heated to 220° C., stirred and reacted for 6 hours. After the reaction was completed, the reaction solution was cooled to room temperature, and then added with 100 mL of dichloromethane for dissolution, and concentrated under reduced pressure. The obtained residue was purified by silica gel column chromatography (eluent: system A) to obtain 1-(4-fluoro-2-hydroxy-3-(2-methylallyl)phenyl)ethan-1-one 13c (1.35 g, yellow oily substance) with a yield of 65%.

MS m/z(ESI): 209.0 [M+1]

Step 3

1-(4-fluoro-2-(iodomethyl)-2-methyl-2,3-dihydrobenzofuran-7-yl)ethan-1-one 1-(4-fluoro-2-hydroxy-3-(2-methylallyl)phenyl)ethan-1-one 13c (5.4 g, 25.96 mmol) was dissolved in 50 mL of tetrahydrofuran, added with N-iodosuccinimide (11.7 g, 51.92 mmol), and reacted at room temperature overnight. After the reaction was completed, the reaction solution was concentrated under reduced pressure, and added with 50 mL of ethyl acetate for dilution, then washed with saturated sodium bisulfite solution (30 mL×2) and saturated sodium chloride solution (20 mL) sequentially, dried with anhydrous sodium sulfate, filtered, and concentrated under reduced pressure. The obtained residue was purified by silica gel column chromatography (eluent: system A) to obtain 1-(4-fluoro-2-(iodomethyl)-2-methyl-2,3-dihydrobenzofuran-7-yl)ethan-1-one 13d (3.4 g, white solid) with a yield of 39%.

MS m/z(ESI): 335.0 [M+1]

Step 4

(R)—N-((E)-1-(4-fluoro-2-(iodomethyl)-2-methyl-2,3-dihydrobenzofuran-7-yl)ethylidene)-2-methylpropane-2-sulfinamide 1-(4-fluoro-2-(iodomethyl)-2-methyl-2,3-dihydrobenzofuran-7-yl)ethan-1-one 13d (2.98 g, 8.92 mmol) was dissolved in 40 mL of tetrahydrofuran, added with (R)-2-methylpropane-2-sulfinamide 1b (2.16 g, 17.8 mmol) and tetraethyl titanate (8.14 g, 35.68 mmol) sequentially, then refluxed and reacted overnight. After the reaction was completed, the reaction solution was cooled to room temperature, added with 40 mL of ethyl acetate and 50 mL of water, and filtered. The filtrate was separated, the organic phase was retained, and the aqueous phase was extracted with ethyl acetate (30 mL×2), then organic phases were combined, dried with anhydrous sodium sulfate, filtered, and concentrated under reduced pressure. The obtained residue was purified by silica gel column chromatography (eluent: system A) to obtain (R)—N-((E)-1-(4-fluoro-2-(iodomethyl)-2-methyl-2,3-dihydrobenzofuran-7-yl)ethylidene)-2-methylpropane-2-sulfinamide 13e (980 mg, yellow oily substance) with a yield of 30%.

MS m/z(ESI): 438.0 [M+1]

Step 5

(R)—N-((1R)-1-(4-fluoro-2-(iodomethyl)-2-methyl-2,3-dihydrobenzofuran-7-yl)ethyl)-2-methylpropane-2-sulfinamide (R)—N-((E)-1-(4-fluoro-2-(iodomethyl)-2-methyl-2,3-dihydrobenzofuran-7-yl)ethylidene)-2-methylpropane-2-sulfinamide 13e (980 mg, 2.24 mmol) was dissolved in 10 mL of tetrahydrofuran, and then added with 9-borabicyclo[3,3,1]-nonane (9 mL, 4.48 mmol, 0.5 mol/L), and reacted at room temperature overnight. After the reaction was completed, the reaction solution was quenched with 30 mL of methanol and concentrated under reduced pressure. The obtained residue was purified by silica gel column chromatography (eluent: system A) to obtain (R)—N-((1R)-1-(4-fluoro-2-(iodomethyl)-2-methyl-2,3-dihydrobenzofuran-7-yl)ethyl)-2-methylpropane-2-sulfinamide 13f (770 mg, white solid) with a yield of 78.3%.

MS m/z(ESI): 440.0 [M+1]

Step 6

(R)—N-((1R)-1-(2-(azidomethyl)-4-fluoro-2-methyl-2,3-dihydrobenzofuran-7-yl)ethyl)-2-methylpropane-2-sulfinamide (R)—N-((1R)-1-(4-fluoro-2-(iodomethyl)-2-methyl-2,3-dihydrobenzofuran-7-yl)ethyl)-2-methylpropane-2-sulfinamide 13f (770 mg, 1.75 mmol) was dissolved in 10 mL of N,N-dimethylformamide, added with sodium azide (228 mg, 3.5 mmol), and reacted at 95° C. overnight. After the reaction was completed, the reaction solution was cooled to room temperature, added with 20 mL of water, and extracted with ethyl acetate (20 mL×3), then organic phases were combined, washed with water (10 mL) and saturated brine (100 mL×2) sequentially, dried with anhydrous sodium sulfate, filtered, and concentrated under reduced pressure. The obtained residue was purified by silica gel column chromatography (eluent: system A) to obtain (R)—N-((1R)-1-(2-(azidomethyl)-4-fluoro-2-methyl-2,3-dihydrobenzofuran-7-yl)ethyl)-2-methylpropane-2-sulfinamide 13g (450 mg, colorless oily substance) with a yield of 72.7%.

MS m/z(ESI): 355.1[M+1]

Step 7

(1R)-1-(2-(azidomethyl)-4-fluoro-2-methyl-2,3-dihydrobenzofuran-7-yl)ethan-1-amine (R)—N-((1R)-1-(2-(azidomethyl)-4-fluoro-2-methyl-2,3-dihydrobenzofuran-7-yl)ethyl)-2-methylpropane-2-sulfinamide 13g (450 mg, 1.27 mmol) was dissolved in 4 mL of dichloromethane, then added with 1 mL of hydrochloride 1,4-dioxane solution (4 mol/L), and reacted at room temperature overnight. After the reaction was completed, the reaction solution was concentrated under reduced pressure to obtain crude product of (1R)-1-(2-(azidomethyl)-4-fluoro-2-methyl-2,3-dihydrobenzofuran-7-yl)ethan-1-amine 13h (317 mg, colorless liquid), which was directly used for the next reaction without purification.

MS m/z(ESI): 234.0[M−16]

Step 8

Ethyl 5-(((1R)-1-(2-(azidomethyl)-4-fluoro-2-methyl-2,3-dihydrobenzofuran-7-yl)ethyl)amino)pyrazolo[1,5-a]pyrimidine-3-carboxylate (1R)-1-(2-(azidomethyl)-4-fluoro-2-methyl-2,3-dihydrobenzofuran-7-yl)ethan-1-amine 13h (317 mg, 1.27 mmol) and ethyl 5-chloropyrazolo[1,5-a]pyrimidine-3-carboxylate 1j (343 mg, 1.52 mmol) were dissolved in 10 mL of n-butanol, and then added with N,N-diisopropylethylamine (1.31 g, 10.16 mmol), heated to 125° C., and reacted for 4 hours. After the reaction was completed, the reaction solution was concentrated under reduced pressure. The obtained residue was purified by silica gel column chromatography (eluent: system A) to obtain ethyl 5-(((1R)-1-(2-(azidomethyl)-4-fluoro-2-methyl-2,3-dihydrobenzofuran-7-yl)ethyl)amino) pyrazolo[1,5-a]pyrimidine-3-carboxylate 13i (380 mg, white solid) with a yield of 68%.

MS m/z(ESI): 440.0 [M+1]

Step 9

Ethyl 5-(((1R)-1-(2-(((tert-butoxycarbonyl)amino)methyl)-4-fluoro-2-methyl-2,3-dihydrobenzofuran-7-yl)ethyl)amino)pyrazolo[1,5-a]pyrimidine-3-carboxylate Ethyl 5-(((1R)-1-(2-(azidomethyl)-4-fluoro-2-methyl-2,3-dihydrobenzofuran-7-yl)ethyl) amino)pyrazolo[1,5-a]pyrimidine-3-carboxylate 13i (380 mg, 0.86 mmol) was dissolved in 10 mL of methanol, and then added with di-tert-butyl dicarbonate (226 mg, 1.04 mmol) and 10% palladium carbon (80 mg, containing 50% of water) sequentially, hydrogen gas was replaced for three times, and a hydrogen balloon was inserted to react at room temperature overnight. After the reaction was completed, the reaction solution was filtered, and the filtrate was concentrated under reduced pressure. The obtained residue was purified by silica gel column chromatography (eluent: system A) to obtain ethyl 5-(((1R)-1-(2-(((tert-butoxycarbonyl)amino)methyl)-4-fluoro-2-methyl-2,3-dihydrobenzofuran-7-yl)ethyl)amino) pyrazolo[1,5-a]pyrimidine-3-carboxylate 13j (200 mg, white solid) with a yield of 45%.

MS m/z(ESI): 514.0 [M+1]

Step 10

5-(((1R)-1-(2-(((tert-butoxycarbonyl)amino)methyl)-4-fluoro-2-methyl-2,3-dihydrobenzofuran-7-yl)ethyl)amino)pyrazolo[1,5-a]pyrimidine-3-carboxylic acid Ethyl 5-(((1R)-1-(2-(((tert-butoxycarbonyl)amino)methyl)-4-fluoro-2-methyl-2,3-dihydrobenzofuran-7-yl)ethyl)amino)pyrazolo[1,5-a]pyrimidine-3-carboxylate 13j (200 mg, 0.39 mmol) was dissolved in 5 mL of mixed solvent of ethanol, tetrahydrofuran and water (V:V:V=2:2:1), added with lithium hydroxide monohydrate (130 mg, 3.1 mmol), heated to 85° C., and reacted for 4 hours. After the reaction was completed, the reaction solution was concentrated under reduced pressure to remove ethanol and tetrahydrofuran, then added with 20 mL of ethyl acetate for dilution, washed with 10% citric acid aqueous solution (20 mL) and saturated brine (20 mL) sequentially, dried with anhydrous sodium sulfate, filtered, and concentrated under reduced pressure to obtain crude product of 5-(((1R)-1-(2-(((tert-butoxycarbonyl)amino)methyl)-4-fluoro-2-methyl-2,3-dihydrobenzofuran-7-yl)ethyl)amino)pyrazolo[1,5-a]pyrimidine-3-carboxylic acid 13k (189 mg, white solid), which was directly used for the next reaction.

MS m/z(ESI): 386.0 [M−100]

Step 11

5-(((1R)-1-(2-(aminomethyl)-4-fluoro-2-methyl-2,3-dihydrobenzofuran-7-yl)ethyl)amino)pyrazolo[1,5-a]pyrimidine-3-carboxylic acid 5-(((1R)-1-(2-(((tert-butoxycarbonyl)amino)methyl)-4-fluoro-2-methyl-2,3-dihydrobenzofuran-7-yl)ethyl)amino) pyrazolo[1,5-a]pyrimidine-3-carboxylic acid 13k (189 mg, 0.39 mmol) was dissolved in 2 mL of dichloromethane, and then added with 0.5 mL of hydrochloride 1,4-dioxane solution (4 mol/L), and reacted at room temperature overnight. After the reaction was completed, the reaction was concentrated under reduced pressure to obtain crude product of 5-(((1R)-1-(2-(aminomethyl)-4-fluoro-2-methyl-2,3-dihydrobenzofuran-7-yl)ethyl)amino)pyrazolo[1,5-a]pyrimidine-3-carboxylic acid 131 (150 mg, red oily substance), which was directly used for the next reaction without purification.

MS m/z(ESI): 386.0 [M+1]

Step 12

(3R)-7-fluoro-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 5-(((1R)-1-(2-(aminomethyl)-4-fluoro-2-methyl-2,3-dihydrobenzofuran-7-yl)ethyl)amino)pyrazolo[1,5-a]pyrimidine-3-carboxylic acid 131 (150 mg, 0.26 mmol), pentafluorophenyl diphenyl phosphinate (119.8 mg, 0.31 mmol) and N,N-diisopropylethylamine (268 mg, 2.08 mmol) were dissolved in 4 mL of mixed solvent of dichloromethane and N,N-dimethylformamide (V:V=1:1), and reacted at room temperature for 4 hours. After the reaction was completed, the reaction solution was concentrated under reduced pressure, dissolved with 10 mL of ethyl acetate, washed with saturated brine (10 mL×2), dried with anhydrous sodium sulfate, filtered, and concentrated under reduced pressure. (3R)-7-fluoro-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 13 (20 mg) with a yield of 21.1% was obtained by preparing a liquid phase (separation column AKZONOBEL Kromasil; 250×21.2 mm I.D.; 5 μm, 20 mL/min; mobile phase A: 0.05% TFA+H$_2$O, and mobile phase B: CH$_3$CN) from the obtained residue.

MS m/z(ESI): 368.0 [M+1]

1H NMR (400 MHz, CDCl$_3$) δ 9.22-9.20 (d, J=8.0 Hz, 1H), 8.22-8.14 (m, 2H), 6.97-6.94 (m, 11H), 6.49-6.44 (m, 1H), 6.14-6.12 (m, 11H), 5.91 (s, 1H), 5.19-5.13 (m, 1H), 4.02-3.96 (m, 11H), 3.43-3.23 (m, 3H), 1.67-1.64 (m, 6H).

Examples 14 and 15

(3R,11S)-6-fluoro-11-(methoxymethyl)-3-methyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 14

(3R,11R)-6-fluoro-11-(methoxymethyl)-3-methyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 15

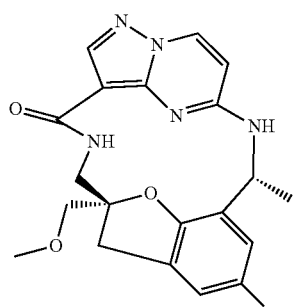

14

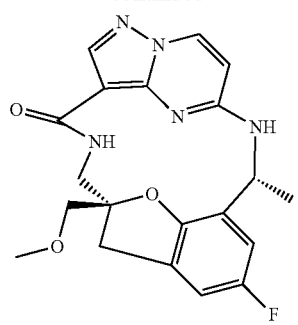

15

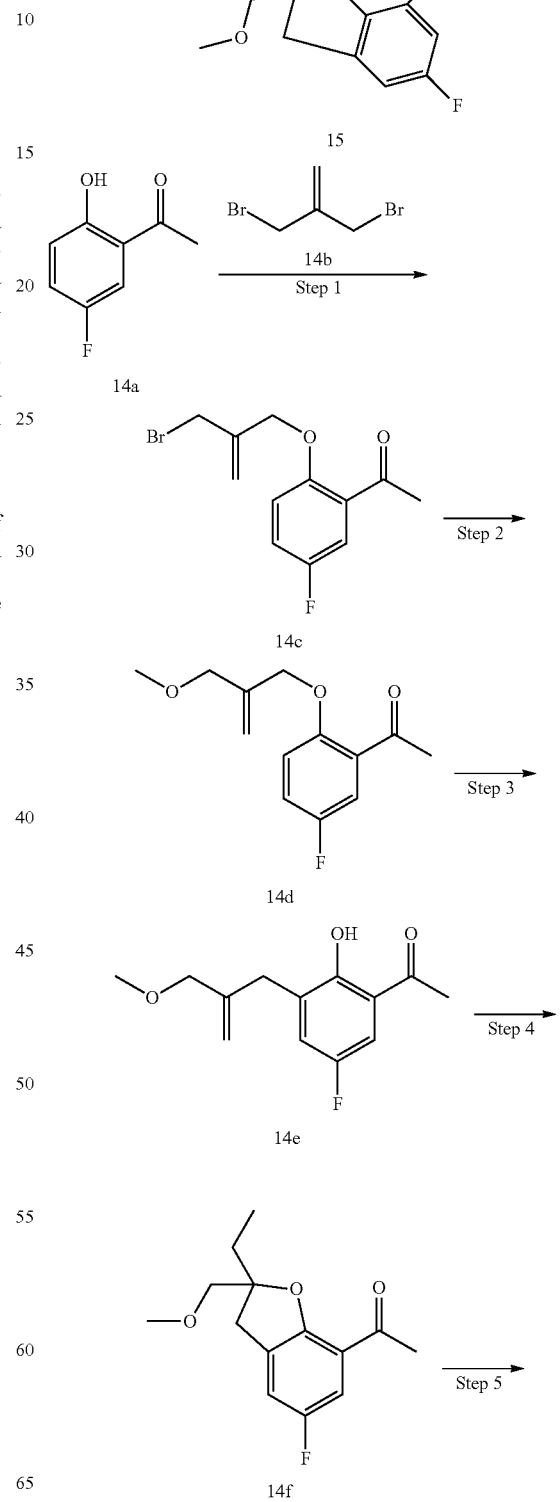

135
-continued
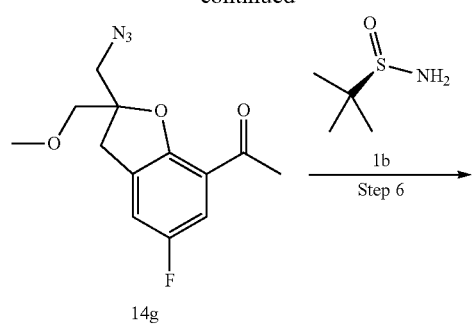
14g
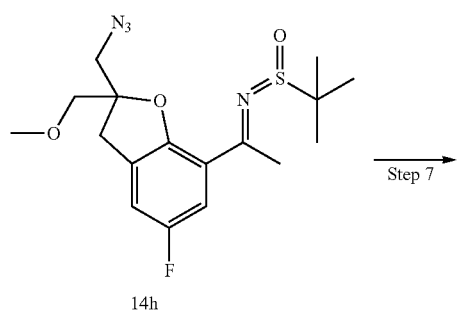
14h
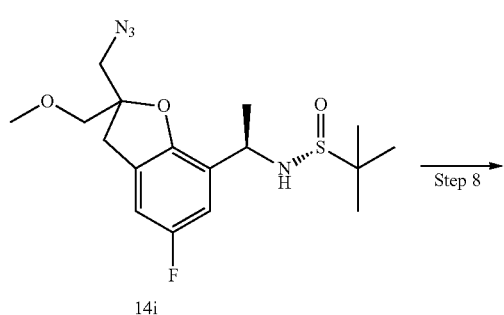
14i
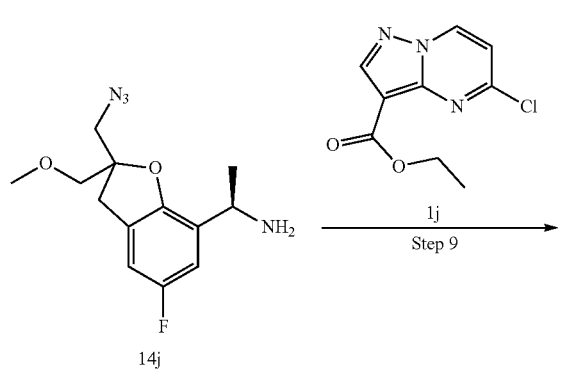
14j
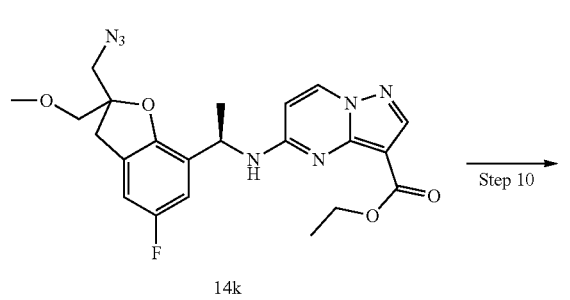
14k
136
-continued
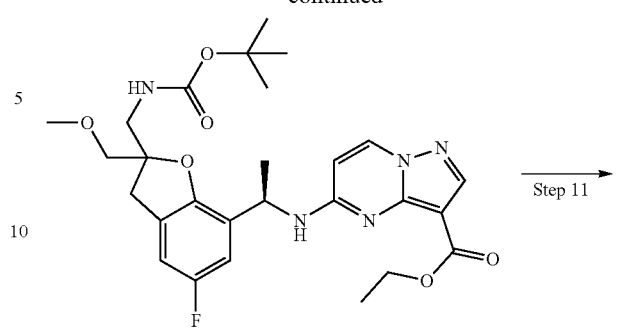
14l
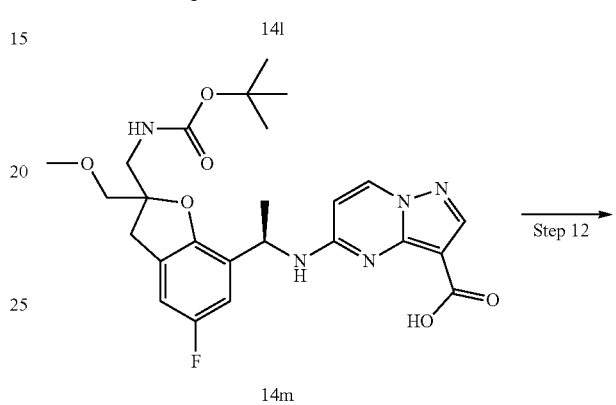
14m
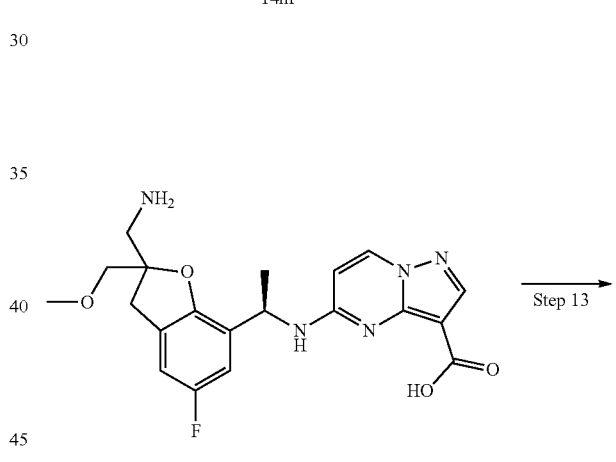
14n
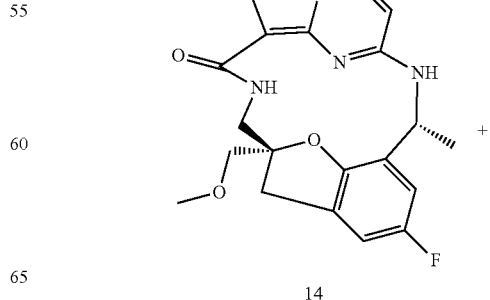
14

-continued

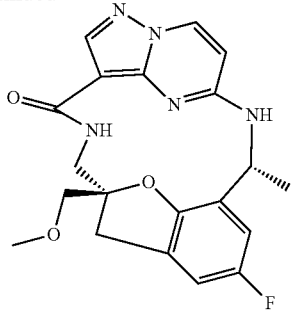

Step 1

1-(2-((2-(bromomethyl)allyl)oxy)-5-fluorophenyl)ethan-1-one 3-bromo-2-(bromomethyl)prop-1-ene 14b (4.28 g, 20 mmol) and potassium carbonate (1.66 g, 12 mmol) were dissolved in 40 mL of N,N-dimethylformamide; 1-(5-fluoro-2-hydroxyphenyl)ethan-1-one 14a (1.54 g, 10 mmol) was dissolved in 15 mL of N,N-dimethylformamide, and then dropwise added in the above-mentioned mixed solution, and reacted at room temperature overnight. After the reaction was completed, the reaction solution was added with 100 mL of water, and extracted with ethyl acetate (50 mL×3), and organic phases were combined, washed with saturated brine (200 mL), dried with anhydrous sodium sulfate, filtered, and concentrated under reduced pressure. The obtained residue was purified by silica gel column chromatography (eluent: system A) to obtain 1-(2-((2-(bromomethyl)allyl)oxy)-5-fluorophenyl)ethan-1-one 14c (1.8 g, grey liquid) with a yield of 62.5%.

MS m/z(ESI): 287.1 [M+1]

Step 2

1-(5-fluoro-2-((2-(methoxymethyl)allyl)oxy)phenyl)ethan-1-one 1-(2-((2-(bromomethyl)allyl)oxy)-5-fluorophenyl)ethan-1-one 14c (1.8 g, 6.29 mmol) was dissolved in 20 mL of methanol, added with sodium methanolate (1.37 g, 25.16 mmol), and reacted at room temperature overnight. After the reaction was completed, the reaction solution was concentrated under reduced pressure, added with 100 mL of water for dissolution, and extracted with ethyl acetate (50 mL×3), then organic phases were combined, washed with saturated brine (200 mL), dried with anhydrous sodium sulfate, filtered, and concentrated under reduced pressure. The obtained residue was purified by silica gel column chromatography (eluent: system A) to obtain 1-(5-fluoro-2-((2-(methoxymethyl)allyl)oxy)phenyl)ethan-1-one 14d (1.1 g, yellow oily substance) with a yield of 73.8%.

MS m/z(ESI): 239.1[M+1]

Step 3

1-(5-fluoro-2-hydroxy-3-(2-(methoxymethyl)allyl)phenyl)ethan-1-one 1-(5-fluoro-2-((2-(methoxymethyl)allyl)oxy)phenyl)ethan-1-one 14d (1.1 g, 4.6 mmol) was heated to 220° C., and then stirred and reacted for 8 hours. After the reaction was completed, the reaction solution was cooled to room temperature to obtain crude product of 1-(5-fluoro-2-hydroxy-3-(2-(methoxymethyl)allyl)phenyl)ethan-1-one 14e (1.1 g, brown viscous substance), which was directly used for the next reaction without purification.

MS m/z(ESI): 239.1[M+1]

Step 4

1-(5-fluoro-2-(iodomethyl)-2-(methoxymethyl)-2,3-dihydrobenzofuran-7-yl)ethan-1-one 1-(5-fluoro-2-hydroxy-3-(2-(methoxymethyl)allyl)phenyl)ethan-1-one 14e (1.1 g, 4.6 mmol) was dissolved in 10 mL of acetonitrile, added with iodine (2.34 g, 9.2 mmol) and sodium bicarbonate (1.55 g, 18.4 mmol), and reacted at room temperature overnight. After the reaction was completed, the reaction solution was added with 100 mL of water, and then slowly added with sodium thiosulfate solid, and stirred for dissolution until the color of the solution was no longer light, then the solution was extracted with ethyl acetate (50 mL×3), then organic phases were combined, washed with 100 mL of saturated brine, dried with anhydrous sodium sulfate, filtered, and concentrated under reduced pressure. The obtained residue was purified by silica gel column chromatography (eluent: system A) to obtain 1-(5-fluoro-2-(iodomethyl)-2-(methoxymethyl)-2,3-dihydrobenzofuran-7-yl)ethan-1-one 14f (1.4 g, brown viscous substance) with a yield of 83.6%.

MS m/z(ESI): 365.0 [M+1]

Step 5

1-(2-(azidomethyl)-5-fluoro-2-(methoxymethyl)-2,3-dihydrobenzofuran-7-yl)ethan-1-one 1-(5-fluoro-2-(iodomethyl)-2-(methoxymethyl)-2,3-dihydrobenzofuran-7-yl)ethan-1-one 14f (1.4 g, 3.84 mmol) was dissolved in 15 mL of N,N-dimethylformamide, added with sodium azide (500 mg, 7.69 mmol), heated to 60° C., and then reacted overnight. After the reaction was completed, the reaction solution was cooled to room temperature and poured into 100 mL of water, and extracted with ethyl acetate (50 mL×3), then organic phases were combined, washed with 100 mL of saturated brine, dried with anhydrous sodium sulfate, filtered, and concentrated under reduced pressure. The obtained residue was purified by silica gel column chromatography (eluent: system A) to obtain 1-(2-(azidomethyl)-5-fluoro-2-(methoxymethyl)-2,3-dihydrobenzofuran-7-yl)ethan-1-one 14g (430 mg, yellow viscous substance) with a yield of 41.2%.

MS m/z(ESI): 280.1 [M+1]

Step 6

(R)—N-((E)-1-(2-(azidomethyl)-5-fluoro-2-(methoxymethyl)-2,3-dihydrobenzofuran-7-yl)ethylidene)-2-methylpropane-2-sulfinamide 1-(2-(azidomethyl)-5-fluoro-2-(methoxymethyl)-2,3-dihydrobenzofuran-7-yl)ethan-1-one 14g (430 mg, 1.54 mmol) was dissolved in 10 mL of tetrahydrofuran, added with (R)-2-methylpropane-2-sulfinamide 1b (373 mg, 3.08 mmol) and tetraethyl titanate (1.41 g, 6.16 mmol) sequentially, then refluxed and reacted for 6 hours. After the reaction was completed, the reaction solution was cooled to room temperature, and concentrated under reduced pressure. The obtained residue was purified by silica gel column chromatography (eluent: system A) to obtain (R)—N-((E)-1-(2-(azidomethyl)-5-fluoro-2-(methoxymethyl)-2,3-dihydrobenzofuran-7-yl)ethylidene)-2-methylpropane-2-sulfinamide 14h (440 mg, yellow viscous substance) with a yield of 74.8%.

MS m/z(ESI): 383.2 [M+1]

Step 7

(R)—N-((1R)-1-(2-(azidomethyl)-5-fluoro-2-(methoxymethyl)-2,3-dihydrobenzofuran-7-yl)ethyl)-2-methylpropane-2-sulfinamide (R)—N-((E)-1-(2-(azidomethyl)-5-fluoro-2-(methoxymethyl)-2,3-dihydrobenzofuran-7-yl)ethylidene)-2-methylpropane-2-sulfinamide 14h (440 mg, 1.15 mmol) was dissolved in 5 mL of tetrahydrofuran, and then added with 9-borabicyclo[3,3,1]-nonane (4.6 mL, 2.31 mmol, 0.5 mol/L), and reacted at room temperature overnight. After the reaction was completed, the reaction solution was quenched with 30 mL of methanol and concentrated under reduced pressure to obtain crude product of (R)—N-((1R)-1-(2-(azidomethyl)-5-fluoro-2-(methoxymethyl)-2,3-dihydrobenzofuran-7-yl)ethyl)-2-methylpropane-2-sulfinamide 14i (440 mg, yellow viscous substance), which was directly used for the next reaction.

MS m/z(ESI): 385.2 [M+1]

Step 8

(1R)-1-(2-(azidomethyl)-5-fluoro-2-(methoxymethyl)-2,3-dihydrobenzofuran-7-yl)ethan-1-amine (R)—N-((1R)-1-(2-(azidomethyl)-5-fluoro-2-(methoxymethyl)-2,3-dihydrobenzofuran-7-yl)ethyl)-2-methylpropane-2-sulfinamide 14i (440 mg, 1.15 mmol) was dissolved in 5 mL of dichloromethane, then added with 3 mL of hydrochloride 1,4-dioxane solution (4 mol/L), and reacted at room temperature for 1 hour. After the reaction was completed, the reaction solution was concentrated under reduced pressure to obtain crude product of (1R)-1-(2-(azidomethyl)-5-fluoro-2-(methoxymethyl)-2,3-dihydrobenzofuran-7-yl)ethan-1-amine 14j (320 mg, yellow viscous substance), which was directly used for the next reaction without purification.

MS m/z(ESI): 281.1 [M+1]

Step 9

Ethyl 5-(((1R)-1-(2-(azidomethyl)-5-fluoro-2-(methoxymethyl)-2,3-dihydrobenzofuran-7-yl)ethyl)amino)pyrazolo[1,5-a]pyrimidine-3-carboxylate (1R)-1-(2-(azidomethyl)-5-fluoro-2-(methoxymethyl)-2,3-dihydrobenzofuran-7-yl)ethan-1-amine 14j (320 mg, 1.14 mmol) and ethyl 5-chloropyrazolo[1,5-a]pyrimidine-3-carboxylate 1j (257 mg, 1.14 mmol) were dissolved in 5 mL of n-butanol, added with N,N-diisopropylethylamine (1.18 g, 9.12 mmol), heated to 135° C., and reacted for 6 hours. After the reaction was completed, the reaction solution was cooled to room temperature, and concentrated under reduced pressure. The obtained residue was purified by silica gel column chromatography (eluent: system A) to obtain ethyl 5-(((1R)-1-(2-(azidomethyl)-5-fluoro-2-(methoxymethyl)-2,3-dihydrobenzofuran-7-yl)ethyl)amino)pyrazolo[1,5-a]pyrimidine-3-carboxylate 14k (170 mg, yellow viscous substance) with a yield of 31.8%.

MS m/z(ESI): 470.3 [M+1]

Step 10

Ethyl 5-(((1R)-1-(2-(((tert-butoxycarbonyl)amino)methyl)-5-fluoro-2-(methoxymethyl)-2,3-dihydrobenzofuran-7-yl)ethyl)amino)pyrazolo[1,5-a]pyrimidine-3-carboxylate Ethyl 5-(((1R)-1-(2-(azidomethyl)-5-fluoro-2-(methoxymethyl)-2,3-dihydrobenzofuran-7-yl)ethyl)amino)pyrazolo[1,5-a]pyrimidine-3-carboxylate 14k (170 mg, 0.36 mmol) was dissolved in 5 mL of methanol, and then added with di-tert-butyl dicarbonate (97 mg, 0.44 mmol) and 10% palladium carbon (50 mg, containing 50% of water) in turn, hydrogen gas was replaced for three times, and a hydrogen balloon was inserted to react at room temperature overnight. After the reaction was completed, the reaction solution was filtered, and the filtrate was concentrated under reduced pressure to obtain crude product of ethyl 5-(((1R)-1-(2-(((tert-butoxycarbonyl)amino)methyl)-5-fluoro-2-(methoxymethyl)-2,3-dihydrobenzofuran-7-yl)ethyl)amino)pyrazolo[1,5-a]pyrimidine-3-carboxylate 14l (197 mg, yellow viscous substance), which was directly used for the next reaction without purification.

MS m/z(ESI): 544.3 [M+1]

Step 11

5-(((1R)-1-(2-(((tert-butoxycarbonyl)amino)methyl)-5-fluoro-2-(methoxymethyl)-2,3-dihydrobenzofuran-7-yl)ethyl)amino)pyrazolo[1,5-a]pyrimidine-3-carboxylic acid Ethyl 5-(((1R)-1-(2-(((tert-butoxycarbonyl)amino)methyl)-5-fluoro-2-(methoxymethyl)-2,3-dihydrobenzofuran-7-yl)ethyl)amino)pyrazolo[1,5-a]pyrimidine-3-carboxylate 14l (197 mg, 0.36 mmol) was dissolved in 7 mL of mixed solvent of ethanol, tetrahydrofuran and water (V:V:V=5:1:1), added with lithium hydroxide monohydrate (152 mg, 3.6 mmol), heated to 90° C., and reacted for 5 hours. After the reaction was completed, the reaction solution was concentrated under reduced pressure to remove ethanol and tetrahydrofuran, then added with 20 mL of water, and adjusted to acidity with 1.0 M diluted hydrochloric acid, and extracted with ethyl acetate (15 mL×3), then organic phases were combined, washed with 50 mL of saturated brine, dried with anhydrous sodium sulfate, filtered, and concentrated under reduced pressure to obtain crude product of 5-(((1R)-1-(2-(((tert-butoxycarbonyl)amino)methyl)-5-fluoro-2-(methoxymethyl)-2,3-dihydrobenzofuran-7-yl)ethyl)amino)pyrazolo[1,5-a]pyrimidine-3-carboxylic acid 14m (187 mg, yellow foam solid), which was directly used for the next reaction without purification.

MS m/z(ESI): 516.2 [M+1]

Step 12

5-(((1R)-1-(2-(aminomethyl)-5-fluoro-2-(methoxymethyl)-2,3-dihydrobenzofuran-7-yl)ethyl)amino)pyrazolo[1,5-a]pyrimidine-3-carboxylic acid 5-(((1R)-1-(2-(((tert-butoxycarbonyl)amino)methyl)-5-fluoro-2-(methoxymethyl)-2,3-dihydrobenzofuran-7-yl)

ethyl)amino)pyrazolo[1,5-a]pyrimidine-3-carboxylic acid 14m (187 mg, 0.36 mmol) was dissolved in 1 mL of dichloromethane, and then added with 3 mL of hydrochloride 1,4-dioxane solution (4 mol/L), and reacted at room temperature for 1 hour. After the reaction was completed, the reaction was concentrated under reduced pressure to obtain crude product of 5-(((1R)-1-(2-(aminomethyl)-5-fluoro-2-(methoxymethyl)-2,3-dihydrobenzofuran-7-yl)ethyl)amino)pyrazolo[1,5-a]pyrimidine-3-carboxylic acid 14n (151 mg), which was directly used for the next reaction without purification.

MS m/z(ESI): 416.2[M+1]

Step 13

(3R,11S)-6-fluoro-11-(methoxymethyl)-3-methyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 14

(3R,11R)-6-fluoro-11-(methoxymethyl)-3-methyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 15

5-(((1R)-1-(2-(aminomethyl)-5-fluoro-2-(methoxymethyl)-2,3-dihydrobenzofuran-7-yl)ethyl)amino)pyrazolo[1,5-a]pyrimidine-3-carboxylic acid 14n (151 mg, 0.36 mmol), pentafluorophenyl diphenyl phosphinate (167 mg, 0.44 mmol) and N,N-diisopropylethylamine (374 mg, 2.93 mmol) were dissolved in 4 mL of mixed solvent of dichloromethane and N,N-dimethylformamide (V:V=3:1), and reacted at room temperature overnight. After the reaction was completed, the reaction solution was added with 50 mL of saturated aqueous ammonium chloride solution and extracted with dichloromethane (30 mL×3), and then organic phases were combined, dried with anhydrous sodium sulfate, filtered, and concentrated under reduced pressure. (3R,11S)-6-fluoro-11-(methoxymethyl)-3-methyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 14 (3.85 mg) with a yield of 2.7% and (3R,11R)-6-fluoro-11-(methoxymethyl)-3-methyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 15 (30 mg) with a yield of 21% were obtained by preparing a liquid phase (separation column AKZONOBEL Kromasil; 250×21.2 mm I.D.; 5 μm, 50 mL/min; mobile phase A: 0.05% TFA+H$_2$O, and mobile phase B: CH$_3$CN) from the obtained residue.

14

MS m/z(ESI): 398.2[M+1]

$^1$H NMR (400 MHz, DMSO-d$_6$) δ 8.66 (d, J=7.6 Hz, 1H), 8.37 (d, J=8.0 Hz, 1H), 8.09 (s, 1H), 7.94 (d, J=9.5 Hz, 1H), 7.03 (d, J=8.0 Hz, 1H), 6.66 (d, J=10.4 Hz, 1H), 6.60 (d, J=7.5 Hz, 1H), 5.48 (t, J=7.3 Hz, 1H), 3.76-3.60 (m, 1H), 3.14 (d, J=14.0 Hz, 2H), 3.03 (s, 1H), 2.99 (s, 1H), 2.92 (s, 3H), 2.73 (s, 1H), 1.56 (d, J=6.9 Hz, 3H).

15

MS m/z(ESI): 398.2[M+1]

$^1$H NMR (400 MHz, DMSO-d$_6$) δ 8.89 (d, J=9.3 Hz, 1H), 8.62 (d, J=4.9 Hz, 1H), 8.54 (d, J=7.6 Hz, 1H), 8.00 (s, 1H), 6.82 (dd, J=8.2, 2.6 Hz, 1H), 6.74 (dd, J=10.1, 2.7 Hz, 1H), 6.37 (d, J=7.6 Hz, 1H), 4.95 (t, J=6.8 Hz, 1H), 3.78-3.68 (m, 1H), 3.67-3.58 (m, 2H), 3.46 (s, 1H), 3.36 (s, 3H), 3.28 (d, J=13.1 Hz, 1H), 2.89 (d, J=16.8 Hz, 1H), 1.54 (d, J=7.0 Hz, 3H).

Example 16

(3R)-6-bromo-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one

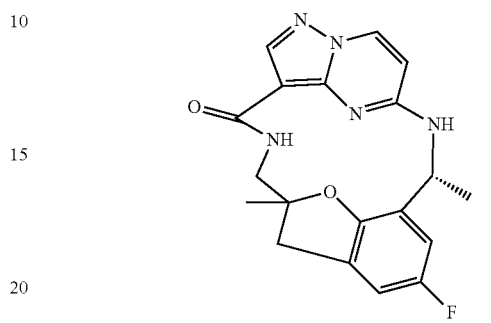

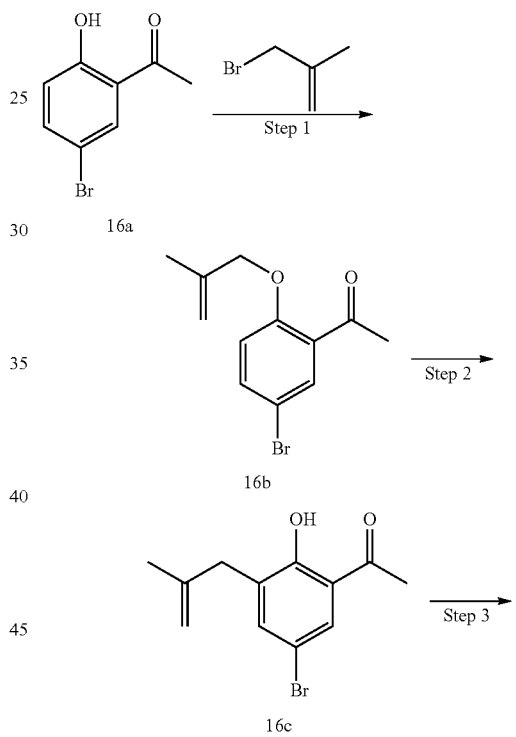

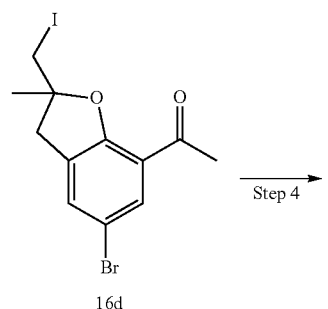

-continued
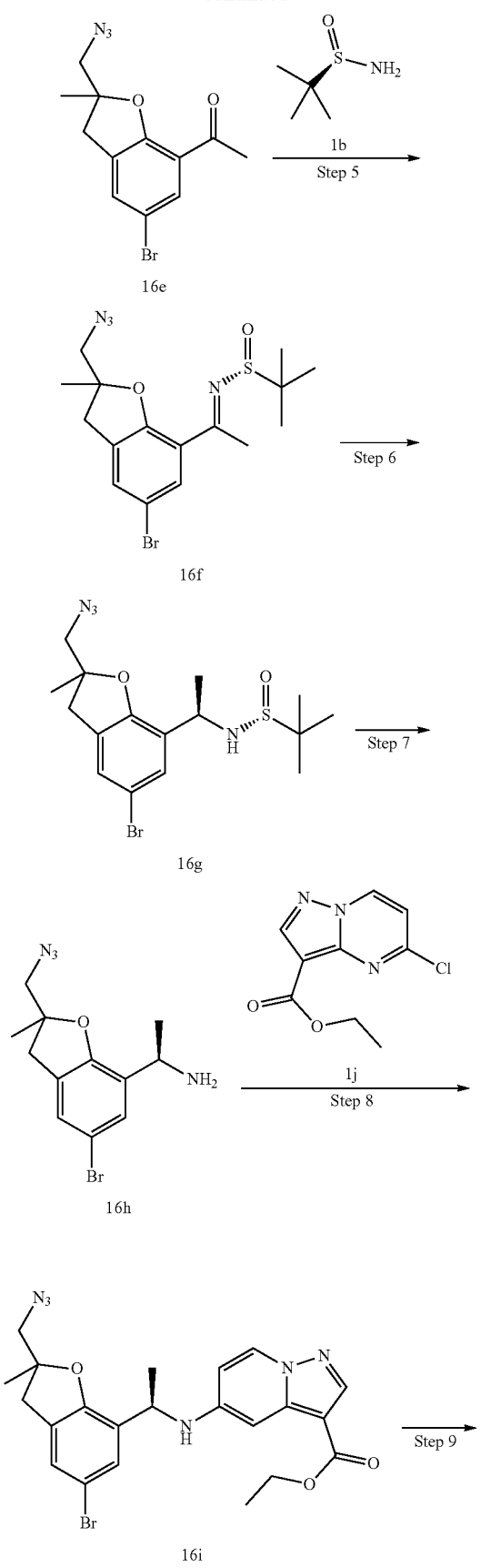
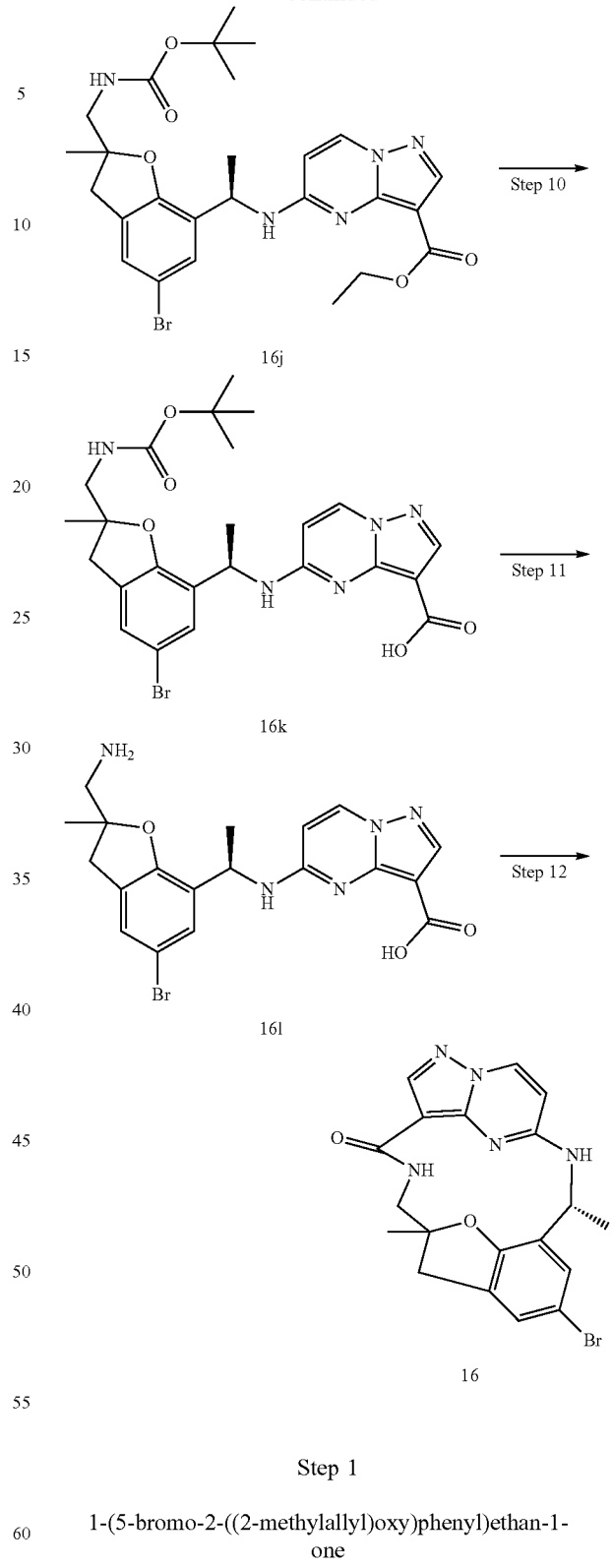
Step 1
1-(5-bromo-2-((2-methylallyl)oxy)phenyl)ethan-1-one
1-(5-bromo-2-hydroxyphenyl)ethan-1-one 16a (10 g, 46.5 mmol) was dissolved in 100 ml of N,N-dimethylformamide, then added with 3-bromo-2-methylpropene (7.53 g, 55.8 mmol) and potassium carbonate (12.8 g, 93 mmol) sequentially, and reacted at room temperature overnight.

After the reaction was completed, the reaction solution was added with 200 mL of water and extracted with ethyl acetate (100 mL), the organic phases were combined, washed with saturated brine (100 mL×2), dried with anhydrous sodium sulfate, filtered, and concentrated under reduced pressure to obtain crude product of 1-(5-bromo-2-((2-methylallyl)oxy) phenyl)ethan-1-one 16b (12.46 g, yellow oily substance), and the product was directly used for the next reaction without further purification.

MS m/z(ESI): 269.0 [M+1]

Step 2

1-(5-bromo-2-hydroxy-3-(2-methylallyl)phenyl) ethan-1-one 1-(5-bromo-2-((2-methylallyl)oxy)phenyl)ethan-1-one 16b (12.46 g, 46.5 mmol) was heated to 220° C., stirred and reacted for 6 hours. After the reaction was completed, the reaction solution was cooled to room temperature, and then added with 100 mL of dichloromethane for dissolution, and concentrated under reduced pressure. The obtained residue was purified by silica gel column chromatography (eluent: system A) to obtain 1-(5-bromo-2-hydroxy-3-(2-methylallyl)phenyl)ethan-1-one 16c (6.97 g, red oily substance) with a yield of 56%.

MS m/z(ESI): 268.9 [M+1]

Step 3

1-(5-bromo-2-(iodomethyl)-2-methyl-2,3-dihydrobenzofuran-7-yl)ethan-1-one 1-(5-bromo-2-hydroxy-3-(2-methylallyl)phenyl)ethan-1-one 16c (11 g, 41 mmol) was dissolved in 200 mL of acetonitrile, added with iodine (20.8 g, 82 mmol) and sodium bicarbonate (13.8 g, 164 mmol), and reacted at room temperature overnight. After the reaction was completed, the reaction solution was concentrated under reduced pressure, and the residue was added with 200 mL of ethyl acetate for dissolution, then washed with 25% saturated sodium bisulfite solution (100 mL×2) and saturated brine (100 mL×2) sequentially, dried with anhydrous sodium sulfate, filtered, and concentrated under reduced pressure. The obtained residue was purified by silica gel column chromatography (eluent: system A) to obtain 1-(5-bromo-2-(iodomethyl)-2-methyl-2,3-dihydrobenzofuran-7-yl)ethan-1-one 16d (15 g, white solid) with a yield of 92.6%.

MS m/z(ESI): 394.5 [M+1]

Step 4

1-(2-(azidomethyl)-5-bromo-2-methyl-2,3-dihydrobenzofuran-7-yl)ethan-1-one 1-(5-bromo-2-(iodomethyl)-2-methyl-2,3-dihydrobenzofuran-7-yl)ethan-1-one 16d (6.4 g, 16.2 mmol) was dissolved in 50 mL of N,N-dimethylformamide, added with sodium azide (2.1 g, 32.4 mmol), heated to 95° C., and then reacted overnight. After the reaction was completed, the reaction solution was cooled to room temperature, then added with 100 mL of water and extracted with ethyl acetate (50 mL×3), then organic phases were combined, washed with saturated brine (50 mL×3), dried with anhydrous sodium sulfate, filtered, and concentrated under reduced pressure. The obtained residue was purified by silica gel column chromatography (eluent: system A) to obtain 1-(2-(azidomethyl)-5-bromo-2-methyl-2,3-dihydrobenzofuran-7-yl)ethan-1-one 16e (3.97 g, white solid) with a yield of 79.4%.

MS m/z(ESI): 310.9 [M+1]

Step 5

(R)—N-((E)-1-(2-(azidomethyl)-5-bromo-2-methyl-2,3-dihydrobenzofuran-7-yl)ethylidene)-2-methyl-propane-2-sulfinamide 1-(2-(azidomethyl)-5-bromo-2-methyl-2,3-dihydrobenzofuran-7-yl)ethan-1-one 16e (3.97 g, 12.8 mmol) was dissolved in 50 mL of tetrahydrofuran, added with (R)-2-methylpropane-2-sulfinamide 1b (3.1 g, 25.6 mmol) and tetraethyl titanate (11.67 g, 51.2 mmol) sequentially, then reacted at 75° C. overnight. After the reaction was completed, the reaction solution was cooled to room temperature, added with 100 mL of water, a large amount of solids were precipitated, filtered. The filter cake was rinsed with 100 mL of ethyl acetate to obtain the filtrate, and then extracted with ethyl acetate (50 mL×3), and then organic phases were combined, dried with anhydrous sodium sulfate, filtered, and concentrated under reduced pressure. The obtained residue was purified by silica gel column chromatography (eluent: system A) to obtain (R)—N-((E)-1-(2-(azidomethyl)-5-bromo-2-methyl-2,3-dihydrobenzofuran-7-yl)ethylidene)-2-methylpropane-2-sulfinamide 16f (5.17 g, white solid) with a yield of 97.8%.

MS m/z(ESI): 413.0 [M+1]

Step 6

(R)—N-((1R)-1-(2-(azidomethyl)-5-bromo-2-methyl-2,3-dihydrobenzofuran-7-yl)ethyl)-2-methyl-propane-2-sulfinamide (R)—N-((E)-1-(2-(azidomethyl)-5-bromo-2-methyl-2,3-dihydrobenzofuran-7-yl)ethylidene)-2-methylpropane-2-sulfinamide 16f (5.17 g, 12.5 mmol) was dissolved in 100 mL of tetrahydrofuran, and then dropwise added with 9-borabicyclo[3,3,1]-nonane (50 mL, 25 mmol, 0.5 mol/L), and reacted at room temperature overnight. After the reaction was completed, the reaction solution was quenched with 100 mL of methanol and concentrated under reduced pressure to obtain (R)—N-((1R)-1-(2-(azidomethyl)-5-bromo-2-methyl-2,3-dihydrobenzofuran-7-yl)ethyl)-2-methylpropane-2-sulfinamide 16g (4.5 g, white solid) with a yield of 86.7%.

MS m/z(ESI): 415.0 [M+1]

Step 7

(1R)-1-(2-(azidomethyl)-5-bromo-2-methyl-2,3-dihydrobenzofuran-7-yl)ethan-1-amine (R)—N-((1R)-1-(2-(azidomethyl)-5-bromo-2-methyl-2,3-dihydrobenzofuran-7-yl)ethyl)-2-methylpropane-2-sulfinamide 16g (4.5 g, 10.8 mmol) was dissolved in 40 mL of dichloromethane, then added with 10 mL of hydrochloride 1,4-dioxane solution (4 mol/L), and reacted at room temperature overnight. After the reaction was completed, the reaction solution was concentrated under reduced pressure to obtain (1R)-1-(2-(azidomethyl)-5-bromo-2-methyl-2,3-dihydrobenzofuran-7-yl)ethan-1-amine 16h (3.36 g, white solid) with a yield of 100%.

MS m/z(ESI): 294.0[M−16]

Step 8

Ethyl 5-(((1R)-1-(2-(azidomethyl)-5-bromo-2-methyl-2,3-dihydrobenzofuran-7-yl)ethyl)amino)pyrazolo[1,5-a]pyrimidine-3-carboxylate (1R)-1-(2-(azidomethyl)-5-bromo-2-methyl-2,3-dihydrobenzofuran-7-yl)ethan-1-amine 16h (3.36 g, 10.8 mmol) and ethyl 5-chloropyrazolo[1,5-a]pyrimidine-3-carboxylate 1j (2.67 g, 11.8 mmol) were dissolved in 60 mL of n-butanol, and then added with N,N-diisopropylethylamine (15 mL, 86.4 mmol), heated to 125° C., and reacted for 5 hours. After the reaction was completed, the reaction solution was concentrated under reduced pressure. The obtained residue was purified by silica gel column chromatography (eluent: system A) to obtain ethyl 5-(((1R)-1-(2-(azidomethyl)-5-bromo-2-methyl-2,3-dihydrobenzofuran-7-yl)ethyl)amino)pyrazolo[1,5-a]pyrimidine-3-carboxylate 16i (4.5 g, white solid) with a yield of 83.3%.

MS m/z(ESI): 501.1 [M+1]

Step 9

Ethyl 5-(((1R)-1-(5-bromo-2-(((tert-butoxycarbonyl)amino)methyl)-2-methyl-2,3-dihydrobenzofuran-7-yl)ethyl)amino)pyrazolo[1,5-a]pyrimidine-3-carboxylate Ethyl 5-(((1R)-1-(2-(azidomethyl)-5-bromo-2-methyl-2,3-dihydrobenzofuran-7-yl)ethyl)amino)pyrazolo[1,5-a]pyrimidine-3-carboxylate 16i (3.19 mg, 6.38 mmol) was dissolved in 25 mL of methanol, added with triphenylphosphine (2.5 g, 9.57 mmol), and reacted at 80° C. for 1.5 hours. After the reaction was completed, the reaction solution was concentrated under reduced pressure, added with 50 mL of ethyl acetate for dilution, and then the pH value was adjusted to 4 with 1.0 M diluted hydrochloric acid. The reaction solution was separated to collect aqueous phases, and the pH value was adjusted to 10 with 25% aqueous sodium hydroxide, then the reaction solution was extracted with ethyl acetate (100 mL×3), and organic phases were combined, washed with saturated brine (100 mL), dried with anhydrous sodium sulfate, filtered, and concentrated under reduced pressure. The obtained residue was dissolved in 100 mL of dichloromethane, added with di-tert-butyl dicarbonate (2.09 g, 9.57 mmol) and triethylamine (1.3 g, 12.76 mmol), and reacted at room temperature overnight. After the reaction was completed, the reaction solution was concentrated under reduced pressure. The obtained residue was purified by silica gel column chromatography (eluent: system A) to obtain ethyl 5-(((1R)-1-(5-bromo-2-(((tert-butoxycarbonyl)amino)methyl)-2-methyl-2,3-dihydrobenzofuran-7-yl)ethyl)amino)pyrazolo[1,5-a]pyrimidine-3-carboxylate 16j (2.776 g, white solid) with a yield of 76%.

MS m/z(ESI): 473.9[M−100]

Step 10

5-(((1R)-1-(5-bromo-(((tert-butoxycarbonyl)amino)methyl)-2-methyl-2,3-dihydrobenzofuran-7-yl)ethyl)amino)pyrazolo[1,5-a]pyrimidine-3-carboxylic acid Ethyl 5-(((1R)-1-(5-bromo-2-(((tert-butoxycarbonyl)amino)methyl)-2-methyl-2,3-dihydrobenzofuran-7-yl)ethyl)amino)pyrazolo[1,5-a]pyrimidine-3-carboxylate 16j (450 mg, 0.78 mmol) was dissolved in 5 mL of mixed solvent of ethanol, tetrahydrofuran and water (V:V:V=2:2:1), added with lithium hydroxide monohydrate (238 mg, 6.28 mmol), heated to 80° C., and reacted for 2 hours. After the reaction was completed, the reaction solution was cooled to room temperature and concentrated under reduced pressure to remove ethanol and tetrahydrofuran, then added with 20 mL of water, and adjusted to acidity with 1.0 M diluted hydrochloric acid, and extracted with ethyl acetate (20 mL×3), then organic phases were combined, washed with 20 mL of saturated brine, dried with anhydrous sodium sulfate, filtered, and concentrated under reduced pressure to obtain crude product of 5-(((1R)-1-(5-bromo-(((tert-butoxycarbonyl)amino)methyl)-2-methyl-2,3-dihydrobenzofuran-7-yl)ethyl)amino)pyrazolo[1,5-a]pyrimidine-3-carboxylic acid 16k (426 mg, white solid), which was directly used for the next reaction without purification.

MS m/z(ESI): 545.9 [M+1]

Step 11

5-(((1R)-1-(2-(aminomethyl)-5-bromo-2-methyl-2,3-dihydrobenzofuran-7-yl)ethyl)amino)pyrazolo[1,5-a]pyrimidine-3-carboxylic acid 5-(((1R)-1-(5-bromo-(((tert-butoxycarbonyl)amino)methyl)-2-methyl-2,3-dihydrobenzofuran-7-yl)ethyl)amino)pyrazolo[1,5-a]pyrimidine-3-carboxylic acid 16k (426 mg, 0.78 mmol) was dissolved in 5 mL of dichloromethane, and then added with 0.5 mL of hydrochloride 1,4-dioxane solution (4 mol/L), and reacted at room temperature for 2 hours. After the reaction was completed, the reaction solution was concentrated under reduced pressure to obtain crude product of 5-(((1R)-1-(2-(aminomethyl)-5-bromo-2-methyl-2,3-dihydrobenzofuran-7-yl)ethyl)amino)pyrazolo[1,5-a]pyrimidine-3-carboxylic acid 16l (348 mg, white solid), which was directly used for the next reaction without purification.

MS m/z(ESI): 445.9[M+1]

Step 12

(3R)-6-bromo-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 5-(((1R)-1-(2-(aminomethyl)-5-bromo-2-methyl-2,3-dihydrobenzofuran-7-yl)ethyl)amino)pyrazolo[1,5-a]pyrimidine-3-carboxylic acid 16l (348 mg, 0.78 mmol), pentafluorophenyl diphenyl phosphinate (360 mg, 0.94 mmol) and N,N-diisopropylethylamine (805 mg, 6.24 mmol) were dissolved in 6 mL of mixed solvent of dichloromethane and N,N-dimethylformamide (V:V=1:1), and reacted at room temperature overnight. After the reaction was completed, the reaction solution was added with 10 mL of water and extracted with ethyl acetate (10 mL×3), and then organic phases were combined, washed with saturated brine (10 mL), dried with anhydrous sodium sulfate, filtered, and concentrated under reduced pressure. (3R)-6-bromo-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 16 (100 mg) with a yield of 29.9% was obtained by preparing a liquid phase (separation column AKZONOBEL Kromasil; 250×21.2 mm I.D.; 5 μm, 10 mL/min; mobile phase A: 0.05% TFA+H$_2$O, and mobile phase B: CH$_3$CN) from the obtained residue.

MS m/z(ESI): 427.9 [M+1]

$^1$H NMR (400 MHz, CDCl$_3$) δ 9.16-9.13 (d, J=12.0 Hz, 1H), 8.23-8.19 (m, 2H), 7.08 (s, 1H), 7.03 (s, 1H), 6.15-6.13 (d, J=8.0 Hz, 1H), 5.72 (s, 1H), 5.19-5.15 (m, 1H), 3.99-3.94 (m, 1H), 3.41-3.15 (m, 3H), 1.66-1.65 (m, 6H).

Example 17

(3R)-6-Cyano-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one

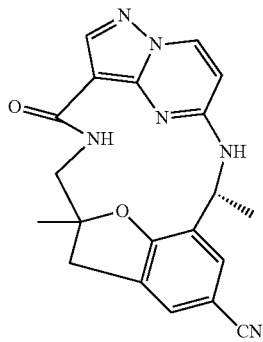

16

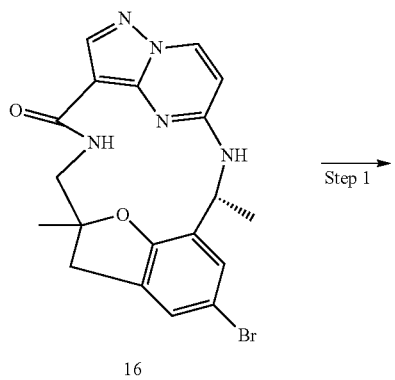

17

Step 1

(3R)-6-Cyano-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one (3R)-6-bromo-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 16 (45 mg, 0.105 mmol), zinc cyanide (62 mg, 0.525 mmol), zinc powder (0.7 mg, 0.0105 mmol), 1,1'-bis(diphenylphosphino)ferrocene (29 mg, 0.053 mmol) and tris(dibenzylideneacetone)dipalladium (19.2 mg, 0.021 mmol) were dissolved in 5 mL of N,N-dimethylaniline, and reacted at 130° C. for 3 hours. After the reaction was completed, the reaction solution was cooled to room temperature, added with 10 mL of water and extracted with ethyl acetate (10 mL×3), then organic phases were combined, washed with saturated brine (30 mL), dried with anhydrous sodium sulfate, filtered, and concentrated under reduced pressure. (3R)-6-Cyano-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 17 (10 mg) with a yield of 25.6% was obtained by preparing a liquid phase (separation column AKZONOBEL Kromasil; 250× 21.2 mm I.D.; 5 μm, 20 mL/min; mobile phase A: 0.05% TFA+H$_2$O, and mobile phase B: CH$_3$CN) from the obtained residue.

MS m/z(ESI): 375.0[M+1]

$^1$H NMR (400 MHz, CDCl$_3$) δ 9.02-9.00 (d, J=8.0 Hz, 1H), 8.22-8.18 (m, 2H), 7.36 (s, 1H), 7.21 (s, 1H), 6.19-6.17 (d, J=8.0 Hz, 1H), 6.03 (s, 1H), 5.23-5.19 (m, 11H), 4.13-4.10 (m, 1H), 3.43-3.29 (m, 3H), 1.69-1.66 (m, 6H).

Example 18

(3R)-6-fluoro-11-(fluoromethyl)-3-methyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one

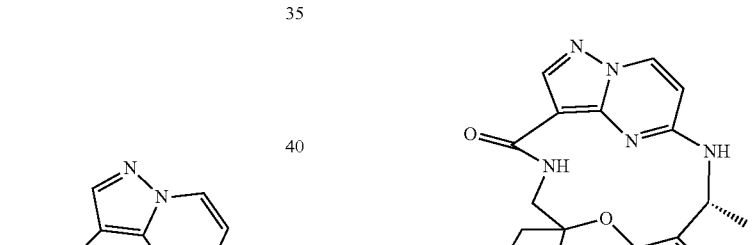

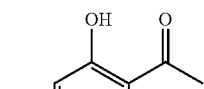
18a

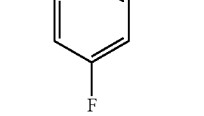
14a

18b

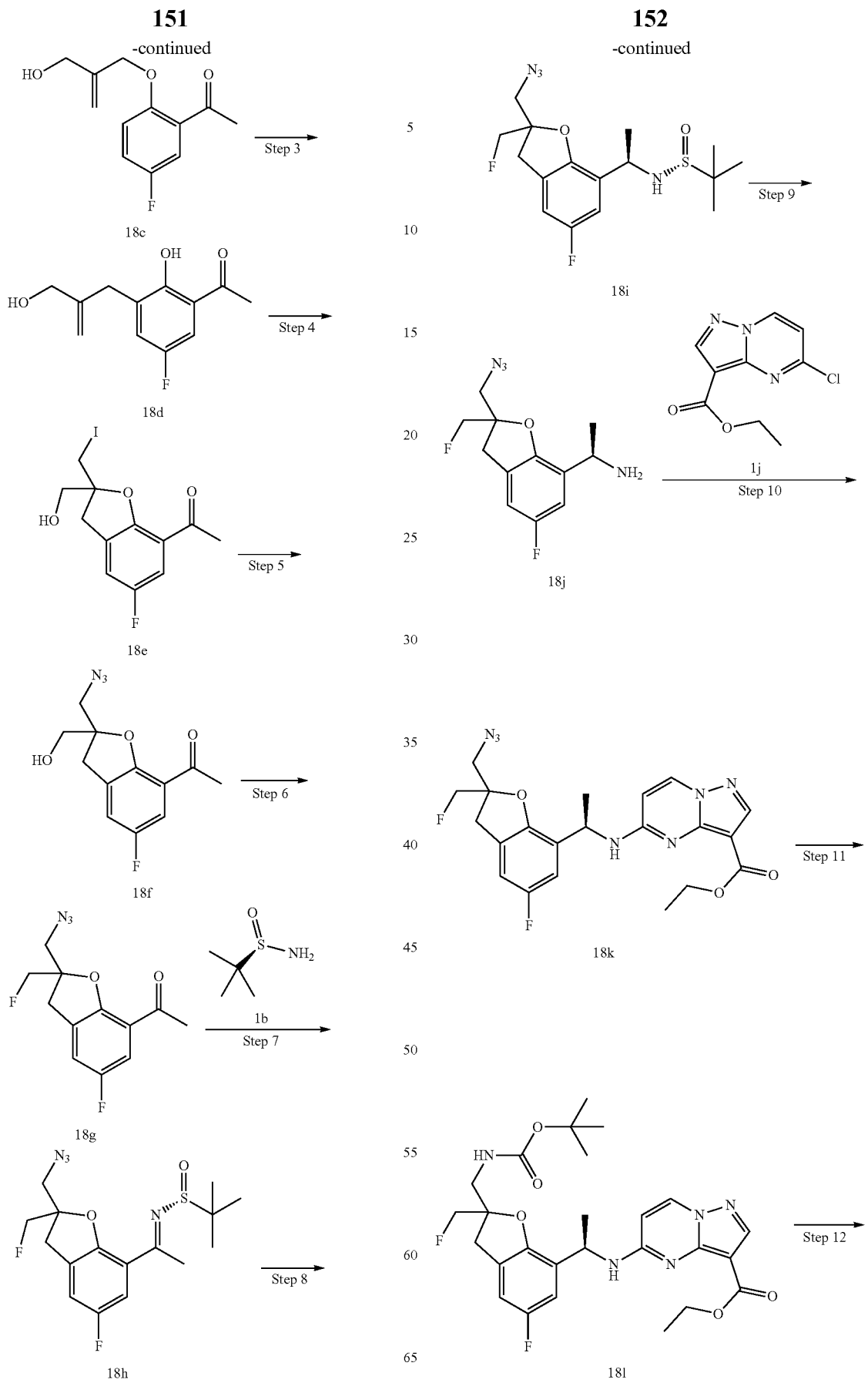

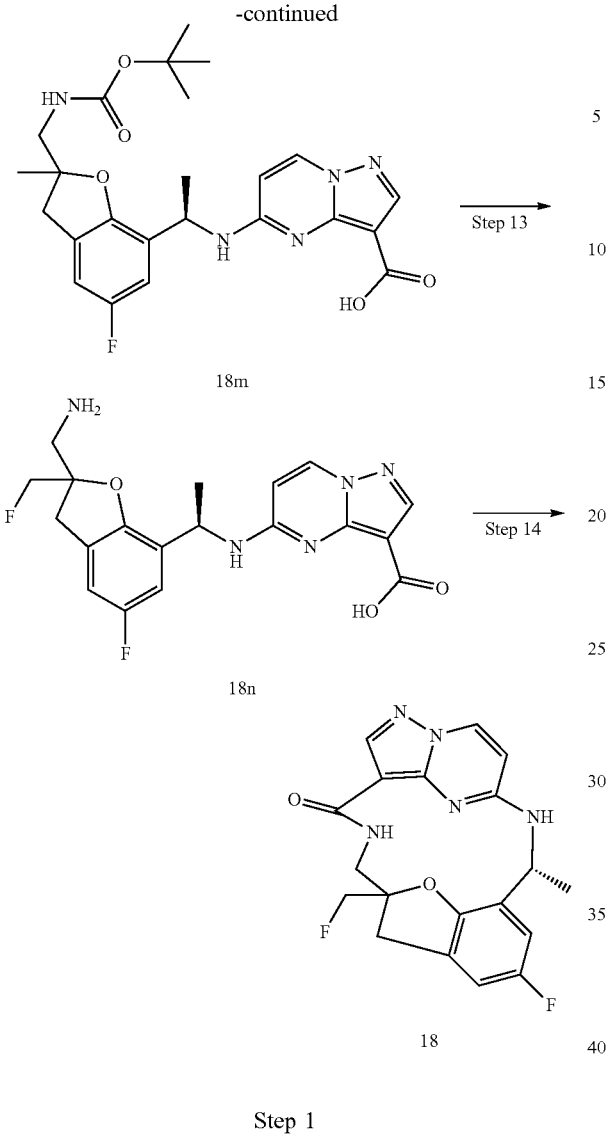

Step 1

5-methylene-1,3,2-dioxathiane-2-oxide 2-methylenepropane-1,3-diol 18a was dissolved in 100 mL of carbon tetrachloride, cooled to 0° C.; thionyl chloride (50.7 g, 426 mmol) was dissolved in 50 mL of carbon tetrachloride, and then dropwise added to the above solution at 0° C., and reacted at 0° C. for 1 hour. After the reaction was completed, the reaction solution was poured into 200 mL of ice water, and extracted with dichloromethane (100 mL×3), then organic phases were combined, washed with saturated brine (200 mL) and saturated sodium bicarbonate solution (200 mL) sequentially, dried with anhydrous sodium sulfate, filtered, and concentrated under reduced pressure to obtain 5-methylene-1,3,2-dioxathiane-2-oxide 18b (28.7 g, yellow liquid), which was directly used for the next reaction.

MS m/z(ESI): 135.0[M+1]

Step 2

1-(5-fluoro-2-((2-(hydroxymethyl)allyl)oxy)phenyl)ethan-1-one 1-(5-fluoro-2-hydroxyphenyl)ethan-1-one 14a (33.0 g, 214 mmol) was dissolved in 100 mL of N,N-dimethylformamide, cooled to 0° C., slowly added with sodium hydride (10.2 g, 256 mmol) in batches, stirred at 0° C. for 0.5 hour, and then dropwise added with 5-methylene-1,3,2-dioxathiane-2-oxide 18b (28.7 g, 214 mmol) at 0° C., then warmed up naturally to room temperature, heated to 50° C. and reacted for 1 hour, and then continuously heated to 100° C. and reacted overnight. After the reaction was completed, the reaction solution was cooled to room temperature. The reaction solution was poured into 300 mL of ice water, and extracted with ethyl acetate (200 mL×3), and then organic phases were combined, dried with anhydrous sodium sulfate, filtered, and concentrated under reduced pressure. The obtained residue was purified by silica gel column chromatography (eluent: system A) to obtain 1-(5-fluoro-2-((2-(hydroxymethyl)allyl)oxy)phenyl)ethan-1-one 18c (20 g, dark brown liquid) with a yield of 41.7%.

MS m/z(ESI): 225.2 [M+1]

Step 3

1-(5-fluoro-2-hydroxy-3-(2-(hydroxymethyl)allyl)phenyl)ethan-1-one 1-(5-fluoro-2-((2-(hydroxymethyl)allyl)oxy)phenyl)ethan-1-one 18c (20 g, 89.2 mmol) was heated to 220° C., and then stirred and reacted for 6 hours. After the reaction was completed, the reaction solution was cooled to room temperature, and then added with 100 mL of ethyl acetate for dissolution, and concentrated under reduced pressure. The obtained residue was purified by silica gel column chromatography (eluent: system A) to obtain 1-(5-fluoro-2-hydroxy-3-(2-(hydroxymethyl)allyl)phenyl)ethan-1-one 18d (5.5 g, yellow liquid) with a yield of 27.5%.

MS m/z(ESI): 225.2 [M+1]

Step 4

1-(5-fluoro-2-(hydroxymethyl)-2-(iodomethyl)-2,3-dihydrobenzofuran-7-yl)ethan-1-one 1-(5-fluoro-2-hydroxy-3-(2-(hydroxymethyl)allyl)phenyl)ethan-1-one 18d (5.5 g, 24.55 mmol) was dissolved in 55 mL of acetonitrile, added with iodine (12.4 g, 49.1 mmol) and sodium bicarbonate (8.24 g, 98.1 mmol), and reacted at room temperature overnight. After the reaction was completed, the reaction solution was added with 100 mL of water, and extracted with ethyl acetate (100 mL×3), organic phases were combined, washed with saturated sodium thiosulfate solution (200 mL×3) until the color of organic phases was no longer light, dried with anhydrous sodium sulfate, filtered, and concentrated under reduced pressure. The obtained residue was purified by silica gel column chromatography (eluent: system A) to obtain 1-(5-fluoro-2-(hydroxymethyl)-2-(iodomethyl)-2,3-dihydrobenzofuran-7-yl)ethan-1-one 18e (5.4 g, yellow solid) with a yield of 62.8%.

MS m/z(ESI): 351.1 [M+1]

Step 5

1-(2-(azidomethyl)-5-fluoro-2-(hydroxymethyl)-2,3-dihydrobenzofuran-7-yl)ethan-1-one 1-(5-fluoro-2-(hydroxymethyl)-2-(iodomethyl)-2,3-dihydrobenzofuran-7-yl)ethan-1-one 18e (5.4 g, 15.4 mmol) was dissolved in 50 mL of N,N-dimethylformamide, added with sodium azide (2.0 g, 30.8 mmol), heated to 85° C., and then reacted overnight. After the reaction was completed, the reaction solution was cooled to room temperature, added with 100 mL of water, and extracted with ethyl acetate (50 mL×3), then organic phases were combined, washed with saturated brine (100 mL×2), dried with anhydrous sodium sulfate, filtered, and concentrated under reduced pressure. The obtained residue was purified by silica gel column chromatography (eluent: system A) to obtain 1-(2-(azidomethyl)-5-fluoro-2-(hydroxymethyl)-2,3-dihydrobenzofuran-7-yl)ethan-1-one 18f (2.9 g, brown viscous substance) with a yield of 70.7%.

MS m/z(ESI): 266.0 [M+1]

Step 6

1-(2-(azidomethyl)-5-fluoro-2-(fluoromethyl)-2,3-dihydrobenzofuran-7-yl)ethan-1-one 1-(2-(azidomethyl)-5-fluoro-2-(hydroxymethyl)-2,3-dihydrobenzofuran-7-yl)ethan-1-one 18f (1 g, 3.77 mmol) was dissolved in 10 mL of dichloromethane, added with diethylaminosulfur trifluoride (728 mg, 4.5 mmol), refluxed and reacted overnight. After the reaction was completed, the reaction solution was cooled to room temperature, and concentrated under reduced pressure. The obtained residue was purified by silica gel column chromatography (eluent: system A) to obtain 1-(2-(azidomethyl)-5-fluoro-2-(fluoromethyl)-2,3-dihydrobenzofuran-7-yl)ethan-1-one 18g (440 mg, yellow liquid) with a yield of 44%.

MS m/z(ESI): 268.1 [M+1]

Step 7

(R)—N-((E)-1-(2-(azidomethyl)-5-fluoro-2-(fluoromethyl)-2,3-dihydrobenzofuran-7-yl)ethylidene)-2-methylpropane-2-sulfinamide 1-(2-(azidomethyl)-5-fluoro-2-(fluoromethyl)-2,3-dihydrobenzofuran-7-yl)ethan-1-one 18g (440 mg, 1.65 mmol) was dissolved in 10 mL of tetrahydrofuran, added with (R)-2-methylpropane-2-sulfinamide 1b (400 mg, 3.3 mmol) and tetraethyl titanate (1.51 g, 6.6 mmol) sequentially, then refluxed and reacted at 90° C. overnight. After the reaction was completed, the reaction solution was cooled to room temperature, and concentrated under reduced pressure. The obtained residue was purified by silica gel column chromatography (eluent: system A) to obtain (R)—N-((E)-1-(2-(azidomethyl)-5-fluoro-2-(fluoromethyl)-2,3-dihydrobenzofuran-7-yl)ethylidene)-2-methylpropane-2-sulfinamide 18h (420 mg, yellow viscous substance) with a yield of 68.9%.

MS m/z(ESI): 371.2 [M+1]

Step 8

(R)—N-((1R)-1-(2-(azidomethyl)-5-fluoro-2-(fluoromethyl)-2,3-dihydrobenzofuran-7-yl)ethyl)-2-methylpropane-2-sulfinamide (R)—N-((E)-1-(2-(azidomethyl)-5-fluoro-2-(fluoromethyl)-2,3-dihydrobenzofuran-7-yl)ethylidene)-2-methylpropane-2-sulfinamide 18h (420 mg, 1.14 mmol) was dissolved in 5 mL of tetrahydrofuran, and then dropwise added with 9-borabicyclo[3,3,1]-nonane (6.8 mL, 3.42 mmol, 0.5 mol/L), and reacted at room temperature overnight. After the reaction was completed, the reaction solution was quenched with 10 mL of methanol and concentrated under reduced pressure to obtain (R)—N-((1R)-1-(2-(azidomethyl)-5-fluoro-2-(fluoromethyl)-2,3-dihydrobenzofuran-7-yl)ethyl)-2-methylpropane-2-sulfinamide 18i (420 mg, yellow viscous substance) with a yield of 100%.

MS m/z(ESI): 373.1[M+1]

Step 9

(1R)-1-(2-(azidomethyl)-5-fluoro-2-(fluoromethyl)-2,3-dihydrobenzofuran-7-yl)ethan-1-amine (R)—N-((1R)-1-(2-(azidomethyl)-5-fluoro-2-(fluoromethyl)-2,3-dihydrobenzofuran-7-yl)ethyl)-2-methylpropane-2-sulfinamide 18i (420 mg, 1.13 mmol) was dissolved in 3 mL of dichloromethane, then added with 5 mL of hydrochloride 1,4-dioxane solution (4 mol/L), and reacted at room temperature overnight. After the reaction was completed, the reaction solution was concentrated under reduced pressure to obtain (1R)-1-(2-(azidomethyl)-5-fluoro-2-(fluoromethyl)-2,3-dihydrobenzofuran-7-yl)ethan-1-amine 18j (303 mg, yellow viscous substance) with a yield of 100%.

MS m/z(ESI): 269.2 [M+1]

Step 10

Ethyl 5-(((1R)-1-(2-(azidomethyl)-5-fluoro-2-(fluoromethyl)-2,3-dihydrobenzofuran-7-yl)ethyl) amino) pyrazolo[1,5-a]pyrimidine-3-carboxylate (1R)-1-(2-(azidomethyl)-5-fluoro-2-(fluoromethyl)-2,3-dihydrobenzofuran-7-yl)ethan-1-amine 18j (303 mg, 1.13 mmol) and ethyl 5-chloropyrazolo[1,5-a]pyrimidine-3-carboxylate 1j (255 mg, 1.13 mmol) were dissolved in 5 mL of n-butanol, added with N,N-diisopropylethylamine (1.17 g, 9 mmol), heated to 130° C., and reacted for 5 hours. After the reaction was completed, the reaction solution was concentrated under reduced pressure. The obtained residue was purified by silica gel column chromatography (eluent: system A) to obtain ethyl 5-(((1R)-1-(2-(azidomethyl)-5-fluoro-2-(fluoromethyl)-2,3-dihydrobenzofuran-7-yl)ethyl)amino)pyrazolo[1,5-a]pyrimidine-3-carboxylate 18k (200 g, white solid) with a yield of 38.7%.

MS m/z(ESI): 458.3 [M+1]

Step 11

Ethyl 5-(((1R)-1-(2-(((tert-butoxycarbonyl)amino) methyl)-5-fluoro-2-(fluoromethyl)-2,3-dihydrobenzofuran-7-yl)ethyl)amino)pyrazolo[1,5-a]pyrimidine-3-carboxylate Ethyl 5-(((1R)-1-(2-(azidomethyl)-5-fluoro-2-(fluoromethyl)-2,3-dihydrobenzofuran-7-yl) ethyl)amino)pyrazolo[1,5-a]pyrimidine-3-carboxylate 18k (200 mg, 0.44 mmol) was dissolved in 5 mL of methanol, and then added with di-tert-butyl dicarbonate (115 mg, 0.52 mmol) and 10% palladium carbon (100 mg, containing 50% of water) sequentially, hydrogen gas was replaced for three times, and a hydrogen balloon was inserted to react at room temperature for 3 hours. After the reaction was completed, the reaction solution was filtered, and the filtrate was concentrated under reduced pressure to obtain ethyl 5-(((1R)-1-(2-(((tert-butoxycarbonyl)amino)methyl)-5-fluoro-2-(fluoromethyl)-2,3-dihydrobenzofuran-7-yl)ethyl)amino)pyrazolo[1, 5-a]pyrimidine-3-carboxylate 18l (232 mg, yellow viscous substance) with a yield of 100%.

MS m/z(ESI): 532.2 [M+1]

Step 12

5-(((1R)-1-(2-(((tert-butoxycarbonyl)amino)methyl)-5-fluoro-2-(fluoromethyl)-2,3-dihydrobenzofuran-7-yl)ethyl)amino)pyrazolo[1,5-a]pyrimidine-3-carboxylic acid Ethyl 5-(((1R)-1-(2-(((tert-butoxycarbonyl)amino)methyl)-5-fluoro-2-(fluoromethyl)-2,3-dihydrobenzofuran-7-yl)ethyl)amino)pyrazolo[1,5-a]pyrimidine-3-carboxylate 18l (232 mg, 0.44 mmol) was dissolved in 5 mL of mixed solvent of ethanol, tetrahydrofuran and water (V:V:V=3:1:1), added with lithium hydroxide monohydrate (185 mg, 4.4 mmol), heated to 95° C., and reacted for 2 hours. After the reaction was completed, the reaction solution was cooled to room temperature and concentrated under reduced pressure to remove ethanol and tetrahydrofuran, then added with 20 mL of water, and adjusted to acidity with 1.0 M diluted hydrochloric acid, and extracted with ethyl acetate (20 mL×3), then organic phases were combined, washed with 20 mL of saturated brine, dried with anhydrous sodium sulfate, filtered, and concentrated under reduced pressure to obtain crude product of 5-(((1R)-1-(2-(((tert-butoxycarbonyl)amino)methyl)-5-fluoro-2-(fluoromethyl)-2,3-dihydrobenzofuran-7-yl)ethyl)amino)pyrazolo[1,5-a]pyrimidine-3-carboxylic acid 18m (222 mg, yellow viscous substance) with a yield of 100%.

MS m/z(ESI): 504.2 [M+1]

Step 13

5-(((1R)-1-(2-(aminomethyl)-5-fluoro-2-(fluoromethyl)-2,3-dihydrobenzofuran-7-yl)ethyl)amino)pyrazolo[1,5-a]pyrimidine-3-carboxylic acid 5-(((1R)-1-(2-(((tert-butoxycarbonyl)amino)methyl)-5-fluoro-2-(fluoromethyl)-2,3-dihydrobenzofuran-7-yl)ethyl)amino)pyrazolo[1,5-a]pyrimidine-3-carboxylic acid 18m (222 mg, 0.44 mmol) was dissolved in 5 mL of dichloromethane, and then added with 4 mL of hydrochloride 1,4-dioxane solution (4 mol/L), and reacted at room temperature for 0.5 hour. After the reaction was completed, the reaction was concentrated under reduced pressure to obtain crude product of 5-(((1R)-1-(2-(aminomethyl)-5-fluoro-2-(fluoromethyl)-2,3-dihydrobenzofuran-7-yl)ethyl)amino)pyrazolo[1,5-a]pyrimidine-3-carboxylic acid 18n (178 mg, yellow viscous substance) with a yield of 100%.

MS m/z(ESI): 404.3 [M+1]

Step 14

(3R)-6-fluoro-11-(fluoromethyl)-3-methyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 5-(((1R)-1-(2-(aminomethyl)-5-fluoro-2-(fluoromethyl)-2,3-dihydrobenzofuran-7-yl)ethyl)amino)pyrazolo[1,5-a]pyrimidine-3-carboxylic acid 18n (178 mg, 0.44 mmol), pentafluorophenyl diphenyl phosphinate (203 mg, 0.88 mmol) and N,N-diisopropylethylamine (340.56 mg, 2.64 mmol) were dissolved in 6 mL of mixed solvent of dichloromethane and N,N-dimethylformamide (V:V=5:1), and reacted at room temperature overnight. After the reaction was completed, the reaction solution was added with 10 mL of dichloromethane, washed with saturated brine (20 mL×3), then dried with anhydrous sodium sulfate, filtered, and concentrated under reduced pressure. (3R)-6-fluoro-11-(fluoromethyl)-3-methyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 18 (90 mg) with a yield of 53.2% was obtained by preparing a liquid phase (separation column AKZONOBEL Kromasil; 250×21.2 mm I.D.; 5 μm, 10 mL/min; mobile phase A: 0.05% TFA+H$_2$O, and mobile phase B: CH$_3$CN) from the obtained residue.

MS m/z(ESI): 386.2 [M+1]

$^1$H NMR (400 MHz, DMSO-d$_6$) δ 8.88 (d, J=9.0 Hz, 1H), 8.65 (d, J=4.8 Hz, 1H), 8.53 (dd, J=7.6, 2.3 Hz, 1H), 8.00 (d, J=2.4 Hz, 1H), 6.91-6.78 (m, 1H), 6.76 (d, J=2.7 Hz, 1H), 6.38 (dd, J=7.6, 2.3 Hz, 1H), 4.96 (t, J=6.5 Hz, 1H), 4.78 (q, J=12.2, 11.4 Hz, 1H), 4.66 (q, J=12.4, 11.5 Hz, 1H), 3.79 (dd, J=13.0, 9.3 Hz, 1H), 3.40 (d, J=16.4 Hz, 1H), 3.29 (s, 1H), 2.96 (d, J=17.1 Hz, 1H), 1.55 (d, J=6.8 Hz, 3H).

Example 19

(3R)-6-fluoro-11-(hydroxymethyl)-3-methyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one

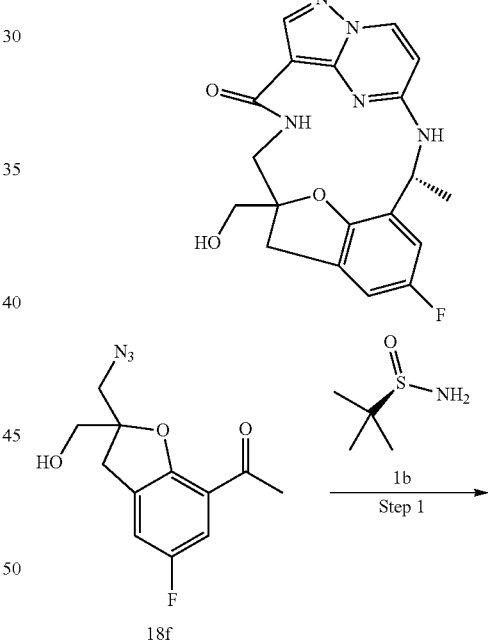

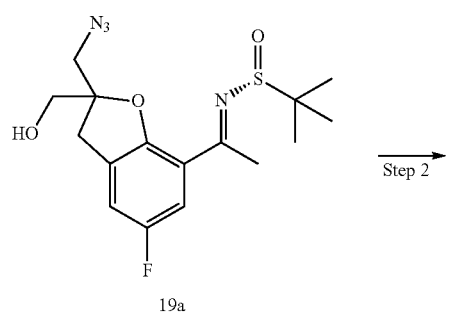

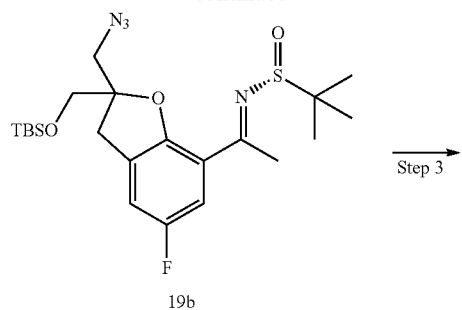

19b

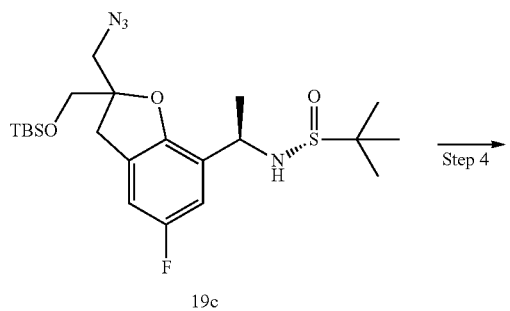

19c

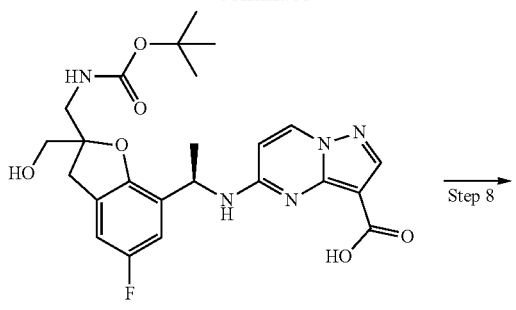

19g

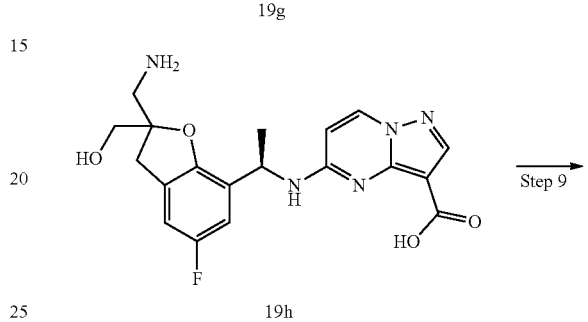

19h

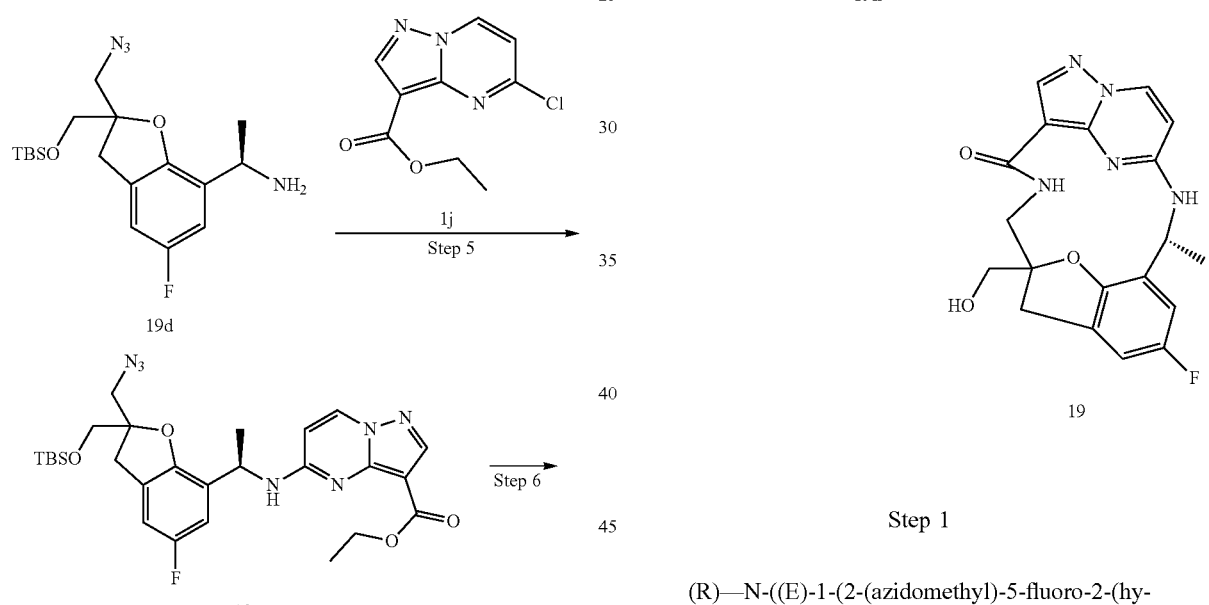

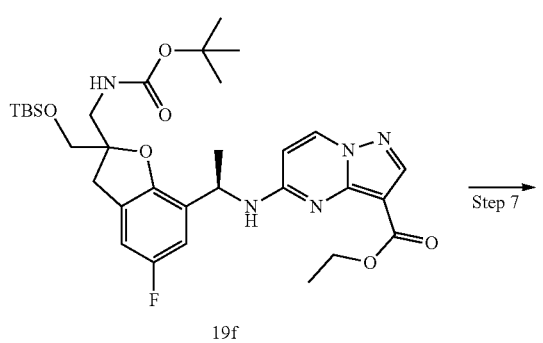

19f

Step 1

(R)—N-((E)-1-(2-(azidomethyl)-5-fluoro-2-(hydroxymethyl)-2,3-dihydrobenzofuran-7-yl)ethylidene)-2-methylpropane-2-sulfinamide 1-(2-(azidomethyl)-5-fluoro-2-(hydroxymethyl)-2,3-dihydrobenzofuran-7-yl)ethan-1-one 18f (500 mg, 1.89 mmol) was dissolved in 5 mL of tetrahydrofuran, added with (R)-2-methylpropane-2-sulfinamide 1b (459 mg, 3.79 mmol) and tetraethyl titanate (1.73 g, 7.59 mmol) sequentially, then refluxed and reacted at 90° C. overnight. After the reaction was completed, the reaction solution was cooled to room temperature. Two reaction solutions were combined and concentrated under reduced pressure. The obtained residue was purified by silica gel column chromatography (eluent: system A) to obtain (R)—N-((E)-1-(2-(azidomethyl)-5-fluoro-2-(hydroxymethyl)-2,3-dihydrobenzofuran-7-yl)ethylidene)-2-methylpropane-2-sulfinamide 19a (278 mg, yellow viscous substance) with an overall yield of 40%.

MS m/z(ESI): 369.1[M+1]

Step 2

(R)—N-((E)-1-(2-(azidomethyl)-2-(((tert-butyldimethylsilyl)oxy)methyl)-5-fluoro-2,3-dihydrobenzofuran-7-yl)ethylidene)-2-methylpropane-2-sulfinamide (R)—N-((E)-1-(2-(azidomethyl)-5-fluoro-2-(hydroxymethyl)-2,3-dihydrobenzofuran-7-yl)ethylidene)-2-methylpropane-2-sulfinamide 19a (50 mg, 0.136 mmol) was dissolved in 5 mL of N,N-dimethylformamide, added with imidazole (19 mg, 0.28 mmol) and tert-butyldimethylsilyl chloride (24 mg, 0.16 mmol), and reacted at 75° C. for 6 hours. After the reaction was completed, the reaction solution was cooled to room temperature, poured into 100 mL of water, and extracted with ethyl acetate (20 mL×3), then organic phases were combined, washed with saturated brine (100 mL), dried with anhydrous sodium sulfate, filtered, and concentrated under reduced pressure to obtain (R)—N-((E)-1-(2-(azidomethyl)-2-(((tert-butyldimethylsilyl)oxy)methyl)-5-fluoro-2,3-dihydrobenzofuran-7-yl)ethylidene)-2-methylpropane-2-sulfinamide 19b (50 mg, yellow viscous substance) with a yield of 76.9%.

MS m/z(ESI): 483.3 [M+1]

Step 3

(R)—N-((1R)-1-(2-(azidomethyl)-2-(((tert-butyldimethylsilyl)oxy)methyl)-5-fluoro-2,3-dihydrobenzofuran-7-yl)ethyl)-2-methylpropane-2-sulfinamide (R)—N-((E)-1-(2-(azidomethyl)-2-(((tert-butyldimethylsilyl)oxy)methyl)-5-fluoro-2,3-dihydrobenzofuran-7-yl)ethylidene)-2-methylpropane-2-sulfinamide 19b (50 mg, 0.1037 mmol) was dissolved in 5 mL of tetrahydrofuran, and then dropwise added with 9-borabicyclo[3,3,1]-nonane (0.4 mL, 0.2 mmol, 0.5 mol/L), and reacted at room temperature overnight. After the reaction was completed, the reaction solution was quenched with 10 mL of methanol and concentrated under reduced pressure to obtain (R)—N-((1R)-1-(2-(azidomethyl)-2-(((tert-butyldimethylsilyl)oxy)methyl)-5-fluoro-2,3-dihydrobenzofuran-7-yl)ethyl)-2-methylpropane-2-sulfinamide 19c (50 mg, yellow viscous substance) with a yield of 100%.

MS m/z(ESI): 485.2[M+1]

Step 4

(1R)-1-(2-(azidomethyl)-2-(((tert-butyldimethylsilyl)oxy)methyl)-5-fluoro-2,3-dihydrobenzofuran-7-yl)ethan-1-amine (R)—N-((1R)-1-(2-(azidomethyl)-2-(((tert-butyldimethylsilyl)oxy)methyl)-5-fluoro-2,3-dihydrobenzofuran-7-yl)ethyl)-2-methylpropane-2-sulfinamide 19c (1 g, 2.1 mmol) was dissolved in 11 mL of mixed solvent of tetrahydrofuran and water (V:V=10:1), added with iodine (105 mg, 0.42 mmol), and reacted at 50° C. for 3 hours. After the reaction was completed, the reaction solution was cooled to room temperature, added with 50 mL of water, and then slowly added with sodium thiosulfate solid, and stirred for dissolution until the color of the solution was no longer light, then the solution was extracted with ethyl acetate (20 mL×3), then organic phases were combined, dried with anhydrous sodium sulfate, filtered, and concentrated under reduced pressure to obtain (1R)-1-(2-(azidomethyl)-2-(((tert-butyldimethylsilyl)oxy)methyl)-5-fluoro-2,3-dihydrobenzofuran-7-yl)ethan-1-amine 19d (yellow viscous substance), which was directly used for the next reaction without further purification.

MS m/z(ESI): 381.2 [M+1]

Step 5

Ethyl 5-(((1R)-1-(2-(azidomethyl)-2-(((tert-butyldimethylsilyl)oxy)methyl)-5-fluoro-2,3-dihydrobenzofuran-7-yl)ethyl)amino)pyrazolo[1,5-a]pyrimidine-3-carboxylate (1R)-1-(2-(azidomethyl)-2-(((tert-butyldimethylsilyl)oxy)methyl)-5-fluoro-2,3-dihydrobenzofuran-7-yl)ethan-1-amine 19d and ethyl 5-chloropyrazolo[1,5-a]pyrimidine-3-carboxylate 1j (489 mg, 2.17 mmol) were dissolved in 5 mL of n-butanol, added with N,N-diisopropylethylamine (2.25 g, 17.44 mmol), heated to 130° C., and reacted for 5 hours. After the reaction was completed, the reaction solution was concentrated under reduced pressure. The obtained residue was purified by silica gel column chromatography (eluent: system A) to obtain ethyl 5-(((1R)-1-(2-(azidomethyl)-2-(((tert-butyldimethylsilyl)oxy)methyl)-5-fluoro-2,3-dihydrobenzofuran-7-yl)ethyl)amino)pyrazolo[1,5-a]pyrimidine-3-carboxylate 19e (110 mg, white solid) with a two-step yield of 9.2%.

MS m/z(ESI): 570.3 [M+1]

Step 6

Ethyl 5-(((1R)-1-(2-(((tert-butoxycarbonyl)amino)methyl)-2-(((tert-butyldimethylsilyl)oxy) methyl)-5-fluoro-2,3-dihydrobenzofuran-7-yl)ethyl)amino) pyrazolo[1,5-a]pyrimidine-3-carboxylate Ethyl 5-(((1R)-1-(2-(azidomethyl)-2-(((tert-butyldimethylsilyl)oxy)methyl)-5-fluoro-2,3-dihydrobenzofuran-7-yl)ethyl)amino)pyrazolo[1,5-a]pyrimidine-3-carboxylate 19e (110 mg, 0.19 mmol) was dissolved in 5 mL of methanol, and then added with di-tert-butyl dicarbonate (51 mg, 0.23 mmol) and 10% palladium carbon (50 mg, containing 50% of water) sequentially, hydrogen gas was replaced for three times, and a hydrogen balloon was inserted to react at room temperature for 3 hours. After the reaction was completed, the reaction solution was filtered, and the filtrate was concentrated under reduced pressure to obtain ethyl 5-(((1R)-1-(2-(((tert-butoxycarbonyl)amino)methyl)-2-(((tert-butyldimethylsilyl)oxy)methyl)-5-fluoro-2,3-dihydrobenzofuran-7-yl)ethyl)amino)pyrazolo[1,5-a]pyrimidine-3-carboxylate 19f (122 mg, yellow viscous substance) with a yield of 100%.

MS m/z(ESI): 644.3 [M+1]

Step 7

5-(((1R)-1-(2-(((tert-butoxycarbonyl)amino)methyl)-5-fluoro-2-(hydroxymethyl)-2,3-dihydrobenzofuran-7-yl)ethyl)amino)pyrazolo[1,5-a]pyrimidine-3-carboxylic acid Ethyl 5-(((1R)-1-(2-(((tert-butoxycarbonyl)amino)methyl)-2-(((tert-butyldimethylsilyl)oxy) methyl)-5-fluoro-2,3-dihydrobenzofuran-7-yl)ethyl)amino)pyrazolo[1,5-a]pyrimidine-3-carboxylate 19f (122 mg, 0.19 mmol) was dissolved in 7 mL of mixed solvent of ethanol, tetrahydrofuran and water (V:V:V=5:1:1), added with lithium hydroxide monohydrate (160 mg, 3.8 mmol), heated to 90° C., and reacted for 2 hours. After the reaction was completed, the reaction solution was cooled to room temperature and concentrated under reduced pressure to remove ethanol and tetrahydrofuran, then added with 20 mL of water, and adjusted to acidity with 1.0 M diluted hydrochloric acid, and extracted with ethyl acetate (20 mL×3), then organic phases were combined, washed with 50 mL of saturated brine, dried with anhydrous sodium sulfate, filtered, and concentrated under reduced pressure to obtain crude product of 5-(((1R)-1-(2-(((tert-butoxycarbonyl)amino)methyl)-5-fluoro-2-(hydroxymethyl)-2,3-dihydrobenzofuran-7-yl)ethyl)amino) pyrazolo[1,5-a]pyrimidine-3-carboxylic acid 19g (95 mg, yellow viscous substance) with a yield of 100%.

MS m/z(ESI): 502.2[M+1]

Step 8

5-(((1R)-1-(2-(aminomethyl)-5-fluoro-2-(hydroxymethyl)-2,3-dihydrobenzofuran-7-yl)ethyl)amino) pyrazolo[1,5-a]pyrimidine-3-carboxylic acid 5-(((1R)-1-(2-(((tert-butoxycarbonyl)amino)methyl)-5-fluoro-2-(hydroxymethyl)-2,3-dihydrobenzofuran-7-yl) ethyl)amino)pyrazolo[1,5-a]pyrimidine-3-carboxylic acid 19g (95 mg, 0.19 mmol) was dissolved in 3 mL of dichloromethane, and then added with 5 mL of hydrochloride 1,4-dioxane solution (4 mol/L), and reacted at room temperature for 0.5 hour. After the reaction was completed, the reaction solution was concentrated under reduced pressure to obtain crude product of 5-(((1R)-1-(2-(aminomethyl)-5-fluoro-2-(hydroxymethyl)-2,3-dihydrobenzofuran-7-yl) ethyl)amino)pyrazolo[1,5-a]pyrimidine-3-carboxylic acid 19h (76 mg), which was directly used for the next reaction without further purification.

MS m/z(ESI): 402.2[M+1]

Step 9

(3R)-6-fluoro-11-(hydroxymethyl)-3-methyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 5-(((1R)-1-(2-(aminomethyl)-5-fluoro-2-(hydroxymethyl)-2,3-dihydrobenzofuran-7-yl)ethyl)amino)pyrazolo[1,5-a]pyrimidine-3-carboxylic acid 19h (76 mg, 0.19 mmol), pentafluorophenyl diphenyl phosphinate (88 mg, 0.228 mmol) and N,N-diisopropylethylamine (196 mg, 1.52 mmol) were dissolved in 6 mL of mixed solvent of dichloromethane and N,N-dimethylformamide (V:V=5:1), and reacted at room temperature overnight. After the reaction was completed, the reaction solution was added with 10 mL of dichloromethane, washed with water (20 mL×3), then dried with anhydrous sodium sulfate, filtered, and concentrated under reduced pressure. (3R)-6-fluoro-11-(hydroxymethyl)-3-methyl-10-oxa-2,13,17,18,21-pentaazapentacyclo [13.5.2.1$^{8,11}$.0$^{4,9}$.0$^{18,22}$]tricosa-1(21),4,6,8,15(22),16,19-heptaen-14-one 19 (14 mg) with a yield of 18.4% was obtained by preparing a liquid phase (separation column AKZONOBEL Kromasil; 250×21.2 mm I.D.; 5 μm, 10 mL/min; mobile phase A: 0.05% TFA+H$_2$O, and mobile phase B: CH$_3$CN) from the obtained residue.

MS m/z(ESI): 384.1[M+1]

Example 20

(3R,11R)-6-fluoro-3,11-dimethyl-10-oxa-2,14,18,19,22-pentaazapentacyclo[14.5.2.1$^{8,11}$.0$^{4,9}$.0$^{19,23}$]tetracosa-1(22),4,6,8,16(23),17,20-heptaen-15-one

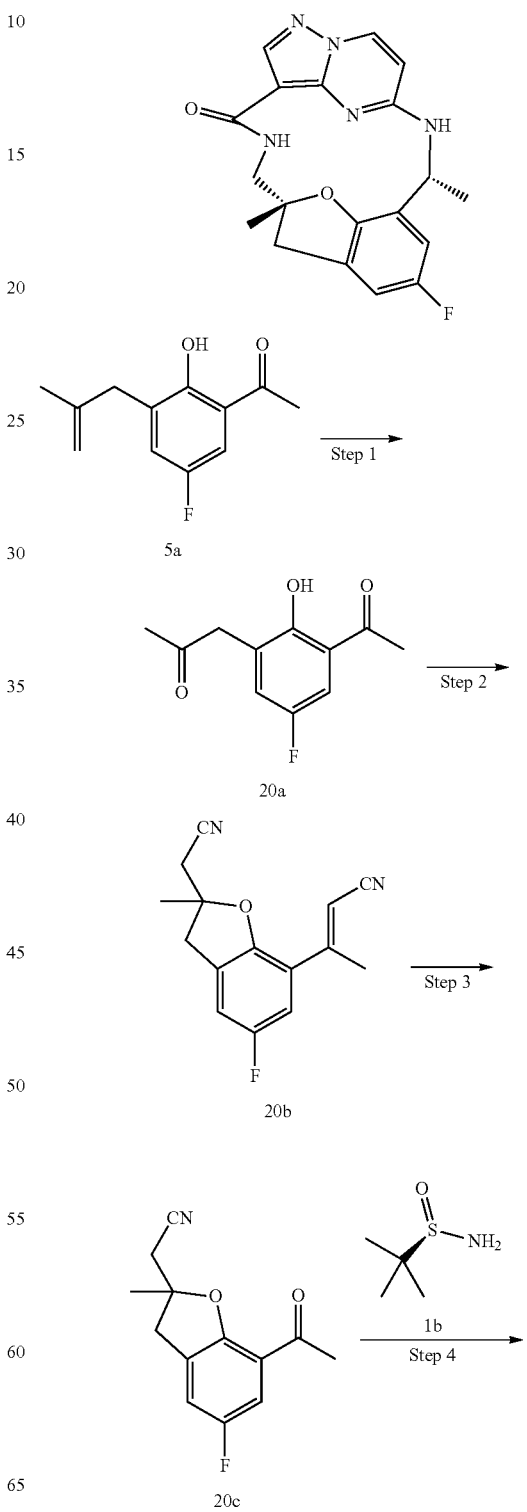

165
-continued
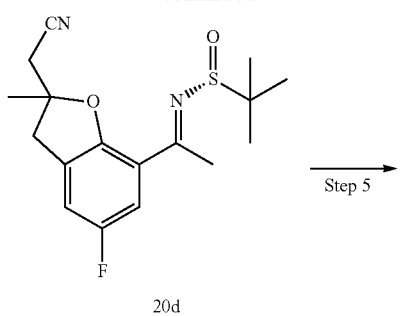
20d
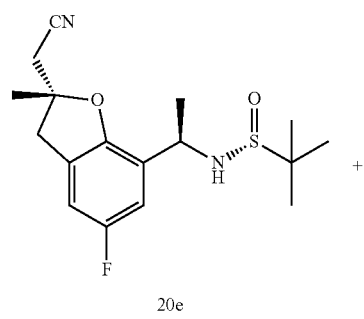
20e
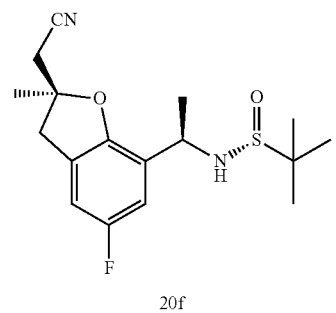
20f
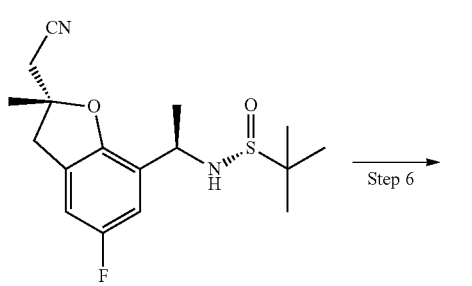
20e
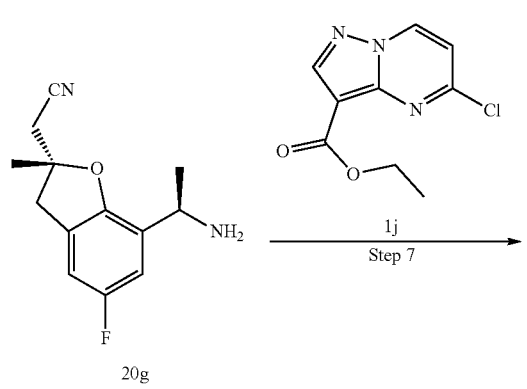
20g
166
-continued
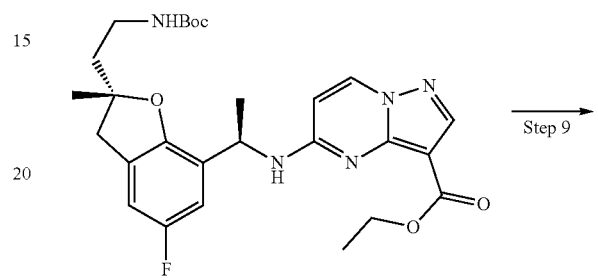
20h
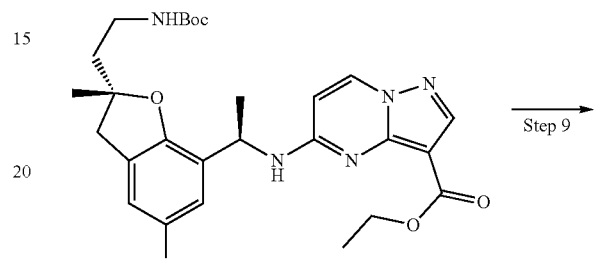
20i
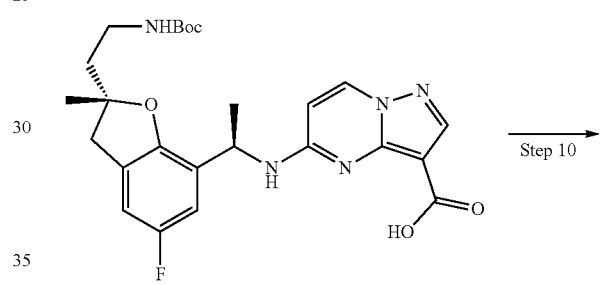
20j
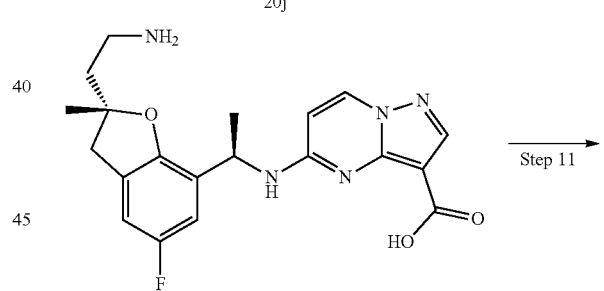
20k
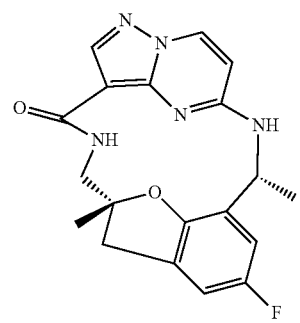
20
Step 5
Step 6
Step 7
Step 8
Step 9
Step 10
Step 11
1j

Step 1

1-(3-acetyl-5-fluoro-2-hydroxyphenyl)propan-2-one 1-(5-fluoro-2-hydroxy-3-(2-methylallyl)phenyl)ethan-1-one 5a (5 g, 24 mmol) was dissolved in 500 mL of dichloromethane, stirred at room temperature, ozone was inlet, and then the obtained solution was reacted at room temperature for 6 hours. After the reaction was completed, the reaction solution was quenched with triphenylphosphine, and concentrated under reduced pressure. The obtained residue was purified by silica gel column chromatography (eluent: system A) to obtain 1-(3-acetyl-5-fluoro-2-hydroxyphenyl)propan-2-one 20a (2 g, yellow solid) with a yield of 39.7%.

MS m/z(ESI): 211.1[M+1]

Step 2

(E)-3-(2-(cyanomethyl)-5-fluoro-2-methyl-2,3-dihydrobenzofuran-7-yl)but-2-enenitrile Diethyl cyanomethylphosphonate (6.3 g, 35.5 mmol) was dissolved in 100 mL of tetrahydrofuran, cooled to 0° C., slowly added with sodium hydride (1.42 g, 35.5 mmol) in batches, reacted at 0° C. for 1 hour, and then added with 1-(3-acetyl-5-fluoro-2-hydroxyphenyl)propan-2-one 20a (5 g, 23.7 mmol), then warmed up to room temperature, continuously reacted overnight. After the reaction was completed, the system was poured into 50 mL of ice water and extracted with ethyl acetate (50 mL×3), and then organic phases were combined, dried with anhydrous sodium sulfate, filtered, and concentrated under reduced pressure. The obtained residue was purified by silica gel column chromatography (eluent: system A) to obtain (E)-3-(2-(cyanomethyl)-5-fluoro-2-methyl-2,3-dihydrobenzofuran-7-yl)but-2-enenitrile 20b (1.1 g, yellow solid) with a yield of 18.1%.

MS m/z(ESI): 257.1 [M+1]

Step 3

2-(7-acetyl-5-fluoro-2-methyl-2,3-dihydrobenzofuran-2-yl)acetonitrile (E)-3-(2-(cyanomethyl)-5-fluoro-2-methyl-2,3-dihydrobenzofuran-7-yl)but-2-enenitrile 20b (1.9 g, 2.4 mmol) was dissolved in 50 mL of dichloromethane, stirred at room temperature, ozone was inlet, and then the obtained solution was continuously reacted at room temperature for 4 hours. After the reaction was completed, the reaction solution was quenched with triphenylphosphine, and concentrated under reduced pressure. The obtained residue was purified by silica gel column chromatography (eluent: system A) to obtain 2-(7-acetyl-5-fluoro-2-methyl-2,3-dihydrobenzofuran-2-yl)acetonitrile 20c (560 mg, off-white solid) with a yield of 56%.

MS m/z(ESI): 234.1 [M+1]

Step 4

(R)—N-((E)-1-(2-(cyanomethyl)-5-fluoro-2-methyl-2,3-dihydrobenzofuran-7-yl)ethylidene)-2-methylpropane-2-sulfinamide 2-(7-acetyl-5-fluoro-2-methyl-2,3-dihydrobenzofuran-2-yl)acetonitrile 20c (1.2 g, 5.15 mmol) was dissolved in 20 mL of tetrahydrofuran, added with (R)-2-methylpropane-2-sulfinamide 1b (1.25 g, 10.3 mmol) and tetraethyl titanate (4.7 g, 20.6 mmol) sequentially, then refluxed and reacted at 90° C. overnight. After the reaction was completed, the reaction solution was cooled to room temperature, and concentrated under reduced pressure. The obtained residue was purified by silica gel column chromatography (eluent: system A) to obtain (R)—N-((E)-1-(2-(cyanomethyl)-5-fluoro-2-methyl-2,3-dihydrobenzofuran-7-yl)ethylidene)-2-methylpropane-2-sulfinamide 20d (1.3 g, yellow viscous substance) with a yield of 75%.

MS m/z(ESI): 337.2 [M+1]

Step 5

(R)—N—((R)-1-((R)-2-(cyanomethyl)-5-fluoro-2-methyl-2,3-dihydrobenzofuran-7-yl)ethyl)-2-methylpropane-2-sulfinamide 20e (R)—N—((R)-1-((S)-2-(cyanomethyl)-5-fluoro-2-methyl-2,3-dihydrobenzofuran-7-yl)ethyl)-2-methylpropane-2-sulfinamide 20f (R)—N-((E)-1-(2-(cyanomethyl)-5-fluoro-2-methyl-2,3-dihydrobenzofuran-7-yl)ethylidene)-2-methylpropane-2-sulfinamide 20d (1.3 g, 3.87 mmol) was dissolved in 15 mL of tetrahydrofuran, and then dropwise added with 9-borabicyclo[3,3,1]-nonane (15 mL, 7.5 mmol, 0.5 mol/L), and reacted at room temperature overnight. After the reaction was completed, the reaction solution was quenched with 10 mL of methanol, and concentrated under reduced pressure. The obtained residue was purified by silica gel column chromatography (eluent: system A) to obtain (R)—N—((R)-1-((R)-2-(cyanomethyl)-5-fluoro-2-methyl-2,3-dihydrobenzofuran-7-yl)ethyl)-2-methylpropane-2-sulfinamide 20e (300 mg, yellow viscous substance) with a yield of 23.1% and (R)—N—((R)-1-((S)-2-(cyanomethyl)-5-fluoro-2-methyl-2,3-dihydrobenzofuran-7-yl)ethyl)-2-methylpropane-2-sulfinamide 20f (530 mg, yellow viscous substance) with a yield of 40.77%.

MS m/z(ESI): 339.0[M+1]

Step 6

2-((R)-7-((R)-1-aminoethyl)-5-fluoro-2-methyl-2,3-dihydrobenzofuran-2-yl)acetonitrile (R)—N—((R)-1-((R)-2-(cyanomethyl)-5-fluoro-2-methyl-2,3-dihydrobenzofuran-7-yl)ethyl)-2-methylpropane-2-sulfinamide 20e (300 mg, 0.89 mmol) was dissolved in 2 mL of dichloromethane, then added with 3 mL of hydrochloride 1,4-dioxane solution (4 mol/L), and reacted at room temperature for 1 hour. After the reaction was completed, the reaction solution was concentrated under reduced pressure to obtain 2-((R)-7-((R)-1-aminoethyl)-5-fluoro-2-methyl-2,3-dihydrobenzofuran-2-yl)acetonitrile 20g (208 mg, yellow viscous substance) with a yield of 100%.

MS m/z(ESI): 235.3[M+1]

Step 7

Ethyl 5-(((R)-1-((R)-2-(cyanomethyl)-5-fluoro-2-methyl-2,3-dihydrobenzofuran-7-yl)ethyl) amino) pyrazolo[1,5-a]pyrimidine-3-carboxylate 2-((R)-7-((R)-1-aminoethyl)-5-fluoro-2-methyl-2,3-dihydrobenzofuran-2-yl)acetonitrile 20g (208 mg, 0.89 mmol) and ethyl 5-chloropyrazolo[1,5-a]pyrimidine-3-carboxylate 1j (240 mg, 1.07 mmol) were dissolved in 5 mL of n-butanol, added with N,N-diisopropylethylamine (918 mg, 7.12 mmol), heated to 80° C., and reacted for 5 hours. 2-((R)-7-((R)-1-aminoethyl)-5-fluoro-2-methyl-2,3-dihydrobenzofuran-2-yl)acetonitrile 20g (1.3 g, 5.56 mmol) and ethyl 5-chloropyrazolo[1,5-a]pyrimidine-3-carboxylate 1j (1.26 g, 5.6 mmol) were dissolved in 10 mL of n-butanol, added with N,N-diisopropylethylamine (5.74 g, 44 mmol), heated to 80° C., and reacted for 5 hours. After the reaction was completed, the two reaction solutions were combined, concentrated under reduced pressure. The obtained residue was purified by silica gel column chromatography (eluent: system A) to obtain ethyl 5-(((R)-1-((R)-2-(cyanomethyl)-5-fluoro-2-methyl-2,3-dihydrobenzofuran-7-yl)ethyl)amino)pyrazolo[1,5-a]pyrimidine-3-carboxylate 20h (678 mg, white solid) with a yield of 24.8%.

MS m/z(ESI): 424.3[M+1]

Step 8

Ethyl 5-(((R)-1-((R)-2-(2-((tert-butoxycarbonyl)amino)ethyl)-5-fluoro-2-methyl-2,3-dihydrobenzofuran-7-yl)ethyl)amino)pyrazolo[1,5-a]pyrimidine-3-carboxylate Ethyl 5-(((R)-1-((R)-2-(cyanomethyl)-5-fluoro-2-methyl-2,3-dihydrobenzofuran-7-yl)ethyl) amino)pyrazolo[1,5-a]pyrimidine-3-carboxylate 20h (678 mg, 1.6 mmol) was dissolved in 5 mL of methanol, and then added with di-tert-butyl dicarbonate (419 mg, 1.92 mmol) and Raney nickel (1 g), hydrogen gas was replaced for three times, and a hydrogen balloon was inserted to react at room temperature overnight. After the reaction was completed, the reaction solution was filtered, and the filtrate was concentrated under reduced pressure to obtain ethyl 5-(((R)-1-((R)-2-(2-((tert-butoxycarbonyl)amino)ethyl)-5-fluoro-2-methyl-2,3-dihydrobenzofuran-7-yl)ethyl)amino)pyrazolo[1,5-a]pyrimidine-3-carboxylate 20i (843 mg, yellow viscous substance) with a yield of 100%.

MS m/z(ESI): 528.4[M+1]

Step 9

5-(((R)-1-((R)-2-(2-((tert-butoxycarbonyl)amino)ethyl)-5-fluoro-2-methyl-2,3-dihydrobenzofuran-7-yl)ethyl)amino)pyrazolo[1,5-a]pyrimidine-3-carboxylic acid Ethyl 5-(((R)-1-((R)-2-(2-((tert-butoxycarbonyl)amino)ethyl)-5-fluoro-2-methyl-2,3-dihydrobenzofuran-7-yl)ethyl)amino)pyrazolo[1,5-a]pyrimidine-3-carboxylate 20i (843 mg, 1.6 mmol) was dissolved in 12 mL of mixed solvent of ethanol, tetrahydrofuran and water (V:V:V=10:10:1), added with lithium hydroxide monohydrate (671 mg, 15.99 mmol), heated to 80° C., and reacted for 2 hours. After the reaction was completed, the reaction solution was cooled to room temperature and concentrated under reduced pressure to remove ethanol and tetrahydrofuran, then added with 50 mL of water, and adjusted to acidity with 1.0 M diluted hydrochloric acid, and extracted with ethyl acetate (50 mL×3), then organic phases were combined, washed with 100 mL of saturated brine, dried with anhydrous sodium sulfate, filtered, and concentrated under reduced pressure to obtain 5-(((R)-1-((R)-2-(2-((tert-butoxycarbonyl)amino)ethyl)-5-fluoro-2-methyl-2,3-dihydrobenzofuran-7-yl)ethyl)amino)pyrazolo[1,5-a]pyrimidine-3-carboxylic acid 20j (720 mg, yellow viscous substance) with a yield of 90%.

MS m/z(ESI): 500.2[M+1]

Step 10

5-(((R)-1-((R)-2-(2-aminoethyl)-5-fluoro-2-methyl-2,3-dihydrobenzofuran-7-yl)ethyl)amino)pyrazolo[1,5-a]pyrimidine-3-carboxylic acid 5-(((R)-1-((R)-2-(2-((tert-butoxycarbonyl)amino)ethyl)-5-fluoro-2-methyl-2,3-dihydrobenzofuran-7-yl)ethyl)amino)pyrazolo[1,5-a]pyrimidine-3-carboxylic acid 20j (720 mg, 1.44 mmol) was dissolved in 5 mL of dichloromethane, and then added with 8 mL of hydrochloride 1,4-dioxane solution (4 mol/L), and reacted at room temperature for 1 hour. After the reaction was completed, the reaction solution was concentrated under reduced pressure to obtain 5-(((R)-1-((R)-2-(2-aminoethyl)-5-fluoro-2-methyl-2,3-dihydrobenzofuran-7-yl)ethyl)amino)pyrazolo[1,5-a]pyrimidine-3-carboxylic acid 20k (574 mg, yellow viscous substance) with a yield of 100%.

MS m/z(ESI): 400.1 [M+1]

Step 11

(3R,11R)-6-fluoro-3,11-dimethyl-10-oxa-2,14,18,19,22-pentaazapentacyclo[14.5.2.1$^{8,11}$.0$^{4,9}$.0$^{19,23}$]tetracosa-1(22),4,6,8,16(23),17,20-heptaen-15-one 5-(((R)-1-((R)-2-(2-aminoethyl)-5-fluoro-2-methyl-2,3-dihydrobenzofuran-7-yl)ethyl)amino)pyrazolo[1,5-a]pyrimidine-3-carboxylic acid 20k (574 mg, 1.44 mmol), pentafluorophenyl diphenyl phosphinate (665 mg, 1.73 mmol) and N,N-diisopropylethylamine (1.49 g, 11.55 mmol) were dissolved in 11 mL of mixed solvent of dichloromethane and N,N-dimethylformamide (V:V=10:1), and reacted at room temperature overnight. After the reaction was completed, the reaction solution was added with 50 mL of dichloromethane, washed with water (50 mL×3), then dried with anhydrous sodium sulfate, filtered, and concentrated under reduced pressure. (3R,11R)-6-fluoro-3,11-dimethyl-10-oxa-2,14,18,19,22-pentaazapentacyclo[4.5.2.1$^{8,11}$.0$^{4,9}$.0$^{19,23}$]tetracosa-1(22),4,6,8,16(23),17,20-heptaen-15-one 20 (100 mg) with a yield of 18.22% was obtained by preparing a liquid phase (separation column AKZONOBEL Kromasil; 250×21.2 mm I.D.; 5 μm, 20 mL/min; mobile phase A: 0.05% TFA+H$_2$O, and mobile phase B: CH$_3$CN) from the obtained residue.

MS m/z(ESI): 382.0[M+1]

$^1$H NMR (400 MHz, DMSO-d$_6$) δ 8.77-8.68 (m, 1H), 8.50 (d, J=7.6 Hz, 2H), 8.05 (d, J=1.9 Hz, 1H), 6.96 (s, 1H), 6.83 (s, 1H), 6.30 (d, J=7.6 Hz, 1H), 4.66-4.47 (m, 1H), 3.61 (s, 2H), 3.26 (d, J=22.3 Hz, 2H), 2.88 (d, J=16.2 Hz, 1H), 2.14 (s, 1H), 1.51-1.40 (m, 3H), 1.43-1.34 (m, 3H).

Example 21

(3R,11S)-6-fluoro-3,11-dimethyl-10-oxa-2,14,18,19,22-pentaazapentacyclo[14.5.2.1$^{8,11}$.0$^{4,9}$.0$^{19,23}$]tetracosa-1(22),4,6,8,16(23),17,20-heptaen-15-one

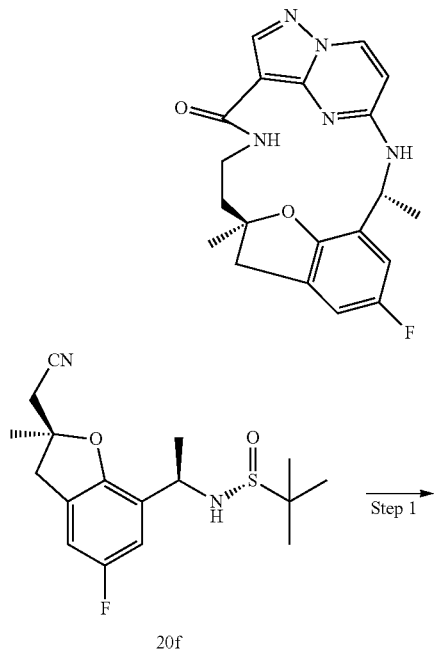

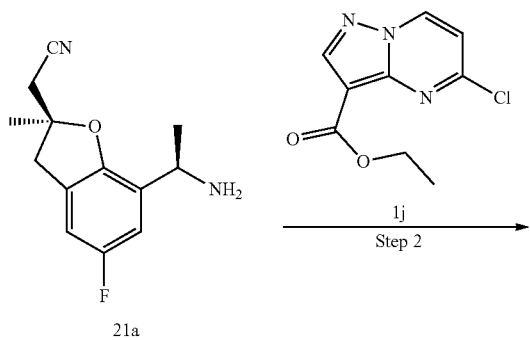

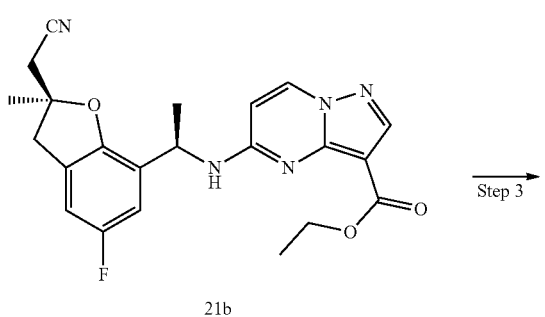

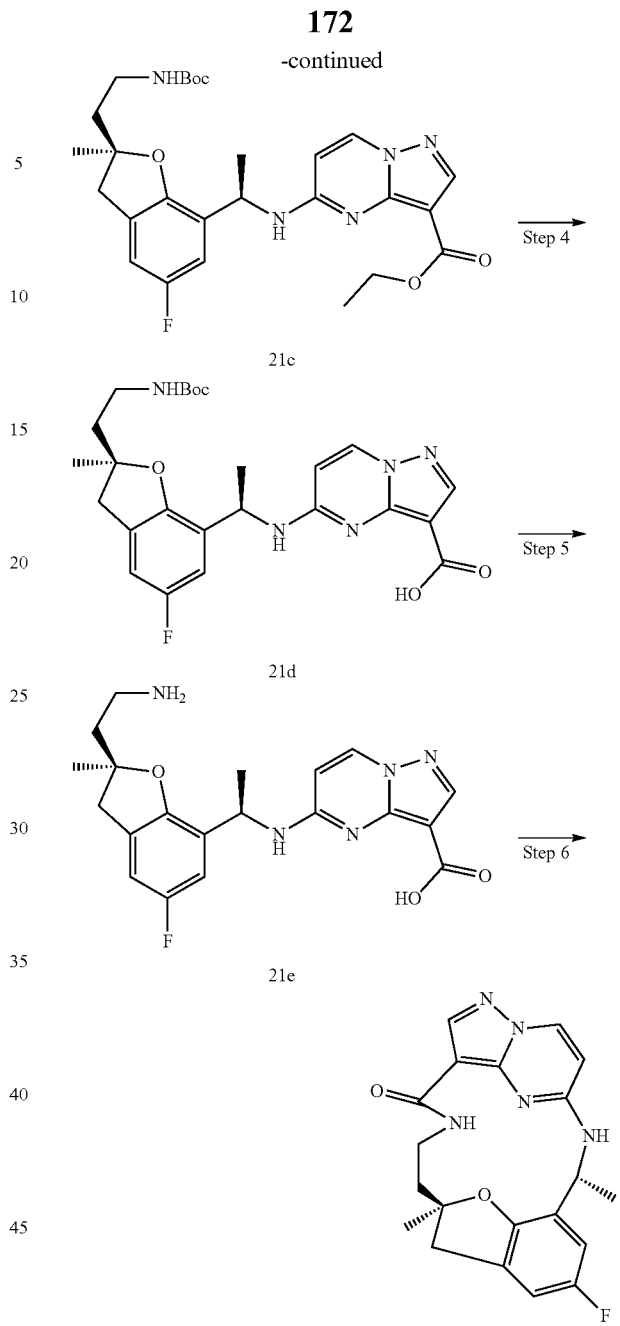

Step 1

2-((R)-7-((S)-1-aminoethyl)-5-fluoro-2-methyl-2,3-dihydrobenzofuran-2-yl)acetonitrile (R)—N—((R)-1-((S)-2-(cyanomethyl)-5-fluoro-2-methyl-2,3-dihydrobenzofuran-7-yl)ethyl)-2-methylpropane-2-sulfinamide 20f (530 mg, 1.57 mmol) was dissolved in 3 mL of dichloromethane, then added with 4 mL of hydrochloride 1,4-dioxane solution (4 mol/L), and reacted at room temperature for 1 hour. After the reaction was completed, the reaction solution was concentrated under reduced pressure to obtain 2-((R)-7-((S)-1-aminoethyl)-5-fluoro-2-methyl-2,3-dihydrobenzofuran-2-yl)acetonitrile 21a (367 mg, yellow viscous substance) with a yield of 100%.

MS m/z(ESI): 235.4[M+1]

Step 2

Ethyl 5-(((R)-1-((S)-2-(cyanomethyl)-5-fluoro-2-methyl-2,3-dihydrobenzofuran-7-yl)ethyl) amino) pyrazolo[1,5-a]pyrimidine-3-carboxylate 2-((R)-7-((S)-1-aminoethyl)-5-fluoro-2-methyl-2,3-dihydrobenzofuran-2-yl)acetonitrile 21a (367 g, 1.57 mmol) and ethyl 5-chloropyrazolo[1,5-a]pyrimidine-3-carboxylate 1j (433 mg, 1.92 mmol) were dissolved in 5 mL of n-butanol, added with N,N-diisopropylethylamine (1.62 g, 12.56 mmol), heated to 80° C., and reacted for 5 hours. 2-((R)-7-((S)-1-aminoethyl)-5-fluoro-2-methyl-2,3-dihydrobenzofuran-2-yl)acetonitrile 21a (831 mg, 3.55 mmol) and ethyl 5-chloropyrazolo[1,5-a]pyrimidine-3-carboxylate 1j (800 mg, 3.56 mmol) were dissolved in 10 mL of n-butanol, added with N,N-diisopropylethylamine (3.67 g, 28.4 mmol), heated to 80° C., and reacted for 5 hours. After the reaction was completed, the two reaction solutions were combined, concentrated under reduced pressure. The obtained residue was purified by silica gel column chromatography (eluent: system A) to obtain ethyl 5-(((R)-1-((S)-2-(cyanomethyl)-5-fluoro-2-methyl-2,3-dihydrobenzofuran-7-yl)ethyl)amino)pyrazolo[1,5-a]pyrimidine-3-carboxylate 21b (1.0 g, white solid) with a yield of 46.18%.

MS m/z(ESI): 424.2[M+1]

Step 3

Ethyl 5-(((R)-1-((S)-2-(2-((tert-butoxycarbonyl)amino)ethyl)-5-fluoro-2-methyl-2,3-dihydrobenzofuran-7-yl)ethyl)amino)pyrazolo[1,5-a]pyrimidine-3-carboxylate Ethyl 5-(((R)-1-((S)-2-(cyanomethyl)-5-fluoro-2-methyl-2,3-dihydrobenzofuran-7-yl)ethyl) amino)pyrazolo[1,5-a]pyrimidine-3-carboxylate 21b (1.0 g, 2.36 mmol) was dissolved in 5 mL of methanol, and then added with di-tert-butyl dicarbonate (618 mg, 2.8 mmol) and Raney nickel (1 g), hydrogen gas was replaced for three times, and a hydrogen balloon was inserted to react at room temperature overnight. After the reaction was completed, the reaction solution was filtered, and the filtrate was concentrated under reduced pressure to obtain ethyl 5-(((R)-1-((S)-2-(2-((tert-butoxycarbonyl)amino)ethyl)-5-fluoro-2-methyl-2,3-dihydrobenzofuran-7-yl)ethyl)amino)pyrazolo[1,5-a]pyrimidine-3-carboxylate 21c (1.24 g, yellow viscous substance) with a yield of 100%.

MS m/z(ESI): 528.3[M+1]

Step 4

5-(((R)-1-((S)-2-(2-((tert-butoxycarbonyl)amino)ethyl)-5-fluoro-2-methyl-2,3-dihydrobenzofuran-7-yl)ethyl)amino)pyrazolo[1,5-a]pyrimidine-3-carboxylic acid Ethyl 5-(((R)-1-((S)-2-(2-((tert-butoxycarbonyl)amino)ethyl)-5-fluoro-2-methyl-2,3-dihydrobenzofuran-7-yl)ethyl)amino)pyrazolo[1,5-a]pyrimidine-3-carboxylate 21c (1.24 g, 2.36 mmol) was dissolved in 12 mL of mixed solvent of ethanol, tetrahydrofuran and water (V:V:V=10:1:1), added with lithium hydroxide monohydrate (994 mg, 23.69 mmol), heated to 80° C., and reacted for 2 hours. After the reaction was completed, the reaction solution was cooled to room temperature and concentrated under reduced pressure to remove ethanol and tetrahydrofuran, then added with 50 mL of water, and adjusted to acidity with 1.0 M diluted hydrochloric acid, and extracted with ethyl acetate (50 mL×3), then organic phases were combined, washed with 10 mL of saturated brine, dried with anhydrous sodium sulfate, filtered, and concentrated under reduced pressure to obtain crude product of 5-(((R)-1-((S)-2-(2-((tert-butoxycarbonyl)amino)ethyl)-5-fluoro-2-methyl-2,3-dihydrobenzofuran-7-yl)ethyl)amino)pyrazolo[1,5-a]pyrimidine-3-carboxylic acid 21d (910 mg, yellow viscous substance) with a yield of 77.27%.

MS m/z(ESI): 500.2[M+1]

Step 5

5-(((R)-1-((S)-2-(2-aminoethyl)-5-fluoro-2-methyl-2,3-dihydrobenzofuran-7-yl)ethyl)amino)pyrazolo[1,5-a]pyrimidine-3-carboxylic acid 5-(((R)-1-((S)-2-(2-((tert-butoxycarbonyl)amino)ethyl)-5-fluoro-2-methyl-2,3-dihydrobenzofuran-7-yl)ethyl)amino)pyrazolo[1,5-a]pyrimidine-3-carboxylic acid 21d (910 mg, 1.8 mmol) was dissolved in 5 mL of dichloromethane, and then added with 8 mL of hydrochloride 1,4-dioxane solution (4 mol/L), and reacted at room temperature for 1 hour. After the reaction was completed, the reaction solution was concentrated under reduced pressure to obtain 5-(((R)-1-((S)-2-(2-aminoethyl)-5-fluoro-2-methyl-2,3-dihydrobenzofuran-7-yl)ethyl)amino)pyrazolo[1,5-a]pyrimidine-3-carboxylic acid 21e (728 mg, yellow viscous substance) with a yield of 100%.

MS m/z(ESI): 400.1[M+1]

Step 6

(3R,11S)-6-fluoro-3,11-dimethyl-10-oxa-2,14,18,19,22-pentaazapentacyclo[14.5.2.1$^{8,11}$.0$^{4,9}$.0$^{19,23}$]tetracosa-1(22),4,6,8,16(23),17,20-heptaen-15-one 5-(((R)-1-((S)-2-(2-aminoethyl)-5-fluoro-2-methyl-2,3-dihydrobenzofuran-7-yl)ethyl)amino)pyrazolo[1,5-a]pyrimidine-3-carboxylic acid 21e (728 mg, 1.8 mmol), pentafluorophenyl diphenyl phosphinate (840 mg, 2.18 mmol) and N,N-diisopropylethylamine (1.89 g, 14.65 mmol) were dissolved in 11 mL of mixed solvent of dichloromethane and N,N-dimethylformamide (V:V=10:1), and reacted at room temperature overnight. After the reaction was completed, the reaction solution was added with 50 mL of dichloromethane, washed with water (50 mL×3), then dried with anhydrous sodium sulfate, filtered, and concentrated under reduced pressure. (3R,11S)-6-fluoro-3,11-dimethyl-10-oxa-2,14,18,19,22-pentaazapentacyclo[14.5.2.1$^{8,11}$.0$^{4,9}$.0$^{19,23}$]tetracosa-1(22),4,6,8,16(23),17,20-heptaen-15-one 21 (230 mg) with a yield of 33.54% was obtained by preparing a liquid phase (separation column AKZONOBEL Kromasil; 250×21.2 mm I.D.; 5 μm, 20 mL/min; mobile phase A: 0.05% TFA+H$_2$O, and mobile phase B: CH$_3$CN) from the obtained residue.

MS m/z(ESI): 382.3 [M+1]

$^1$H NMR (400 MHz, DMSO-d$_6$) δ 8.63 (d, J=6.4 Hz, 1H), 8.55 (d, J=7.6 Hz, 1H), 8.47 (t, J=5.8 Hz, 11H), 8.05 (s, 1H), 6.96-6.90 (m, 1H), 6.85 (dd, J=10.0, 2.8 Hz, 1H), 6.37 (d, J=7.6 Hz, 1H), 5.25-5.06 (m, 1H), 3.75 (dt, J=15.2, 7.7 Hz, 1H), 3.70-3.62 (m, 1H), 3.48 (dt, J=13.3, 5.5 Hz, 1H), 3.22 (d, J=16.6 Hz, 1H), 3.03 (d, J=16.5 Hz, 1H), 2.17-2.05 (m, 1H), 1.49 (s, 3H), 1.43 (d, J=7.1 Hz, 3H).

Example 22
(3R)-6-chloro-3,11-dimethyl-10-oxa-2,13,17,18,21-pentaazapentacyclo[13.5.2.1$^{8,11}$.0$^{4,9}$.0$^{11,22}$]tricosa-1(21),4,6,8,15(22),16,19-heptaen-14-one
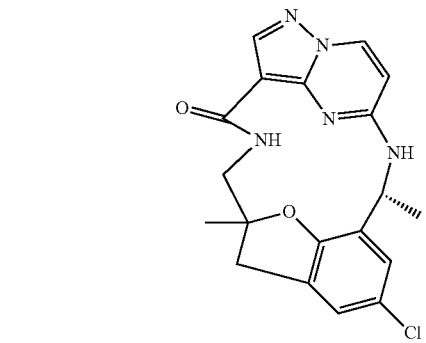
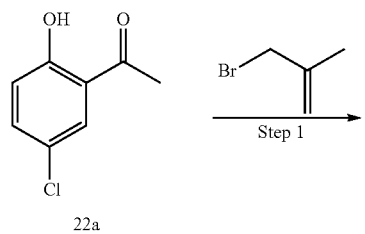
22a
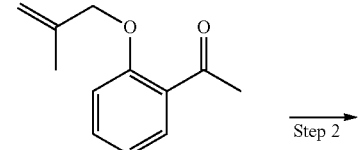
22b
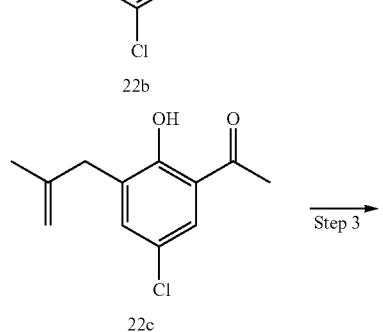
22c
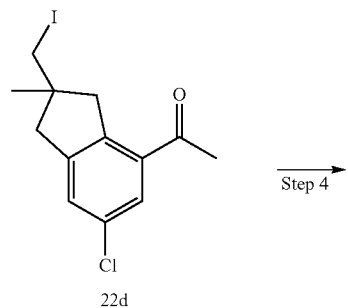
22d
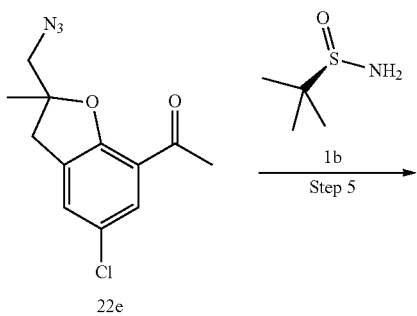
22e
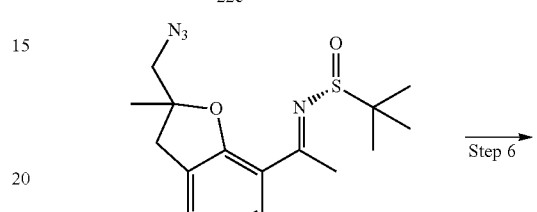
22f
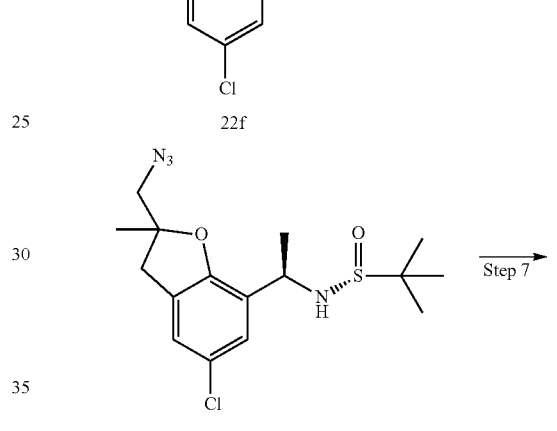
22g
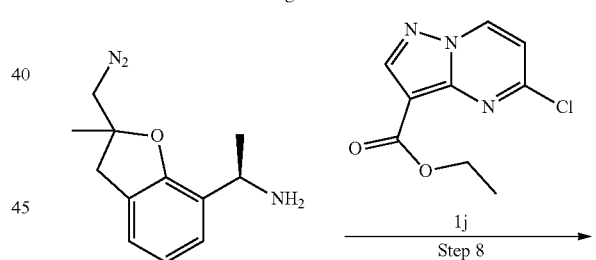
22h
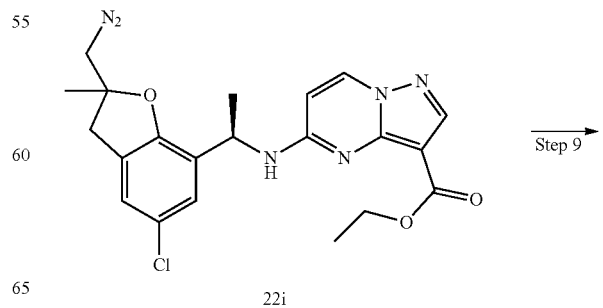
22i

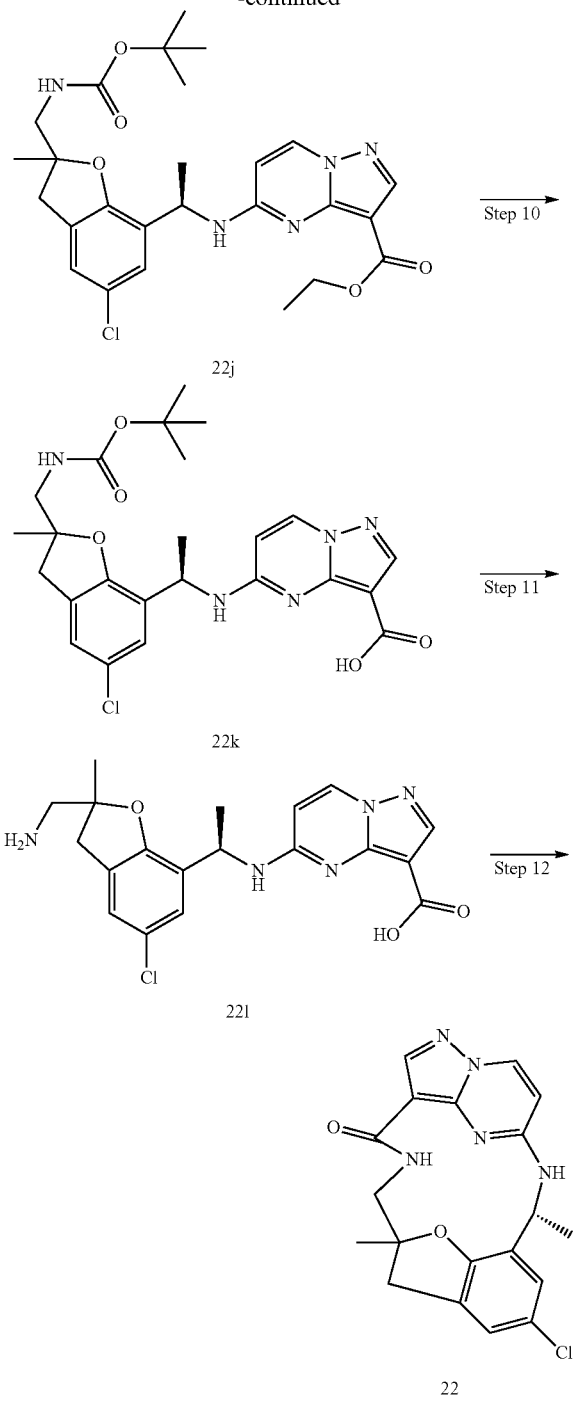

with 100 mL of water and extracted with ethyl acetate (50 mL×3), organic phases were combined, washed with saturated brine (50 mL×2), dried with anhydrous sodium sulfate, filtered, and concentrated under reduced pressure to obtain 1-(5-chloro-2-((2-methylallyl)oxy)phenyl)ethan-1-one 22b (6.72 g, yellow oily substance), and the product was directly used for the next reaction without further purification.

MS m/z(ESI): 225.0 [M+1]

Step 2

1-(5-chloro-2-hydroxy-3-(2-methylallyl)phenyl)ethan-1-one 1-(5-chloro-2-((2-methylallyl)oxy)phenyl)ethan-1-one 22b (6.72 g, 30 mmol) was heated to 220° C., and then stirred and reacted for 5.5 hours. After the reaction was completed, the reaction solution was cooled to room temperature, and then added with 100 mL of dichloromethane for dissolution, and concentrated under reduced pressure. The obtained residue was purified by silica gel column chromatography (eluent: system A) to obtain 1-(5-chloro-2-hydroxy-3-(2-methylallyl)phenyl)ethan-1-one 22c (6.72 g, red oily substance) with a yield of 100%.

MS m/z(ESI): 224.9 [M+1]

Step 3

1-(5-chloro-2-(iodomethyl)-2-methyl-2,3-dihydrobenzofuran-7-yl)ethan-1-one 1-(5-chloro-2-hydroxy-3-(2-methylallyl)phenyl)ethan-1-one 22c (1 g, 4.46 mmol) was dissolved in 30 mL of tetrahydrofuran, added with iodosuccinimide (2 g, 8.93 mmol), and reacted at room temperature overnight. After the reaction was completed, the reaction solution was concentrated under reduced pressure. The residue was added with 30 mL of dichloromethane for dissolution, then washed with 25% sodium bisulfite solution (20 mL×2) and saturated brine (20 mL×2) sequentially, dried with anhydrous sodium sulfate, filtered, and concentrated under reduced pressure. The obtained residue was purified by silica gel column chromatography (eluent: system A) to obtain 1-(5-chloro-2-(iodomethyl)-2-methyl-2,3-dihydrobenzofuran-7-yl)ethan-1-one 22d (1.34 g, white solid) with a yield of 85.9%.

MS m/z(ESI): 351.0 [M+1].

Step 4

1-(2-(azidomethyl)-5-chloro-2-methyl-2,3-dihydrobenzofuran-7-yl)ethan-1-one 1-(5-chloro-2-(iodomethyl)-2-methyl-2,3-dihydrobenzofuran-7-yl)ethan-1-one 22d (1.34 g, 3.82 mmol) was dissolved in 20 mL of N,N-dimethylformamide, added with sodium azide (496 mg, 7.64 mmol), heated to 95° C., and then reacted overnight. LC-MS showed that the reaction was incomplete, and the reaction was continued at 115° C. for 3 hours. After the reaction was completed, the reaction solution was cooled to room temperature, then added with 50 mL of water and extracted with ethyl acetate (30 mL×3), then organic phases were combined, washed with saturated brine (30 mL), dried with anhydrous sodium sulfate, filtered, and concentrated under reduced pressure. The obtained residue was further separated and purified by silica gel column chromatography (eluent: system A) to obtain 1-(2-(azidomethyl)-5-chloro-2-methyl-2,3-dihydrobenzofuran-7-yl)
ethan-1-one 22e (1g, yellow oily substance) with a yield of
100%.

MS m/z(ESI): 265.9 [M+1]

Step 5

(R)—N-((E)-1-(2-(azidomethyl)-5-chloro-2-methyl-
2,3-dihydrobenzofuran-7-yl)ethylidene)-2-methyl-
propane-2-sulfinamide 1-(2-(azidomethyl)-5-chloro-2-methyl-2,3-dihydrobenzofuran-7-yl)ethan-1-one 22e (940 mg, 3.55 mmol) was dissolved in 20 mL of tetrahydrofuran, added with (R)-2-methylpropane-2-sulfinamide 1b (858 mg, 7.09 mmol) and tetraethyl titanate (3.24 g, 14.2 mmol) sequentially, then reacted at 75° C. overnight. After the reaction was completed, the reaction solution was cooled to room temperature, poured into 50 mL of water, added with 50 mL of ethyl acetate, and then filtered. The filtrate was concentrated under reduced pressure, and extracted with ethyl acetate (50 mL×2), and then organic phases were combined, dried with anhydrous sodium sulfate, filtered, and concentrated under reduced pressure. The obtained residue was purified by silica gel column chromatography (eluent: system A) to obtain (R)—N-((E)-1-(2-(azidomethyl)-5-chloro-2-methyl-2,3-dihydrobenzofuran-7-yl)ethylidene)-2-methylpropane-2-sulfinamide 22f (360 mg, white solid) with a yield of 27.7%.

MS m/z(ESI): 368.9 [M+1]

Step 6

(R)—N-((1R)-1-(2-(azidomethyl)-5-chloro-2-
methyl-2,3-dihydrobenzofuran-7-yl)ethyl)-2-methyl-
propane-2-sulfinamide (R)—N-((E)-1-(2-(azidomethyl)-5-chloro-2-methyl-2,3-dihydrobenzofuran-7-yl)ethylidene)-2-methylpropane-2-sulfinamide 22f (360 mg, 1 mmol) was dissolved in 10 mL of tetrahydrofuran, and then dropwise added with 9-borabicyclo[3,3,1]-nonane (4 mL, 2 mmol, 0.5 mol/L), and reacted at room temperature overnight. After the reaction was completed, the reaction solution was concentrated under reduced pressure to obtain (R)—N-((1R)-1-(2-(azidomethyl)-5-chloro-2-methyl-2,3-dihydrobenzofuran-7-yl)ethyl)-2-methylpropane-2-sulfinamide 22g (271 mg, white solid) with a yield of 73%.

MS m/z(ESI): 371.0 [M+1]

Step 7

(1R)-1-(2-(azidomethyl)-5-chloro-2-methyl-2,3-
dihydrobenzofuran-7-yl)ethan-1-amine (R)—N-((1R)-1-(2-(azidomethyl)-5-chloro-2-methyl-2,3-dihydrobenzofuran-7-yl)ethyl)-2-methylpropane-2-sulfinamide 22g (271 mg, 0.73 mmol) was dissolved in 3 mL of dichloromethane, then added with 4 mL of hydrochloride 1,4-dioxane solution (4 mol/L), and reacted at room temperature overnight. After the reaction was completed, the reaction solution was concentrated under reduced pressure to obtain (1R)-1-(2-(azidomethyl)-5-chloro-2-methyl-2,3-dihydrobenzofuran-7-yl)ethan-1-amine 22h (195 mg, white solid) with a yield of 100%.

MS m/z(ESI): 250.0 [M−16]

Step 8

Ethyl 5-(((1R)-1-(2-(azidomethyl)-5-chloro-2-
methyl-2,3-dihydrobenzofuran-7-yl)ethyl) amino)
pyrazolo[1,5-a]pyrimidine-3-carboxylate (1R)-1-(2-(azidomethyl)-5-chloro-2-methyl-2,3-dihydrobenzofuran-7-yl)ethan-1-amine 22h (525 mg, 1.97 mmol) and ethyl 5-chloropyrazolo[1,5-a]pyrimidine-3-carboxylate 1j (443 mg, 1.97 mmol) were dissolved in 10 mL of n-butanol, and then added with N,N-diisopropylethylamine (2.7 mL, 15.76 mmol), heated to 125° C., and reacted for 5 hours. After the reaction was completed, the reaction solution was concentrated under reduced pressure. The obtained residue was purified by silica gel column chromatography (eluent: system A) to obtain ethyl 5-(((1R)-1-(2-(azidomethyl)-5-chloro-2-methyl-2,3-dihydrobenzofuran-7-yl)ethyl)amino)pyrazolo[1,5-a]pyrimidine-3-carboxylate 22i (731 mg, yellow solid) with a yield of 81%.

MS m/z(ESI): 456.1 [M+1]

Step 9

Ethyl 5-(((1R)-1-(2-(((tert-butoxycarbonyl)amino)
methyl)-5-chloro-2-methyl-2,3-dihydrobenzofuran-
7-yl)ethyl)amino)pyrazolo[1,5-a]pyrimidine-3-car-
boxylate Ethyl 5-(((1R)-1-(2-(azidomethyl)-5-chloro-2-methyl-2,3-dihydrobenzofuran-7-yl)ethyl) amino)pyrazolo[1,5-a]pyrimidine-3-carboxylate 22i (731 mg, 1.6 mmol) was dissolved in 10 mL of methanol, and then added with di-tert-butyl dicarbonate (420 mg, 1.93 mmol) and 10% palladium carbon (100 mg, containing 50% of water) sequentially, hydrogen gas was replaced for three times, and a hydrogen balloon was inserted to reacted at room temperature overnight. After the reaction was completed, the reaction solution was filtered with diatomite, and the filtrate was concentrated under reduced pressure. The obtained residue was purified by silica gel column chromatography to obtain ethyl 5-(((1R)-1-(2-(((tert-butoxycarbonyl)amino)methyl)-5-chloro-2-methyl-2,3-dihydrobenzofuran-7-yl)ethyl)amino)pyrazolo[1,5-a]pyrimidine-3-carboxylate 22j (350 mg, white solid) with a yield of 41%.

MS m/z(ESI): 530.2 [M+1]

Step 10

5-(((1R)-1-(2-(((tert-butoxycarbonyl)amino)methyl)-
5-chloro-2-methyl-2,3-dihydrobenzofuran-7-yl)
ethyl)amino)pyrazolo[1,5-a]pyrimidine-3-carboxylic
acid Ethyl 5-(((1R)-1-(2-(((tert-butoxycarbonyl)amino)methyl)-5-chloro-2-methyl-2,3-dihydrobenzofuran-7-yl)ethyl)amino)pyrazolo[1,5-a]pyrimidine-3-carboxylate 22j (350 mg, 0.66 mmol) was dissolved in 5 mL of mixed solvent of ethanol, tetrahydrofuran and water (V:V:V=2:2:1), added with lithium hydroxide monohydrate (222 mg, 5.29 mmol), heated to 85° C., and reacted for 6 hours. After the reaction was completed, the reaction solution was cooled to room temperature, added with 15 mL of ethyl acetate to dilute the reaction solution, washed with 10% citric acid aqueous solution (10 mL), dried with anhydrous sodium sulfate, filtered, and concentrated under reduced pressure to obtain 5-(((1R)-1-(2-(((tert-butoxycarbonyl)amino)methyl)-5-chloro-2-methyl-2,3-dihydrobenzofuran-7-yl)ethyl)amino)pyrazolo[1,5-a]pyrimidine-3-carboxylic acid 22k (330 mg, yellow oily substance) with a yield of 100%.

MS m/z(ESI): 502.2 [M+1]

Step 11

5-(((1R)-1-(2-(aminomethyl)-5-chloro-2-methyl-2,3-dihydrobenzofuran-7-yl)ethyl)amino)pyrazolo[1,5-a]pyrimidine-3-carboxylic acid 5-(((1R)-1-(2-(((tert-butoxycarbonyl)amino)methyl)-5-chloro-2-methyl-2,3-dihydrobenzofuran-7-yl)ethyl)amino)pyrazolo[1,5-a]pyrimidine-3-carboxylic acid 22k (330 mg, 0.66 mmol) was dissolved in 5 mL of dichloromethane, and then added with 2 mL of hydrochloride 1,4-dioxane solution (4 mol/L), and reacted at room temperature overnight. After the reaction was completed, the reaction solution was concentrated under reduced pressure to obtain 5-(((1R)-1-(2-(aminomethyl)-5-chloro-2-methyl-2,3-dihydrobenzofuran-7-yl)ethyl)amino)pyrazolo[1,5-a]pyrimidine-3-carboxylic acid 22l (264 mg, white solid) with a yield of 100%.

MS m/z(ESI): 401.8 [M+1]

Step 12

(3R)-6-chloro-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 5-(((1R)-1-(2-(aminomethyl)-5-chloro-2-methyl-2,3-dihydrobenzofuran-7-yl)ethyl)amino)pyrazolo[1,5-a]pyrimidine-3-carboxylic acid 22l (264 mg, 0.66 mmol), pentafluorophenyl diphenyl phosphinate (304 mg, 0.79 mmol) and N,N-diisopropylethylamine (0.5 mL, 2.44 mmol) were dissolved in 6 mL of mixed solvent of dichloromethane and N,N-dimethylformamide (V:V=1:1), and reacted at 35° C. for 4 hours. After the reaction was completed, the reaction solution was added with 10 mL of water and extracted with ethyl acetate (10 mL×3), and then organic phases were combined, washed with saturated brine (10 mL), dried with anhydrous sodium sulfate, filtered, and concentrated under reduced pressure. (3R)-6-chloro-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 22 (50 mg) with a yield of 19.8% was obtained by preparing a liquid phase (separation column AKZONOBEL Kromasil; 250× 21.2 mm I.D.; 5 μm, 20 mL/min; mobile phase A: 0.05% TFA+H$_2$O, and mobile phase B: CH$_3$CN) from the obtained residue.

MS m/z(ESI): 384.0 [M+1]

1H NMR (400 MHz, CDCl$_3$) δ 9.18-9.16 (d, J=8.0 Hz, 1H), 8.22-8.13 (m, 2H), 6.97 (s, 1H), 6.88 (s, 1H), 6.59 (s, 1H), 6.25-6.23 (d, J=8.0 Hz, 1H), 5.17-5.15 (m, 11H), 3.99-3.93 (m, 1H), 3.43-3.14 (m, 3H), 1.66-1.63 (m, 6H).

Examples 23 and 24

(2R,14R)-19-fluoro-2,14-dimethyl-16,22-dioxa-3,5,7,8,12-pentaazapentacyclo[12.6.2.2$^{4,7}$.0$^{6,10}$.0$^{17,21}$]tetracosa-1(20),4,6(10),8,17(21),18,23-heptaen-11-one 23

(2R,14S)-19-fluoro-2,14-dimethyl-16,22-dioxa-3,5,7,8,12-pentaazapentacyclo[12.6.2.2$^{4,7}$.0$^{6,10}$.0$^{17,21}$]tetracosa-1(20),4,6(10),8,17(21),18,23-heptaen-11-one 24

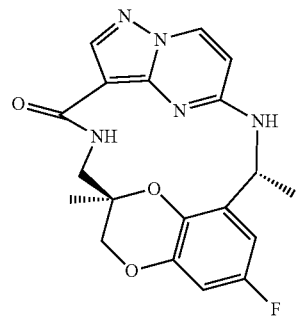

23

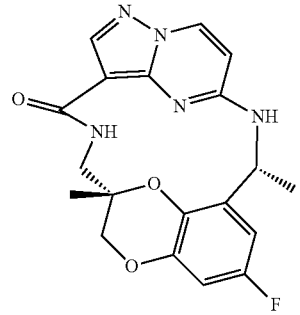

24

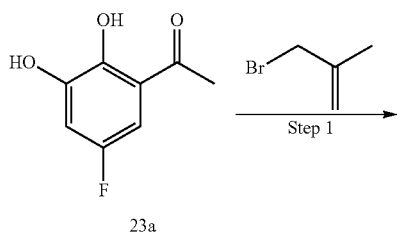

23a

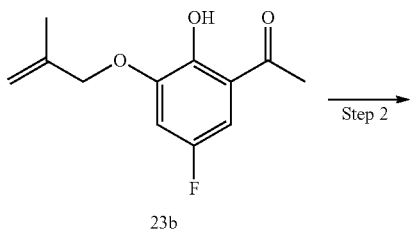

23b

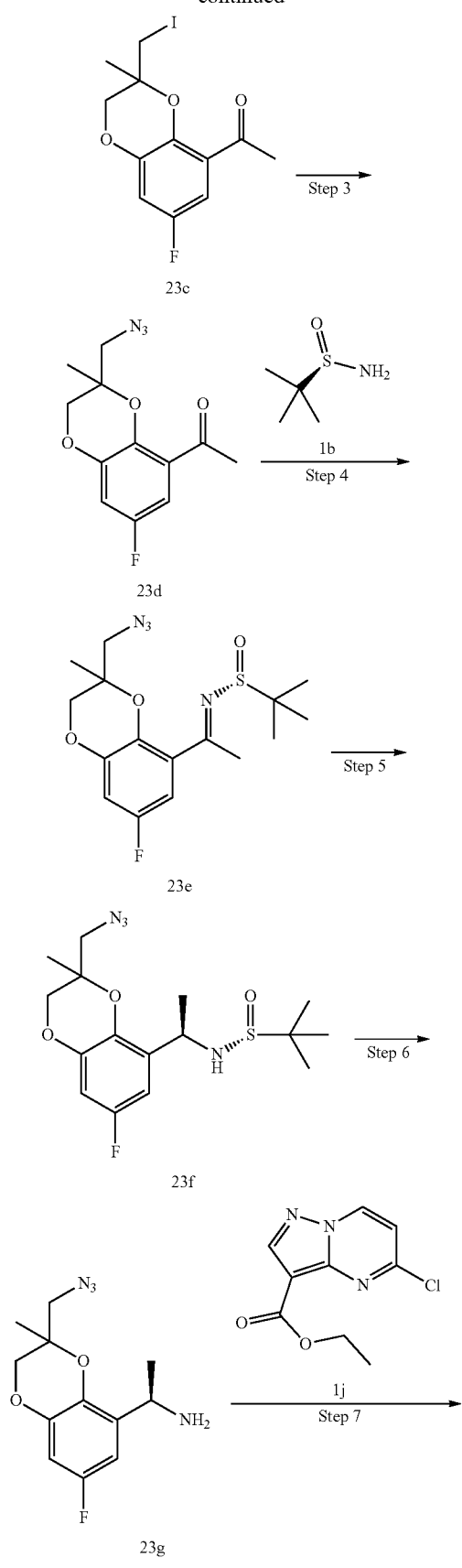
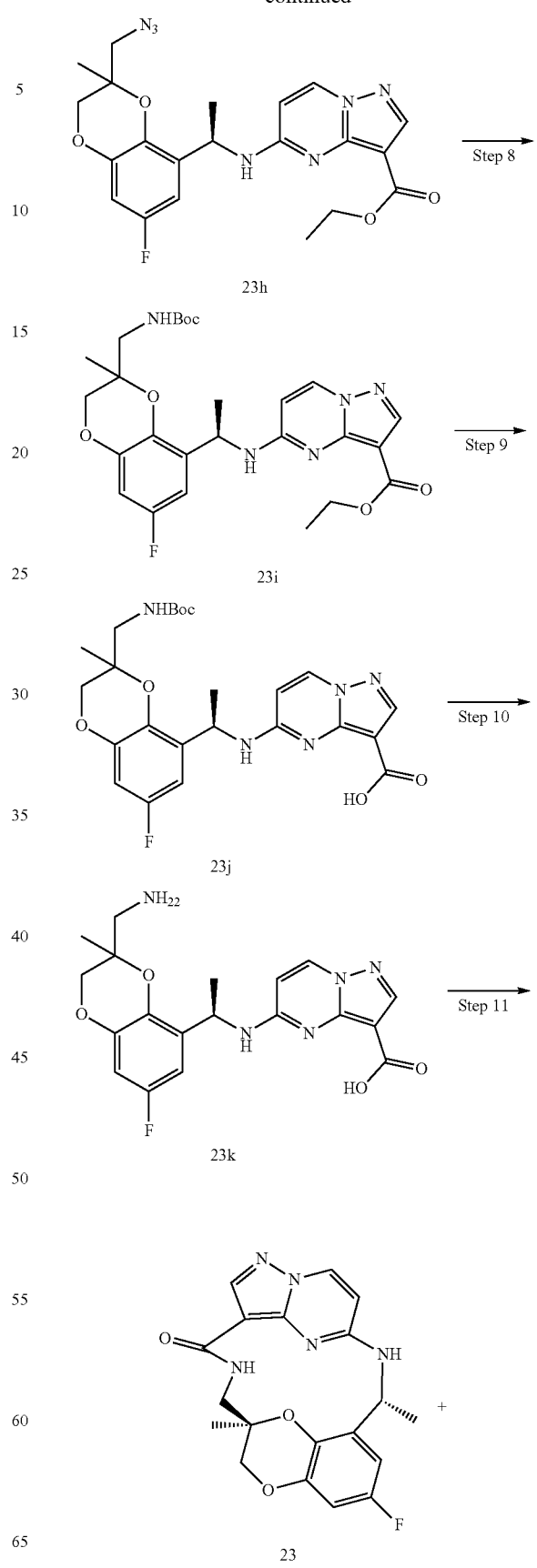

185
-continued

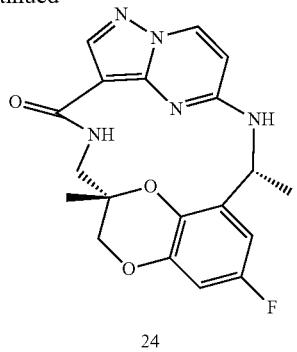

24

Step 1

1-(5-fluoro-2-hydroxy-3-((2-methylallyl)oxy)phenyl)ethan-1-one 1-(5-fluoro-2,3-dihydroxyphenyl)ethan-1-one 23a (1.7 g, 10 mmol) was dissolved in 20 mL of N,N-dimethylformamide, added with potassium carbonate (1.52 g, 11 mmol), and stirred at room temperature; 3-bromo-2-methylpropene (1.35 g, 10 mmol) was dissolved in 15 mL of N,N-dimethylformamide, and then dropwise added in the above-mentioned mixed solution, and warmed up to 50° C. and reacted at 50° C. overnight. After the reaction was completed, the reaction solution was added with 100 mL of water and extracted with ethyl acetate (50 mL×3), then organic phases were combined, washed with saturated brine (100 mL×2), dried with anhydrous sodium sulfate, filtered, and concentrated under reduced pressure. The obtained residue was purified by silica gel column chromatography (eluent: system A) to obtain 1-(5-fluoro-2-hydroxy-3-((2-methylallyl) oxy)phenyl)ethan-1-one 23b (430 mg, yellow oily substance) with a yield of 19.1%.

Step 2

1-(7-fluoro-3-(iodomethyl)-3-methyl-2,3-dihydrobenzo[b][1,4]dioxin-5-yl)ethan-1-one 1-(5-fluoro-2-hydroxy-3-((2-methylallyl)oxy)phenyl) ethan-1-one 23b (130 mg, 0.58 mmol) and sodium bicarbonate (97 mg, 1.16 mmol) were dissolved in 5 mL of acetonitrile, added with iodine (176 mg, 0.7 mmol), reacted at 60° C. for 4 hours; warmed up to 85° C., and continuously reacted for 3 hours. After the reaction was completed, the reaction solution was cooled to room temperature then was added with 50 mL of water, and then slowly added with sodium thiosulfate solid, and stirred for dissolution until the color of the solution was no longer light, then the solution was extracted with ethyl acetate (20 mL×3), then organic phases were combined, washed with saturated brine (50 mL), dried with anhydrous sodium sulfate, filtered, and concentrated under reduced pressure. The obtained residue was purified by silica gel column chromatography (eluent: system A) to obtain 1-(7-fluoro-3-(iodomethyl)-3-methyl-2, 3-dihydrobenzo[b][1,4]dioxin-5-yl)ethan-1-one 23c (190 mg, faint yellow solid) with a yield of 93.6%.

MS m/z(ESI): 351.0[M+1]

186

Step 3

1-(3-(azidomethyl)-7-fluoro-3-methyl-2,3-dihydrobenzo[b][1,4]dioxin-5-yl)ethan-1-one 1-(7-fluoro-3-(iodomethyl)-3-methyl-2,3-dihydrobenzo [b][1,4]dioxin-5-yl)ethan-1-one 23c (190 mg, 0.54 mmol) was dissolved in 3 mL of N,N-dimethylformamide, and then added with sodium azide (71 mg, 1.09 mmol), heated to 75° C., and reacted overnight. After the reaction was completed, the reaction solution was cooled to room temperature, added with 50 mL of water, and extracted with ethyl acetate (30 mL×3), then organic phases were combined, washed with saturated brine (30 mL), dried with anhydrous sodium sulfate, filtered, and concentrated under reduced pressure to obtain 1-(3-(azidomethyl)-7-fluoro-3-methyl-2,3-dihydrobenzo[b][1,4]dioxin-5-yl)ethan-1-one 23d (143 mg) with a yield of 98%.

MS m/z(ESI): 266.2[M+1]

Step 4

(R)—N-((E)-1-(3-(azidomethyl)-7-fluoro-3-methyl-2,3-dihydrobenzo[b][1,4]dioxin-5-yl)ethylene)-2-methylpropane-2-sulfinamide 1-(3-(azidomethyl)-7-fluoro-3-methyl-2,3-dihydrobenzo [b][1,4]dioxin-5-yl)ethan-1-one 23d (143 mg, 0.54 mmol) was dissolved in 5 mL of tetrahydrofuran, added with (R)-2-methylpropane-2-sulfinamide 1b (131 mg, 1.08 mmol) and tetraethyl titanate (492 mg, 2.16 mmol) sequentially, and then reacted at 95° C. overnight. After the reaction was completed, the reaction solution was cooled to room temperature, and concentrated under reduced pressure. The obtained residue was purified by silica gel column chromatography (eluent: system A) to obtain (R)—N-((E)-1-(3-(azidomethyl)-7-fluoro-3-methyl-2,3-dihydrobenzo[b][1,4] dioxin-5-yl)ethylidene)-2-methylpropane-2-sulfinamide 23e (90 mg, yellow liquid) with a yield of 45.5%.

MS m/z(ESI): 369.0 [M+1]

Step 5

(R)—N-((1R)-1-(3-(azidomethyl)-7-fluoro-3-methyl-2,3-dihydrobenzo[b][1,4]dioxo-5-yl)ethyl)-2-methylpropane-2-sulfinamide (R)—N-((E)-1-(3-(azidomethyl)-7-fluoro-3-methyl-2,3-dihydrobenzo[b][1,4]dioxin-5-yl)ethylidene)-2-methylpropane-2-sulfinamide 23e (90 mg, 0.24 mmol) was dissolved in 5 mL of tetrahydrofuran, and then dropwise added with 9-borabicyclo[3,3,1]-nonane (1 mL, 0.48 mmol, 0.5 mol/L), and reacted at room temperature overnight. After the reaction was completed, the reaction solution was quenched with 10 mL of methanol and concentrated under reduced pressure to obtain (R)—N-((1R)-1-(3-(azidomethyl)-7-fluoro-3-methyl-2,3-dihydrobenzo[b][1,4]dioxo-5-yl)ethyl)-2-methylpropane-2-sulfinamide 23f (90 mg, yellow viscous substance) with a yield of 100%.

MS m/z(ESI): 371.4[M+1]

Step 6

(1R)-1-(3-(azidomethyl)-7-fluoro-3-methyl-2,3-dihydrobenzo[b][1,4]dioxin-5-yl)ethan-1-amine (R)—N-((1R)-1-(3-(azidomethyl)-7-fluoro-3-methyl-2,3-dihydrobenzo[b][1,4]dioxo-5-yl)ethyl)-2-methylpropane-2- sulfinamide 23f (90 mg, 0.24 mmol) was dissolved in 2 mL of dichloromethane, and then added with 2 mL of hydrochloride 1,4-dioxane solution (4 mol/L), and reacted at room temperature for 1 hour. After the reaction was completed, the reaction solution was concentrated under reduced pressure to obtain (1R)-1-(3-(azidomethyl)-7-fluoro-3-methyl-2,3-dihydrobenzo[b][1,4]dioxin-5-yl)ethan-1-amine 23g (65 mg, white solid) with a yield of 100%.

MS m/z(ESI): 267.0[M+1]

Step 7

Ethyl 5-(((1R)-1-(3-(azidomethyl)-7-fluoro-3-methyl-2,3-dihydrobenzo[b][1,4]dioxin-5-yl)ethyl) amino)pyrazolo[1,5-a]pyrimidine-3-carboxylate (1R)-1-(3-(azidomethyl)-7-fluoro-3-methyl-2,3-dihydrobenzo[b][1,4]dioxin-5-yl)ethan-1-amine 23g (65 mg, 0.24 mmol) and ethyl 5-chloropyrazolo[1,5-a]pyrimidine-3-carboxylate 1j (55 mg, 0.24 mmol) were dissolved in 5 mL of n-butanol, added with N,N-diisopropylethylamine (248 mg, 1.92 mmol), heated to 130° C., and reacted for 6 hours. After the reaction was completed, the reaction solution was concentrated under reduced pressure. The obtained residue was purified by silica gel column chromatography (eluent: system A) to obtain ethyl 5-(((1R)-1-(3-(azidomethyl)-7-fluoro-3-methyl-2,3-dihydrobenzo[b][1,4]dioxin-5-yl)ethyl) amino)pyrazolo[1,5-a]pyrimidine-3-carboxylate 23h (50 mg, yellow viscous substance) with a yield of 45.87%.

MS m/z(ESI): 456.3[M+1]

Step 8

Ethyl 5-(((1R)-1-(3-(((tert-butoxycarbonyl)amino) methyl)-7-fluoro-3-methyl-2,3-dihydrobenzo [b][1, 4]dioxin-5-yl)ethyl)amino)pyrazolo[1,5-a]pyrimidine-3-carboxylate Ethyl 5-(((1R)-1-(3-(azidomethyl)-7-fluoro-3-methyl-2, 3-dihydrobenzo[b][1,4]dioxin-5-yl) ethyl)amino)pyrazolo [1,5-a]pyrimidine-3-carboxylate 23h (50 mg, 0.1098 mmol) was dissolved in 3 mL of methanol, and then added with di-tert-butyl dicarbonate (29 mg, 0.13 mmol) and 10% palladium carbon (10 mg, containing 50% of water) sequentially, hydrogen gas was replaced for three times, and a hydrogen balloon was inserted to react at room temperature overnight. After the reaction was completed, the reaction solution was filtered with diatomite, and the filtrate was concentrated under reduced pressure to obtain ethyl 5-(((1R)-1-(3-(((tert-butoxycarbonyl)amino)methyl)-7-fluoro-3-methyl-2,3-dihydrobenzo[b][1,4]dioxin-5-yl) ethyl)amino)pyrazolo[1,5-a]pyrimidine-3-carboxylate 23i (58 mg, yellow viscous substance) with a yield of 100%.

MS m/z(ESI): 530.1[M+1]

Step 9

5-(((1R)-1-(3-(((tert-butoxycarbonyl)amino)methyl)-7-fluoro-3-methyl-2,3-dihydrobenzo[b][1,4]dioxin-5-yl)ethyl)amino)pyrazolo[1,5-a]pyrimidine-3-carboxylic acid Ethyl 5-(((1R)-1-(3-(((tert-butoxycarbonyl)amino) methyl)-7-fluoro-3-methyl-2,3-dihydrobenzo[b][1,4]dioxin-5-yl)ethyl)amino)pyrazolo[1,5-a]pyrimidine-3-carboxylate 23i (58 mg, 0.11 mmol) was dissolved in 4 mL of mixed solvent of ethanol, tetrahydrofuran and water (V:V: V=2:1:1), added with lithium hydroxide monohydrate (41 mg, 1.1 mmol), heated to 85° C., and reacted for 6 hours. After the reaction was completed, the reaction solution was cooled to room temperature, added with 5 mL of ethyl acetate to dilute the reaction solution, washed with 10% citric acid aqueous solution (10 mL), dried with anhydrous sodium sulfate, filtered, and concentrated under reduced pressure to obtain 5-(((1R)-1-(3-(((tert-butoxycarbonyl) amino)methyl)-7-fluoro-3-methyl-2,3-dihydrobenzo[b][1,4] dioxin-5-yl)ethyl)amino)pyrazolo[1,5-a]pyrimidine-3-carboxylic acid 23j (55 mg, yellow viscous substance) with a yield of 100%.

MS m/z(ESI): 502.1[M+1]

Step 10

5-(((1R)-1-(3-(aminomethyl)-7-fluoro-3-methyl-2,3-dihydrobenzo[b][1,4]dioxin-5-yl)ethyl)amino)pyrazolo[1,5-a]pyrimidine-3-carboxylic acid 5-(((1R)-1-(3-(((tert-butoxycarbonyl)amino)methyl)-7-fluoro-3-methyl-2,3-dihydrobenzo[b][1,4]dioxin-5-yl) ethyl)amino)pyrazolo[1,5-a]pyrimidine-3-carboxylic acid 23j (55 mg, 0.11 mmol) was dissolved in 2 mL of dichloromethane, and then added with 2 mL of hydrochloride 1,4-dioxane solution (4 mol/L), and reacted at room temperature for 1 hour. After the reaction was completed, the reaction solution was concentrated under reduced pressure to obtain 5-(((1R)-1-(3-(aminomethyl)-7-fluoro-3-methyl-2, 3-dihydrobenzo[b][1,4]dioxin-5-yl)ethyl)amino)pyrazolo[1, 5-a]pyrimidine-3-carboxylic acid 23k (44 mg, yellow viscous substance) with a yield of 100%.

MS m/z(ESI): 402.2[M+1]

Step 11

(2R,14R)-19-fluoro-2,14-dimethyl-16,22-dioxa-3,5, 7,8,12-pentaazapentacyclo[12.6.2.2$^{4,7}$.0$^{6,10}$.0$^{17,21}$] tetracosa-1(20),4,6(10),8,17(21),18,23-heptaen-11-one 23

(2R,14S)-19-fluoro-2,14-dimethyl-16,22-dioxa-3,5, 7,8,12-pentaazapentacyclo[12.6.2.2$^{4,7}$.0$^{6,10}$.0$^{17,21}$] tetracosa-1(20),4,6(10),8,17(21),18,23-heptaen-11-one 24

5-(((1R)-1-(3-(aminomethyl)-7-fluoro-3-methyl-2,3-dihydrobenzo[b][1,4]dioxin-5-yl)ethyl)amino)pyrazolo[1,5-a] pyrimidine-3-carboxylic acid 23k (44 mg, 0.11 mmol), pentafluorophenyl diphenyl phosphinate (51 mg, 0.13 mmol) and N,N-diisopropylethylamine (114 mg, 0.88 mmol) were dissolved in 4 mL of mixed solvent of dichloromethane and N.N-dimethylformamide (V:V=3:1), and reacted at room temperature overnight. After the reaction was completed, the reaction solution was added with 10 mL of water and extracted with dichloromethane (10 mL×3), and then organic phases were combined, washed with saturated brine (10 mL), dried with anhydrous sodium sulfate, filtered, and concentrated under reduced pressure. (2R,14R)-19-fluoro-2,14-dimethyl-16,22-dioxa-3,5,7,8,12-pentaazapentacyclo[12.6.2.2$^{4,7}$.0$^{6,10}$.0$^{7,21}$]tetracosa-1(20),4,6(10),8, 17(21),18,23-heptaen-11-one 23 (10 mg) with a yield of 23.8% and (2R,14S)-19-fluoro-2,14-dimethyl-16,22-dioxa-3,5,7,8,12-pentaazapentacyclo[12.6.2.2$^{4,7}$.0$^{6,10}$.0$^{17,21}$]tetracosa-1(20),4,6(10),8,17(21),18,23-heptaen-11-one 24 (4.1 mg) with a yield of 9.3% were obtained by preparing a liquid phase (separation column AKZONOBEL Kromasil; 250×

21.2 mm I.D.; 5 μm, 20 mL/min; mobile phase A: 0.05% TFA+H₂O, and mobile phase B: CH₃CN) from the obtained residue.
23
MS m/z(ESI): 384.1[M+1]
24
MS m/z(ESI): 384.1[M+1]
Example 25
(3R,11R)-16-amino-6-fluoro-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one
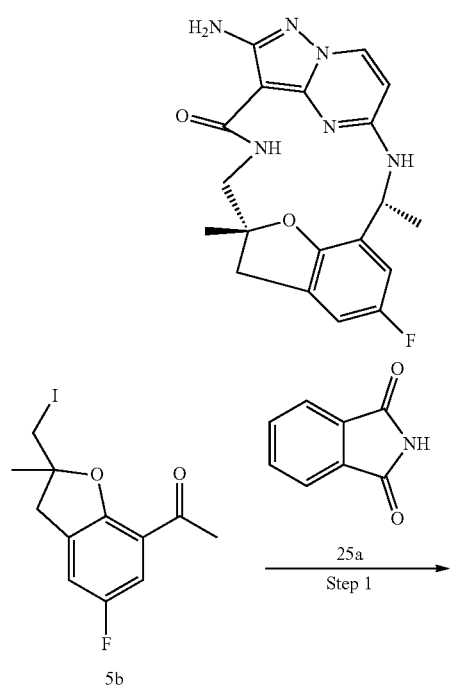
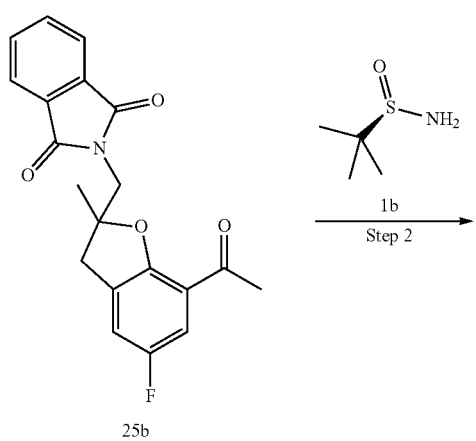
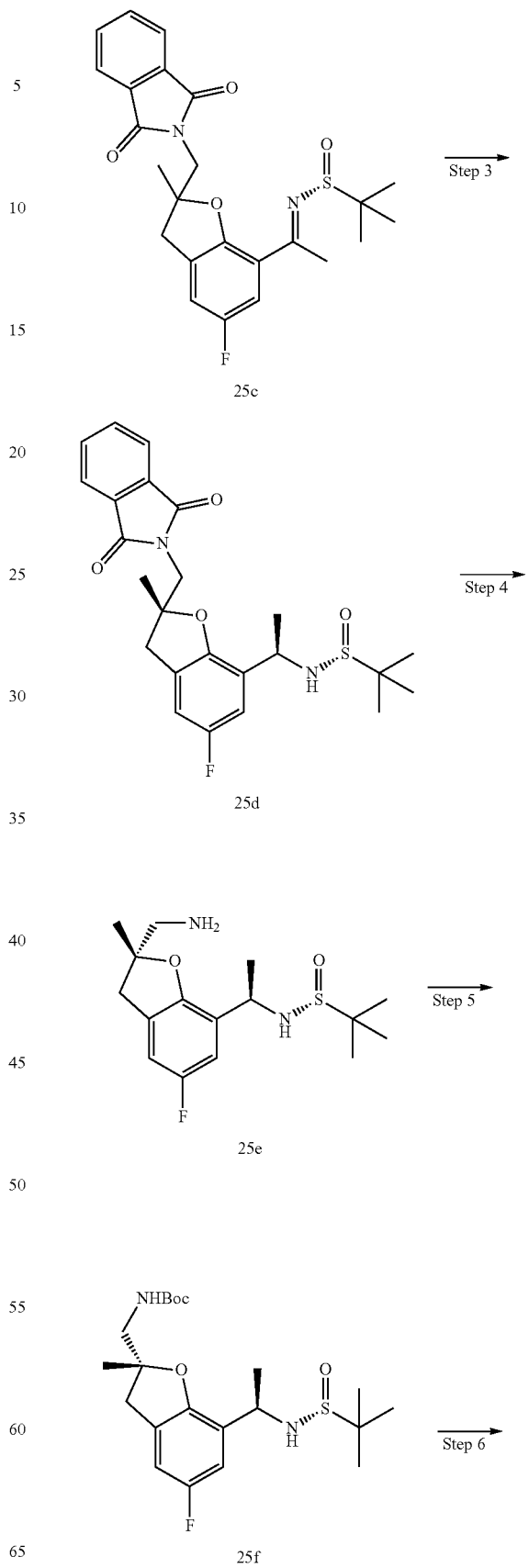

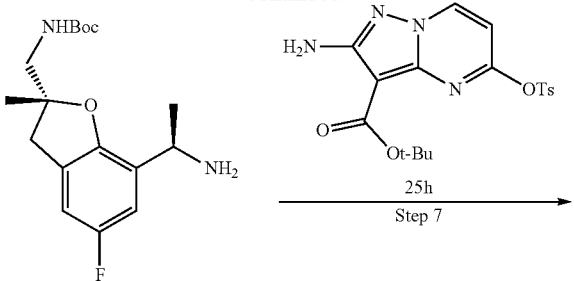

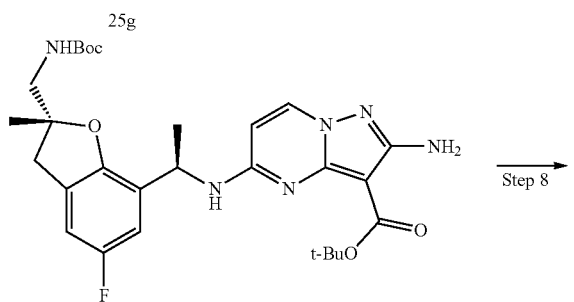

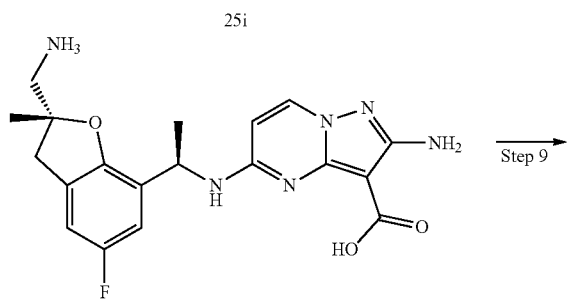

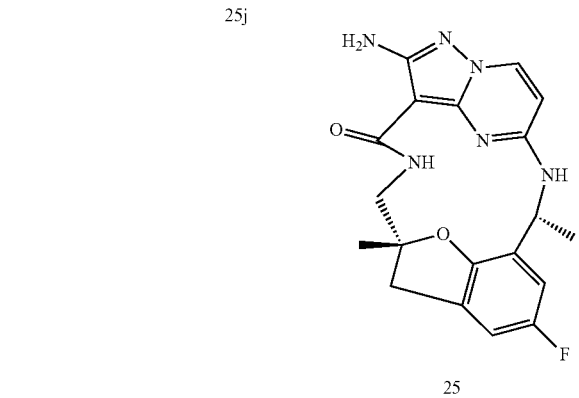

was purified by silica gel column chromatography (eluent: system A) to obtain 2-((7-acetyl-5-fluoro-2-methyl-2,3-dihydrobenzofuran-2-yl)methyl)isoindoline-1,3-dione 25b (22 g, white solid) with a yield of 62.8%.

MS m/z(ESI): 354.1[M+1]

Step 2

(R)—N-((E)-1-(2-((1,3-dioxoisoindolin-2-yl)methyl)-5-fluoro-2-methyl-2,3-dihydrobenzofuran-7-yl)ethylidene)-2-methylpropane-2-sulfinamide 2-((7-acetyl-5-fluoro-2-methyl-2,3-dihydrobenzofuran-2-yl)methyl)isoindoline-1,3-dione 25b (21.3 g, 60 mmol) was dissolved in 250 mL of tetrahydrofuran, added with (R)-2-methylpropane-2-sulfinamide 1b (14.6 g, 120 mmol) and tetraethyl titanate (54.7 g, 240 mmol) sequentially, and then reacted at 75° C. overnight. After the reaction was completed, the reaction solution was cooled to room temperature, and concentrated under reduced pressure. The obtained residue was purified by silica gel column chromatography (eluent: system A) to obtain (R)—N-((E)-1-(2-((1,3-dioxoisoindolin-2-yl)methyl)-5-fluoro-2-methyl-2,3-dihydrobenzofuran-7-yl)ethylidene)-2-methylpropane-2-sulfinamide 25c (21.4 g, yellow solid) with a yield of 78.2%.

MS m/z(ESI): 457.1[M+1]

Step 3

(R)—N—((R)-1-((R)-2-((1,3-dioxoisoindolin-2-yl)methyl)-5-fluoro-2-methyl-2,3-dihydrobenzofuran-7-yl)ethyl)-2-methylpropane-2-sulfinamide (R)—N-((E)-1-(2-((1,3-dioxoisoindolin-2-yl)methyl)-5-fluoro-2-methyl-2,3-dihydrobenzofuran-7-yl)ethylidene)-2-methylpropane-2-sulfinamide 25c (21.4 g, 47 mmol) was dissolved in 250 mL of tetrahydrofuran, and then dropwise added with 9-borabicyclo[3,3,1]-nonane (188 mL, 94 mmol, 0.5 mol/L), and reacted at room temperature overnight. After the reaction was completed, the reaction solution was quenched with 100 mL of methanol and concentrated under reduced pressure to obtain (R)—N—((R)-1-((R)-2-((1,3-dioxoisoindolin-2-yl)methyl)-5-fluoro-2-methyl-2,3-dihydrobenzofuran-7-yl)ethyl)-2-methylpropane-2-sulfinamide 25d (4.5 g, yellow viscous substance) with a yield of 21%.

MS m/z(ESI): 459.2 [M+1]

Step 4

(R)—N—((R)-1-((R)-2-(aminomethyl)-5-fluoro-2-methyl-2,3-dihydrobenzofuran-7-yl)ethyl)-2-methylpropane-2-sulfinamide (R)—N—((R)-1-((R)-2-((1,3-dioxoisoindolin-2-yl)methyl)-5-fluoro-2-methyl-2,3-dihydrobenzofuran-7-yl)ethyl)-2-methylpropane-2-sulfinamide 25d (4.5 g, 10 mmol) and hydrazine hydrate (2.5 g, 50 mmol) were dissolved in 100 mL of ethanol, and then refluxed and reacted for 2 hours. After the reaction was completed, the reaction solution was filtered, the filter cake was washed with ethanol (50 mL×3), and the filtrate was concentrated under reduced pressure, added with 500 mL of water, and extracted with ethyl acetate (200 mL×3), then organic phases were combined, dried with anhydrous sodium sulfate, filtered, and concentrated under reduced pressure to obtain (R)—N—((R)-1-((R)-2-(aminomethyl)-5-fluoro-2-methyl-2,3-dihydrobenzofuran-7-yl)

Step 1

2-((7-acetyl-5-fluoro-2-methyl-2,3-dihydrobenzofuran-2-yl)methyl)isoindoline-1,3-dione 1-(5-fluoro-2-(iodomethyl)-2-methyl-2,3-dihydrobenzofuran-7-yl)ethan-1-one 5b (33.4 g, 100 mmol) and potassium phthalimide salt 25a (22 g, 120 mmol) were dissolved in 200 mL of N,N-dimethylformamide, and reacted at 145° C. for 6 hours. After the reaction was completed, the reaction solution was added with 1 L of water, and extracted with ethyl acetate (300 mL×3), and then organic phases were combined, dried with anhydrous sodium sulfate, filtered, and concentrated under reduced pressure. The obtained residue ethyl)-2-methylpropane-2-sulfinamide 25e (2.9 g, yellow oily substance) with a yield of 88%.

MS m/z(ESI): 329.1 [M+1]

Step 5

Tert-butyl (((R)-7-((R)-1-(((R)-tert-butylsulfinyl)amino)ethyl)-5-fluoro-2-methyl-2,3-dihydrobenzofuran-2-yl)methyl)carbamate (R)—N—((R)-1-((R)-2-(aminomethyl)-5-fluoro-2-methyl-2,3-dihydrobenzofuran-7-yl)ethyl)-2-methylpropane-2-sulfinamide 25e (2.9 g, 8.84 mmol) was dissolved in 20 mL of dichloromethane, added with di-tert-butyl dicarbonate (2.1 g, 9.7 mmol) and triethylamine (2.4 mL, 17.68 mmol), and reacted at room temperature overnight. After the reaction was completed, the reaction solution was added with 300 mL of water and extracted with dichloromethane (100 mL×3), then organic phases were combined, dried with anhydrous sodium sulfate, filtered, and concentrated under reduced pressure. The obtained residue was purified by silica gel column chromatography (eluent: system A) to obtain tert-butyl (((R)-7-((R)-1-(((R)-tert-butylsulfinyl)amino)ethyl)-5-fluoro-2-methyl-2,3-dihydrobenzofuran-2-yl)methyl)carbamate 25f (1.4 g, yellow oily substance) with a yield of 33.6%.

MS m/z(ESI): 329.0 [M−100]

Step 6

Tert-butyl (((R)-7-((R)-1-aminoethyl)-5-fluoro-2-methyl-2,3-dihydrobenzofuran-2-yl) methyl)carbamate Tert-butyl (((R)-7-((R)-1-(((R)-tert-butylsulfinyl)amino)-5-fluoro-2-methyl-2,3-dihydrobenzofuran-2-yl)methyl)carbamate 25f (1.4 g, 3 mmol) and iodine (152 mg, 0.6 mmol) were dissolved in 15 mL of mixed solvent of tetrahydrofuran and water (V:V=4:1), and reacted at 50° C. for 3 hours. After the reaction was completed, the reaction solution was added with 100 mL of water, and extracted with ethyl acetate (15 mL×3), then organic phases were combined, and dried with anhydrous sodium sulfate, filtered, and concentrated under reduced pressure to obtain tert-butyl (((R)-7-((R)-1-aminoethyl)-5-fluoro-2-methyl-2,3-dihydrobenzofuran-2-yl)methyl)carbamate 25g (0.9 g, yellow oily substance) with a yield of 92%.

MS m/z(ESI): 325.1 [M+1]

Step 7

Tert-butyl 2-amino-5-(((R)-1-((R)-2-2-(((tert-butoxycarbonyl)amino)methyl)-5-fluoro-2-methyl-2,3-dihydrobenzofuran-7-yl)ethyl)amino)pyrazolo[1,5-a]pyrimidine-3-carboxylate Tert-butyl (((R)-7-((R)-1-aminoethyl)-5-fluoro-2-methyl-2,3-dihydrobenzofuran-2-yl) methyl)carbamate 25g (3.7 g, 11.41 mmol), tert-butyl 2-amino-5-(p-tosyloxy)pyrazolo[1,5-a]pyrimidine-3-carboxylate 25h (4.61 g, 11.41 mmol, prepared according to published patent WO 2019023417A1) and N,N-diisopropylethylamine (11.79 g, 91.25 mmol) were dissolved in 35 mL of tertiary butyl alcohol, heated to 100° C., and reacted overnight. After the reaction was completed, the reaction solution was concentrated under reduced pressure. The obtained residue was purified by thin layer chromatography (developing agent: system A) to obtain tert-butyl 2-amino-5-(((R)-1-((R)-2-(((tert-butoxycarbonyl)amino)methyl)-5-fluoro-2-methyl-2,3-dihydrobenzofuran-7-yl)ethyl)amino)pyrazolo[1,5-a]pyrimidine-3-carboxylate 25i (2.4 g, yellow foamy solid) with a yield of 37.8%.

MS m/z(ESI): 557.1 [M+1]

Step 8

2-amino-5-(((R)-1-((R)-2-(aminomethyl)-5-fluoro-2-methyl-2,3-dihydrobenzofuran-7-yl)ethyl)amino)pyrazolo[1,5-a]pyrimidine-3-carboxylic acid Tert-butyl 2-amino-5-(((R)-1-((R)-2-(((tert-butoxycarbonyl)amino)methyl)-5-fluoro-2-methyl-2,3-dihydrobenzofuran-7-yl)ethyl)amino)pyrazolo[1,5-a]pyrimidine-3-carboxylate 25i (2.4 g, 4.31 mmol) was dissolved in 25 mL of dichloromethane, and then added with 10 mL of hydrochloride 1,4-dioxane solution (4 mol/L), and reacted at room temperature for 1 hour. After the reaction was completed, the reaction solution was concentrated under reduced pressure to obtain 2-amino-5-(((R)-1-((R)-2-(aminomethyl)-5-fluoro-2-methyl-2,3-dihydrobenzofuran-7-yl)ethyl)amino)pyrazolo[1,5-a]pyrimidine-3-carboxylic acid 25j (1.73 g, yellow viscous substance) with a yield of 100%.

MS m/z(ESI): 401.1 [M+1]

Step 9

(3R,11R)-16-amino-6-fluoro-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 2-amino-5-(((R)-1-((R)-2-(aminomethyl)-5-fluoro-2-methyl-2,3-dihydrobenzofuran-7-yl)ethyl)amino)pyrazolo[1,5-a]pyrimidine-3-carboxylic acid 25j (1.73 g, 4.32 mmol) was dissolved in 30 mL of mixed solvent of dichloromethane and N,N-dimethylformamide (V:V=5:1), added with pentafluorophenyl diphenyl phosphinate (1.99 g, 5.18 mmol) and N,N-diisopropylethylamine (4.47 g, 34.56 mmol), and reacted at room temperature for 2 hours. After the reaction was completed, the reaction solution was added with 100 mL of dichloromethane, and the system was washed with saturated brine (100 mL×2), dried with anhydrous sodium sulfate, filtered, and concentrated under reduced pressure. (3R,11R)-16-amino-6-fluoro-3,11-dimethyl-10-oxa-2,13,17,18,21-pentaazapentacyclo[13.5.2.1$^{8,11}$.0$^{4,9}$.0$^{18,22}$]tricosa-1(21),4,6,8,15(22),16,19-heptaen-14-one 25 (700 mg) with a yield of 42.37% was obtained by preparing a liquid phase (separation column AKZONOBEL Kromasil; 250×21.2 mm I.D.; 5 m, 20 mL/min; mobile phase A: 0.05% TFA+H$_2$O, and mobile phase B: CH$_3$CN) from the obtained residue.

MS m/z(ESI): 383.0 [M+1]

$^1$H NMR (400 MHz, DMSO-d$_6$) δ 8.68 (d, J=9.7 Hz, 1H), 8.28 (d, J=5.1 Hz, 1H), 8.16 (d, J=7.5 Hz, 11H), 6.79 (dd, J=8.1, 2.7 Hz, 1H), 6.71 (dd, J=10.0, 2.8 Hz, 1H), 6.09 (d, J=7.4 Hz, 1H), 4.90 (ddd, J=7.0, 5.0, 2.0 Hz, 1H), 3.75 (dd, J=13.1, 9.8 Hz, 1H), 3.23 (d, J=16.8 Hz, 11H), 3.18 (d, J=13.1 Hz, 1H), 3.00 (d, J=16.8 Hz, 1H), 1.58 (s, 3H), 1.51 (d, J=7.0 Hz, 3H).

Example 26

(3R,11R)-6-fluoro-3,11-dimethyl-10-oxa-2,13,17,21,22-pentaazapentacyclo[13.5.2.1$^{8,11}$.0$^{4,9}$.0$^{18,22}$]tricosa-1(21),4,6,8,15,17,19-heptaen-14-one

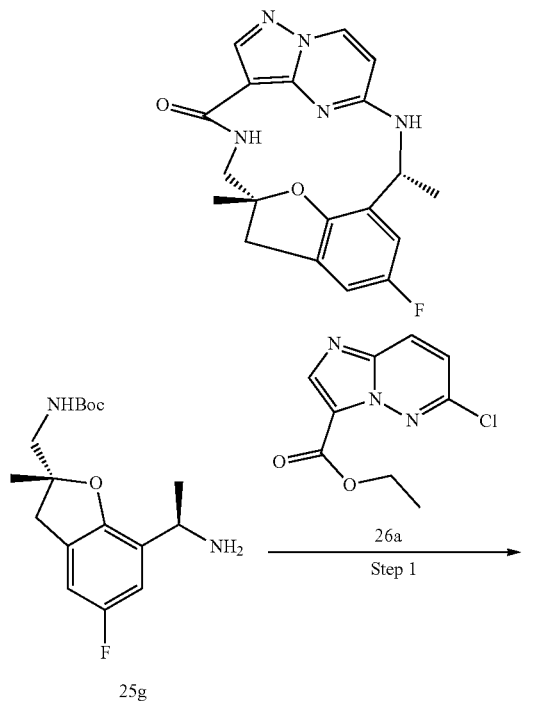

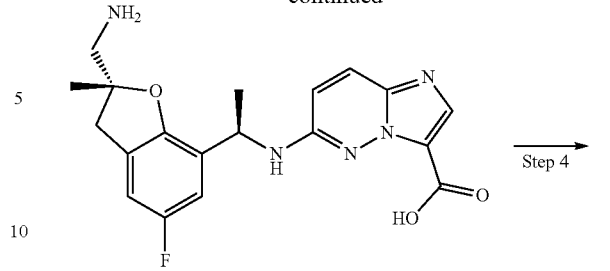

26d

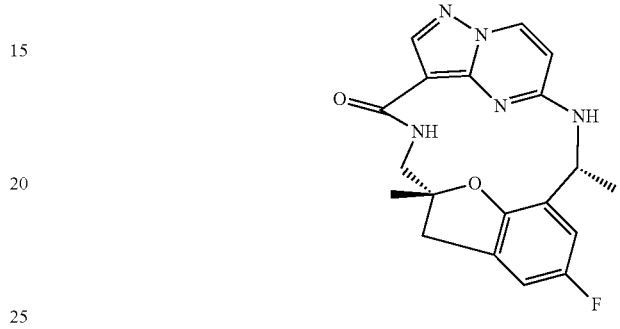

26

Step 1

Ethyl 6-(((R)-1-((R)-2-(((tert-butoxycarbonyl)amino)methyl)-5-fluoro-2-methyl-2,3-dihydrobenzofuran-7-yl)ethyl)amino)imidazo[1,2-b]pyridazine-3-carboxylate Tert-butyl (((R)-7-((R)-1-aminoethyl)-5-fluoro-2-methyl-2,3-dihydrobenzofuran-2-yl) methyl)carbamate 25g (500 mg, 1.54 mmol), ethyl 6-chloroimidazo[1,2-b]pyridazine-3-carboxylate 26a (417.33 mg, 1.85 mmol) and potassium fluoride (447.76 mg, 7.71 mmol) were dissolved in 10 mL of dimethylsulfoxide, heated to 120° C., and reacted overnight. After the reaction was completed, the reaction solution was added with 100 mL of water, and extracted with ethyl acetate (100 mL), then organic phases were washed with saturated brine (100 mL×2), dried with anhydrous sodium sulfate, filtered, and concentrated under reduced pressure. The obtained residue was purified by thin layer chromatography (developing agent: system A) to obtain ethyl 6-(((R)-1-((R)-2-(((tert-butoxycarbonyl)amino)methyl)-5-fluoro-2-methyl-2,3-dihydrobenzofuran-7-yl)ethyl)amino)imidazo[1,2-b]pyridazine-3-carboxylate 26b (230 mg, yellow foamy solid) with a yield of 29.1%.

MS m/z(ESI): 514.3[M+1]

Step 2

6-(((R)-1-((R)-2-(((tert-butoxycarbonyl)amino)methyl)-5-fluoro-2-methyl-2,3-dihydrobenzofuran-7-yl)ethyl)amino)imidazo[1,2-b]pyridazine-3-carboxylic acid Ethyl 6-(((R)-1-((R)-2-(((tert-butoxycarbonyl)amino)methyl)-5-fluoro-2-methyl-2,3-dihydrobenzofuran-7-yl)ethyl)amino)imidazo[1,2-b]pyridazine-3-carboxylate 26b (230 mg, 0.447 mmol) was dissolved in 7 mL of mixed solvent of ethanol, tetrahydrofuran and water (V:V:V=5:1:

1), added with lithium hydroxide monohydrate (187.92 mg, 4.48 mmol), heated to 85° C., and reacted overnight. After the reaction was completed, the reaction solution was cooled to room temperature, concentrated under reduced pressure, added with 100 mL of water, adjusted to acidity with 1M diluted hydrochloric acid, extracted with ethyl acetate (100 mL), dried with anhydrous sodium sulfate, filtered, and concentrated under reduced pressure to obtain 6-(((R)-1-((R)-2-(((tert-butoxycarbonyl)amino)methyl)-5-fluoro-2-methyl-2,3-dihydrobenzofuran-7-yl)ethyl)amino)imidazo[1,2-b]pyridazine-3-carboxylic acid 26c (217 mg, yellow viscous substance) with a yield of 99.8%.

MS m/z(ESI): 486.2[M+1]

Step 3

6-(((R)-1-((R)-2-(aminomethyl)-5-fluoro-2-methyl-2,3-dihydrobenzofuran-7-yl)ethyl)amino)imidazole[1,2-b]pyridazine-3-carboxylic acid 6-(((R)-1-((R)-2-(((tert-butoxycarbonyl)amino)methyl)-5-fluoro-2-methyl-2,3-dihydrobenzofuran-7-yl)ethyl)amino)imidazo[1,2-b]pyridazine-3-carboxylic acid 26c (217 mg, 0.447 mmol) was dissolved in 5 mL of dichloromethane, and then added with 0.11 mL of hydrochloride 1,4-dioxane solution (4 mol/L), and reacted at room temperature for 1 hour. After the reaction was completed, the reaction solution was concentrated under reduced pressure to obtain crude product of 6-(((R)-1-((R)-2-(aminomethyl)-5-fluoro-2-methyl-2,3-dihydrobenzofuran-7-yl)ethyl)amino)imidazole[1,2-b]pyridazine-3-carboxylic acid 26d (172 mg, yellow solid), which was directly used for the next reaction.

MS m/z(ESI): 386.2 [M+1]

Step 4

(3R,11R)-6-fluoro-3,11-dimethyl-10-oxa-2,13,17,21,22-pentaazapentacyclo[13.5.2.1$^{8,11}$.0$^{4,9}$.0$^{18,22}$]tricosa-1(21),4,6,8,15,17,19-heptaen-14-one 6-(((R)-1-((R)-2-(aminomethyl)-5-fluoro-2-methyl-2,3-dihydrobenzofuran-7-yl)ethyl)amino)imidazole[1,2-b]pyridazine-3-carboxylic acid 26d (172 mg, 0.447 mmol) was dissolved in 6 mL of mixed solvent of dichloromethane and N,N-dimethylformamide (V:V=5:1), added with pentafluorophenyl diphenyl phosphinate (172 mg, 0.447 mmol) and N,N-diisopropylethylamine (0.461 mg, 3.57 mmol), and reacted at room temperature for 2 hours. After the reaction was completed, the reaction solution was added with 50 mL of dichloromethane, washed with saturated brine (50 mL×3), then dried with anhydrous sodium sulfate, filtered, and concentrated under reduced pressure. (3R,11R)-6-fluoro-3,11-dimethyl-10-oxa-2,13,17,21,22-pentaazapentacyclo[13.5.2.1$^{8,11}$.0$^{4,9}$.0$^{18,22}$]tricosa-1(21),4,6,8,15,17,19-heptaen-14-one 26 (80 mg) with a yield of 26% was obtained by preparing a liquid phase (separation column AKZONOBEL Kromasil; 250×21.2 mm I.D.; 5 μm, 20 mL/min; mobile phase A: 0.05% TFA+H$_2$O, and mobile phase B: CH$_3$CN) from the obtained residue.

MS m/z(ESI): 368.1[M+1]

$^1$H NMR (400 MHz, DMSO-d$_6$) δ 9.34 (d, J=9.4 Hz, 1H), 8.07 (d, J=5.3 Hz, 1H), 7.88-7.72 (m, 2H), 6.86-6.73 (m, 3H), 4.89-4.74 (m, 1H), 3.93 (dd, J=13.5, 9.6 Hz, 1H), 3.33-3.25 (m, 2H), 3.06 (d, J=16.9 Hz, 1H), 1.63 (s, 3H), 1.55 (d, J=6.9 Hz, 3H).

Biological Evaluation

Test Example 1 Determination of the Compounds of the Present Invention on Activities of TRKA, TRKB, TRKC, TRKA(G595R), TRKA(G667C) and TRKC(G623R) Kinases The following method was used to determine the inhibition degrees of the compounds of the present invention on the activity of recombinant human NTRK family kinase in vitro. In this method, HTRF® KinEASE-TK tyrosine kinase kit (article number: 62TK0PEB) of Cisbio company was used, and the principle of the kit was based on time-resolved fluorescence resonance energy transfer (TF-FRET), and the inhibition of the compounds on the activity of the NTRK kinase was reflected by determining a phosphorylation degree of a biotinylated polypeptide substrate mediated by NTRK kinase. For detailed experimental operation, please refer to the kit instruction. Recombinant human wild-type NTRK proteins were purchased from Carna bioscience (the article numbers were TRKA #08-186, TRKB #08-187 and TRKC #08-197 respectively), and recombinant human mutant NTRK proteins were purchased from SignalChem (the article numbers were TRKA G595R #N16-12BG-10, TRKA G667C #N16-12CG-10, and TRKC G623R #N18-12CH-10 respectively).

The experimental methods were operated according to the steps in the kit instruction, and were briefly described as follows: a test compound was first dissolved in DMSO to prepare a storage solution, and then diluted in gradient with a buffer provided in the kit. A final concentration of the test compound in the reaction system ranged from 1,000 nM to 0.004 nM. An ATP Km value concentration of each NTRK protein was determined by using an ATP solution diluted in gradient (Sangon Biotech (Shanghai) Co., Ltd., A600311). According to the Km value obtained, the ATP concentrations in the reaction system were set as 100 μM for TRKA, 10 μM for TRKB, 50 μM for TRKC, 7 μM for TRKA(G595R), 1 μM for TRKA(G667C) and 100 μM for TRKC(G623R). The reaction was carried out in a 384-well microplate. Firstly, the compound and a certain amount of corresponding NTRK protein were added to the wells and incubated for 5 minutes to 10 minutes at room temperature. Then, the ATP solution and the biotinylated polypeptide substrate solution were added to the reaction solution and incubated with shaking at room temperature for 60 minutes. Then, an anti-phosphorylated tyrosine antibody coupled with a europium compound and streptavidin coupled with modified allophycocyanin XL665 were added to the reaction, and continuously incubated with shaking at room temperature for 1 hour. After incubation, fluorescence intensity values of each well at an excitation wavelength of 304 nm, and emission wavelengths of 620 nM and 665 nM were determined in a TF-FRET mode on a microplate reader. Compared with the fluorescence intensity ratio of a control group (0.1% DMSO), the percentage inhibition rates of the compound at each concentration were calculated, and the IC$_{50}$ value of the compound was obtained by performing nonlinear regression analysis for logarithmic value of the compound concentration-inhibition rate by GraphPad Prism 5 software, which can be seen in Table 1.

TABLE 1

IC$_{50}$ data of the compounds of the present invention on TRK enzyme activity inhibition

| Compound No. | TRKA | TRKB | TRKC | TRKA (G595R) | TRKA (G667C) | TRKC (G623R) |
|---|---|---|---|---|---|---|
| 1 | 1.66 | 0.29 | 0.5 | 11.3 | — | — |
| 3 | 1.7 | 0.33 | 0.47 | 3.31 | — | — |
| 5 | 0.92 | 0.76 | 2.63 | 4.31 | — | 14.5 |
| 6 | 1.05 | 0.34 | — | 11.3 | — | — |
| 7 | 2.05 | 0.32 | — | 2.65 | 21.1 | 25.3 |
| 8 | 0.56 | 0.45 | 0.22 | 2.03 | — | 13.5 |
| 11 | 4.5 | — | 0.63 | — | — | — |
| 15 | 2.8 | — | 0.37 | — | — | — |
| 18 | 0.63 | 0.17 | 1.37 | 3.9 | 6.11 | — |
| 19 | 3.4 | 0.25 | 1.16 | 19.28 | — | — |
| 20 | 5.9 | — | — | — | 4.2 | — |
| 21 | 18.46 | — | — | — | 24.58 | — |
| 22 | 0.98 | 0.36 | 0.52 | 4.97 | 4.6 | 7.4 |
| 23 | 4.83 | — | — | 15.31 | — | — |
| 25 | 0.82 | 1.17 | 0.70 | 5.4 | 9.5 | — |
| 26 | 0.97 | 1.30 | 0.80 | 8.6 | 15.47 | — |

Conclusion: the compounds of the present invention have good inhibitory effects on both wild-type and mutant TRKA, TRKB and TRKC.

Test Example 2 Determination of the Compounds of the Present Invention on Cell Proliferation Activities of BAF3 LMNA-TRKA$^{WT}$ and BAF3 LMNA-TRKA$^{G667C}$ The following method was used to determine the effects of the compounds of the present invention on cell proliferation. BAF3 cells were purchased from National Infrastructure of Cell Line Resource (Beijing Headquarter). For TRKA, BAF3 cells were used to construct three stable cell lines of BAF3 LMNA-TRKA$^{WT}$ and BAF3 LMNA-TRKA$^{G667C}$ The above three cell lines were used to determine the inhibition of the compounds on cell activities. The cells were cultured in an RPMI 1640 medium containing 10% fetal bovine serum, 100 U penicillin and 100 μg/mL streptomycin. The cells were cultured in a 5% CO$_2$ incubator at 37° C. The activities of the cells were determined by CellTiter-Glo® Luminescent Cell Viability Assay kit (Promega, article number: G7573).

The experimental methods were operated according to the steps in the kit instruction, and were briefly described as follows: a test compound was first dissolved in DMSO to prepare a storage solution, and then diluted in gradient with the corresponding cell culture medium to prepare a test sample. A final concentration of the compound ranged from 1 μM to 0.15 nM. Cells in logarithmic growth phase were inoculated into a 96-well cell culture plate at a suitable density, and the cells were cultured in a 5% CO$_2$ incubator at 37° C. overnight. After adding the sample of the test compound, the cells were continuously cultured for 72 hours. After the culture, 50 μL of CellTiter-Glo detection solution was added to each well, shaken for 5 minutes, and then stood for 10 minutes, and the luminescence values of each well were read on the microplate reader using a Luminance mode. By comparing with the absorbance value of a control group (0.3% DMSO), the percentage inhibition rates of the compound at each concentration were calculated, and the IC$_{50}$ value of the compound on inhibiting cell proliferation was obtained by performing nonlinear regression analysis for logarithmic value of the compound concentration-inhibition rate by GraphPad Prism 5 software, which can be seen in Table 2.

TABLE 2

IC$_{50}$ data of the compounds of the present invention on inhibiting activities of BAF3 LMNA-TRKA$^{WT}$ and BAF3 LMNA-TRKA$^{G667C}$

| Compound No. | BAF3 LMNA-TRKA$^{WT}$ | BAF3 LMNA-TRKAG$^{667C}$ |
|---|---|---|
| 8 | 1.5 | 77.6 |
| 25 | 1.2 | 46.7 |

Conclusion: the compounds of the present invention have significant inhibitory effects on proliferation for BAF3 LMNA-TRKA$^{WT}$ and BAF3 LMNA-TRKA$^{G667C}$ stably transferred cell lines.

Test Example 3 Determination of the Compounds of the Present Invention on Cell Proliferation Activity of BAF3 LMNA-TRKA$^{G595R}$ The following method was used to determine the effects of the compounds of the present invention on cell proliferation. BAF3 cells were purchased from National Infrastructure of Cell Line Resource (Beijing Headquarter). For TRKA, BAF3 LMNA-TRKA$^{G595R}$ stably transformed cell line was constructed by BAF3 cells. The above cell line was used to determine the inhibition of the compounds on cell activity. The cells were cultured in an RPMI 1640 medium containing 10% fetal bovine serum, 100 U penicillin and 100 μg/mL streptomycin. The cells were cultured in a 5% CO$_2$ incubator at 37° C. The activity of the cells were determined by CellTiter-Glo® Luminescent Cell Viability Assay kit (Promega, article number: G7573).

The experimental methods were operated according to the steps in the kit instruction, and were briefly described as follows: a test compound was first dissolved in DMSO to prepare a storage solution, and then diluted in gradient with the corresponding cell culture medium to prepare a test sample. A final concentration of the compound ranged from 1 μM to 0.15 nM. Cells in logarithmic growth phase were inoculated into a 96-well cell culture plate at a suitable density, and the cells were cultured in a 5% CO$_2$ incubator at 37° C. overnight. After adding the sample of the test compound, the cells were continuously cultured for 72 hours. After the culture, 50 L of CellTiter-Glo detection solution was added to each well, shaken for 5 minutes, and then stood for 10 minutes, and the luminescence values of each well were read on the microplate reader using a Luminance mode. By comparing with the absorbance value of a control group (0.3% DMSO), the percentage inhibition rates of the compound at each concentration were calculated, and the IC$_{50}$ value of the compound on inhibiting cell proliferation was obtained by performing nonlinear regression analysis for logarithmic value of the compound concentration-inhibition rate by GraphPad Prism 5 software, which can be seen in Table 3.

TABLE 3

IC$_{50}$ data of the compounds of the present invention on inhibiting activity of BAF3 LMNA-TRKA$^{G595R}$

| Compound No. | IC$_{50}$ (nM) BAF3 LMNA-TRKA$^{G595R}$ |
|---|---|
| repotrectinib | 9.0 |
| 8 | 3.1 |
| 25 | 2.2 |

Conclusion: compared with repotrectinib, the compounds of the present invention have significant inhibitory effects on proliferation for BAF3 LMNA-TRKA$^{G595R}$ stably transferred cell line. Compounds 8 and 25 have unexpected inhibitory effects on BAF3 LMNA-TRKA$^{G595}$ stably transformed cell line, which are 2.9-4.1 times that of repotrectinib.

Test Example 4 Determination of the Compounds of the Present Invention on Activity of ALK Kinase The following method was used to determine the inhibition degrees of the compounds of the present invention on the activity of recombinant human ALK kinase in vitro. In this method, HTRF® KinEASE-TK tyrosine kinase kit (article No. 62TK0PEB) of Cisbio company was used, the principle of the kit was based on time-resolved fluorescence resonance energy transfer (TF-FRET), and the inhibition of the compounds on the activity of the ALK kinase was reflected by determining a phosphorylation degree of a biotinylated polypeptide substrate mediated by ALK kinase. For detailed experimental operation, please refer to the kit instruction. The recombinant human ALK was purchased from SignalChem (article number was ALK #A19-11G-10).

The experimental flow was briefly described as follows: a test compound was first dissolved in DMSO to prepare a storage solution, and then diluted in gradient with a buffer provided in the kit. A final concentration of the test compound in the reaction system ranged from 1000 nM to 0.004 nM. An ATP Km value concentration of each ALK protein was determined by using an ATP solution diluted in gradient (Sangon Biotech (Shanghai) Co., Ltd., A600311). According to the Km value obtained, the ATP concentrations in the reaction system were set as 1 µM for ALK, 10 µM for ALK(G1202R) and 25 µM for ALK(L1196M, G1202R). The reaction was carried out in a 384-well microplate. Firstly, the compound and a certain amount of corresponding ALK protein were added to the wells and incubated for 5 minutes to 10 minutes at room temperature. Then, the ATP solution and the biotinylated polypeptide substrate solution were added to the reaction solution and incubated with shaking at room temperature for 60 minutes. Then, an anti-phosphorylated tyrosine antibody coupled with a europium compound and streptavidin coupled with modified allophycocyanin XL665 were added to the reaction, and continuously incubated with shaking at room temperature for 1 hour. After incubation, fluorescence intensity values of each well at an excitation wavelength of 304 nM, and emission wavelengths of 620 nM and 665 nM were determined in a TF-FRET mode on a microplate reader, and the fluorescence intensity ratio 665/620 of each well was calculated. By comparing with the fluorescence intensity ratio of a control group (0.1% DMSO), the percentage inhibition rates of the compound at each concentration were calculated, and the IC$_{50}$ value of the compound was obtained by performing nonlinear regression analysis for logarithmic value of the compound concentration-inhibition rate by GraphPad Prism 5 software, which can be seen in Table 4.

TABLE 4

IC$_{50}$ data of the compounds of the present invention on inhibiting activity of ALK enzyme

| Compound No. | IC$_{50}$ (nM) ALK |
|---|---|
| repotrectinib | 9.45 |
| 8 | 2.02 |
| 25 | 1.93 |

Conclusion: compared with repotrectinib, the compounds of the present invention have preferable inhibitory effects on ALK. Compounds 8 and 25 have unexpected inhibitory effects on ALK, which are 4.7-4.9 times that of repotrectinib.

Test Example 5 Determination of the Compounds of the Present Invention on Activities of ALK(G1202R) and ALK(L1196M, G1202R) Kinases The following method was used to determine the inhibition degrees of the compounds of the present invention on the activities of recombinant human ALK(G1202R) and ALK(L1196M, G1202R) kinases in vitro. In this method, HTRF® KinEASE-TK tyrosine kinase kit (article No. 62TK0PEB) of Cisbio company was used, the principle of the kit was based on time-resolved fluorescence resonance energy transfer (TF-FRET), and the inhibitions of the compounds on the activities of the ALK(G1202R) and ALK(L1196M, G1202R) kinases were reflected by determining a phosphorylation degree of a biotinylated polypeptide substrate mediated by ALK kinase. For detailed experimental operation, please refer to the kit instruction. The recombinant human ALK(G1202R) and ALK(L1196M, G1202R) were both purchased from SignalChem (the article numbers were ALK(G1202R) #A 19-12HG-10, and ALK (L 1196M, G1202R) #A 19-12NG-10 respectively).

The experimental flow was briefly described as follows: a test compound was first dissolved in DMSO to prepare a storage solution, and then diluted in gradient with a buffer provided in the kit. A final concentration of the test compound in the reaction system ranged from 1000 nM to 0.004 nM. An ATP Km value concentration of each ALK protein was determined by using an ATP solution diluted in gradient (Sangon Biotech (Shanghai) Co., Ltd., A600311). According to the Km value obtained, the ATP concentrations in the reaction system were set as 10 µM for ALK(G1202R) and 25 µM for ALK(L1196M, G1202R). The reaction was carried out in a 384-well microplate. Firstly, the compound and a certain amount of corresponding ALK protein were added to the wells and incubated for 5 minutes to 10 minutes at room temperature. Then, the ATP solution and the biotinylated polypeptide substrate solution were added to the reaction solution and incubated with shaking at room temperature for 60 minutes. Then, an anti-phosphorylated tyrosine antibody coupled with a europium compound and streptavidin coupled with modified allophycocyanin XL665 were added to the reaction, and continuously incubated with shaking at room temperature for 1 hour. After incubation, fluorescence intensity values of each well at an excitation wavelength of 304 nM, and emission wavelengths of 620 nM and 665 nM were determined in a TF-FRET mode on a microplate reader, and the fluorescence intensity ratio 665/620 of each hole was calculated. By comparing with the fluorescence intensity ratio of a control group (0.1% DMSO), the percentage inhibition rates of the compound at each concentration were calculated, and the IC$_{50}$ value of the compound was obtained by performing nonlinear regression analysis for logarithmic value of the compound concentration-inhibition rate by GraphPad Prism 5 software, which can be seen in Table 5.

TABLE 5

IC$_{50}$ data of the compounds of the present invention on inhibiting activities of ALK(G1202R) and ALK(L1196M, G1202R) kinases

| | IC$_{50}$ (nM) | |
|---|---|---|
| Compound No. | ALK(G1202R) | ALK(L1196M, G1202R) |
| 8 | 13.2 | 20.7 |
| 25 | 13.6 | 24.2 |

Conclusion: the compounds of the present invention have preferable inhibitory effects on both ALK(G1202R) and ALK(L1196M, G1202R) kinases.

Test Example 6 Determination of the Compounds of the Present Invention on Activities of ROS1 and ROS1(G2032R) Kinases The following method was used to determine the inhibition degrees of the compounds of the present invention on the activity of recombinant human ROS1 kinase in vitro. In this method, HTRF® KinEASE-TK tyrosine kinase kit (article No. 62TK0PEB) of Cisbio company was used, the principle of the kit was based on time-resolved fluorescence resonance energy transfer (TF-FRET), and the inhibition of the compounds on the activity of the ROS1 kinase was reflected by determining a phosphorylation degree of a biotinylated polypeptide substrate mediated by ROS1 kinase. For detailed experimental operation, please refer to the kit instruction. The recombinant human ROS1 and ROS1(G2032R) were both purchased from SignalChem (the article numbers were R14-11G-10 and ROS1(G2032R) #R14-12BG-10 respectively).

The experimental flow was briefly described as follows: a test compound was first dissolved in DMSO to prepare a storage solution, and then diluted in gradient with a buffer provided in the kit. A final concentration of the test compound in the reaction system ranged from 1000 nM to 0.004 nM. An ATP Km value concentration of each ROS1 protein was determined by using an ATP solution diluted in gradient (Sangon Biotech (Shanghai) Co., Ltd., A600311). According to the Km value obtained, the ATP concentrations in the reaction system were set as 1 μM for ROS1 and 0.5 μM for ROS1(G2032R). The reaction was carried out in a 384-well microplate. Firstly, the compound and a certain amount of corresponding ROS1 protein were added to the wells and incubated for 5 minutes to 10 minutes at room temperature. Then, the ATP solution and the biotinylated polypeptide substrate solution were added to the reaction solution and incubated with shaking at room temperature for 60 minutes. Then, an anti-phosphorylated tyrosine antibody coupled with a europium compound and streptavidin coupled with modified allophycocyanin XL665 were added to the reaction, and continuously incubated with shaking at room temperature for 1 hour. After incubation, fluorescence intensity values of each well at an excitation wavelength of 304 nM, and emission wavelengths of 620 nM and 665 nM were determined in a TF-FRET mode on a microplate reader, and the fluorescence intensity ratio 665/620 of each hole was calculated. By comparing with the fluorescence intensity ratio of a control group (0.1% DMSO), the percentage inhibition rates of the compound at each concentration were calculated, and the IC$_{50}$ value of the compound was obtained by performing nonlinear regression analysis for logarithmic value of the compound concentration-inhibition rate by GraphPad Prism 6 software, which can be seen in Table 6.

TABLE 6

IC$_{50}$ data of compounds of the present invention on inhibiting activity of ROS1 enzyme

| | IC$_{50}$ (nM) | |
|---|---|---|
| Compound No. | ROS1 | ROS1(G2032R) |
| 8 | 0.36 | 0.34 |
| 25 | 0.84 | 2.11 |

Conclusion: the compounds of the present invention have preferable inhibitory effects on both ROS1 and ROS1(G2032R) kinases.

Test Example 7 Determination of the Compounds of the Present Invention on Cell Proliferation Activities of H2228 (Human Lung Cancer Cells) and KARPAS-299 (Human Anaplastic Large Cell Lymphoma Cell)

The following method was used to determine the effects of the compounds of the present invention on cell proliferation. H2228 cells (containing EML4-ALK fusion) were purchased from Cell Resource Center of Shanghai Institutes for Biological Sciences, Chinese Academy of Sciences. KARPAS-299 cells (containing NPM-ALK fusion) were purchased from Nanjing COBIOER Biotechnology Co., Ltd. The above two cell lines were used to determine the inhibition of the compounds on cell activities. The cells were cultured in an RPMI 1640 medium containing 10% fetal bovine serum, 100 U penicillin, 100 g/mL streptomycin, and 1 mM Sodium Pyruvate. The cells were cultured in a 5% $CO_2$ incubator at 37° C. The activity of the cells was determined by CellTiter-Glo® Luminescent Cell Viability Assay kit (Promega, article number: G7573).

The experimental methods were operated according to the steps in the kit instruction, and were briefly described as follows: a test compound was first dissolved in DMSO to prepare a storage solution, and then diluted in gradient with the corresponding cell culture medium to prepare a test sample. A final concentration of the compound ranged from 10 μM to 1.5 nM. Cells in logarithmic growth phase were inoculated into a 96-well cell culture plate at a suitable density, and the cells were cultured in a 5% $CO_2$ incubator at 37° C. overnight. After adding the sample of the test compound, the cells were continuously cultured for 72 hours. After the culture, 50 μL of CellTiter-Glo detection solution was added to each well, shaken for 5 minutes, and then stood for 10 minutes, and the luminescence values of each well were read on the microplate reader using a Luminance mode. By comparing with the numerical value of a control group (0.3% DMSO), the percentage inhibition rates of the compound at each concentration were calculated, and the IC$_{50}$ value of the compound on inhibiting cell proliferation was obtained by performing nonlinear regression analysis for logarithmic value of the compound concentration-inhibition rate by GraphPad Prism 5 software, which can be seen in Table 7.

TABLE 7

IC$_{50}$ data of the compounds of the present invention on inhibiting activities of H2228 and KARPAS-299

| Compound No. | IC$_{50}$ (nM) H2228 | IC$_{50}$ (nM) KARPAS-299 |
|---|---|---|
| 8 | 164.4 | 65.5 |
| 25 | — | 52.7 |

Conclusion: the compounds of the present invention have both preferable inhibitory effects on proliferation for H2228 cells and KARPAS-299 cells.

Test Example 8 Pharmacokinetic Study of the Compounds of the Present Invention on ICR Mice 1. Experimental Purpose In this study, ICR mice were used as test animals, and LC/MS/MS method was used to determine the drug concentrations in plasma of mice injected intravenously or administered intragastrically with repotrectinib and the compounds of the present invention, and to study the pharmacokinetic characteristics of the compounds of the present invention in mice.

2. Experimental Solution 2.1 Experimental Drugs and Animals

Repotrectinib, the compound of Example 5, the compound of Example 8 and the compound of Example 25.

ICR mice, male, 29.0 g to 33.8g, purchased from Beijing Charles River Laboratory Animal Technology Co., Ltd.

Animal quality certificate number: 33000800001184.

2.2 Drug Preparation

Intravenous injection group: an appropriate amount of drug was weighed, and added with mixed solvent (DMA: 30% Solutol HS-15: Saline=10:10:80 (v/v/v)) to prepare the drug with a final concentration of 0.2 mg/mL.

Oral gavage administration group: an appropriate amount of drug was weighed, added with an appropriate amount of sodium carboxymethyl cellulose (CMC-Na, containing 0.5% Tween 80), vortex shaked, and ultrasonically prepared into 0.5 mg/kg suspension.

2.3 Administration

For ICR mice, each compound to be tested was divided into an intravenous injection group (9 mice in each group) and an intragastric group (9 mice in each group). The ICR mice were fasted overnight and then administered by orbital intravenous injection (administration dose of 1 mg/kg, and administration volume of 5 mL/kg) and administered by intragastric injection (administration dose of 5 mg/kg, and administration volume of 10 mL/kg), and ate 4 hours after administration. 3. Operation About 0.2 mL of blood was collected via jugular vein before administration and 0.083 hour, 0.25 hour, 0.5 hour, 1 hour, 2 hours, 4 hours, 8 hours, 12 hours and 24 hours after administration, and heparin sodium was used for anticoagulation. The collected blood samples were placed on ice, and plasma was separated by centrifugation (centrifugation condition: 1500 g, 10 minutes). The collected plasma was stored at −40° C. to −20° C. before analysis.

LC-MS/MS was used to determine the contents of different compounds to be tested in mouse plasma after intravenous injection and intragastric administration.

4. Results of Pharmacokinetic Parameters

The pharmacokinetic parameters of the compounds of the present invention and the positive control can be seen in Table 8.

TABLE 8

Results of pharmacokinetic parameters

| Compound | Administration mode and administration dose | Blood concentration Cmax (ng/mL) | Area under curve AUC$_{0-\infty}$ (ng · h/mL) | Half-life T½(h) | Clearance rate ml/kg/min | Bioavailability F(%) |
|---|---|---|---|---|---|---|
| repotrectinib | 5 mg/kg, oral intake | 154 13 | 530 | 2.93 | N/A | 13 |
| | 1 mg/kg, injection | N/A | 824 | 3.90 | 20.2 | |
| Example 5 | 5 mg/kg, oral intake | 2600 65 | 6040 | 2.03 | N/A | 65 |
| | 1 mg/kg, injection | N/A | 1850 | 1.79 | 9.0 | |
| Example 8 | 5 mg/kg, oral intake | 2260 | 5620 | 1.54 | N/A | 53 |
| | 1 mg/kg, injection | N/A | 2100 | 1.47 | 7.9 | |
| Example 25 | 5 mg/kg, oral intake | 1050 | 4850 | 3.15 | N/A | 47 |
| | 1 mg/kg, injection | N/A | 2060 | 1.54 | 8.11 | |

Remarks: N/A means no relevant results.

Conclusion: compared with repotrectinib, the compound of Example 5, the compound of Example 8 and the compound of Example 25 of the present invention have significantly higher Cmax and $AUC_{0-\infty}$, lower clearance rates, significantly improved bioavailabilities, good pharmacokinetic absorption and better pharmacokinetic properties. Especially, compared with repotrectinib, the Cmax, $Auc_{0-\infty}$ and bioavailability of the compound of Example 8 are respectively 14.7 times, 10.6 times and 4.1 times that of repotrectinib, which well confirms that when ring B in general formula (I) of the present invention is benzoheterocyclyl, the pharmacokinetic absorption of the compound will be improved significantly, and the compound of the present invention has pharmacokinetic advantages.

Remarks: repotrectinib was prepared according to patent application WO2017007759, and its specific structure was as follows:

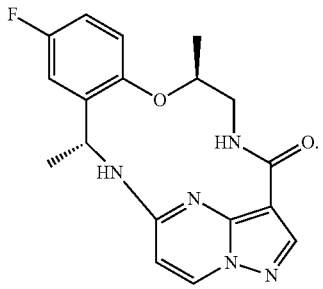 [SMILES: C[C@H]1CNC(=O)c2cnn3ccc(nc23)N[C@H](C)c2cc(F)ccc2O1]

The invention claimed is:

1. A compound represented by general formula (I) or a stereoisomer or a tautomer thereof, or a pharmaceutically acceptable salt thereof,

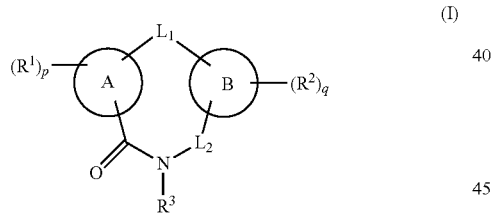

(I)

wherein:
ring A is selected from bicyclic heteroaryl;
ring B is selected from bicyclic aryl, bicyclic heteroaryl and bicyclic fused ring, wherein the bicyclic fused ring is preferably a fused ring of aryl or heteroaryl and monocyclic heterocyclyl or monocyclic cycloalkyl;
$L_1$ is selected from $-(CR^aR^b)_m-$, wherein any one of $-(CR^aR^b)-$ is optionally further replaced by $-N(R^c)-$, $-O-$ or $-S(O)_r-$;
$L_2$ is selected from $-(CR^dR^e)_n-$, wherein any one of $-(CR^dR^e)-$ is optionally further replaced by $-N(R^f)-$, $-O-$ or $-S(O)_r-$;
each $R^a$, $R^b$, $R^d$ and $R^e$ are the same or different and are each independently selected from hydrogen atom, deuterium, halogen, hydroxyl, alkoxy, alkyl, alkenyl, alkynyl, cycloalkyl, heterocyclyl, aryl, heteroaryl and $-NR^5R^6$, wherein the alkyl, alkenyl, alkynyl, cycloalkyl, heterocyclyl, aryl or heteroaryl is optionally further substituted by one or more substituents selected from hydroxyl, halogen, nitro, cyano, alkoxy, cycloalkyl, heterocyclyl, aryl, heteroaryl, $-C(O)R^4$, $-C(O)OR^4$, $-OC(O)R^4$, $-NR^5R^6$, $-C(O)NR^5R^6$, $-SO_2NR^5R^6$ and $-NR^5C(O)R^6$;

alternatively, $R^a$ and $R^b$ together with the same carbon atom bound therewith form a $C_3$-$C_8$ cycloalkyl or 3-8 membered heterocyclyl, wherein the 3-8 membered heterocyclyl internally contains one or more N, O or $S(O)_r$, and the $C_3$-$C_8$ cycloalkyl or 3-8 membered heterocyclyl is optionally further substituted by one or more substituents selected from hydroxyl, halogen, nitro, cyano, alkyl, alkoxy, cycloalkyl, heterocyclyl, aryl, heteroaryl, =O, $-C(O)R^4$, $-C(O)OR^4$, $-OC(O)R^4$, $-NR^5R^6$, $-C(O)NR^5R^6$, $-SO_2NR^5R^6$ and $-NR^5C(O)R^6$;

alternatively, any two $R^a$ together with different carbon atoms respectively bound therewith form a $C_3$-$C_8$ cycloalkyl or 3-8 membered heterocyclyl, wherein the 3-8 membered heterocyclyl internally contains one or more N, O or $S(O)_r$, and the $C_3$-$C_8$ cycloalkyl or 3-8 membered heterocyclyl is optionally further substituted by one or more substituents selected from hydroxyl, halogen, nitro, cyano, alkyl, alkoxy, cycloalkyl, heterocyclyl, aryl, heteroaryl, =O, $-C(O)R^4$, $-C(O)OR^4$, $-OC(O)R^4$, $-NR^5R^6$, $-C(O)NR^5R^6$, $-SO_2NR^5R^6$ of and $-NR^5C(O)R^6$;

alternatively, $R^d$ and $R^e$ together with the same carbon atom bound therewith form a $C_3$-$C_8$ cycloalkyl or 3-8 membered heterocyclyl, wherein the 3-8 membered heterocyclyl internally contains one or more N, O or $S(O)_r$, and the $C_3$-$C_8$ cycloalkyl or 3-8 membered heterocyclyl is optionally further substituted by one or more substituents selected from hydroxyl, halogen, nitro, cyano, alkyl, alkoxy, cycloalkyl, heterocyclyl, aryl, heteroaryl, =O, $-C(O)R^4$, $-C(O)OR^4$, $-OC(O)R^4$, $-NR^5R^6$, $-C(O)NR^5R^6$, $-SO_2NR^5R^6$ and $-NR^5C(O)R^6$;

alternatively, any two $R^d$ together with different carbon atoms respectively bound therewith form a $C_3$-$C_8$ cycloalkyl or 3-8 membered heterocyclyl, wherein the 3-8 membered heterocyclyl internally contains one or more N, O or $S(O)_r$, and the $C_3$-$C_8$ cycloalkyl or 3-8 membered heterocyclyl is optionally further substituted by one or more substituents selected from hydroxyl, halogen, nitro, cyano, alkyl, alkoxy, cycloalkyl, heterocyclyl, aryl, heteroaryl, =O, $-C(O)R^4$, $-C(O)OR^4$, $-OC(O)R^4$, $-NR^5R^6$, $-C(O)NR^5R^6$, $-SO_2NR^5R^6$ and $-NR^5C(O)R^6$;

each $R^c$ and $R^f$ are the same or different, and are each independently selected from hydrogen atom, alkyl and cycloalkyl, wherein the alkyl or cycloalkyl is optionally further substituted by one or more substituents selected from halogen, hydroxy, alkoxy and cycloalkyl; and $R^c$ and $R^f$ are preferably selected from hydrogen atom;

alternatively, when one $-(CR^aR^b)-$ is replaced by $-N(R^c)-$, $R^a$ or $R^b$ and $R^c$ together with the carbon atom and nitrogen atom respectively bound therewith form a 3-8 membered heterocyclyl, wherein the 3-8 membered heterocyclyl internally contains one or more N, O or $S(O)_r$, and the 3-8 membered heterocyclyl is optionally further substituted by one or more substituents selected from hydroxyl, halogen, nitro, cyano, alkyl, alkoxy, cycloalkyl, heterocyclyl, aryl, heteroaryl, =O, $-C(O)R^4$, $-C(O)OR^4$, $-OC(O)R^4$, $-NR^5R^6$, $-C(O)NR^5R^6$, $-SO_2NR^5R^6$ of and $-NR^5C(O)R^6$;

alternatively, when one —(CR$^d$R$^e$)— is replaced by —N(R')—, R$^d$ or R$^c$ and R$^f$ together with the carbon atom and nitrogen atom respectively bound therewith form a 3-8 membered heterocyclyl, wherein the 3-8 membered heterocyclyl internally contains one or more N, O or S(O)$_r$, and the 3-8 membered heterocyclyl is optionally further substituted by one or more substituents selected from hydroxyl, halogen, nitro, cyano, alkyl, alkoxy, cycloalkyl, heterocyclyl, aryl, heteroaryl, =O, —C(O)R$^4$, —C(O)OR$^4$, —OC(O)R$^4$, —NR$^5$R$^6$, —C(O)NR$^5$R$^6$, —SO$_2$NR$^5$R$^6$ and —NR$^5$C(O)R$^6$;

each R$^1$ and R$^2$ are the same or different, and are each independently selected from hydrogen atom, hydroxyl, halogen, nitro, cyano, alkyl, alkoxy, cycloalkyl, heterocyclyl, aryl, heteroaryl, —C(O)R$^4$, —C(O)OR$^4$, —OC(O)R$^4$, —NR$^5$R$^6$, —C(O)NR$^5$R$^6$, —SO$_2$NR$^5$R$^6$ and —NR$^5$C(O)R$^6$, wherein the alkyl, alkoxy, cycloalkyl, heterocyclyl, aryl or heteroaryl is optionally further substituted by one or more substituents selected from hydroxy, halogen, nitro, cyano, alkoxy, cycloalkyl, heterocyclyl, aryl, heteroaryl, =O, —C(O)R$^4$, —C(O)OR$^4$, —OC(O)R$^4$, —NR$^5$R$^6$, —C(O)NR$^5$R$^6$, —SO$_2$NR$^5$R$^6$ and —NR$^5$C(O)R$^6$; preferably, R$^1$ and R$^2$ are each independently selected from hydrogen atom, halogen, amino, cyano, alkyl, alkoxy, haloalkyl, haloalkoxy, hydroxyalkyl and alkoxyalkyl; and more preferably, R$^1$ and R$^2$ are each independently selected from hydrogen atom, amino, cyano, F, Cl, Br, methyl, hydroxymethyl, halomethyl and methoxymethyl;

R$^3$ is selected from hydrogen atom, alkyl and cycloalkyl, wherein the alkyl or cycloalkyl is optionally further substituted by one or more substituents selected from halogen, hydroxy, alkoxy and cycloalkyl;

R$^4$, R$^5$ and R$^6$ are each independently selected from hydrogen atom, hydroxy, halogen, alkyl, alkoxy, cycloalkyl, heterocyclyl, aryl and heteroaryl, wherein the alkyl, alkoxy, cycloalkyl, heterocyclyl, aryl or heteroaryl is optionally further substituted by one or more substituents selected from hydroxyl, halogen, nitro, cyano, alkyl, alkoxy, cycloalkyl, heterocyclyl, aryl, heteroaryl, =O, —C(O)R$^7$, —C(O)OR$^7$, —OC(O)R$^7$, —NR$^8$R$^9$, —C(O)NR$^8$R$^9$, —SO$_2$NR$^8$R$^9$ and —NR$^8$C(O)R$^9$;

alternatively, R$^5$ and R$^6$ together with the atom bound therewith form a 4-8 membered heterocyclyl, wherein the 4-8 membered heterocyclyl internally contains one or more N, O or S(O)$_r$, and the 4-8 membered heterocyclyl is optionally further substituted by one or more substituents selected from hydroxyl, halogen, nitro, cyano, alkyl, alkoxy, cycloalkyl, heterocyclyl, aryl, heteroaryl, =O, —C(O)R$^7$, —C(O)OR$^7$, —OC(O)R$^7$, —NR$^8$R$^9$, —C(O)NR$^8$R$^9$, —SO$_2$NR$^8$R$^9$ and —NR$^8$C(O)R$^9$;

R$^7$, R$^1$ and R$^9$ are each independently selected from hydrogen atom, alkyl, cycloalkyl, heterocyclyl, aryl and heteroaryl, wherein the alkyl, cycloalkyl, heterocyclyl, aryl or heteroaryl is optionally further substituted by one or more substituents selected from hydroxyl, halogen, nitro, cyano, alkyl, alkoxy, cycloalkyl, heterocyclyl, aryl, heteroaryl, carboxyl and carboxylate;

m and n are the same or different and are each independently selected from 1, 2, 3 and 4;

p and q are the same or different and are each independently selected from 0, 1, 2, 3, 4 and 5; and r is selected from 0, 1 and 2.

2. The compound or the stereoisomer or the tautomer thereof, or the pharmaceutically acceptable salt thereof according to claim 1, which is a compound represented by general formula (II) or a stereoisomer or a tautomer thereof, or a pharmaceutically acceptable salt thereof,

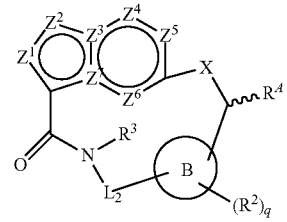

(II)

wherein:
ring B is selected from:

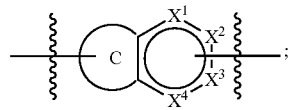

ring C is selected from monocyclic cycloalkyl, monocyclic heterocyclyl, monocyclic aryl and monocyclic heteroaryl, wherein ring C is bound with L$_2$;

X is selected from —N(R$^c$)—, —O— and —S(O)$_r$—; and preferably —NH—;

Z$^1$, Z$^2$, and Z$^4$ to Z$^6$ are the same or different and are each independently selected from N, NH, C(=O) and C(R');

Z$^3$ and Z$^7$ are the same or different and are each independently selected from N and C;

at least one of Z$^1$ to Z$^7$ is not selected from N and NH;

X$^1$ to X$^4$ are the same or different and are each independently selected from bonds, N, NH, C(=O) and C(R$^2$); at least one of X$^1$ to X$^4$ is not selected from N and NH; and at most one of X$^1$ to X$^4$ is selected from bonds;

R$^A$ is selected from hydrogen atom and alkyl, wherein the alkyl is optionally further substituted by one or more substituents selected from halogen, hydroxy, alkoxy and cycloalkyl; and R$^A$ is preferably methyl;

R$^c$ is selected from hydrogen atom, alkyl and cycloalkyl, wherein the alkyl or cycloalkyl is optionally further substituted by one or more substituents selected from halogen, hydroxy, alkoxy and cycloalkyl;

alternatively, when X is selected from —N(R$^c$)—, R$^A$ and R$^c$ together with the carbon atom and nitrogen atom respectively bound therewith form a 4-8 membered heterocyclyl, wherein the 4-8 membered heterocyclyl internally contains one or more N, O or S(O)$_r$, and the 4-8 membered heterocyclyl is optionally further substituted by one or more substituents selected from hydroxyl, halogen, nitro, cyano, alkyl, alkoxy, cycloalkyl, heterocyclyl, aryl, heteroaryl, =O, —C(O)R$^4$, —C(O)OR$^4$, —OC(O)R$^4$, —NR$^5$R$^6$, —C(O)NR$^5$R$^6$, —SO$_2$NR$^5$R$^6$ and —NR$^5$C(O)R$^6$; and R$^1$ to R$^6$, L$_2$, q and r are defined as in claim 1.

3. The compound or the stereoisomer or the tautomer thereof, or the pharmaceutically acceptable salt thereof according to claim 2, which is a compound represented by general formula (III) or a stereoisomer or a tautomer thereof, or a pharmaceutically acceptable salt thereof,

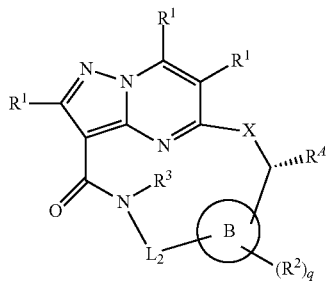

(III)

wherein: ring B, X, L$_2$, R$^1$ to R$^3$, R$^4$ and q are defined as in claim 2.

4. The compound or the stereoisomer or the tautomer thereof, or the pharmaceutically acceptable salt thereof according to claim 1, wherein ring B is selected from a 8-10 membered bicyclic fused ring, and preferably selected from:

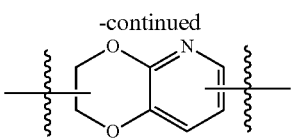
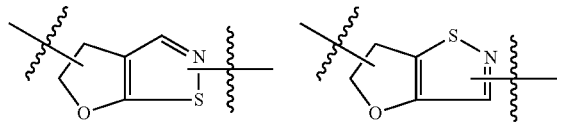
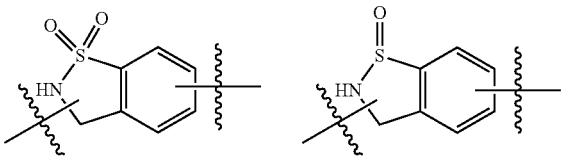
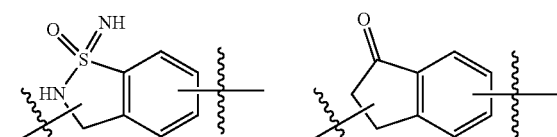
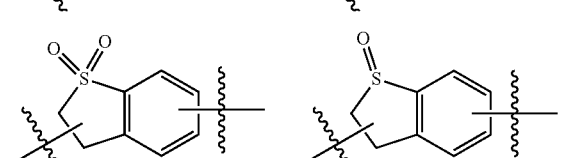
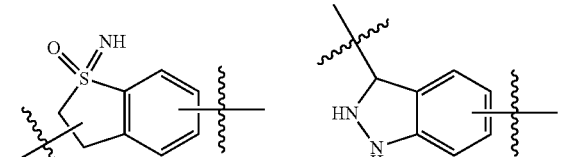
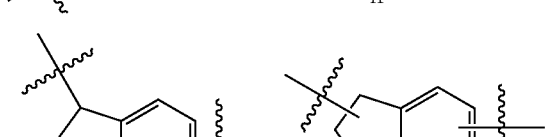
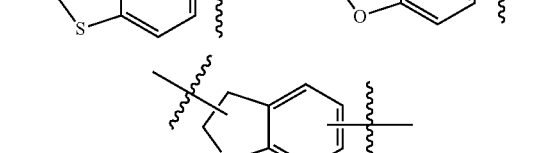
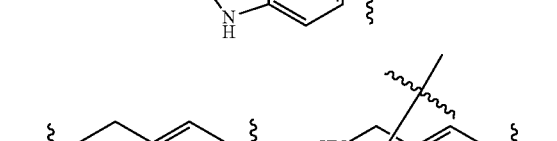
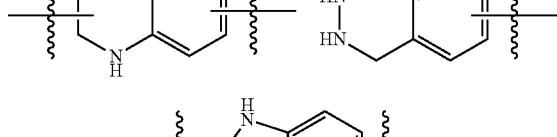
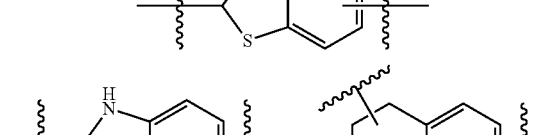
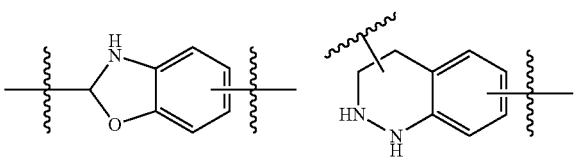

213
-continued
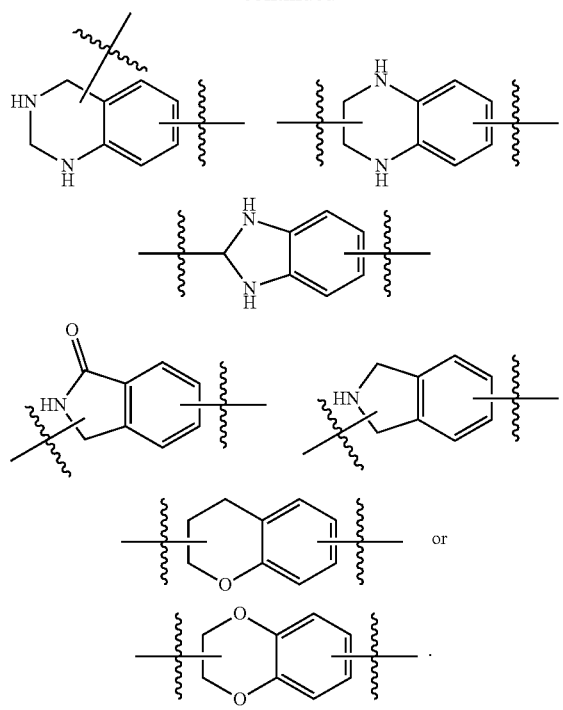
5. The compound or the stereoisomer or the tautomer thereof, or the pharmaceutically acceptable salt thereof according to claim 1, wherein ring B is selected from a 8-10 membered bicyclic heteroaryl, and preferably selected from:

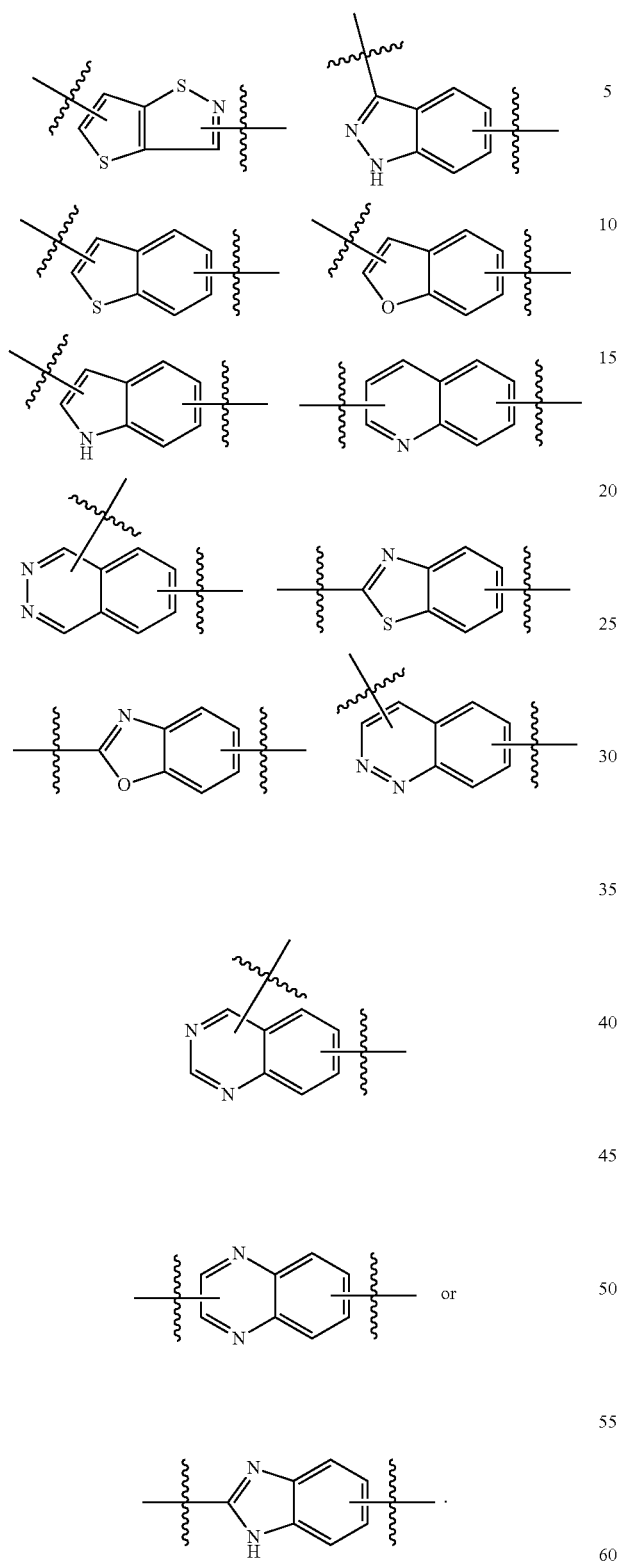

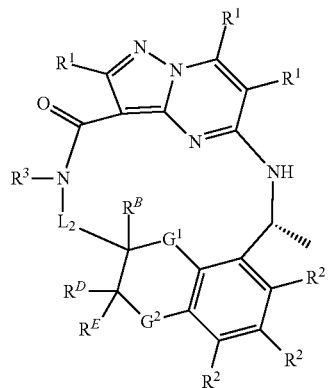

(IV)

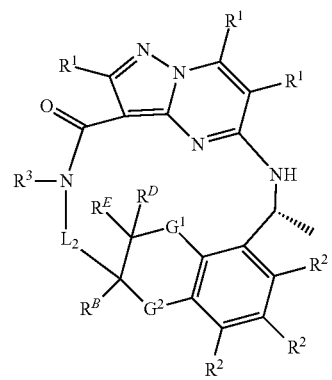

(V)

wherein:
G¹ and G² are the same or different, and are each independently selected from bonds, —N(R$^g$)—, —(CR$^h$R$^i$)— and —O—;

R$^g$ is selected from hydrogen atom, alkyl and cycloalkyl, wherein the alkyl or cycloalkyl is optionally further substituted by one or more substituents selected from halogen, hydroxy and alkoxy;

R$^h$ and R$^i$ are the same or different and are each independently selected from hydrogen atom, deuterium, halogen, hydroxy, alkoxy, alkyl, alkenyl, alkynyl, cycloalkyl, heterocyclyl, aryl and heteroaryl, wherein the alkyl, alkenyl, alkynyl, cycloalkyl, heterocyclyl, aryl or heteroaryl is optionally further substituted by one or more substituents selected from hydroxy, halogen, nitro, cyano, alkoxy, cycloalkyl, heterocyclyl, aryl, heteroaryl, —C(O)R⁴, —C(O)OR⁴, —OC(O)R⁴, —NR⁵R⁶, —C(O)NR⁵R⁶, —SO₂NR⁵R⁶ and —NR⁵C(O)R⁶;

alternatively, R$^h$ and R$^i$ together with the carbon atom bound therewith form a C₃-C₈ cycloalkyl or 3-8 membered heterocyclyl, wherein the 3-8 membered heterocyclyl internally contains one or more N, O or S(O)$_r$, and the C₃-C₈ cycloalkyl or 3-8 membered heterocyclyl is optionally further substituted by one or more substituents selected from hydroxyl, halogen, nitro, cyano, alkyl, alkoxy, cycloalkyl, heterocyclyl, aryl, heteroaryl, =O, —C(O)R⁴, —C(O)OR⁴, —OC(O)R⁴, —NR⁵R⁶, —C(O)NR⁵R⁶, —SO₂NR⁵R⁶ and —NR⁵C(O)R⁶;

6. The compound or the stereoisomer or the tautomer thereof, or the pharmaceutically acceptable salt thereof according to claim 3, which is a compound represented by general formula (IV) or (V) or a stereoisomer or a tautomer thereof, or a pharmaceutically acceptable salt thereof, each $R^1$ and $R^2$ are the same or different, and are each independently selected from hydrogen atom, hydroxyl, halogen, nitro, cyano, alkyl, alkoxy, cycloalkyl, heterocyclyl, aryl, heteroaryl, —C(O)$R^4$, —C(O)O$R^4$, —OC(O)$R^4$, —N$R^5R^6$, —C(O)N$R^5R^6$, —SO$_2$N$R^5R^6$ and —N$R^5$C(O)$R^6$, wherein the alkyl, alkoxy, cycloalkyl, heterocyclyl, aryl or heteroaryl is optionally further substituted by one or more substituents selected from hydroxy, halogen, nitro, cyano, alkoxy, cycloalkyl and heterocyclyl; preferably, $R^1$ and $R^2$ are each independently selected from hydrogen atom, halogen, amino, cyano, alkyl, alkoxy, haloalkyl, haloalkoxy, hydroxyalkyl and alkoxyalkyl; and more preferably, $R^1$ and $R^2$ are each independently selected from hydrogen atom, amino, cyano, F, Cl, Br, methyl, hydroxymethyl, halomethyl and methoxymethyl;

$R^B$ is selected from hydrogen atom, alkyl and alkoxy, wherein the alkyl or alkoxy is substituted by one or more substituents selected from hydroxy, halogen, nitro, cyano, alkoxy, cycloalkyl, heterocyclyl, aryl, heteroaryl, —C(O)$R^4$, —C(O)O$R^4$, —OC(O)$R^4$, —N$R^5R^6$, —C(O)N$R^5R^6$, —SO$_2$N$R^5R^6$(w and —N$R^5$C(O)$R^6$; and $R^B$ is preferably selected from hydrogen atom and methyl, wherein the methyl is optionally further substituted by one or more substituents selected from halogen, hydroxy, cycloalkyl, alkoxy and —N$R^5R^6$;

$R^D$ and $R^E$ are the same or different, and are each independently selected from hydrogen atom, deuterium, halogen, hydroxy, alkoxy, alkyl, alkenyl, alkynyl, cycloalkyl, heterocyclyl, aryl, heteroaryl, —C(O)$R^4$, —C(O)O$R^4$, —OC(O)$R^4$, —N$R^5R^6$, —C(O)N$R^5R^6$, —SO$_2$N$R^5R^6$ and —N$R^5$C(O)$R^6$, wherein the alkyl, alkenyl, alkynyl, cycloalkyl, heterocyclyl, aryl or heteroaryl is optionally further substituted by one or more substituents selected from hydroxy, halogen, nitro, cyano, alkoxy, cycloalkyl, heterocyclyl, aryl, heteroaryl-C(O)$R^4$, —C(O)O$R^4$, —OC(O)$R^4$, —N$R^5R^6$, —C(O)N$R^5R^6$, —SO$_2$N$R^5R^6$ and —N$R^5$C(O)$R^6$;

alternatively, $R^D$ and $R^E$ together with the carbon atom bound therewith form a $C_3$-$C_6$ cycloalkyl or 3-6 membered heterocyclyl, wherein the 3-6 membered heterocyclyl internally contains one or more N, O or S(O)$_r$, and the $C_3$-$C_6$ cycloalkyl or 3-6 membered heterocyclyl is optionally further substituted by one or more substituents selected from hydroxyl, halogen, nitro, cyano, alkyl, alkoxy, cycloalkyl, heterocyclyl, aryl, heteroaryl, =O, —C(O)$R^4$, —C(O)O$R^4$, —OC(O)$R^4$, —N$R^5R^6$, —C(O)N$R^5R^6$, —SO$_2$N$R^5R^6$ and —N$R^5$C(O)$R^6$; and $L_2$, r, and $R^3$ to $R^6$ are defined as in claim 3.

7. The compound or the stereoisomer or the tautomer thereof, or the pharmaceutically acceptable salt thereof according to claim 6, which is a compound represented by general formula (VI), (VII), (VIII) or (IX) or a stereoisomer or a tautomer thereof, or a pharmaceutically acceptable salt thereof,

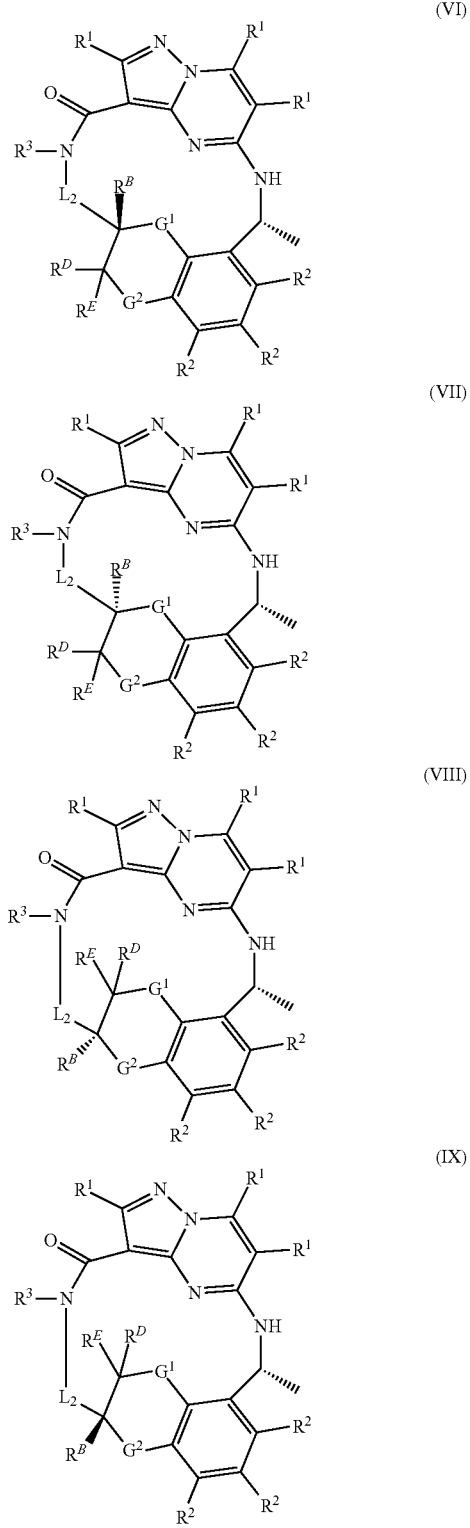

wherein: $L_2$, $G^1$, $G^2$, $R^1$ to $R^3$, $R^B$, $R^D$ and $R^E$ are defined as in claim 6.

8. The compound or the stereoisomer or the tautomer thereof, or the pharmaceutically acceptable salt thereof according to claim 1, wherein:

$L_2$ is selected from —(C$R^dR^e$)$_n$—;

$R^d$ is selected from hydrogen atom;

$R^e$ is selected from hydrogen atom, alkyl and alkoxy, and preferably hydrogen atom or methyl, wherein the alkyl or alkoxy is substituted by one or more halogens; and
n is 1, 2 or 3.
9. The compound or the stereoisomer or the tautomer thereof, or the pharmaceutically acceptable salt thereof according to claim 1, wherein the compound is selected from:
1
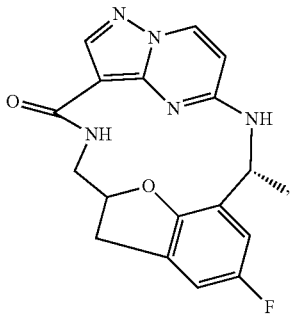
2
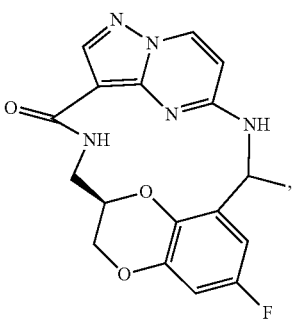
3
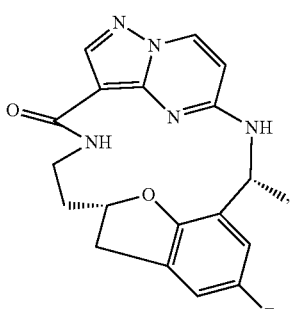
4
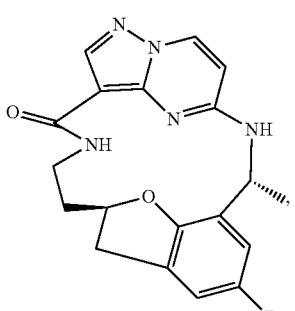
-continued
5
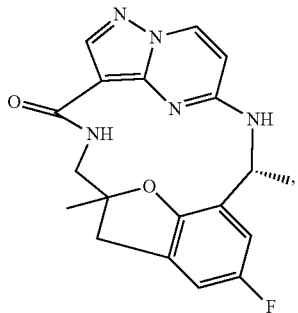
6
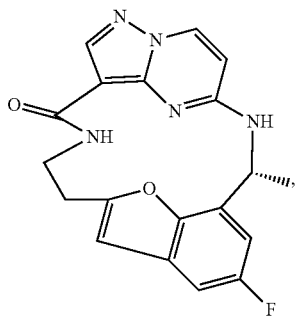
7
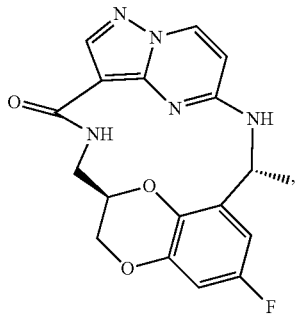
8
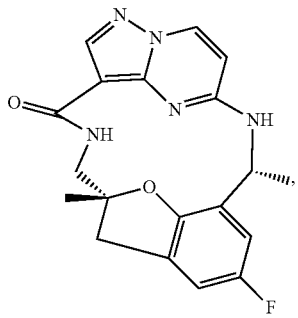
9
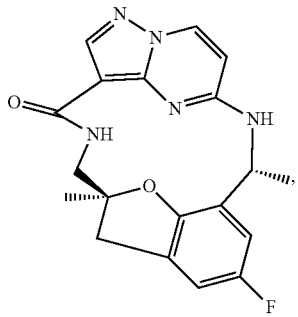

221
-continued
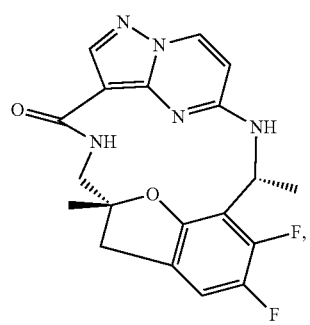
10
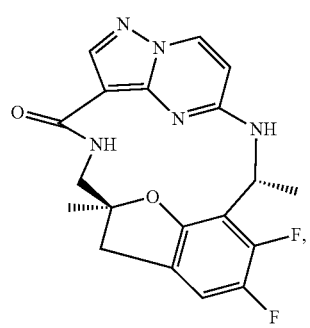
11
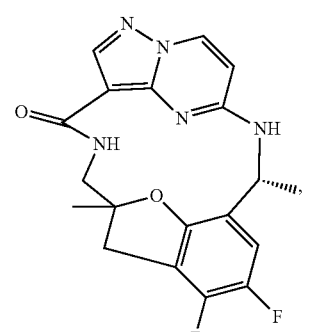
12
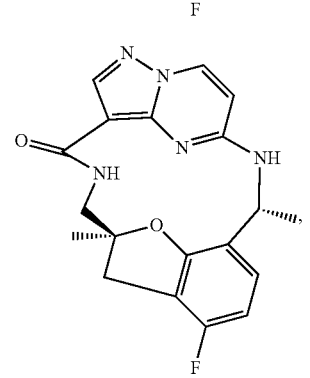
13
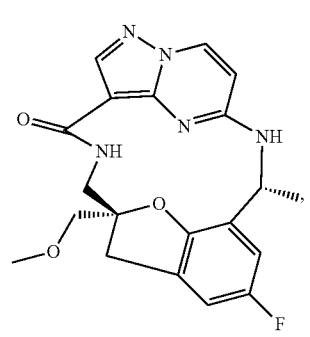
14
222
-continued
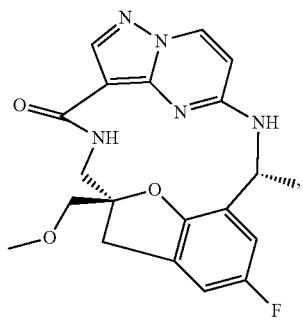
15
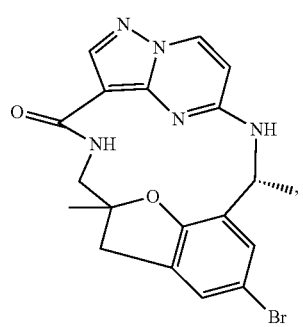
16
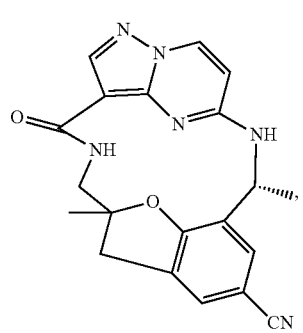
17
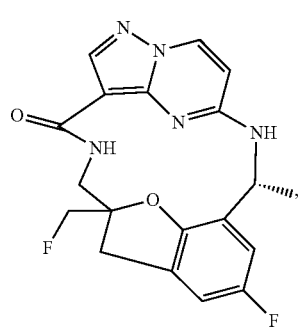
18
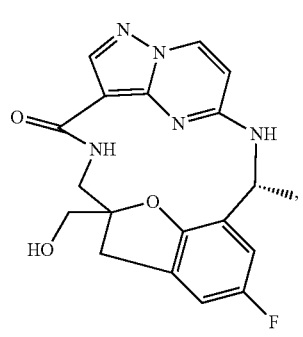
19

223
-continued

20
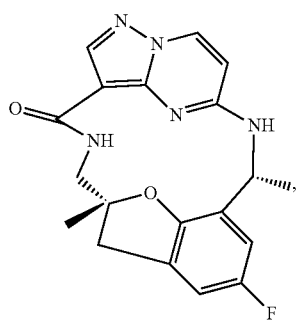

21
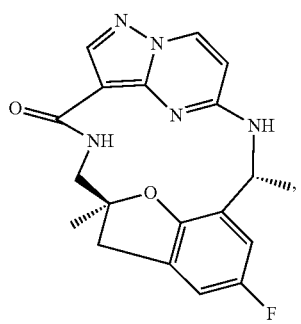

22
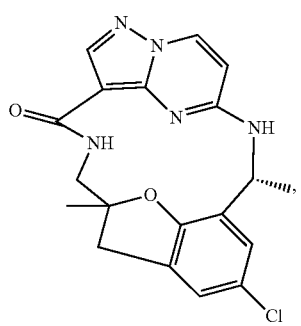

23
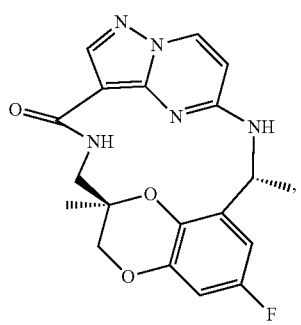

24
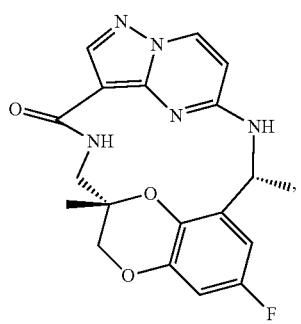

224
-continued

25
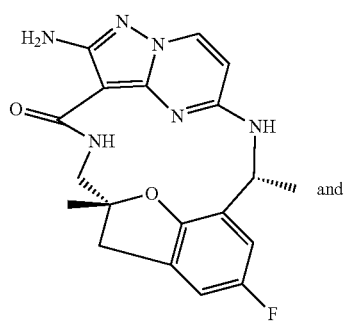
and

26
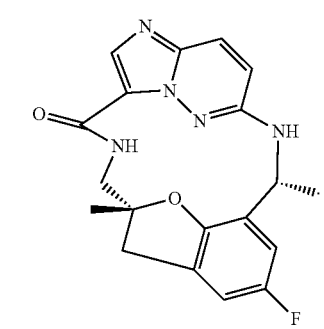

10. A preparation method of the compound represented by general formula (I) or the stereoisomer or the tautomer thereof, or the pharmaceutically acceptable salt thereof according to claim 1, wherein the method comprises:

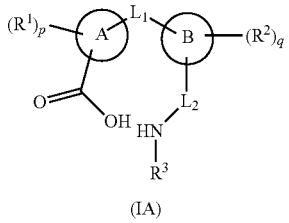

(IA)

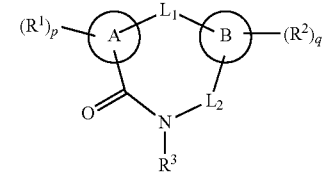

(I)

subjecting a compound represented by general formula (IA) to a condensation reaction under basic conditions to obtain a compound represented by general formula (I);

wherein: ring A, ring B, $R^1$ to $R^3$, $L_1$, $L_2$, p and q are defined as in claim 1.

11. A preparation method of the compound represented by general formula (I) or the stereoisomer or the tautomer thereof, or the pharmaceutically acceptable salt thereof according to claim 1, wherein the method comprises:

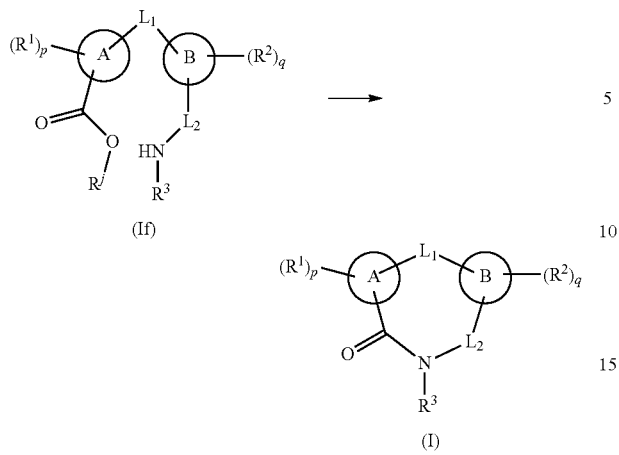

subjecting a compound represented by general formula (If) to a condensation reaction under basic conditions to obtain a compound represented by general formula (I); wherein:
$R^j$ is selected from alkyl; and
ring A, ring B, $R^1$ to $R^3$, $L_1$, $L_2$, p and q are defined as in claim 1.

12. A compound represented by general formula (IA) or a stereoisomer or a tautomer thereof,

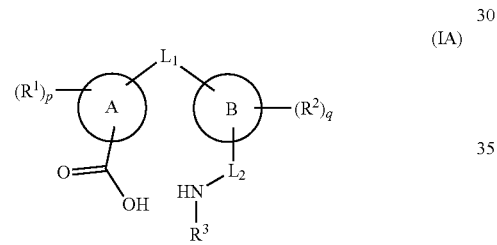

wherein:
$L_1$ is —X—$CHR^A$;
X is selected from —N($R^c$)—, —O— or and —S(O)$_r$—; and preferably —NH—;
$R^A$ is selected from hydrogen atom and alkyl, wherein the alkyl is optionally further substituted by one or more substituents selected from halogen, hydroxy, alkoxy and cycloalkyl; and $R^A$ is preferably methyl;
$R^c$ is selected from hydrogen atom, alkyl and cycloalkyl, wherein the alkyl or cycloalkyl is optionally further substituted by one or more substituents selected from halogen, hydroxy, alkoxy and cycloalkyl;
alternatively, when X is selected from —N($R^c$)—, $R^A$ and $R^c$ together with the carbon atom and nitrogen atom respectively bound therewith form a 4-8 membered heterocyclyl, wherein the 4-8 membered heterocyclyl internally contains one or more N, O or S(O)$_r$, and the 4-8 membered heterocyclyl is optionally further substituted by one or more substituents selected from hydroxyl, halogen, nitro, cyano, alkyl, alkoxy, cycloalkyl, heterocyclyl, aryl, heteroaryl, =O, —C(O)$R^4$, —C(O)O$R^4$, —OC(O)$R^4$, —N$R^5R^6$, —C(O)N$R^5R^6$, —SO$_2$N$R^5R^6$ and —N$R^5$C(O)$R^6$; and
ring A, ring B, $R^1$ to $R^6$, $L_2$, M q and r are defined as in claim 1.

13. The compound or the stereoisomer or the tautomer thereof according to claim 12, wherein the compound is selected from:

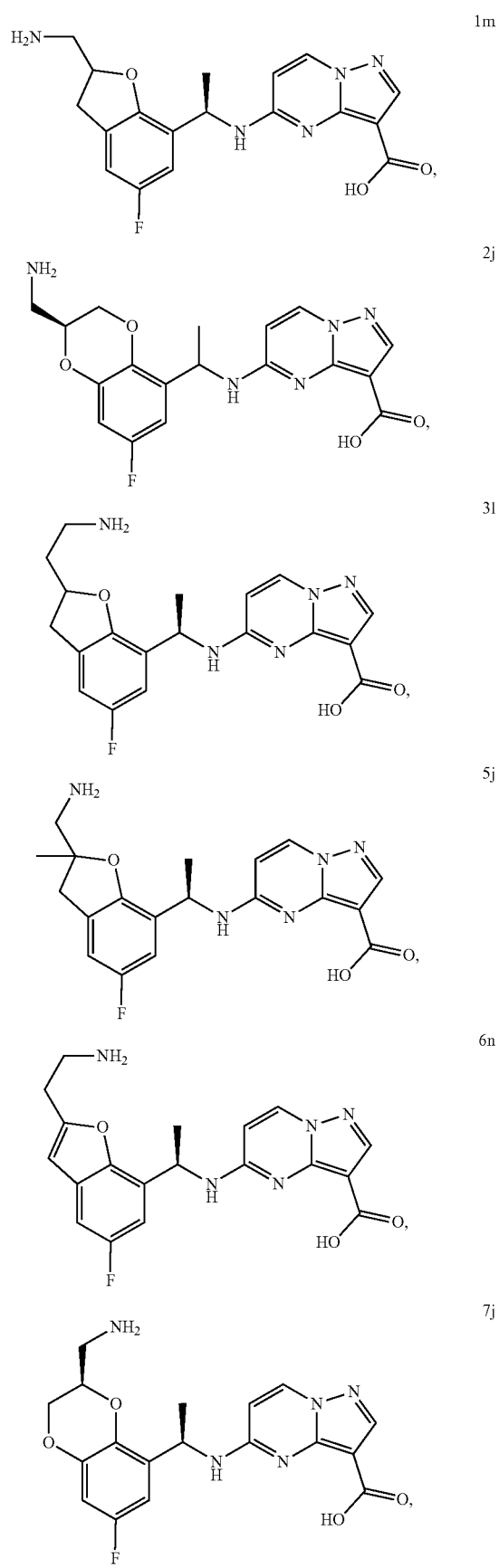

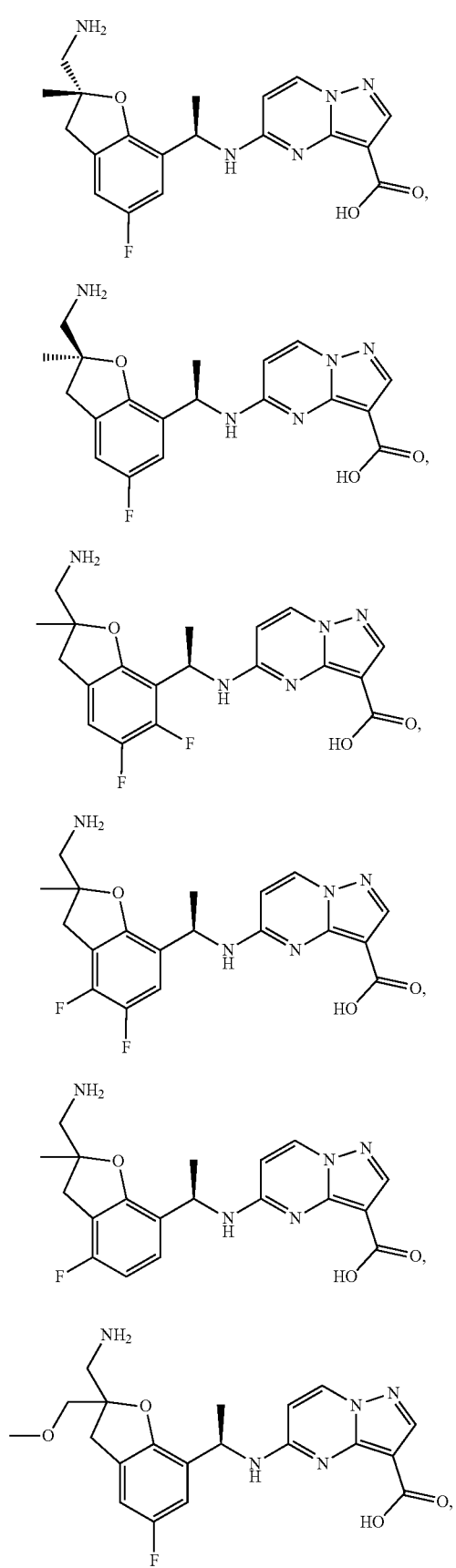
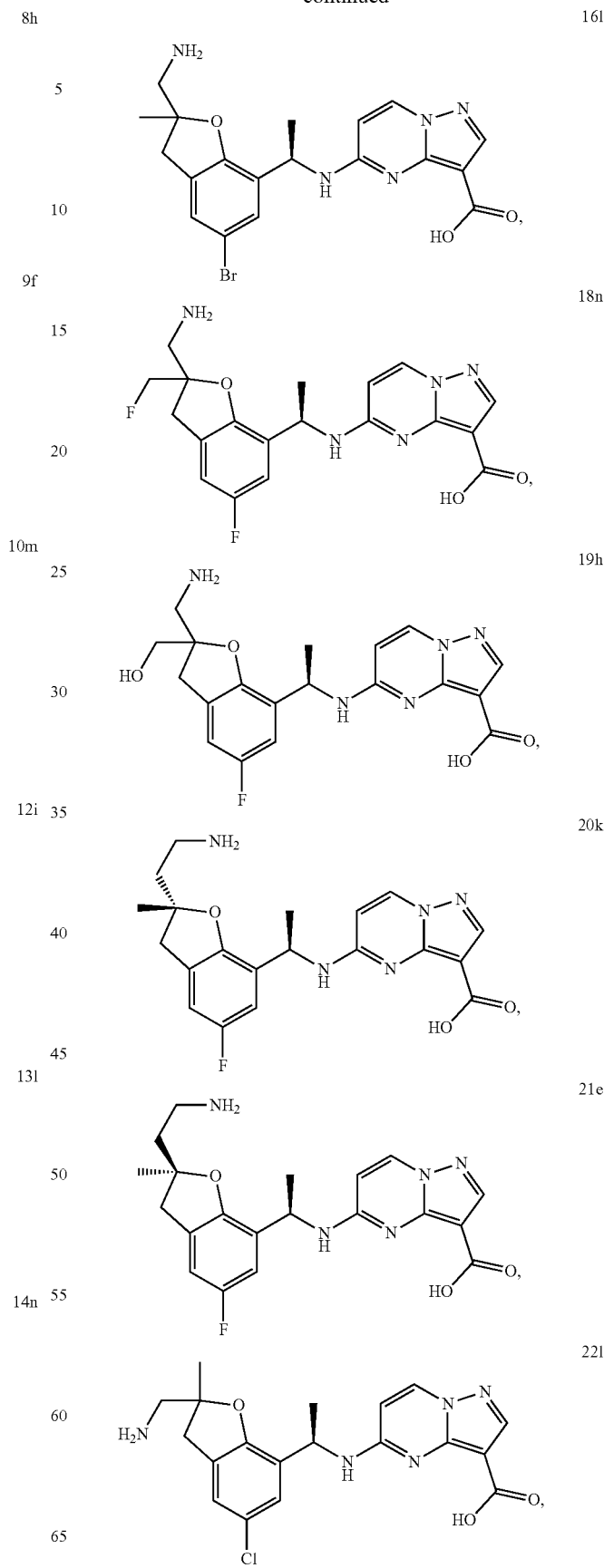

-continued

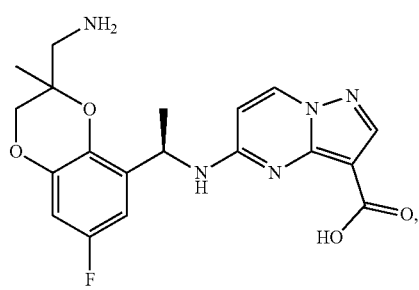
23k

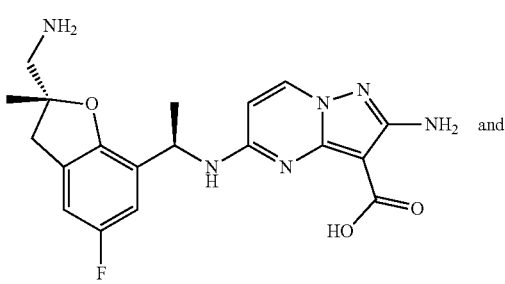
25j

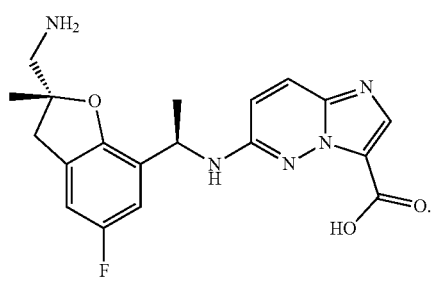
26d

14. A preparation method of the compound represented by general formula (IA) or the stereoisomer or the tautomer thereof according to claim 12, wherein the method comprises:

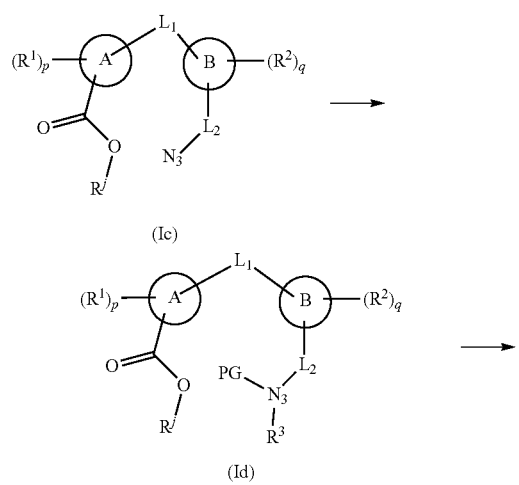

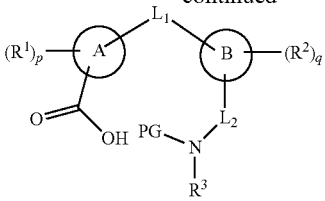
(Ie)

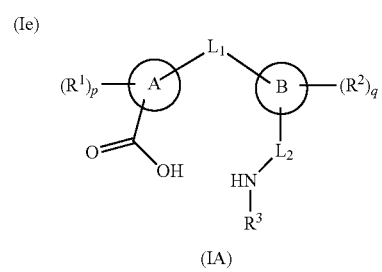
(IA)

reacting a compound represented by general formula (Ic) in the presence of di-tert-butyl dicarbonate under the conditions of hydrogen and catalyst to obtain a compound represented by general formula (Id); subjecting the compound represented by general formula (Id) to hydrolysis under basic conditions to obtain a compound represented by general formula (Ie); and further removing the protecting group PG from the compound represented by general formula (Ie) to obtain a compound represented by general formula (IA);

wherein:

$R^3$ is selected from hydrogen atom;

$R^j$ is selected from alkyl;

PG is an amino protecting group, and is preferably tert-butoxycarbonyl; and ring A, ring B, $R^1$ to $R^2$, $L_1$, $L_2$, p and q are defined as in claim 12.

15. A pharmaceutical composition, wherein the pharmaceutical composition comprises an effective amount of the compound or the stereoisomer or the tautomer thereof, or the pharmaceutically acceptable salt thereof according to claim 1, and a pharmaceutically acceptable carrier, an excipient or a combination thereof.

16. A method for inhibiting an activity of one or more protein kinases of TRK, ALK and ROS1, comprising administering a therapeutically effective amount of the compound or the stereoisomer or the tautomer thereof, or the pharmaceutically acceptable salt thereof according to claim 1 to a patient in need.

17. A method for treating a disease symptom of pain, inflammation, neurodegenerative diseases or trypanosome infection, comprising administering a therapeutically effective amount of the compound or the stereoisomer or the tautomer thereof, or the pharmaceutically acceptable salt thereof according to claim 1.

18. A method for treating a cancer, comprising administering a therapeutically effective amount of the compound or the stereoisomer or the tautomer thereof, or the pharmaceutically acceptable salt thereof according to claim 1 to a patient in need, wherein the cancer is preferably neurocytoma, ovarian cancer, breast cancer, prostate cancer, gastric cancer, gastrointestinal cancer, liver cancer, cholangiocarcinoma, pancreatic cancer, multiple myeloma, astrocytoma, medulloblastoma, neuroglioma, melanoma, thyroid cancer, lung cancer, magnocellular neuroendocrine tumor, colorectal cancer, mammary analogue secretory carcinoma, sarcoma, head and neck tumor, and renal carcinoma.

\* \* \* \* \*